United States Patent
Yan et al.

(10) Patent No.: US 12,240,861 B2
(45) Date of Patent: Mar. 4, 2025

(54) IMIDAZO NITROGEN HETEROCYCLIC COMPOUND AND APPLICATION THEREOF

(71) Applicant: GUANGDONG AGLAIA OPTOELECTRONIC MATERIALS CO., LTD, Guangdong (CN)

(72) Inventors: Liangliang Yan, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 673 days.

(21) Appl. No.: 17/432,335

(22) PCT Filed: Mar. 28, 2020

(86) PCT No.: PCT/CN2020/081895
§ 371 (c)(1),
(2) Date: Aug. 19, 2021

(87) PCT Pub. No.: WO2020/228430
PCT Pub. Date: Nov. 19, 2020

(65) Prior Publication Data
US 2022/0169661 A1    Jun. 2, 2022

(30) Foreign Application Priority Data
May 13, 2019   (CN) .......................... 201910393579.5

(51) Int. Cl.
| | |
|---|---|
| *C07D 519/00* | (2006.01) |
| *H01L 51/00* | (2006.01) |
| *H10K 85/60* | (2023.01) |
| *H10K 50/11* | (2023.01) |
| *H10K 50/16* | (2023.01) |
| *H10K 50/18* | (2023.01) |
| *H10K 101/10* | (2023.01) |

(52) U.S. Cl.
CPC ......... *C07D 519/00* (2013.01); *H10K 85/626* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/16* (2023.02); *H10K 50/18* (2023.02); *H10K 2101/10* (2023.02)

(58) Field of Classification Search
CPC .............. C07D 519/00; H01L 51/0072; H01L 51/0067; H01L 51/0073; H01L 51/0058; H01L 51/5016; H01L 51/0074
See application file for complete search history.

(56) References Cited

U.S. PATENT DOCUMENTS

2014/0225100 A1   8/2014   Yokoyama et al.

FOREIGN PATENT DOCUMENTS

| | | |
|---|---|---|
| CN | 101186608 A | 5/2008 |
| CN | 102070632 A | 5/2011 |
| CN | 103709180 A | 4/2014 |
| CN | 103709181 A | 4/2014 |
| CN | 103788087 A | 5/2014 |
| CN | 103788116 A | 5/2014 |
| CN | 103828485 A | 5/2014 |
| TW | 201506128 B | 2/2015 |
| WO | 2017111366 A1 | 6/2017 |

OTHER PUBLICATIONS

Li et al., "New Type of 2,6-bis(imidazo[1,2-a]pyridene-based ruthenium complexes: active catalysts for transfer hydrogenation of ketones," Organometallics, vol. 34, No. 7, Mar. 17, 2015, pp. 1170-1176 (Year: 2015).*
Cao et al., "NNN Pincer Ru(II)-Complex-Catalyzed a-alkylation of ketones with alcohols," The Journal of Organic Chemistry, vol. 83, Mar. 13, 2018, pp. 3657-3668 (Year: 2018).*
Xiao-Niu Cao et al., "NNN Pincer Ru(II)-Complex-Catalyzed a-Alkylation of Ketones with Alcohols", The Journal of Organic Chemistry, vol. 83, Mar. 13, 2018, pp. 3657-3668.
Ke Li et al., "New Type of 2, 6-Bis(imidazo[1, 2-a]pyridine-Based Ruthenium Complexes: Active Catalysts for Transfer Hydrogenation of Ketones", Organometallics, vol. 34, No. 7, Mar. 17, 2015, pp. 1170-1176.

* cited by examiner

*Primary Examiner* — Robert D Harlan
(74) *Attorney, Agent, or Firm* — Maschoff Brennan

(57) ABSTRACT

The present invention relates to an imidazoazacyclo compound and an application thereof. The compound of the present invention has a structure as shown in a formula I. The imidazoazacyclo compound of the present invention has the advantages of low sublimation temperature, good light stability, electrical stability and thermal stability, high refractive index, small difference of refractive index in a visible light area and the like, and an apparatus prepared by the compound has the advantages of low voltage, long service life, high luminous efficiency and the like and can be used in an organic luminescent apparatus. In particular, as an electron transmission material, a hole barrier layer material and a light extraction layer material, the imidazoazacyclo compound has the probability of being applied to an AMOLED industry.

14 Claims, No Drawings

IMIDAZO NITROGEN HETEROCYCLIC COMPOUND AND APPLICATION THEREOF

TECHNICAL FIELD

The present invention relates to the technical field of organic electroluminescent materials, in particular to an imidazoazacyclo compound and an application thereof in an organic electroluminescent apparatus.

BACKGROUND

At present, an organic electroluminescent apparatus (Organic Light Emitting Diode) as a new generation display technology gains increasing attention in display and illumination technologies, and its application prospect is quite wide. However, compared with a market application requirement, it is still needed to further enhance and improve performance of the OLED apparatus, such as luminous efficiency, driving voltage and service life.

Generally speaking, a basic structure of the OLED apparatus is structured such that organic functional material films with various different functions are entrained between metal electrodes like a sandwich structure. Driven under a current, holes and electrons are injected respectively from the cathode and the anode, and the holes and the electrons moving at a certain distance are compounded on a luminous layer and are released in form of light or heat, such that illumination of the OLED is generated. However, the organic functional material is a core composition of the organic electroluminescent apparatus, and thermal stability, light chemical stability, electrochemical stability, quantum yield, film forming stability, crystallinity, color saturation and the like of the material are major factors that affect apparatus performance.

On the one hand, how to shorten the huge difference between internal and external quantum efficiencies of the OLED apparatus and how to reduce the total emission effect and improve the optical coupling extraction proportion in the apparatus attract wide attention of people. The refractive indexes of materials of current light extraction layers are relatively low, in particular the refractive index of a red light wave band is smaller than 1.85, the refractive index of a very few of the materials is greater than 1.90 and the refractive index of fewer materials is greater than 2.0. In addition, the current light extraction materials are hugely different in refractive index in red, green and blue wave band regions, causing a huge optimum thickness difference of the three color lights, thereby not reflecting performance of the light extraction material fully. As far as a top emission apparatus is concerned, the greater the refractive index of the light extraction layer material is, the higher the corresponding external quantum efficiency is and the higher the luminous efficiency of the apparatus is. Thus, it is in particular important to develop the light extraction layer material with the high refractive index. CN103828485 and TW201506128 disclose a light extraction layer material taking polyphenylenediamine as a core, but the refractive index is slightly low, in particular, the refractive index in red light needs to be further improved.

On the other hand, how to reduce the working voltage of the apparatus, lower the product power consumption, prolong the service life of the apparatus and improve the luminous efficiency is also an orientation of improving the OLED apparatus continuously. CN101186608 discloses a compound structured by bonding imidazopyridine and an anthracene ring. It is needed to improve the triplet state energy level of the compound, the glass-transition temperature and the service life of the apparatus. Qiu et al. discloses a series of compounds structured by bonding imidazopyridine and a fused aromatic ring in CN103709180, CN103709181, CN103788087 and CN103788116. It is also needed to further improve the triplet state energy level of the compound, the glass-transition temperature and the service life of the apparatus.

SUMMARY

Aiming at the defects in the field, the present invention provides an imidazoazacyclo compound. The compound has a structure shown in a formula I. The compound has the advantages of low sublimation temperature, good light stability, electrical stability and thermal stability, high refractive index, small difference of refractive index in a visible light area and the like, and can be used in an organic luminescent apparatus.

The present invention further provides an application of the imidazoazacyclo compound in an OLED, and in particular, as an electron transmission material, a hole barrier layer material and a light extraction layer material, the compound enables the apparatus to have the characteristics of high luminous efficiency, low voltage and long service life and has the probability of being applied to an AMOLED industry.

A structural formula (I) thereof being as shown in:

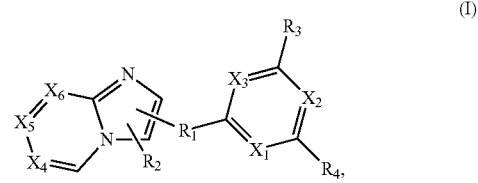

wherein R1 is a single bond, alkyl, heteroalkyl, cycloalkyl, substituted or unsubstituted C6-C30 non-fused ring aryl and substituted or unsubstituted C3-C27 non-fused ring aryl;

R2, R3 and R4 are independently selected from hydrogen, deuterium, halogen, alkyl, heteroalkyl, cycloalkyl, alkoxyl, aryloxy, amino, silicyl, nitrile, isonitrile, phosphino, substituted or unsubstituted C6-C60 aryl, substituted or unsubstituted C1-C60 heteroaryl, substituted or unsubstituted monocyclic or polycyclic C3-C60 aliphatic ring or aromatic ring and at least one of R3 and R4 is substituted or unsubstituted C6-C60 aryl, substituted or unsubstituted C1-C60 heteroaryl, substituted or unsubstituted monocyclic or polycyclic C3-C60 aliphatic ring or aromatic ring, where one or more carbon atoms in the heteroalkyl or heteroaryl can be substituted by at least one heteroatom selected from O, S, N, Se, Si and Ge; the being substituted is being substituted by deuterium, halogen, C1-C30 alkyl, C1-C30 heteroalkyl, C3-C30 cycloalkyl, amino, silicyl, nitrile, isonitrile, phosphino, C6-C60 aryl and C1-C60 heteroaryl; and X1, X2 and X3 independently represent CH or N; X4, X5 and X6 independently represent CR0 or N, R0 is independently selected from hydrogen, deuterium, halogen, alkyl, heteroalkyl, aralkyl, alkoxyl, aryloxy, amino, silicyl, aryl, heteroaryl, nitrile, isonitrile and phosphino, and adjacent R0 can be bonded to form a fused ring.

Preferably, R1 is a single bond, C1-C30 alkyl, C1-C30 heteroalkyl, C3-C30 cycloalkyl, substituted or unsubstituted C6-C30 non-fused ring aryl and substituted or unsubstituted C3-C27 non-fused ring aryl;

R2, R3 and R4 are independently selected from hydrogen, deuterium, halogen, C1-C30 alkyl, C1-C30 heteroalkyl, C3-C30 cycloalkyl, amino, silicyl, nitrile, isonitrile, phosphino, substituted or unsubstituted C6-C60 aryl, substituted or unsubstituted C1-C60 heteroaryl, substituted or unsubstituted monocyclic or polycyclic C3-C60 aliphatic ring or aromatic ring and at least one of R3 and R4 is substituted or unsubstituted C6-C60 aryl, substituted or unsubstituted C1-C60 heteroaryl, substituted or unsubstituted monocyclic or polycyclic C3-C60 aliphatic ring or aromatic ring, where one or more carbon atoms in the heteroalkyl or heteroaryl can be substituted by at least one heteroatom selected from O, S and N; the being substituted is being substituted by deuterium, halogen, C1-C30 alkyl, C1-C30 heteroalkyl, C3-C30 cycloalkyl, amino, silicyl, nitrile, isonitrile, phosphino, C6-C60 aryl and C1-C60 heteroaryl;

X1, X2 and X3 independently represent CH or N; X4, X5 and X6 independently represent CR0 or N, R0 is independently selected from hydrogen, deuterium, halogen, C1-C30 alkyl, C1-C30 heteroalkyl, aralkyl, amino, silicyl, aryl, heteroaryl, nitrile, isonitrile and phosphino, and adjacent R0 can be bonded to form a fused ring.

Further, at least one of X1, X2 and X3 is N.

Further preferably, at least one of R3 or R4 includes a structural formula (II), wherein R1 is a single bond, alkyl, heteroalkyl, cycloalkyl, C1-C30 alkyl substituted or unsubstituted C6-C30 non-fused ring aryl and C1-C30 alkyl substituted or unsubstituted C3-C27 non-fused ring heteroaryl, wherein R2 is hydrogen, deuterium, halogen, alkyl, heteroaryl, cycloaryl, C1-C30 alkyl substituted or unsubstituted C6-C30 aryl and C1-C30 alkyl substituted or unsubstituted C1-C60 heteroaryl,

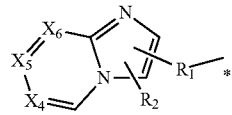

Formula (II)

Further preferably, one of R3 and R4 is a structure shown in the formula (II) and the other one is C1-C4 alkyl substituted or unsubstituted C6-C18 aryl, C1-C4 alkyl substituted or unsubstituted C3-C15 heteroaryl; R1 is C1-C4 alkyl substituted or unsubstituted C6-C18 non-fused ring aryl, C1-C4 alkyl substituted or unsubstituted C3-C15 non-fused ring heteroaryl; and R2 is C1-C4 alkyl substituted or unsubstituted C6-C18 aryl and C1-C4 alkyl substituted or unsubstituted C3-C15 heteroaryl.

Preferably, the compound according to claim 5, wherein R1 is C6-C18 non-fused ring aryl or C5-C15 non-fused ring heteroaryl; and R2 is C6-C18 aryl or C5-C15 heteroaryl.

The preferred compound is the following compounds:

A1

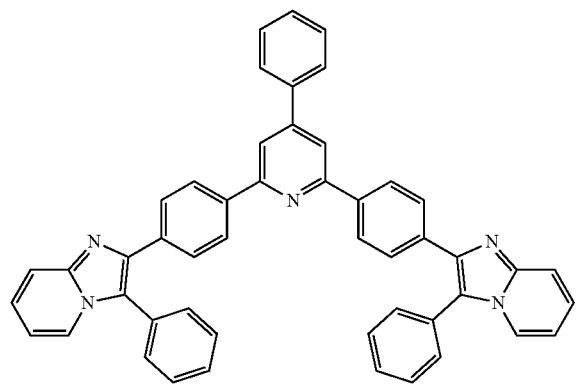

A2

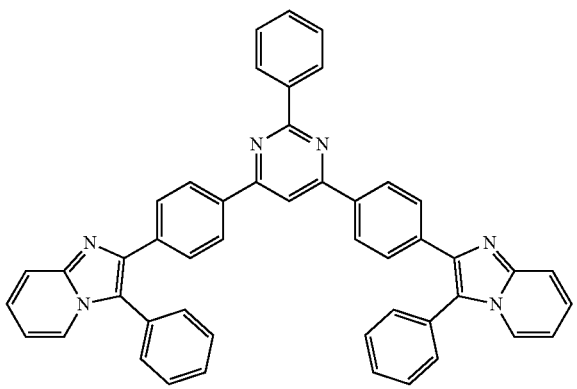

A3

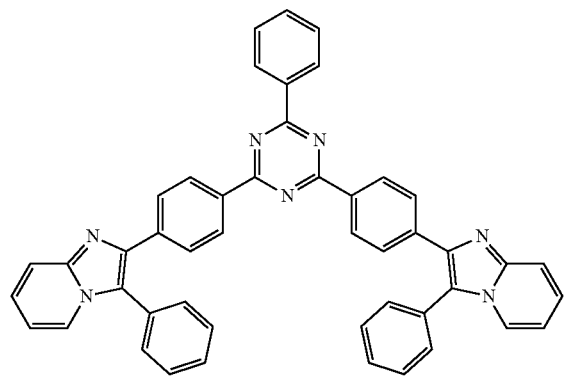

A4

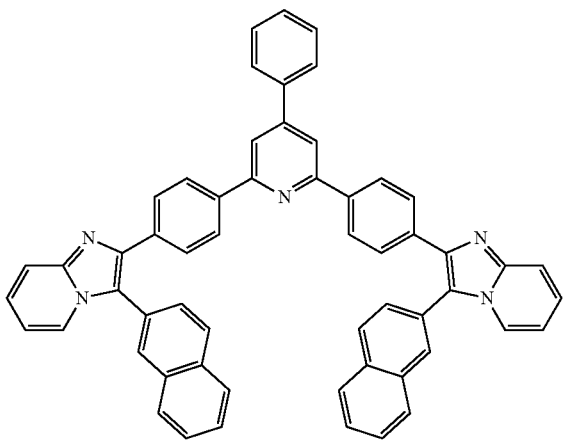

-continued
A 5
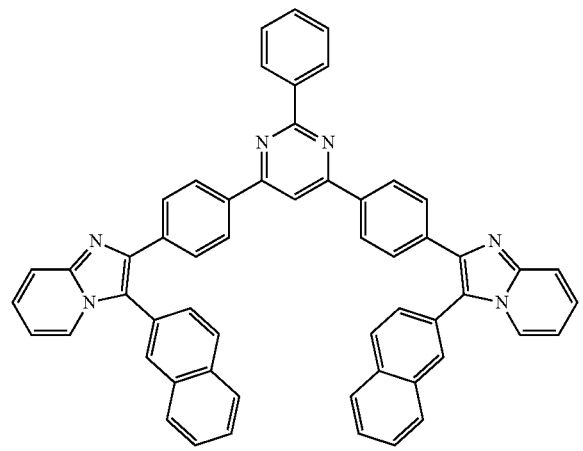
A 6
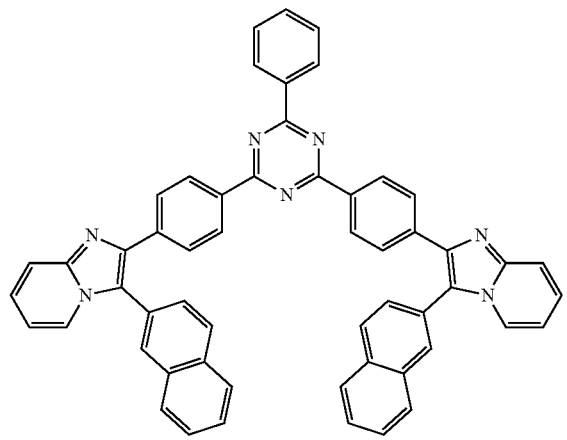
A 7
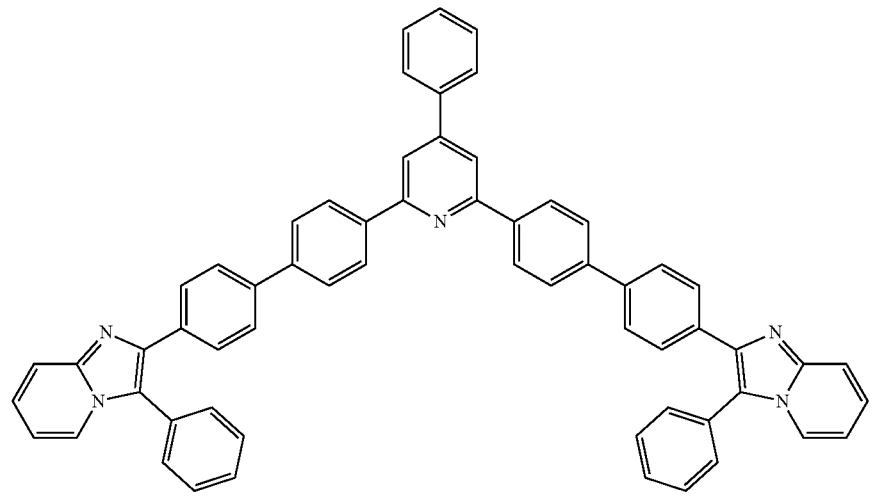
A 8
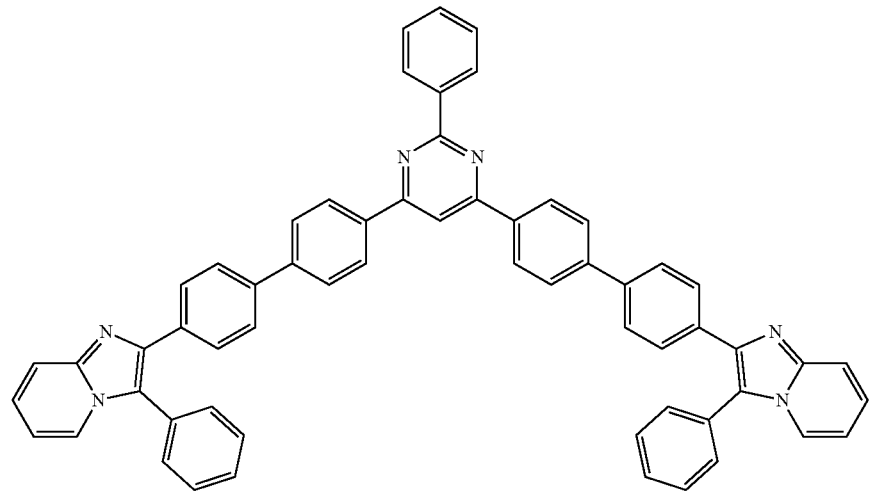

-continued
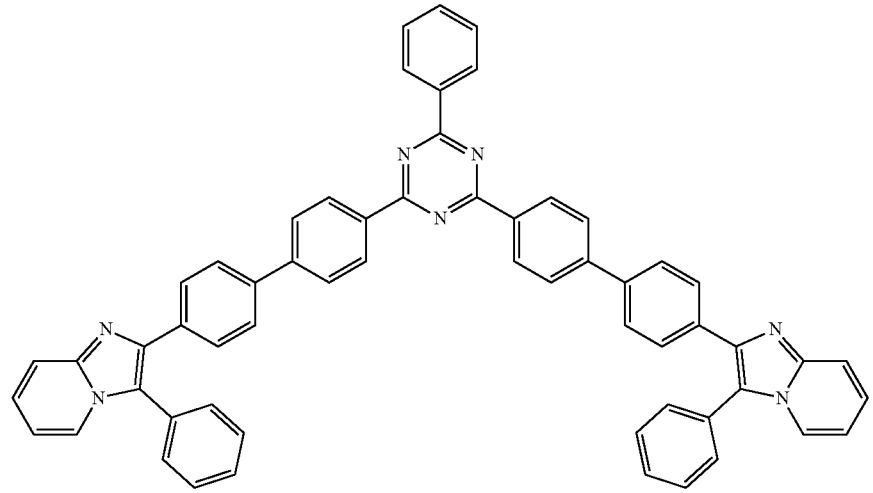
A 9
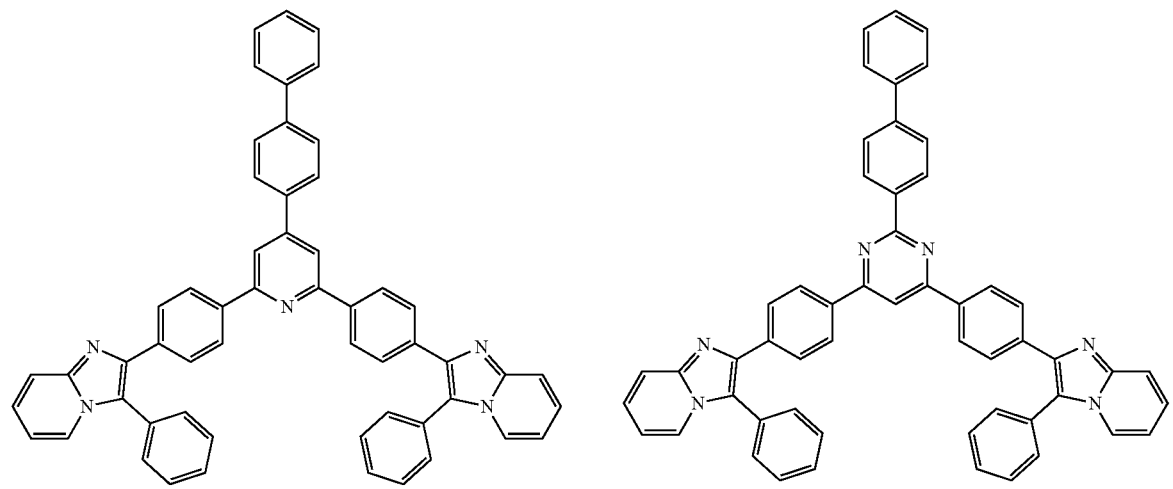
A 10
A 11
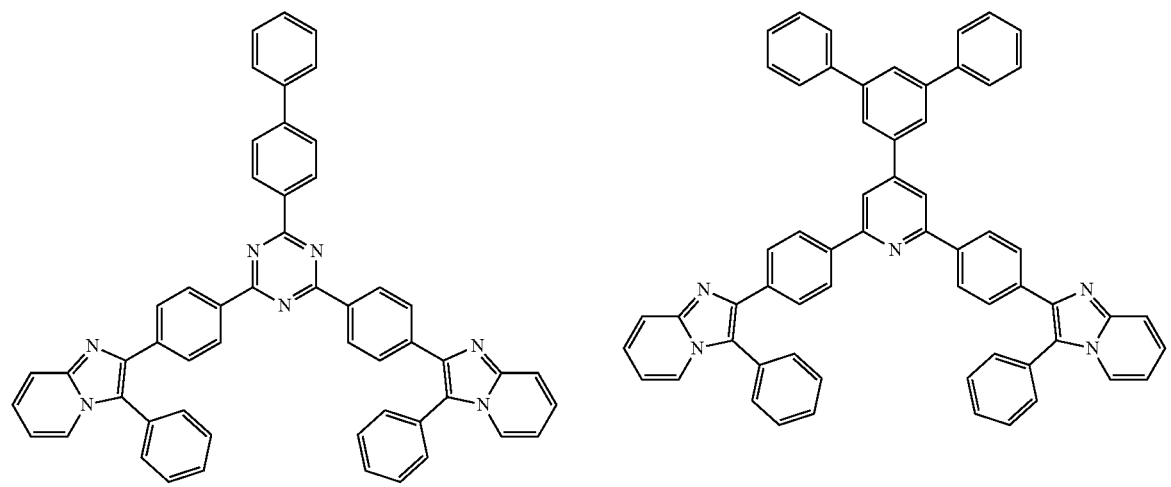
A 12
A 13

-continued
A 14
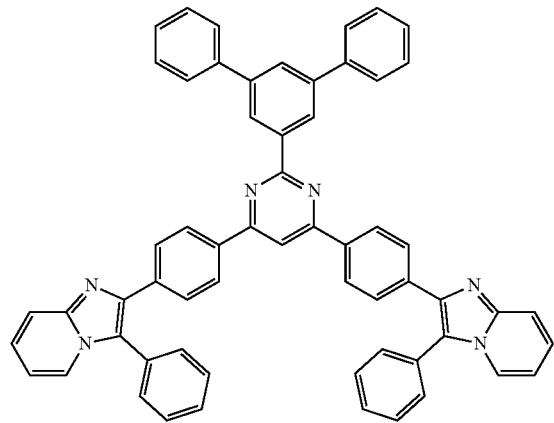
A 15
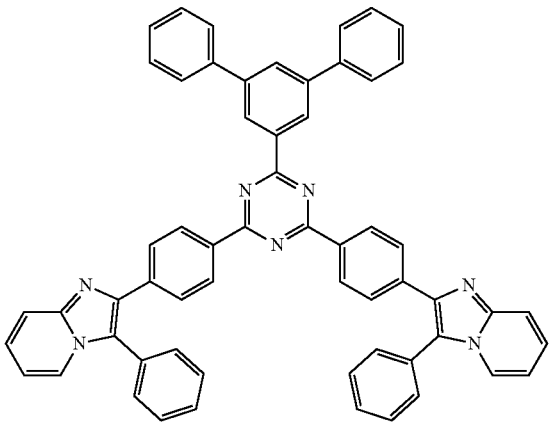
A 16
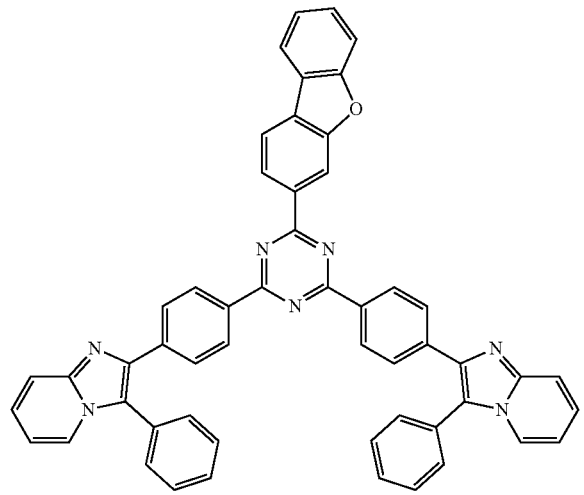
A 17
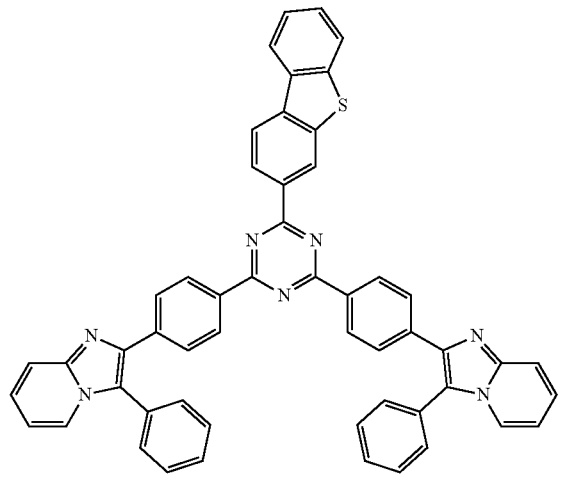
A 18
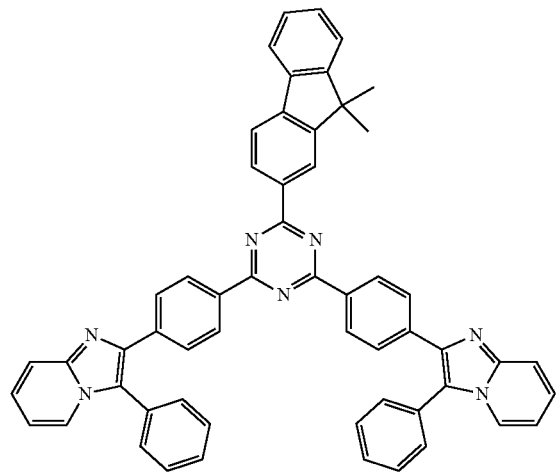
A 19
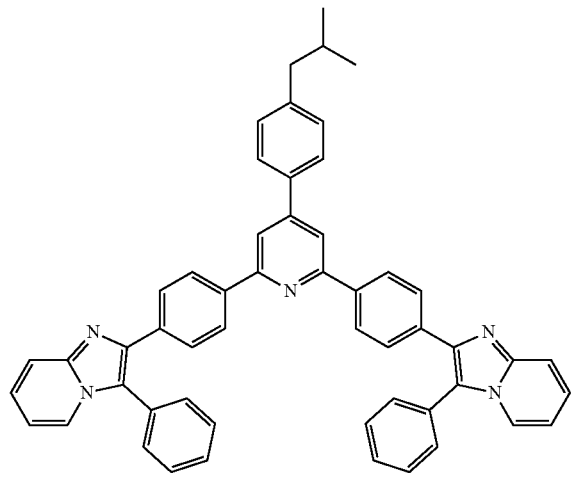

-continued
A 20
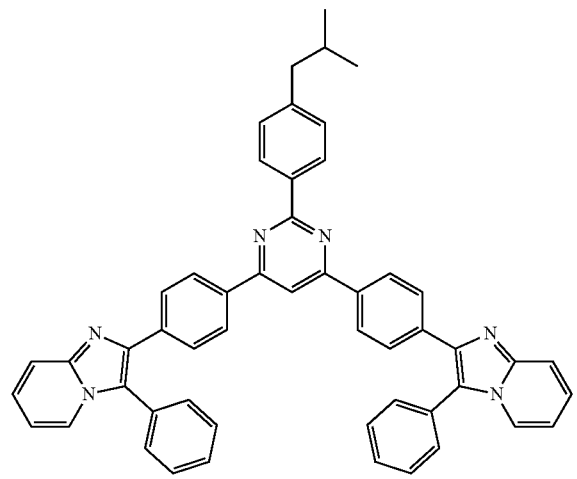
A 21
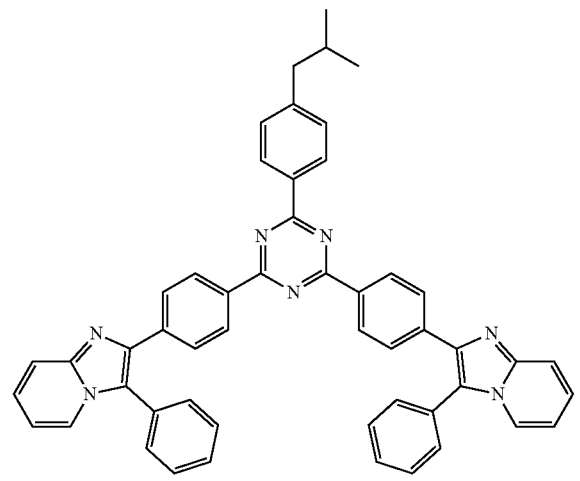
A 22
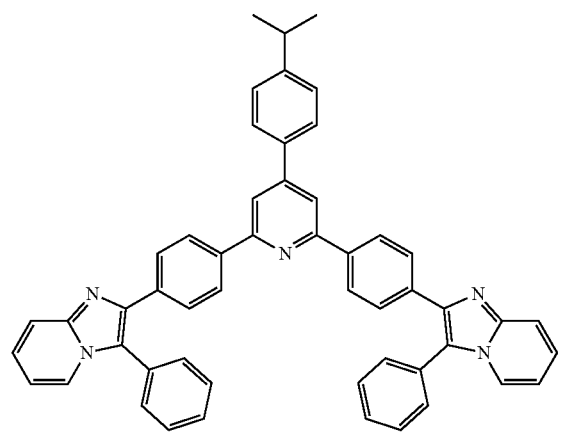
A 23
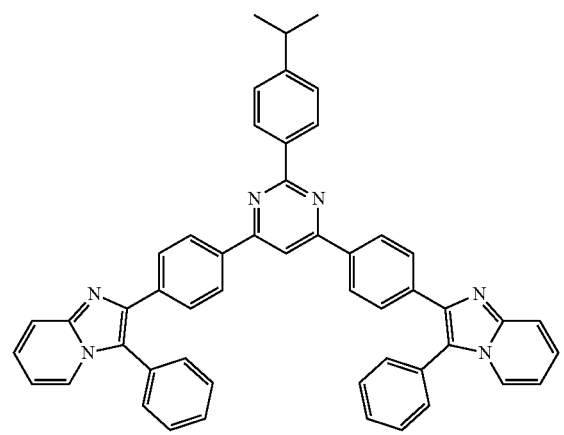
A 24
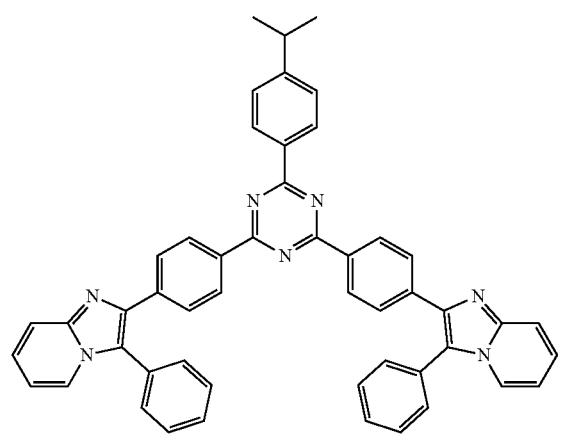
A 25
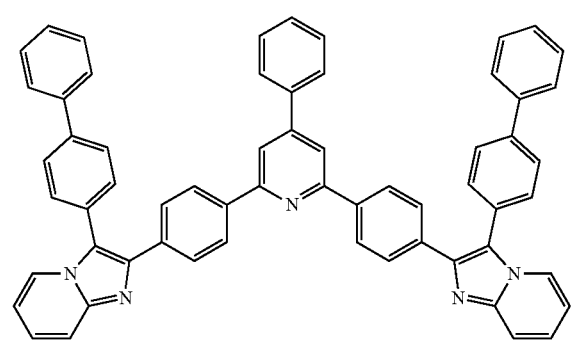

-continued
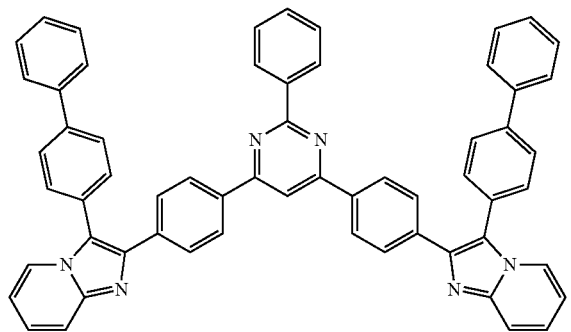
A 26
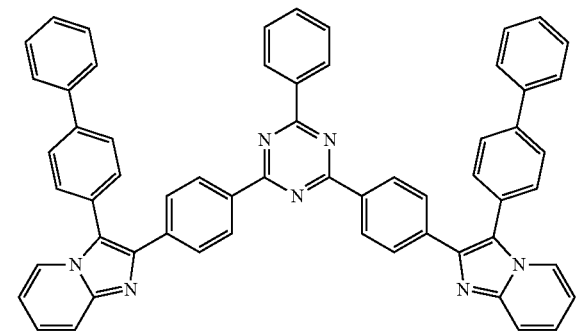
A 27
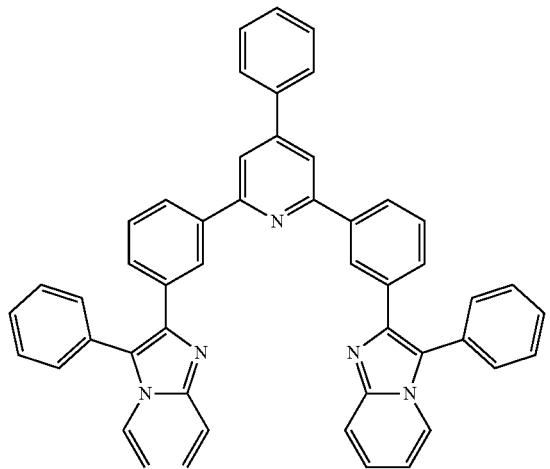
A 28
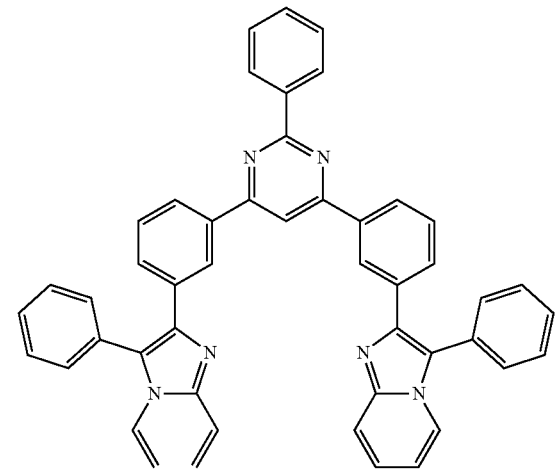
A 29
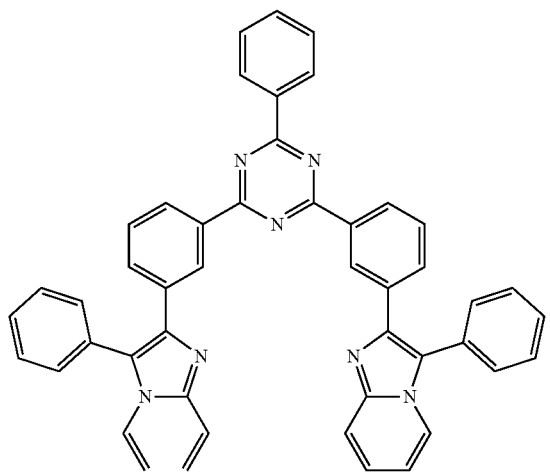
A 30
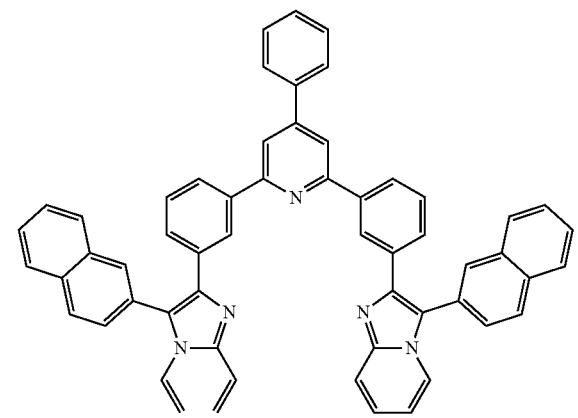
A 31

-continued
A 32
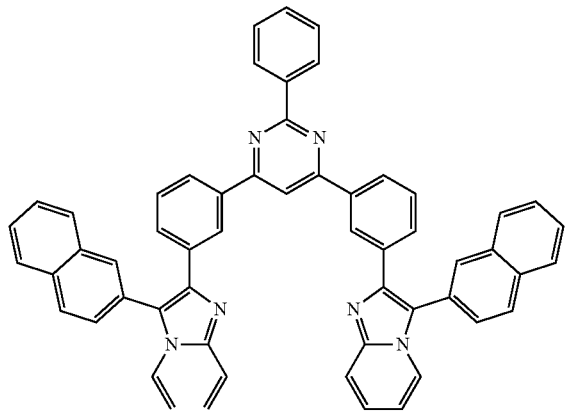
A 33
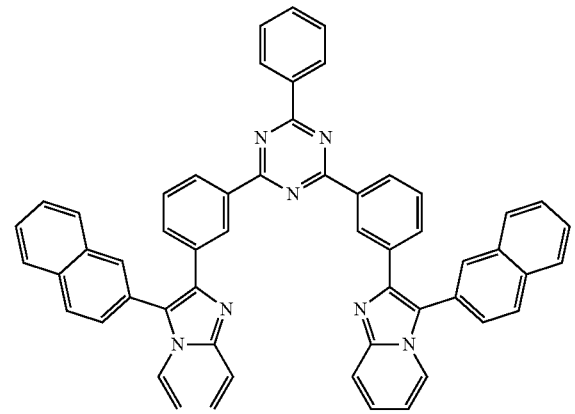
A 34
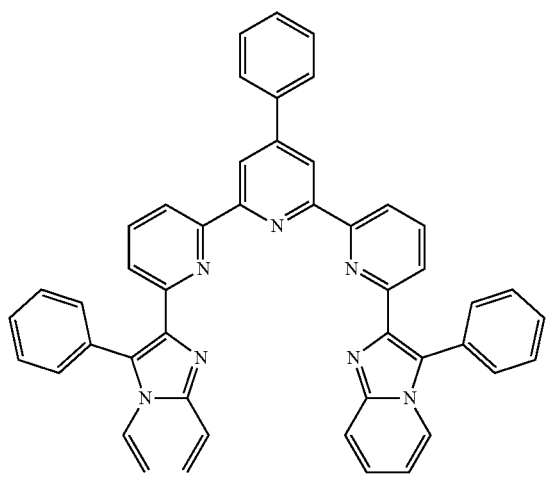
A 35
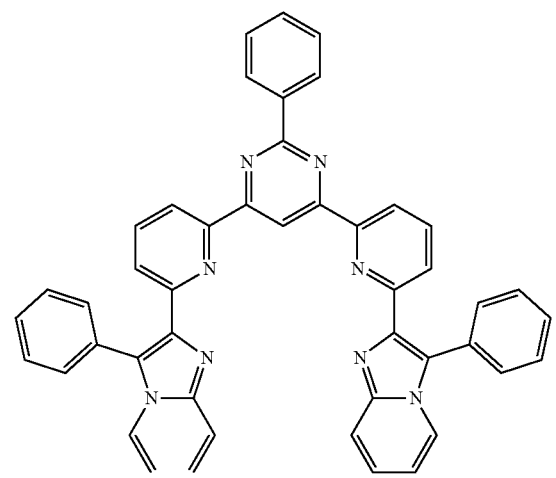
A 36
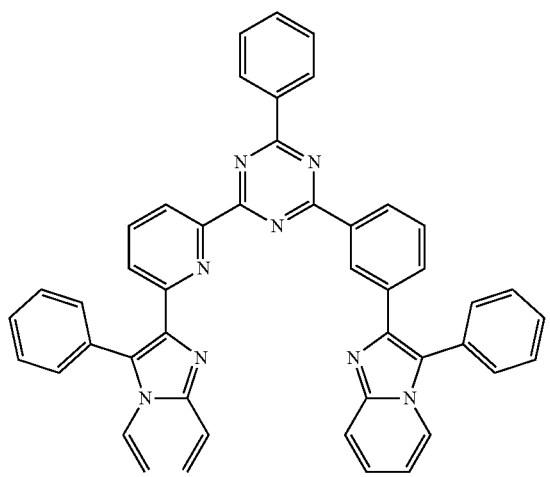
A 37
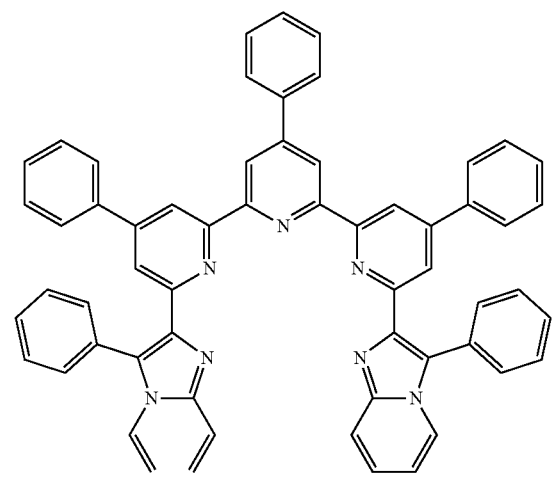

-continued
A 38
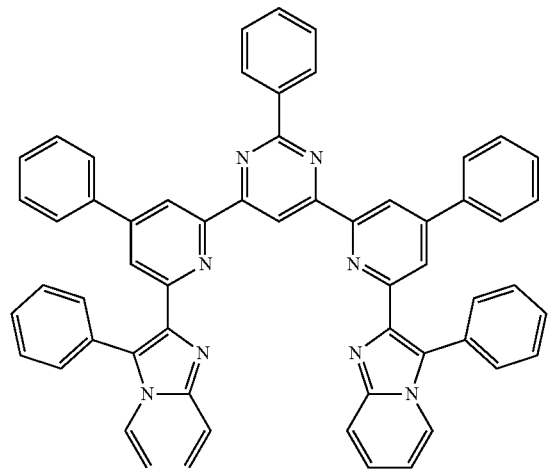
A 39
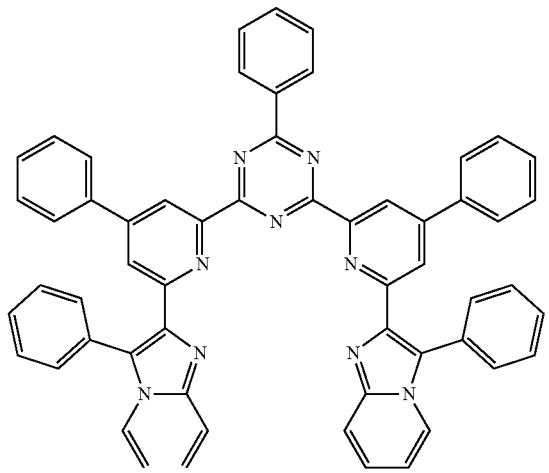
A 40
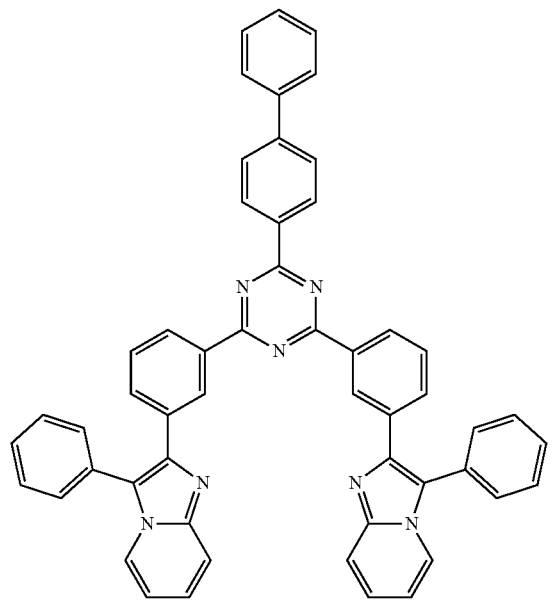
A 41
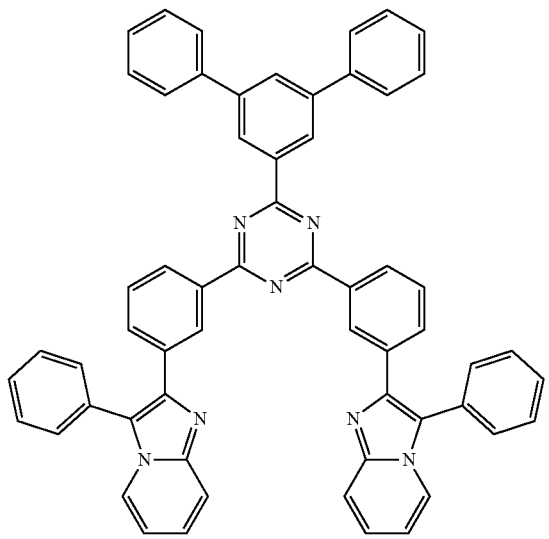
A 42
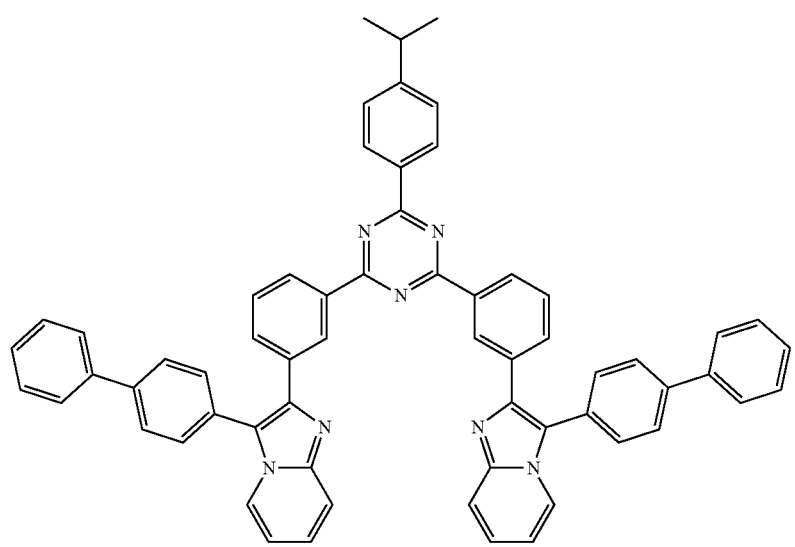

-continued
A 43
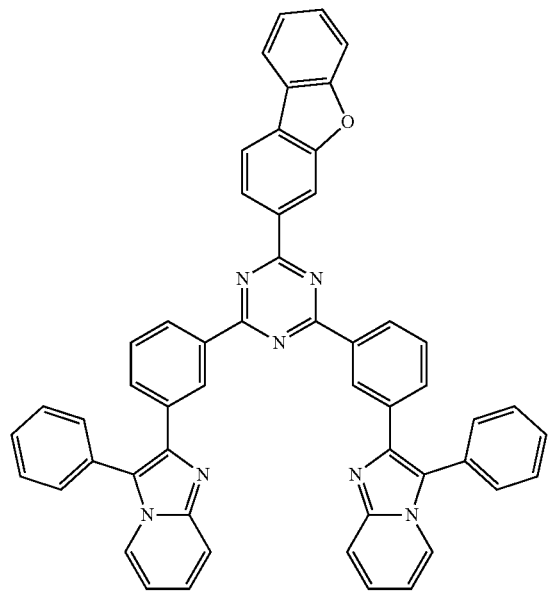
A 44
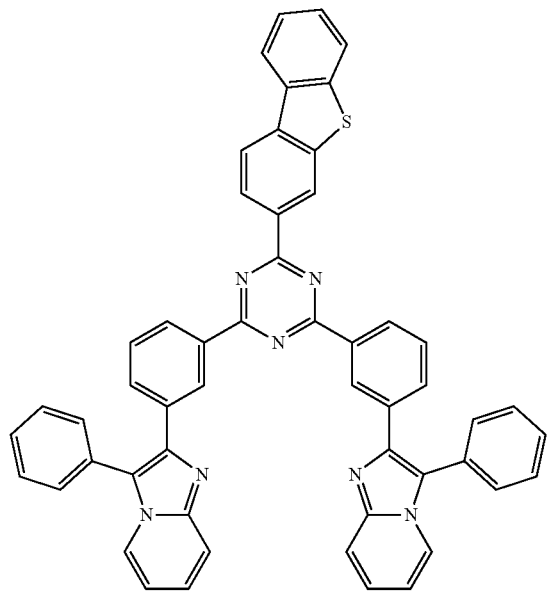
A 45
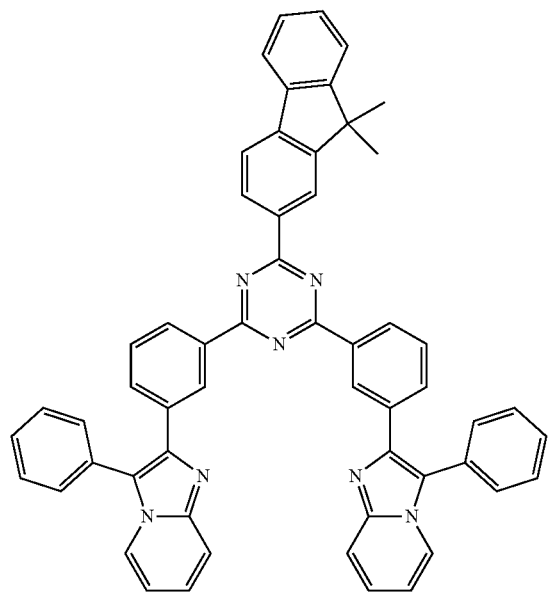
A 46
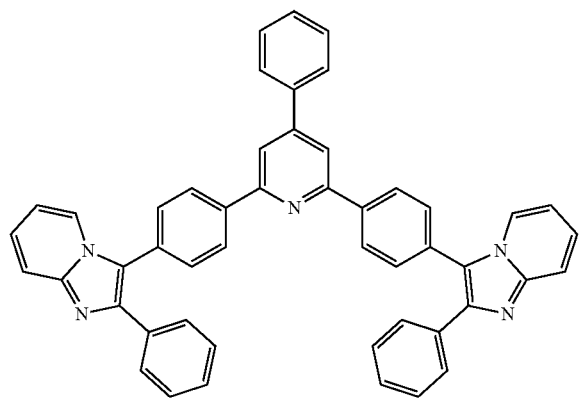
A 47
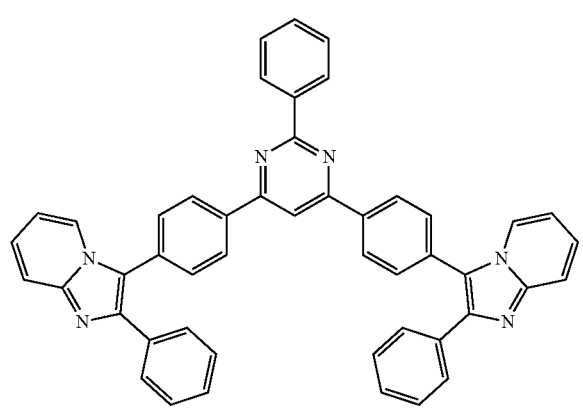
A 48
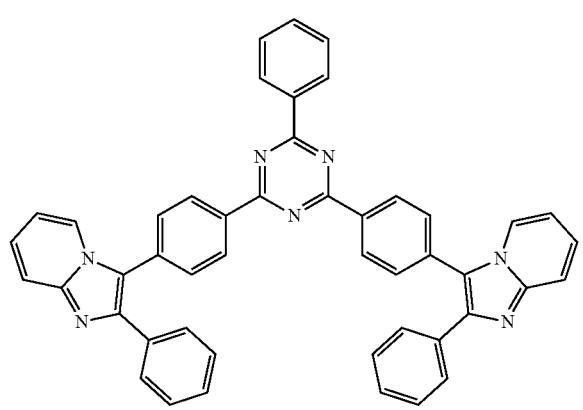

-continued
A 49
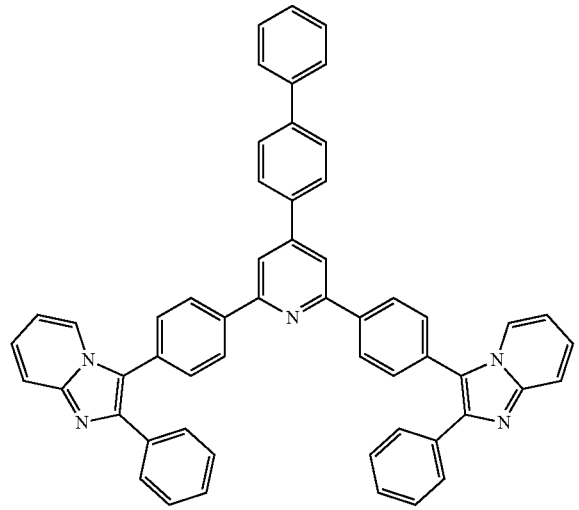
A 50
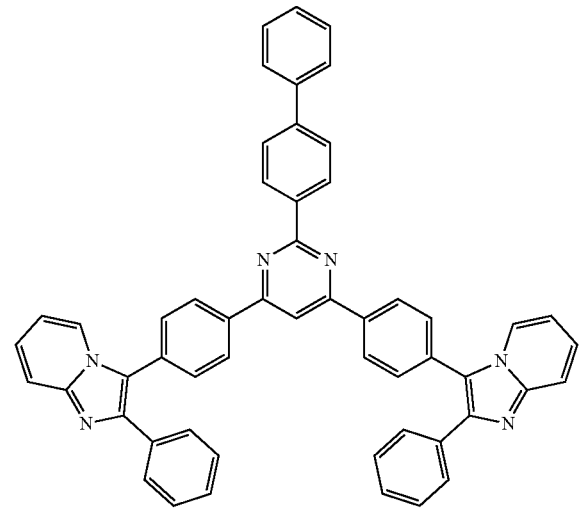
A 51
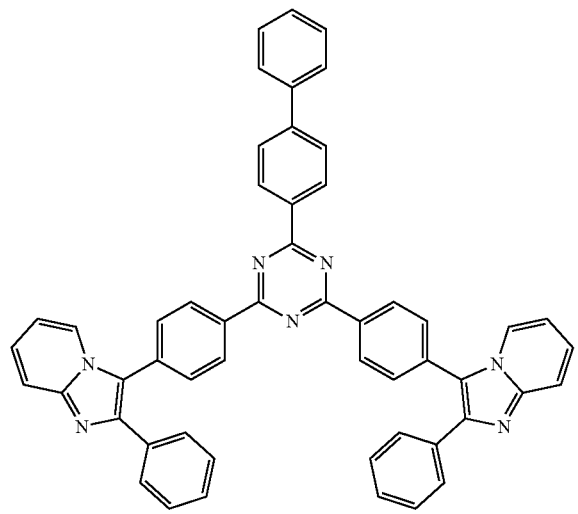
A 52
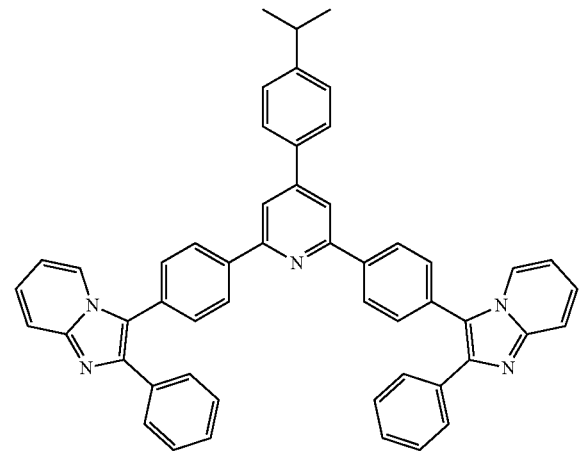
A 53
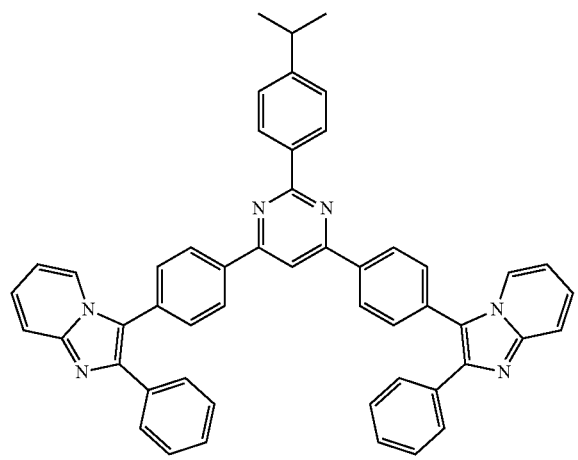
A 54
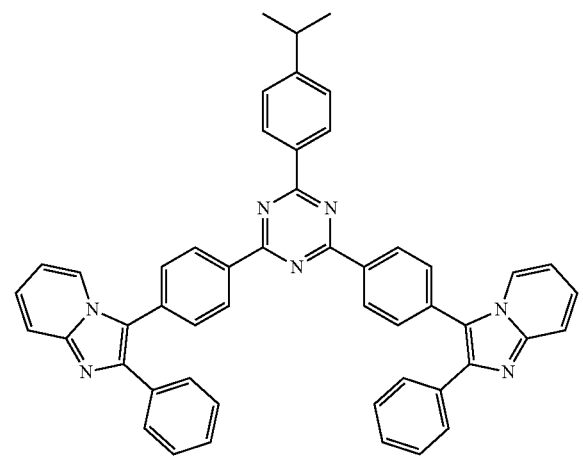

-continued
A 55
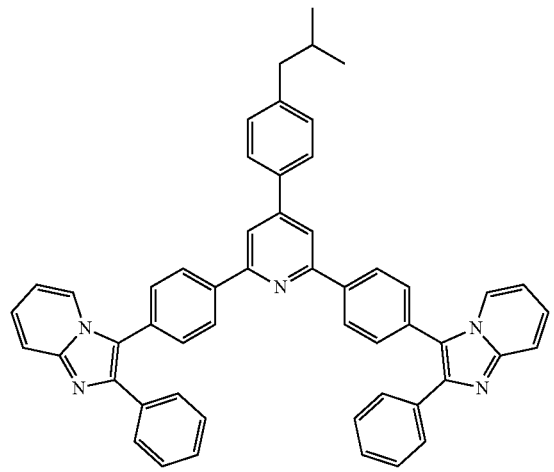
A 56
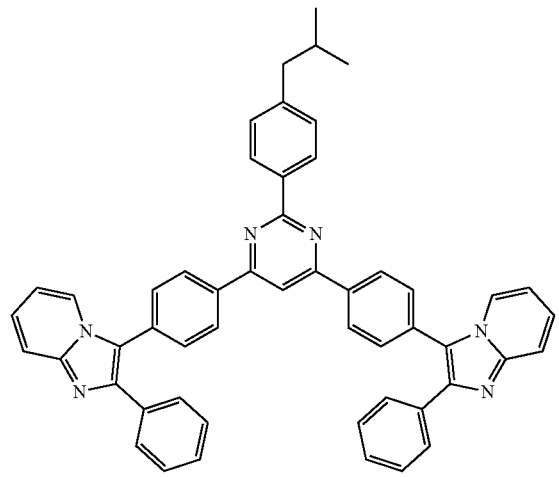
A 57
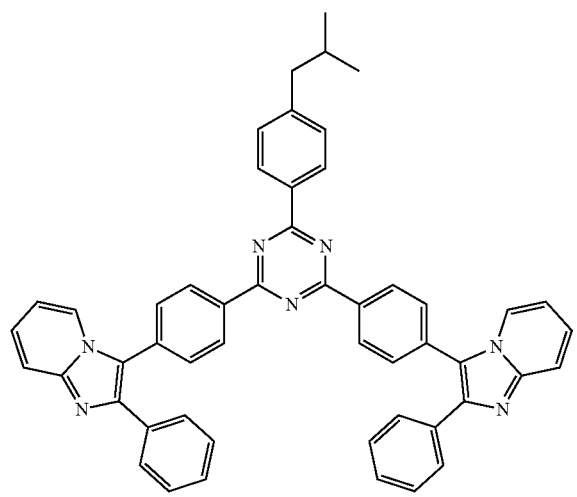
A 58
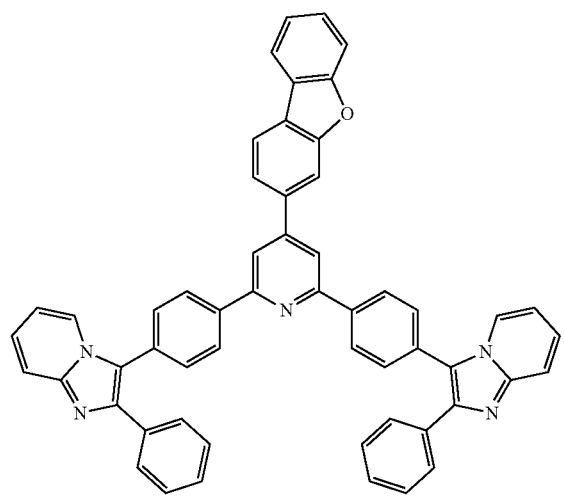
A 59
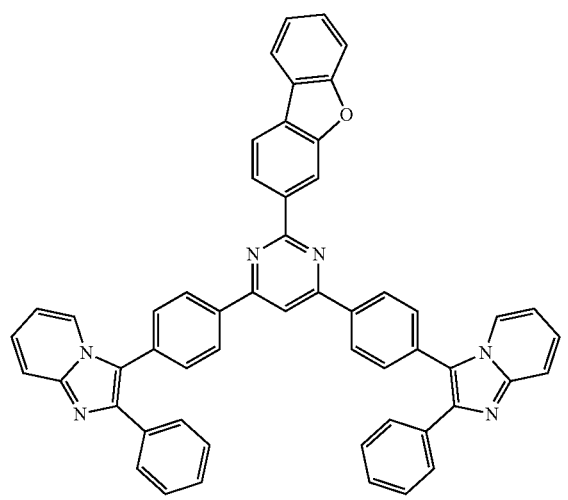
A 60
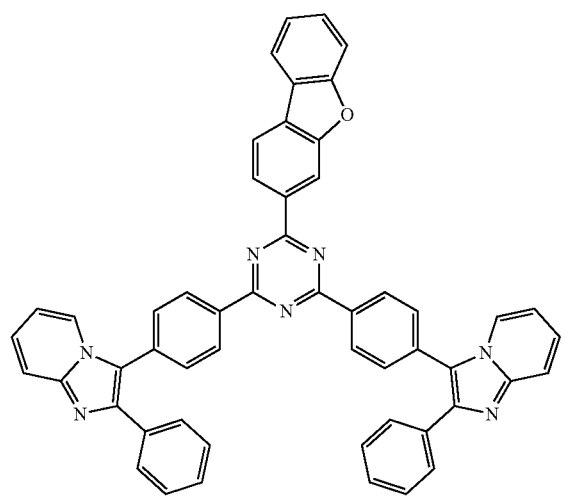

-continued
A 61
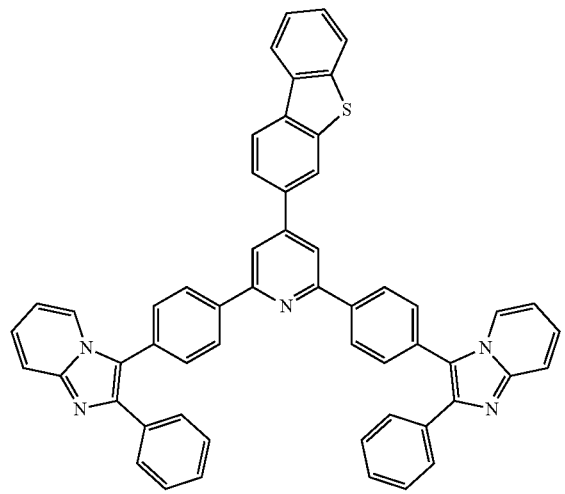
A 62
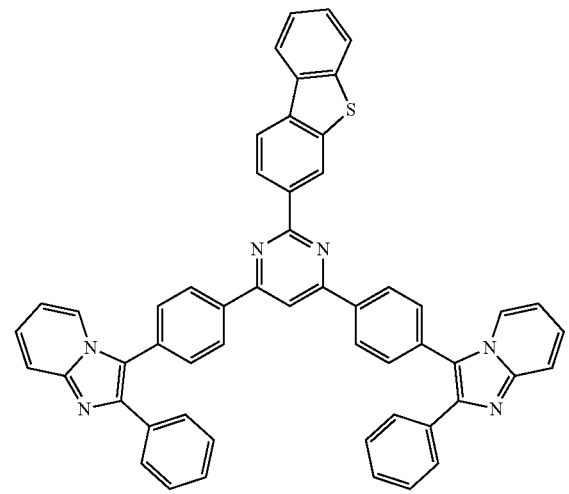
A 63
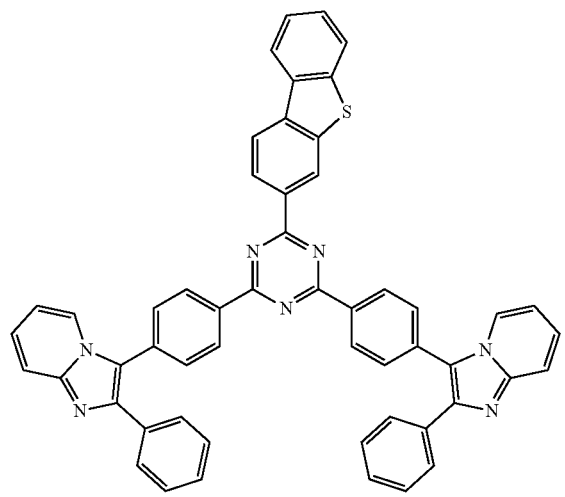
A 64
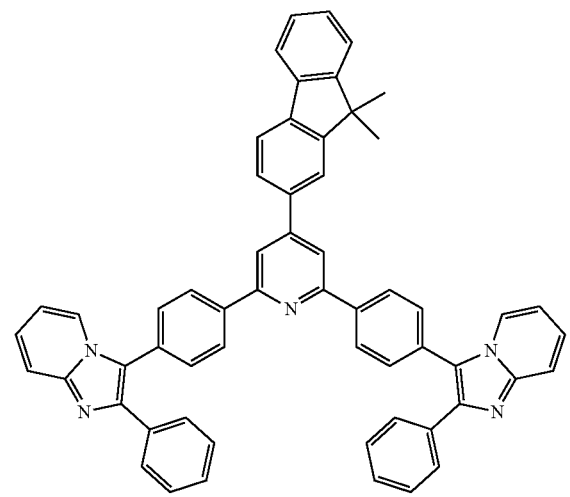
A 65
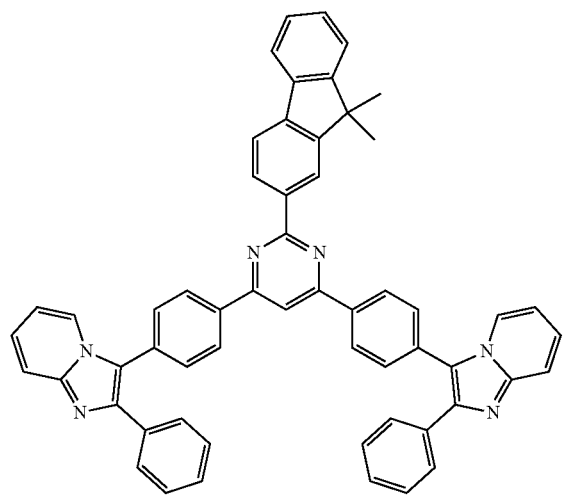
A 66
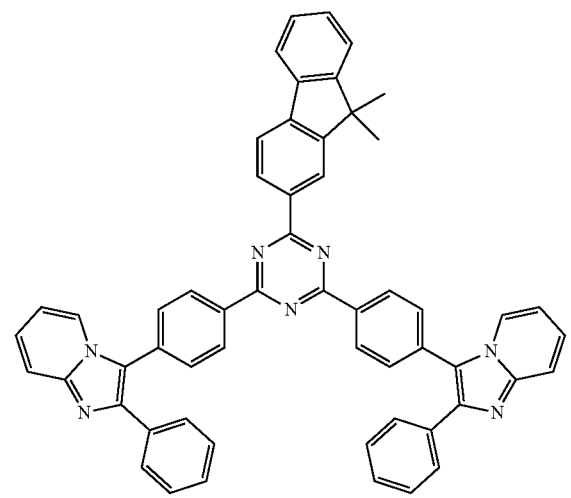

-continued
A 67
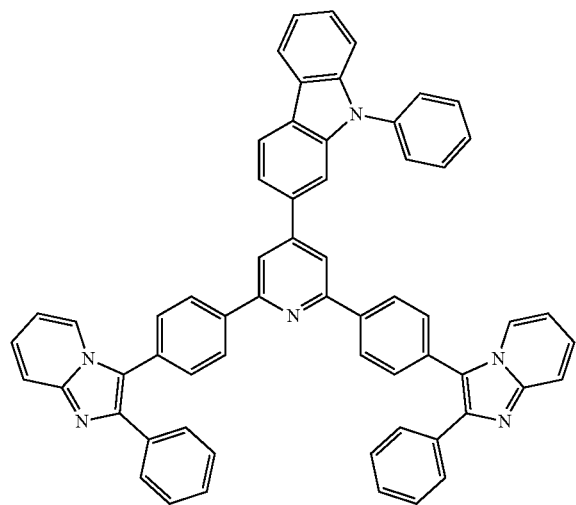
A 68
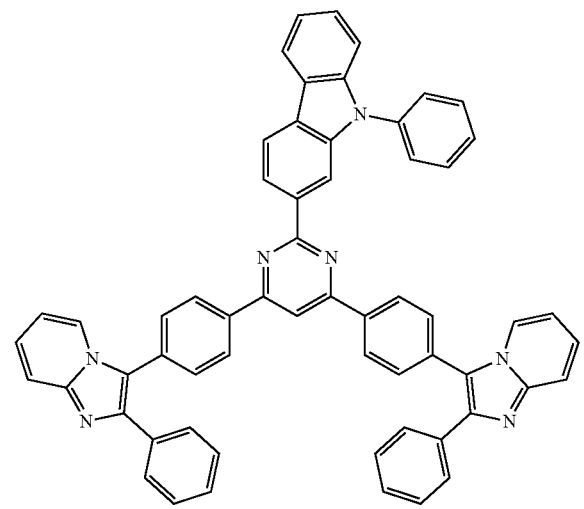
A 69
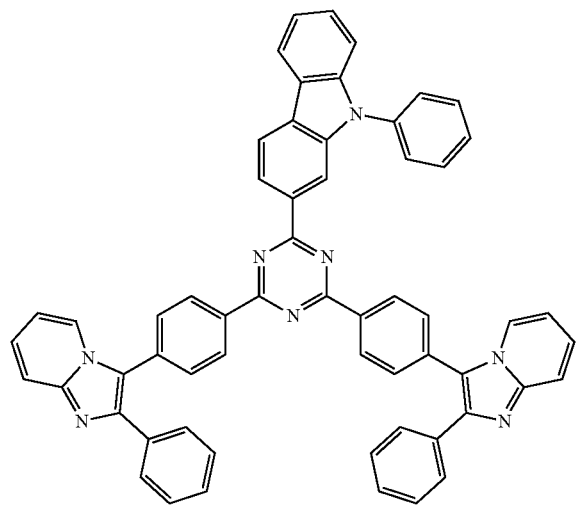
A 70
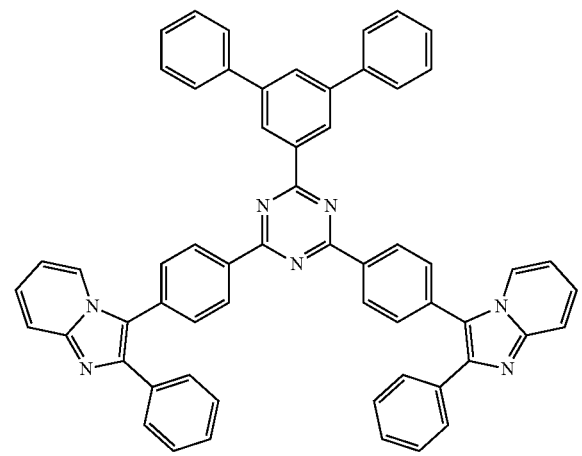
A 71
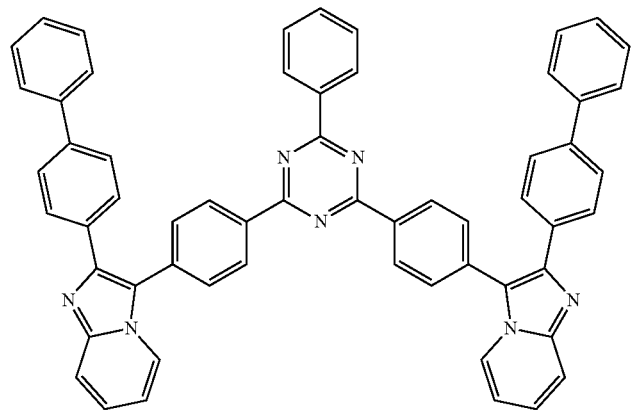

A 72
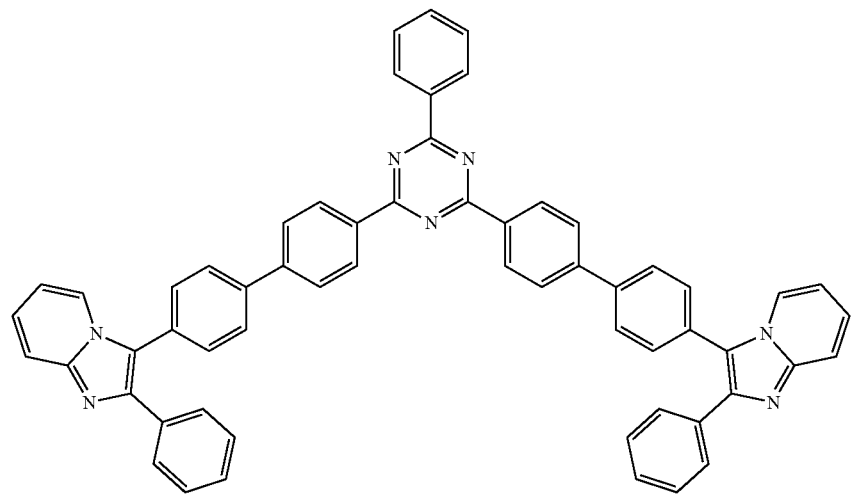
A 73  A 74
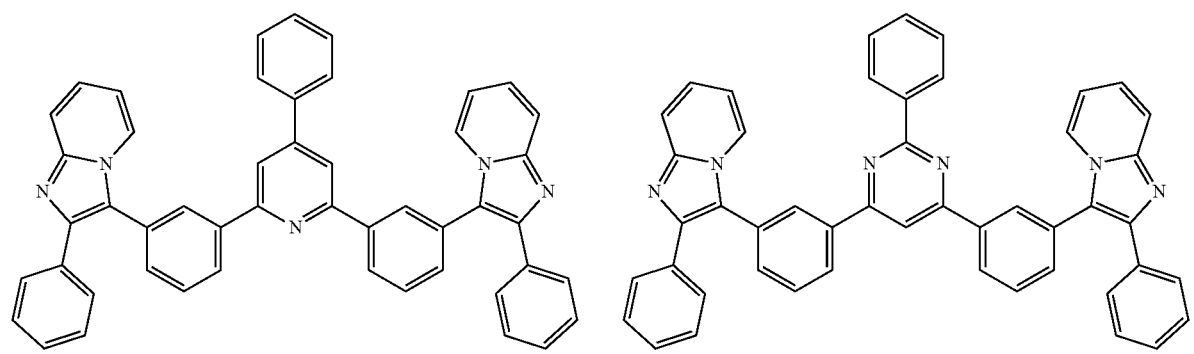
A 75  A 76
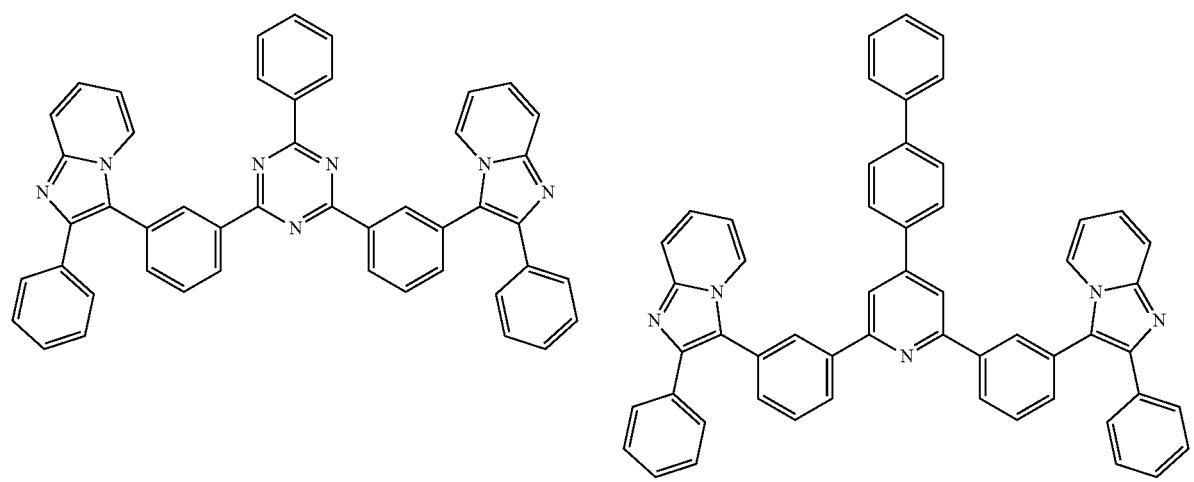

-continued
A 77
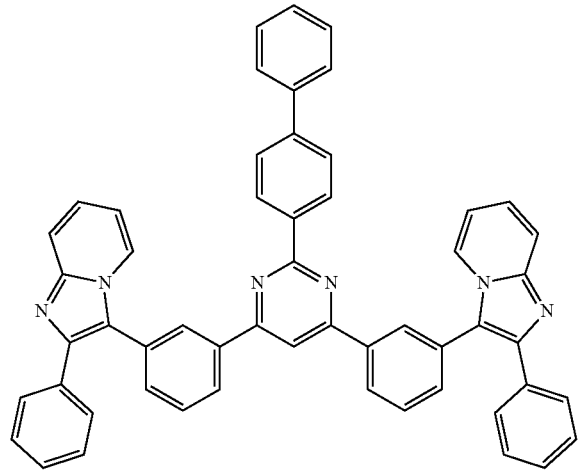
A 78
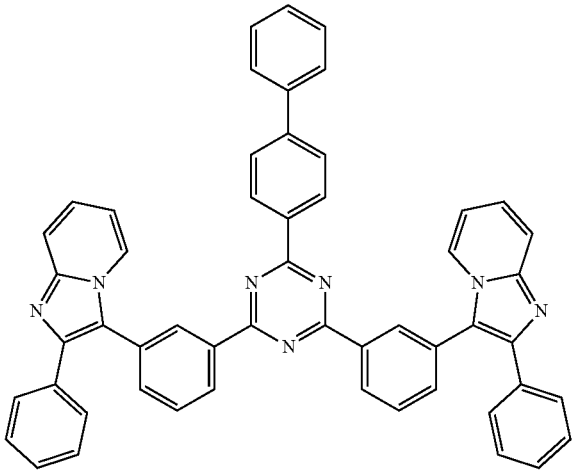
A 79
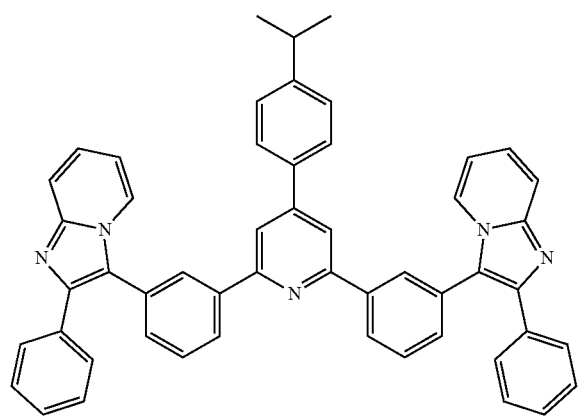
A 80
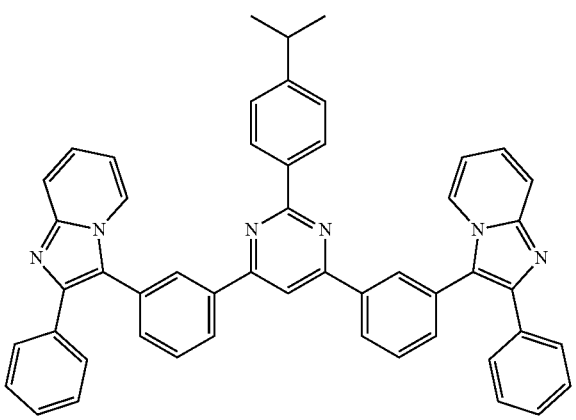
A 81
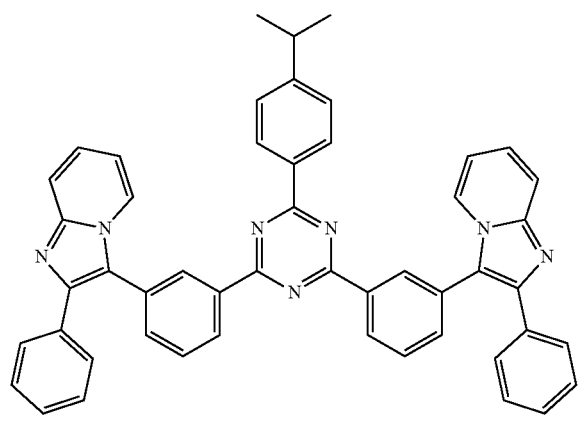
A 82
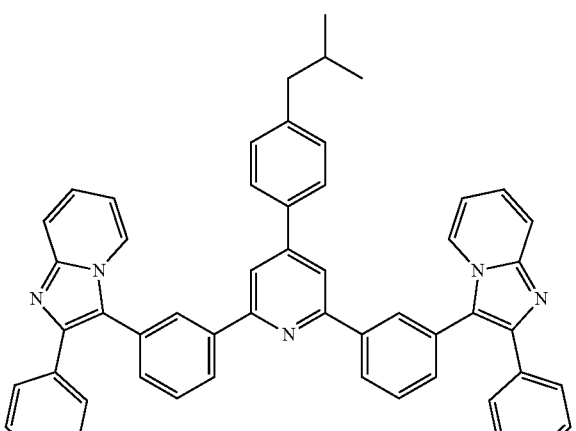

-continued
A 83
A 84
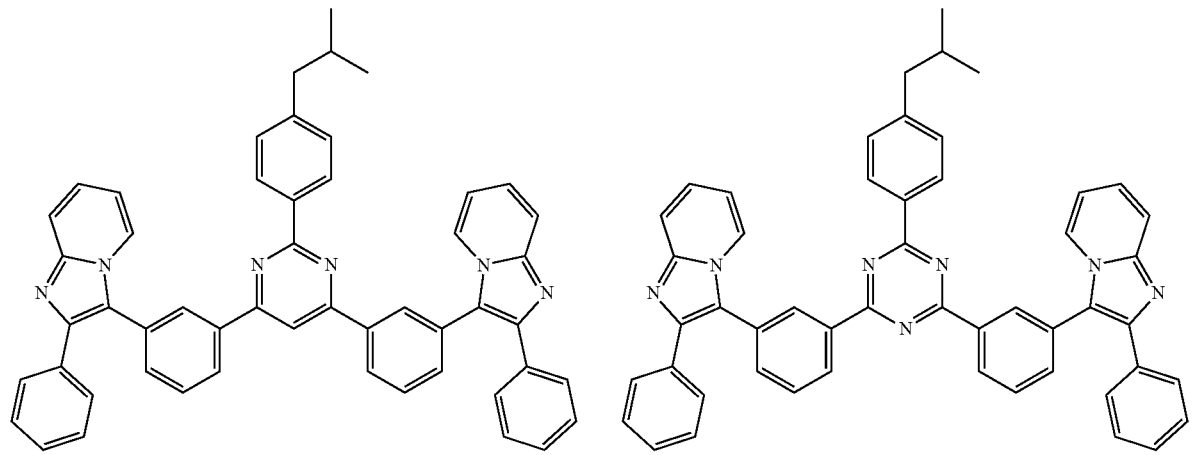
A 85
A 86
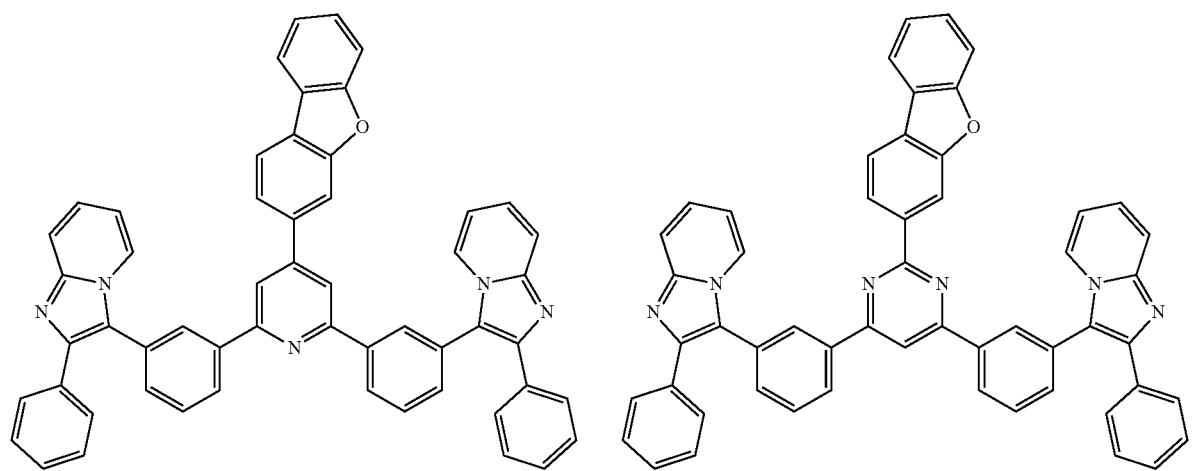
A 87
A 88
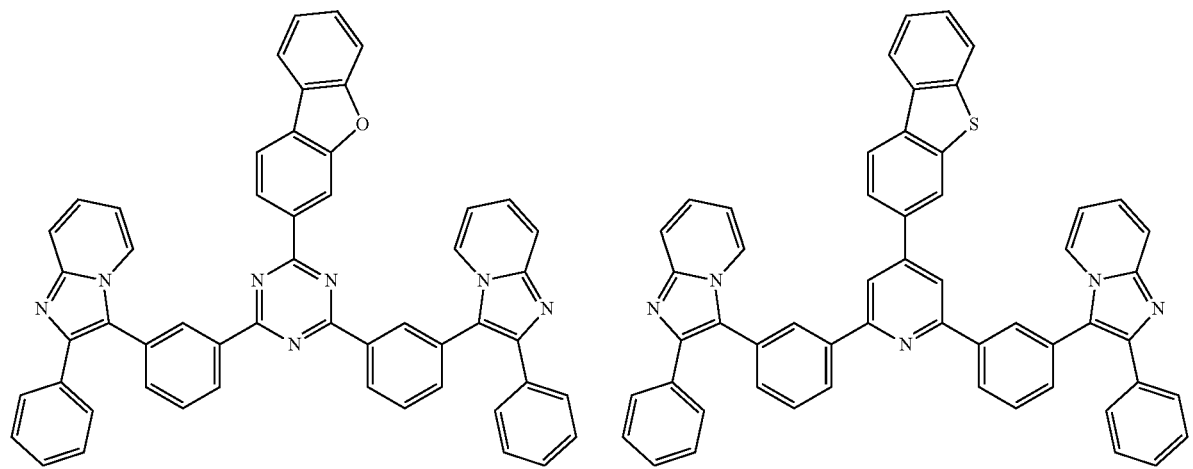

-continued
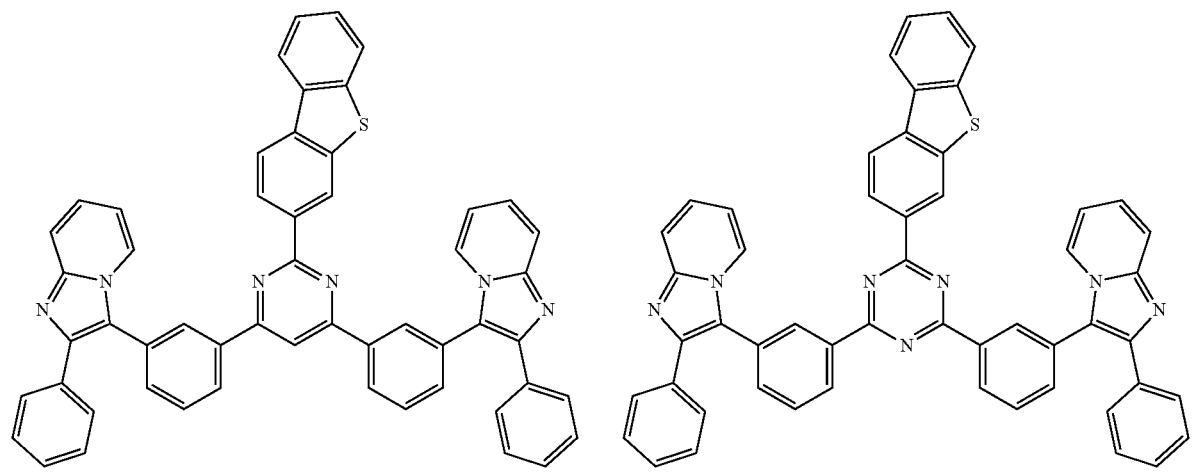
A 89
A 90

A 91
A 92
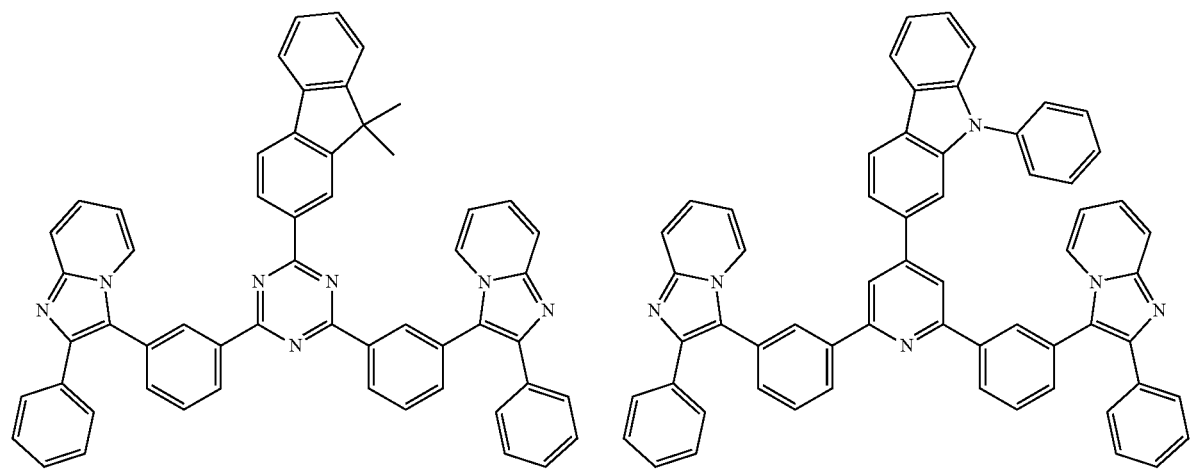
A 93
A 94

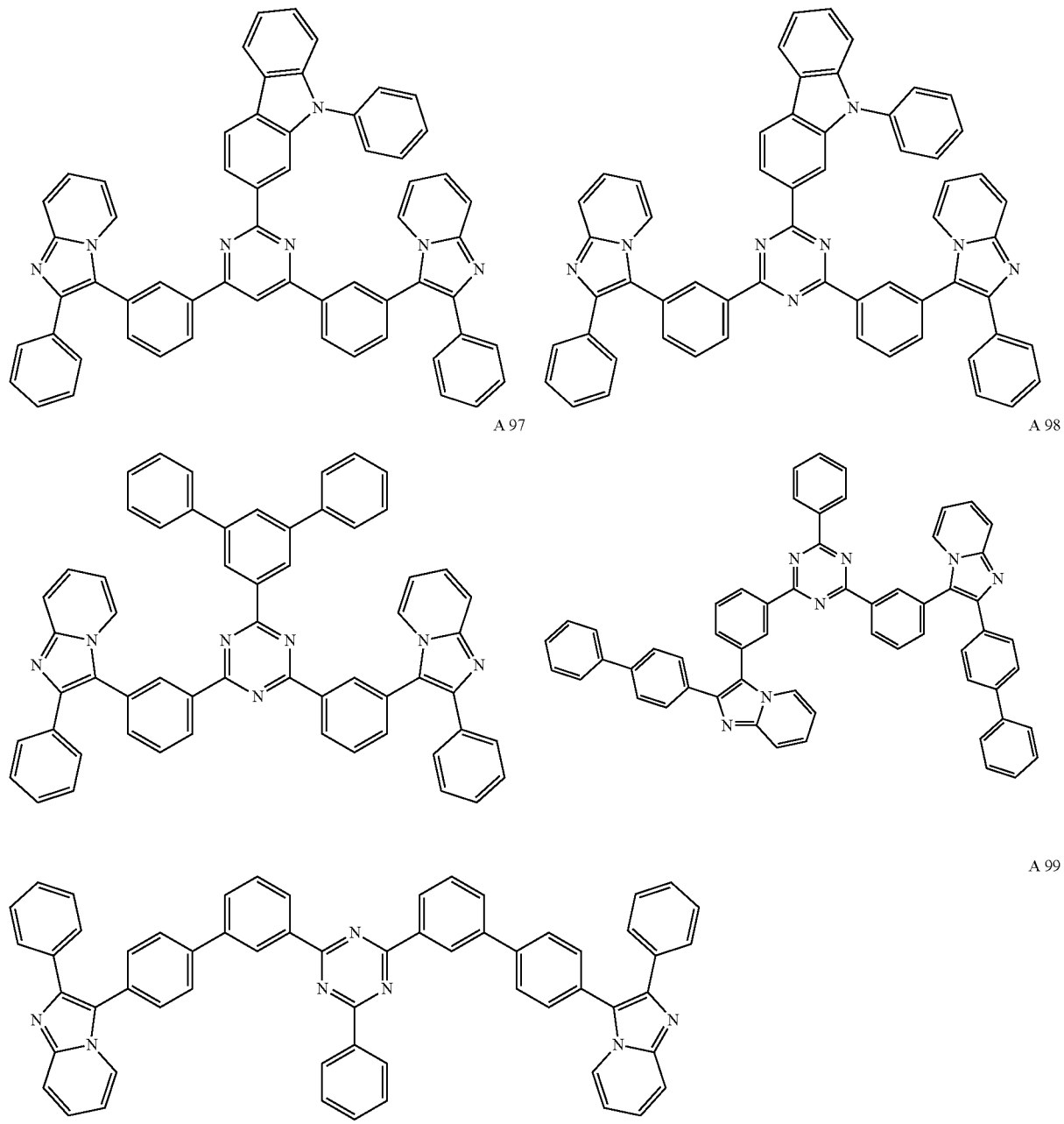

Preferably, the compound as shown in the formula (I), wherein X1, X2 and X3 are represented as N.

Further preferably, R1 is a single bond, C1-C30 alkyl substituted or non-substituted C6-C30 non-fused ring aryl, C1-C30 substituted or non-substituted C3-C27 non-fused ring heteroaryl; R2 is C1-C30 substituted or non-substituted C6-C60 aryl, C1-C30 substituted or non-substituted C1-C60 heteroaryl; R3 and R4 are hydrogen, deuterium, halogen, alkyl, heteroalkyl, cycloalkyl, C1-C30 substituted or non-substituted C6-C60 aryl, C1-C30 substituted or non-substituted C1-C60 heteroaryl, substituted or non-substituted monocyclic or polycyclic C3-C60 aliphatic ring or aromatic ring, and at least one of R3 and R4 is C1-C30 substituted or non-substituted C6-C60 aryl, C1-C30 substituted or non-substitute C1-C60 heteroaryl and substituted or non-substitute monocyclic or polycyclic C3-C60 aliphatic ring or aromatic ring.

Further preferably, R1 is a single bond, C1-C4 alkyl substituted or non-substituted C6-C18 non-fused ring aryl, C1-C4 substituted or non-substituted C3-C15 non-fused ring heteroaryl; R2 is C1-C4 substituted or non-substituted C6-C18 aryl, C1-C4 substituted or non-substituted C3-C15 heteroaryl; R3 and R4 are hydrogen, deuterium, halogen, alkyl, C1-C4 substituted or non-substituted C6-C18 aryl, C1-C4 substituted or non-substituted C3-C15 heteroaryl, substituted or non-substituted monocyclic or polycyclic C3-C18 aliphatic ring or aromatic ring, and R3 and R4 are different.

Further preferably, R1 is a single bond, C6-C18 non-fused ring aryl or C3-C15 non-fused ring heteroaryl; and R2 is C6-C18 aryl or C3-C15 heteroaryl.
The preferred compound is the following compounds:
B 1
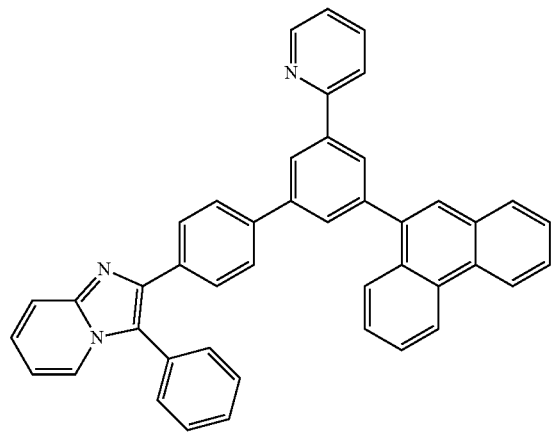
B 2
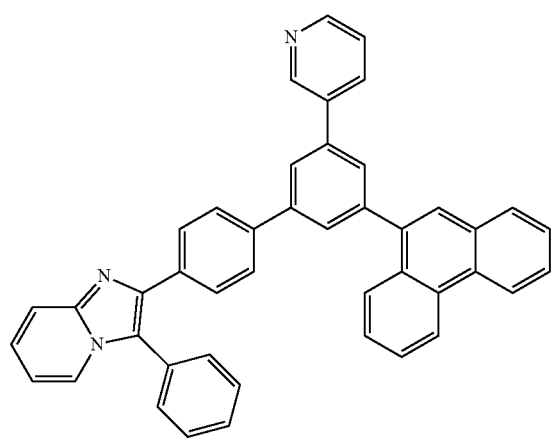
B 3
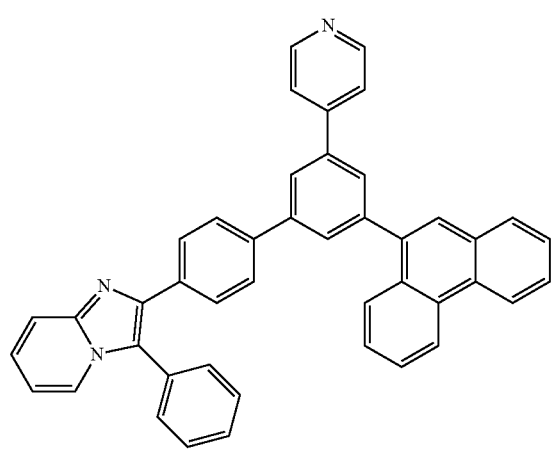
-continued
B 4
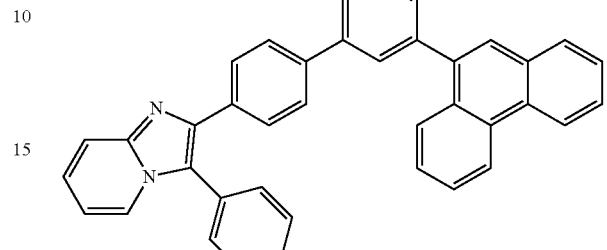
B 5
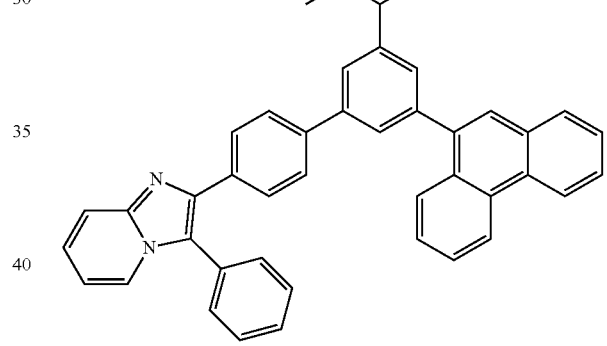
B 6
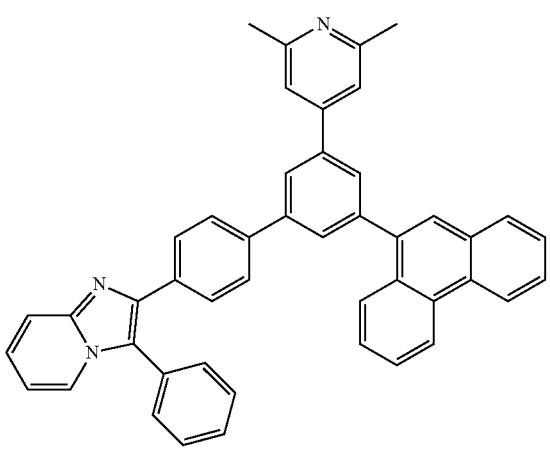

B 7
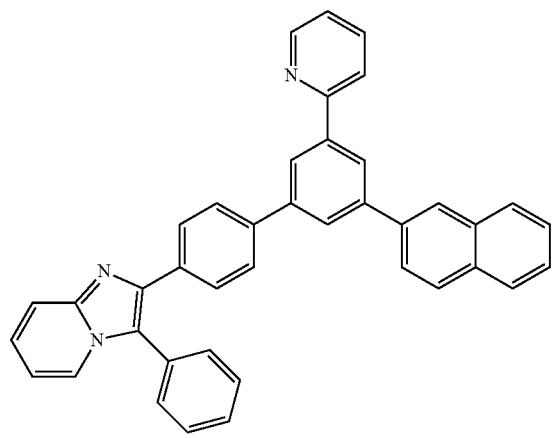
B 8
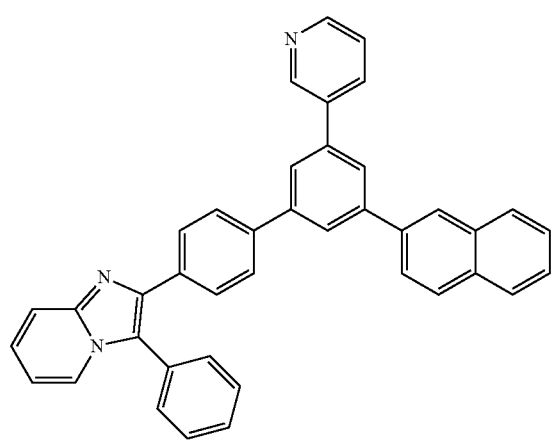
B 9
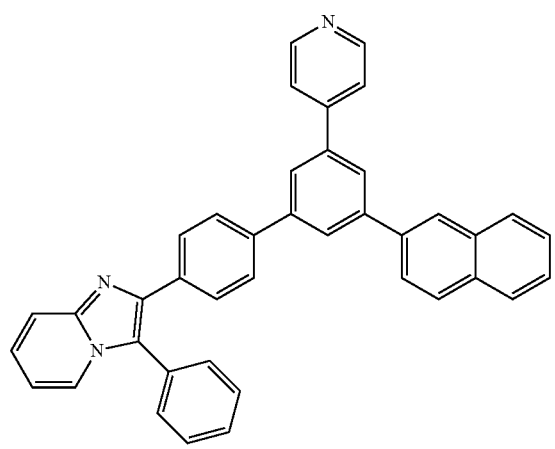
B 10
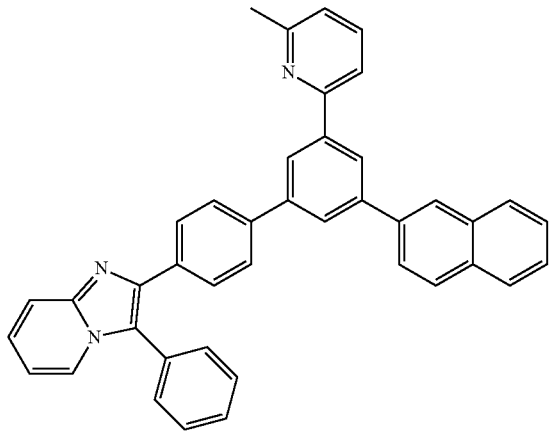
B 11
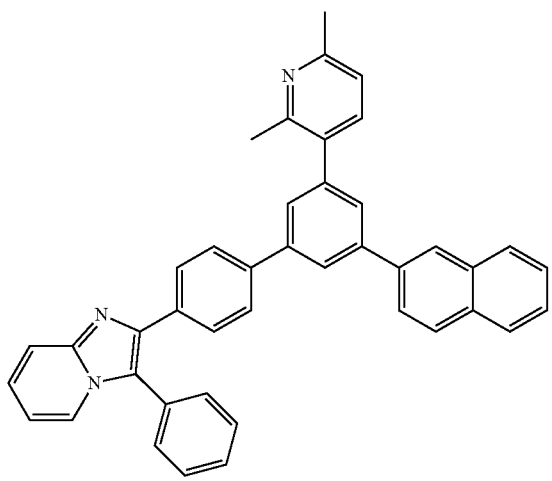
B 12
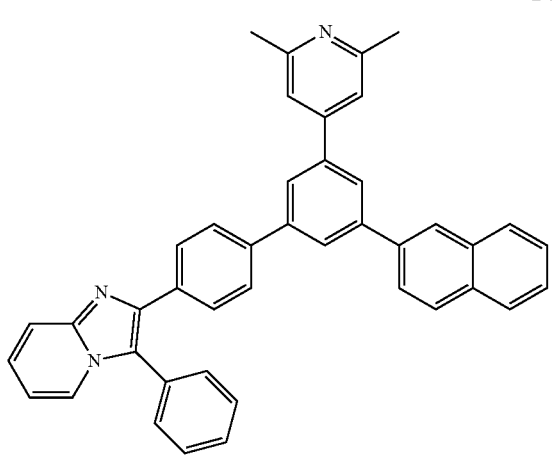

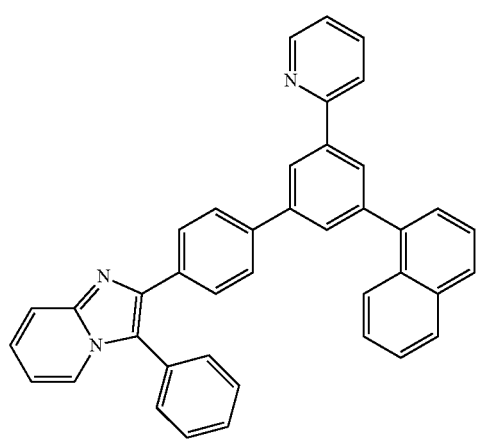
B 13
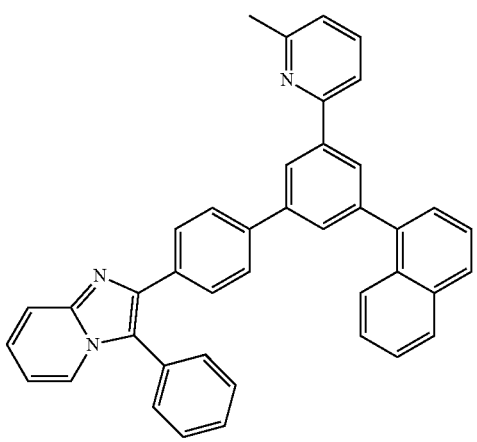
B 16
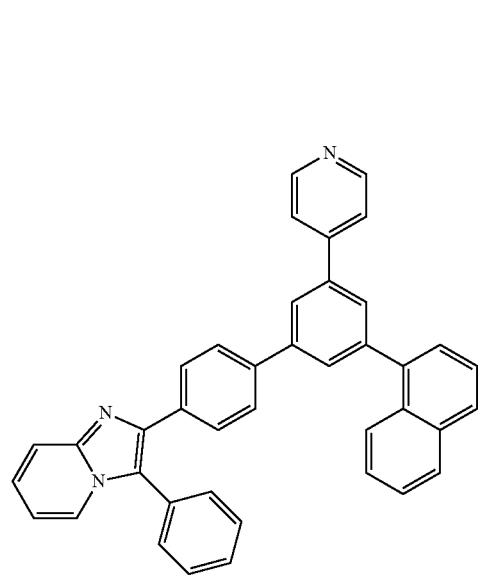
B 14
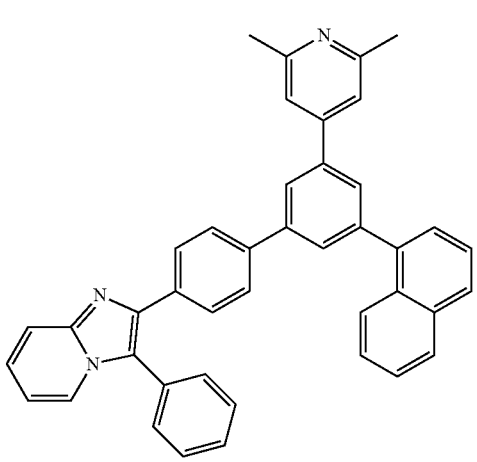
B 17
B 15
B 18

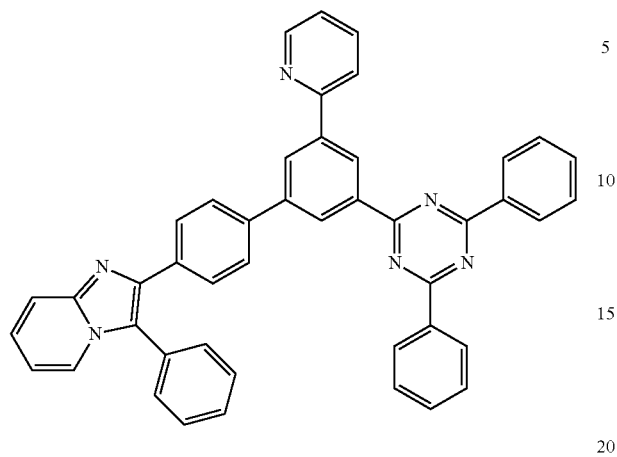
B 19
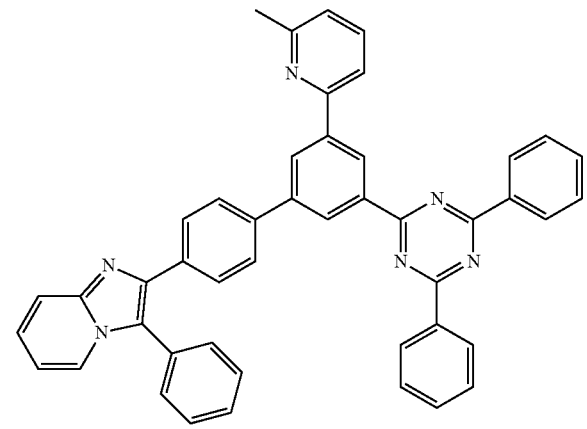
B 22
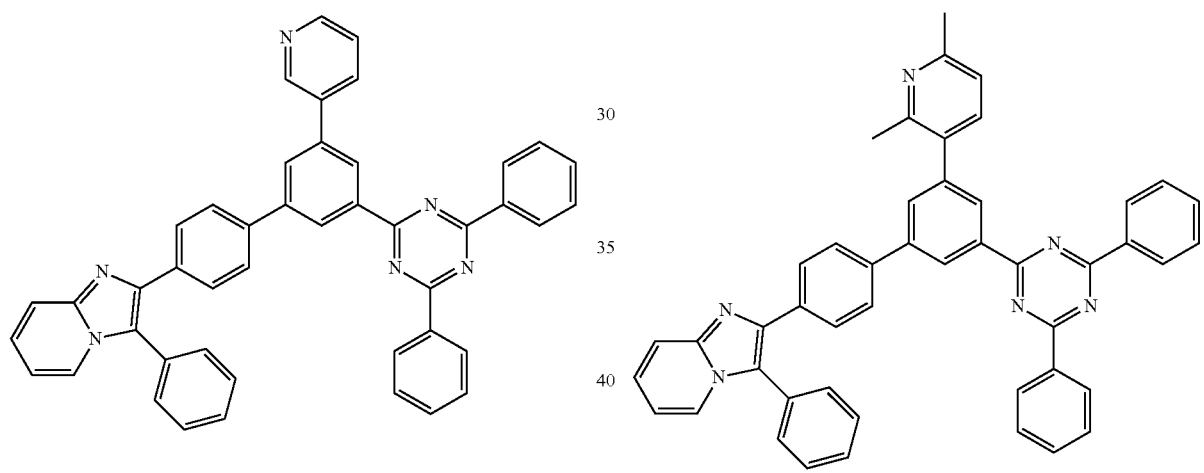
B 20
B 23
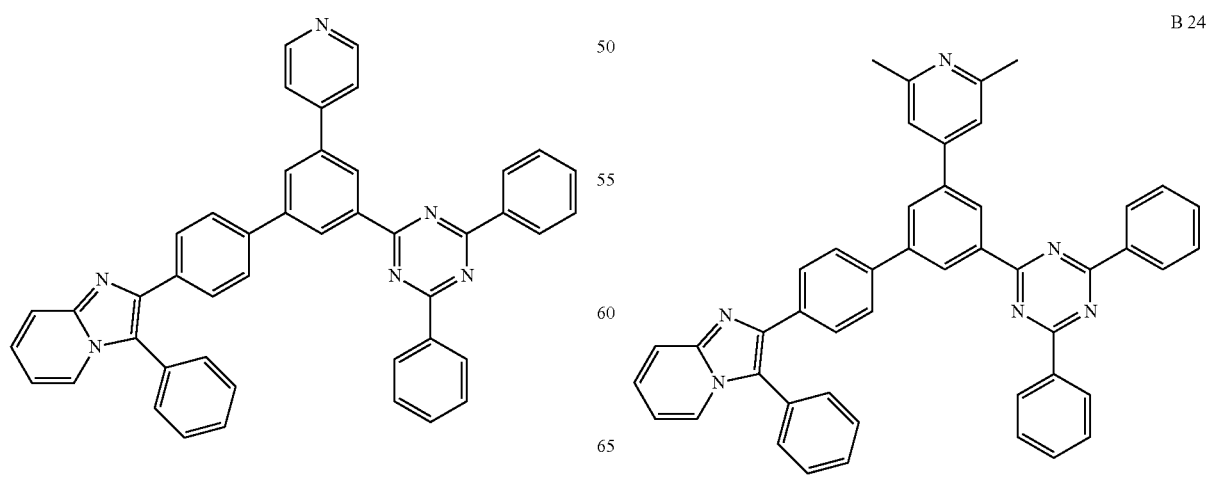
B 21
B 24

B 25
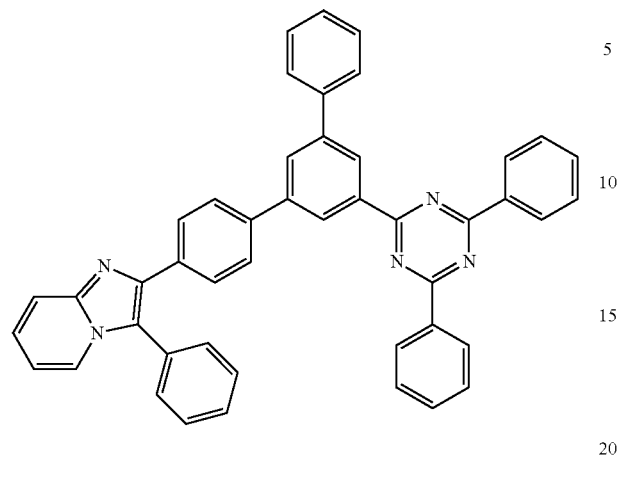
B 26
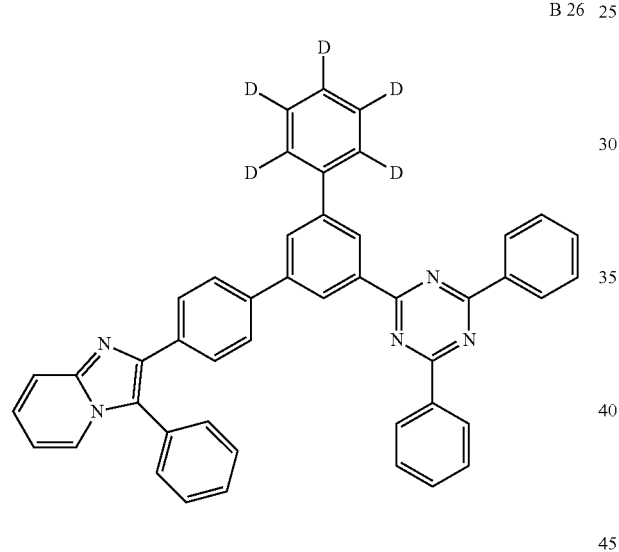
B 27
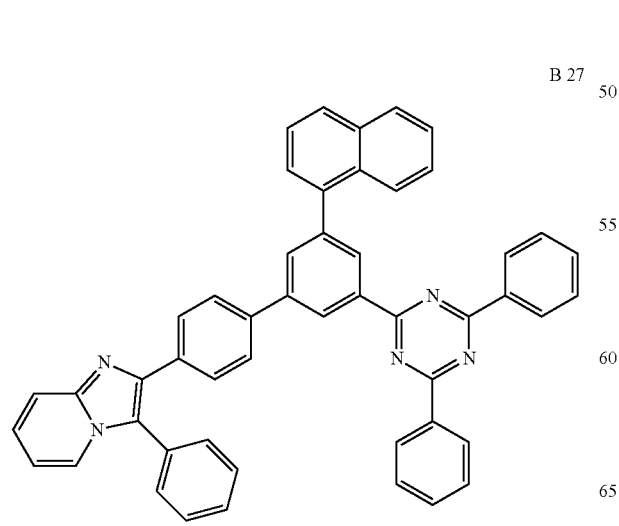
B 28
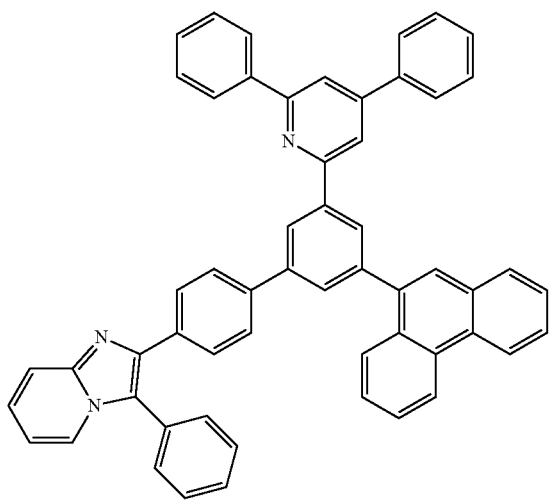
B 29
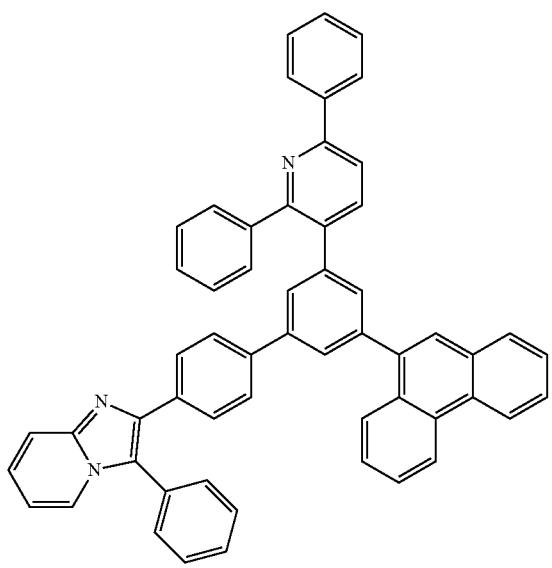
B 30
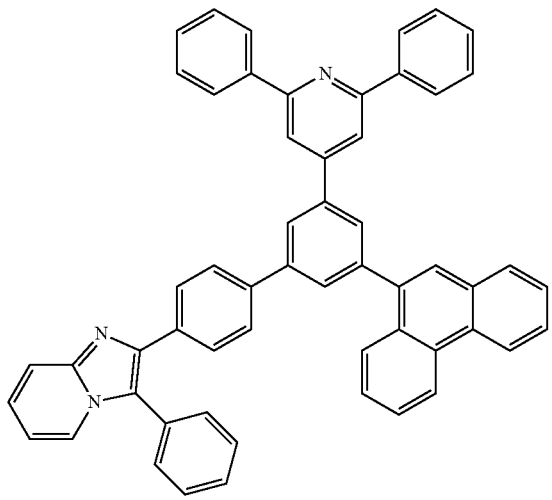

B 31
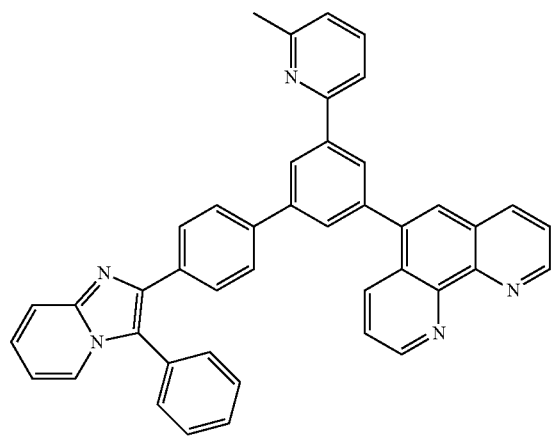
B 34
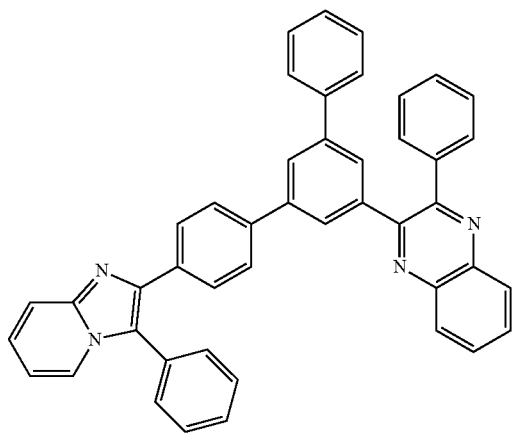
B 32
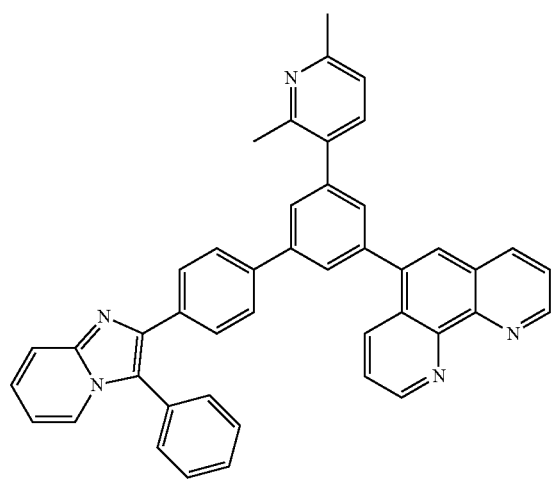
B 35
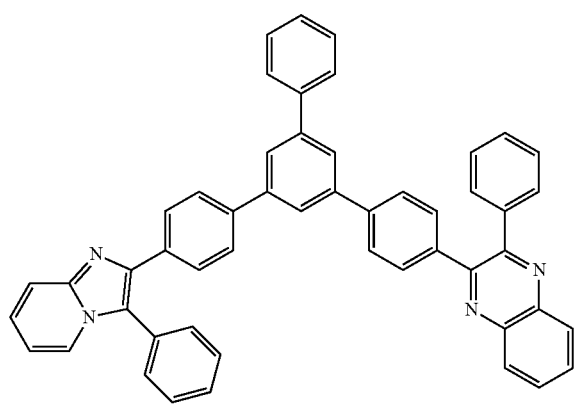
B 33
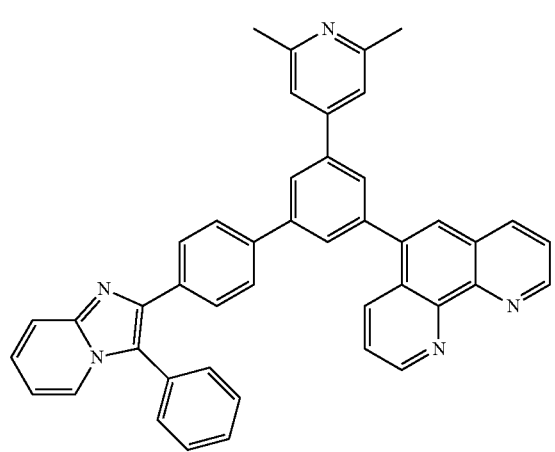
B 36
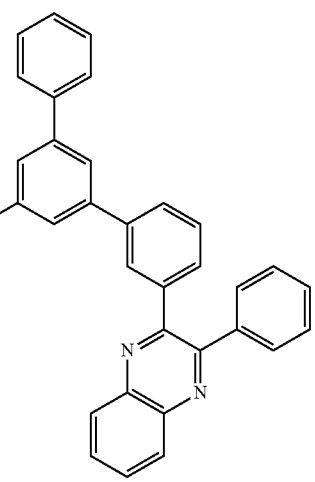

B 37
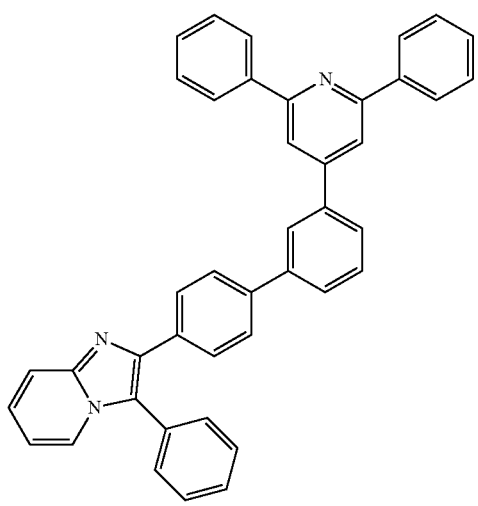
B 38
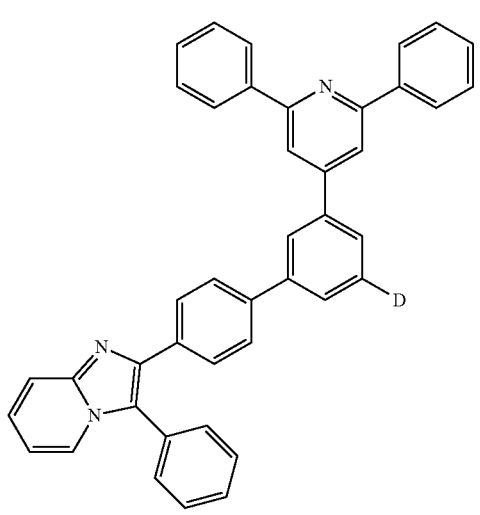
B 39
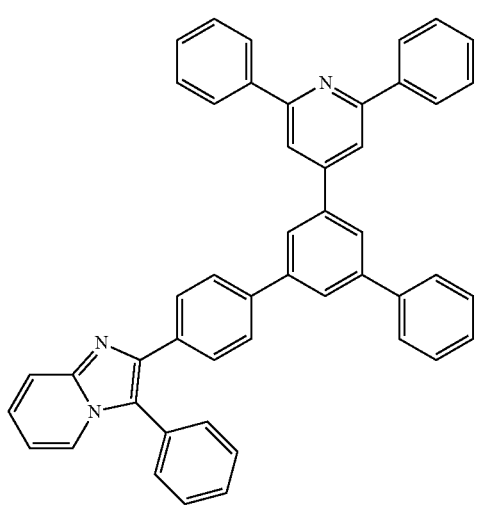
B 40
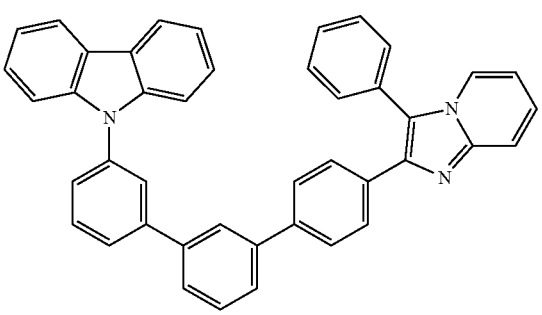
B 41
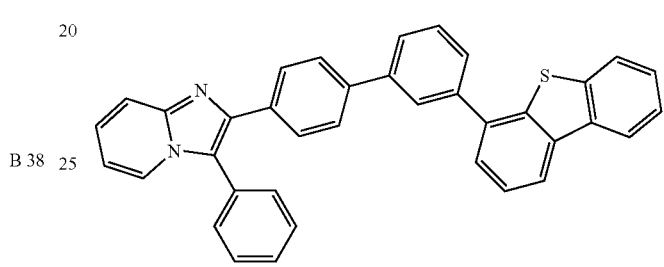
B 42
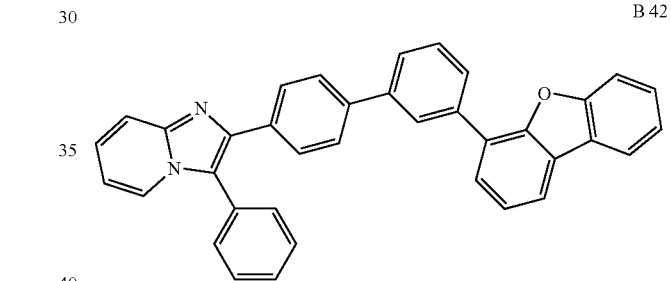
B 43
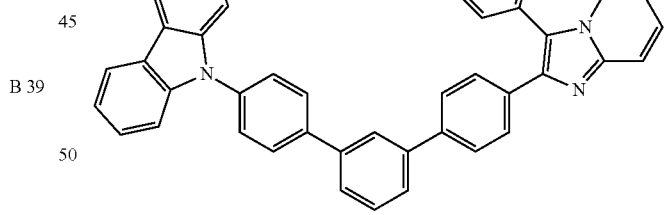
B 44
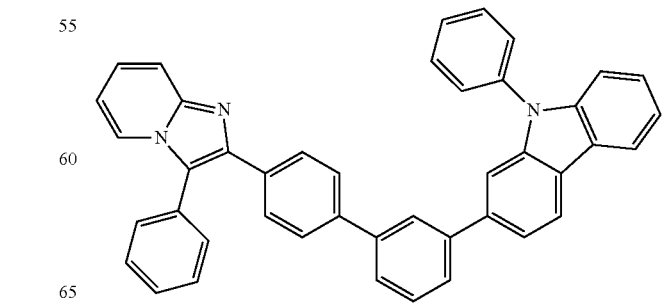

B 45
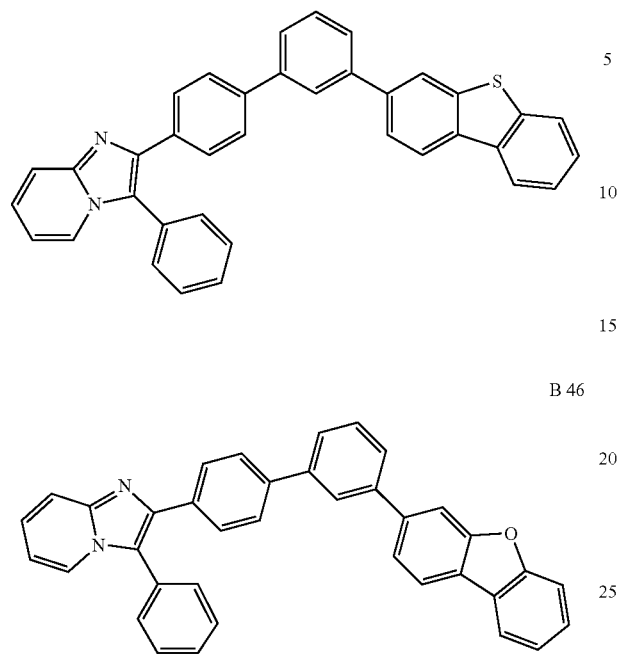
B 46
B 47
B 48
B 49
B 50
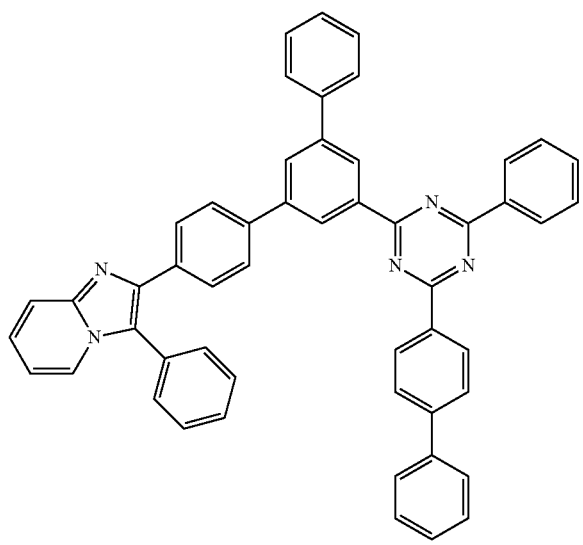
B 51
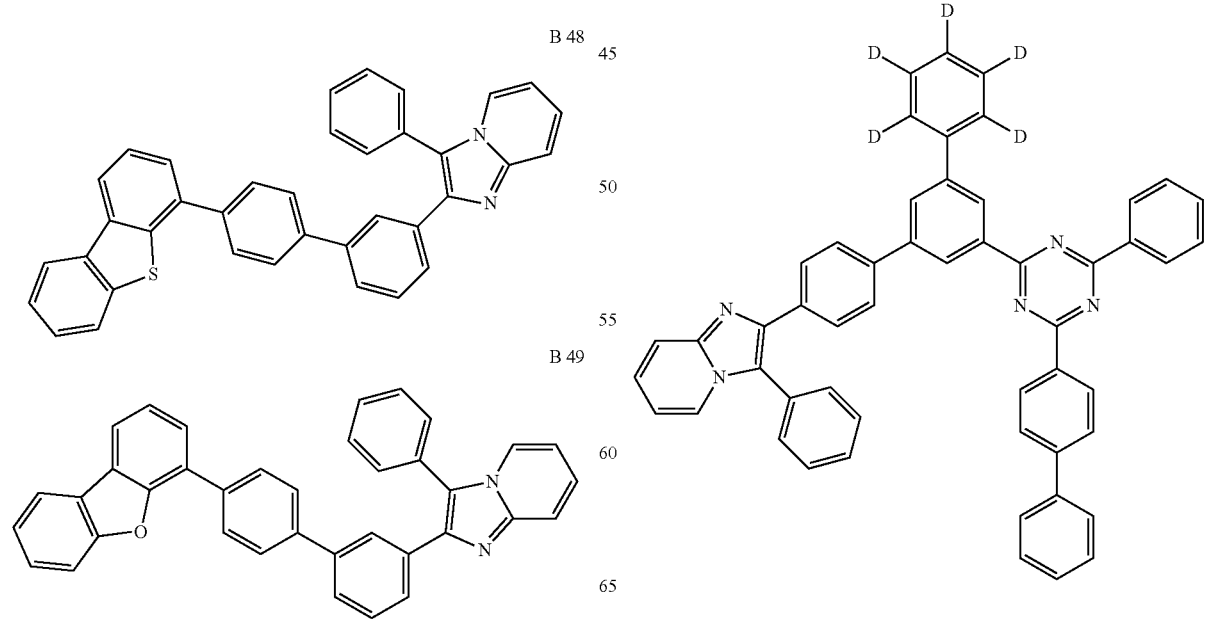

B 52
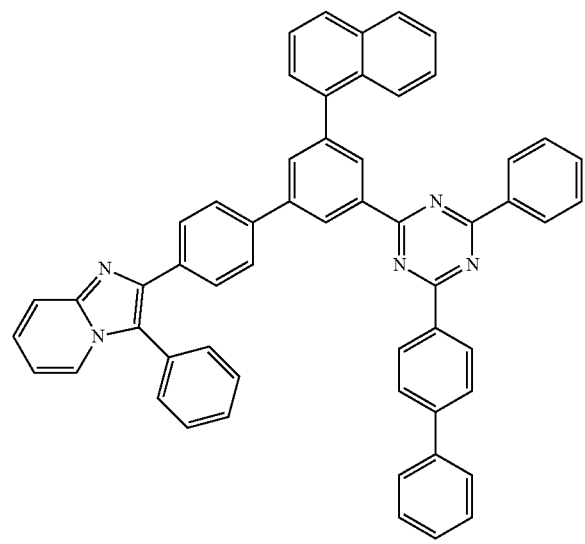
B 55
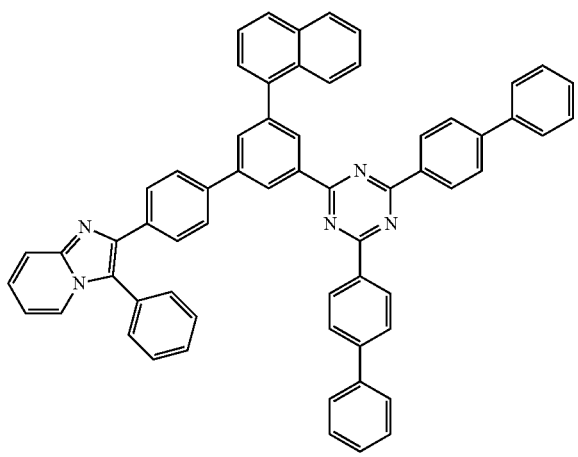
B 53
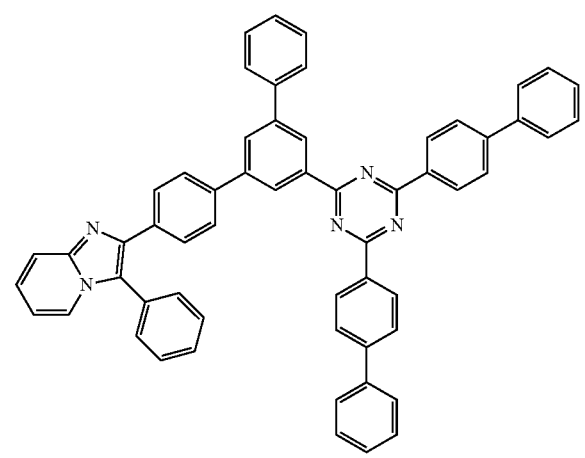
B 56
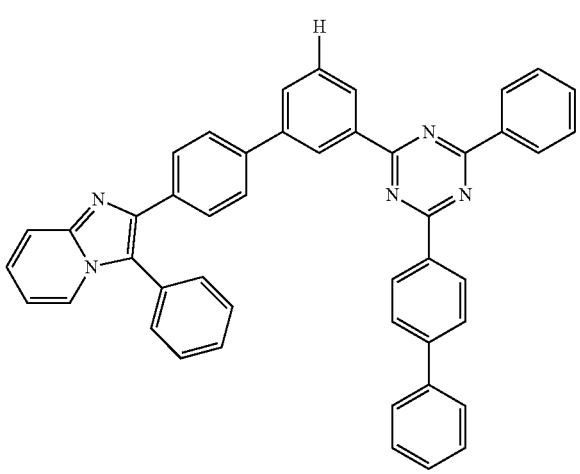
B 54
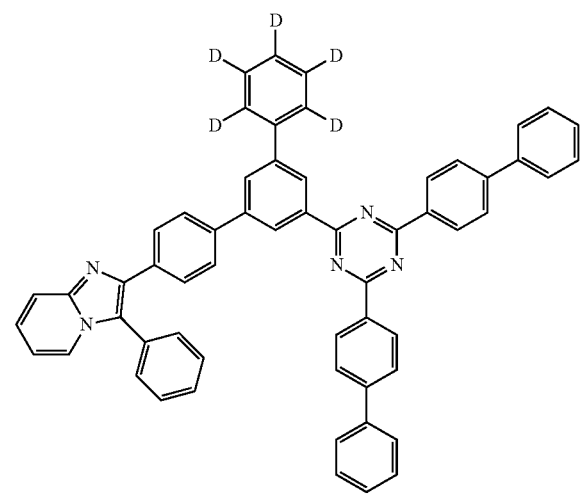
B 57
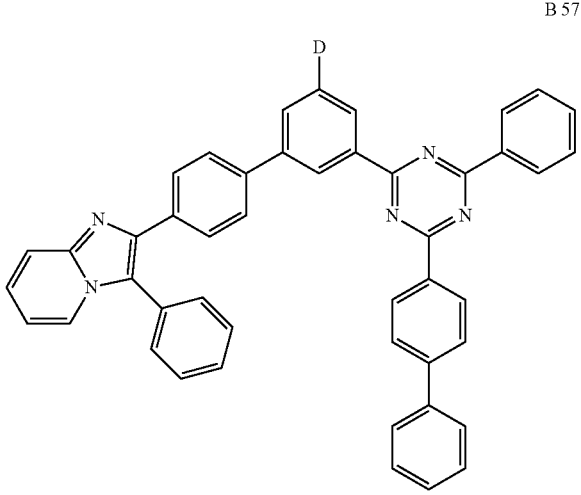

-continued
B 58
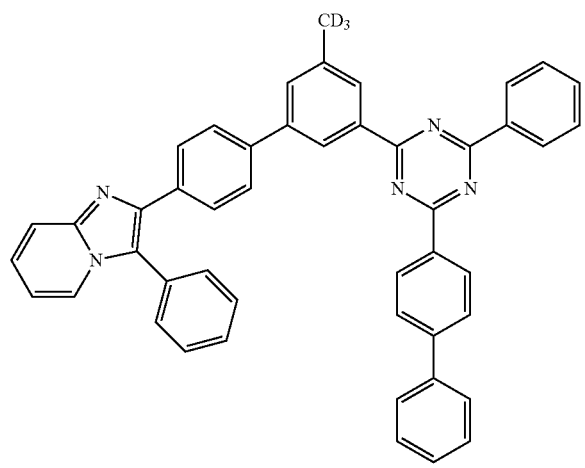
B 59
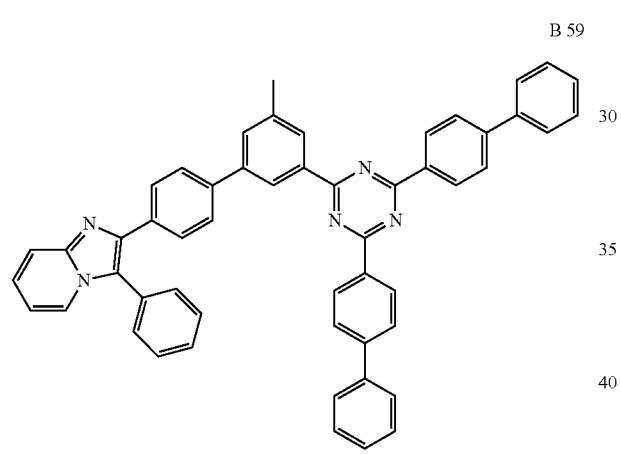
B 60
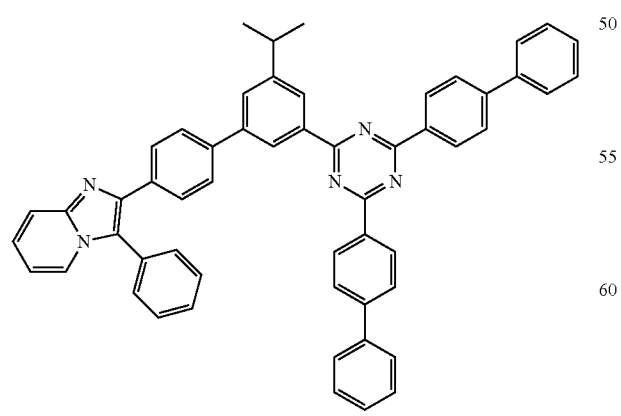
-continued
B 61
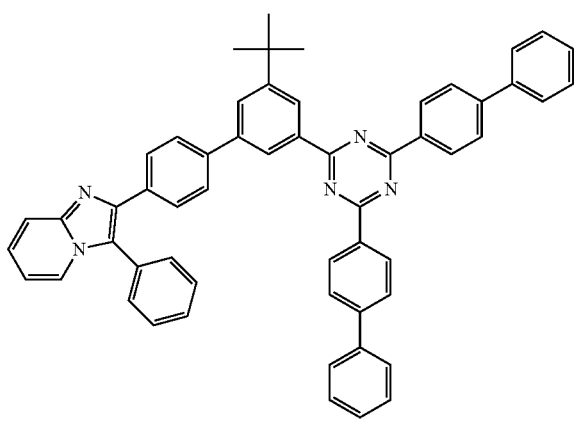
B 62
B 63
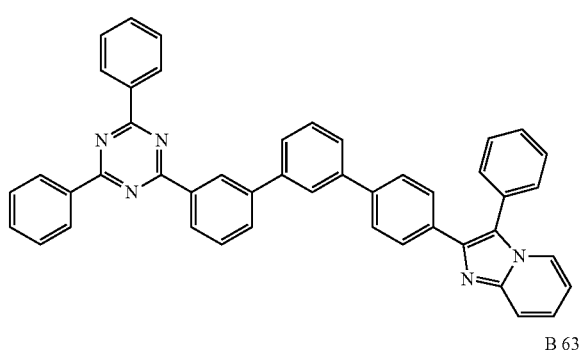
B 64
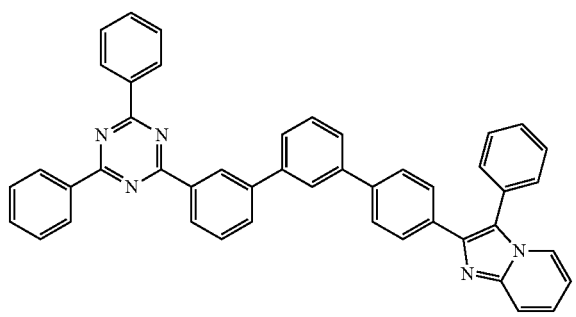

-continued
B 65
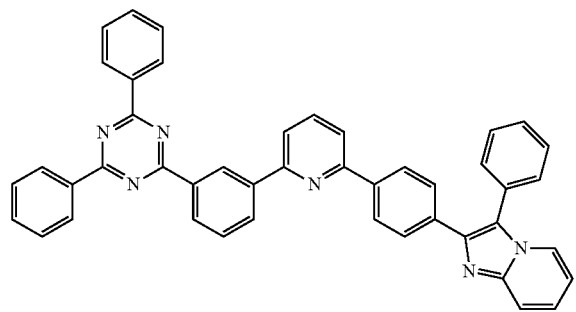
B 66
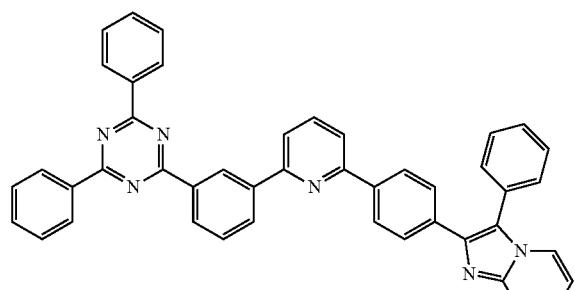
B 67
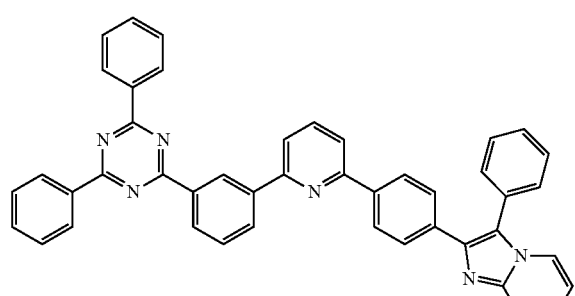
B 68
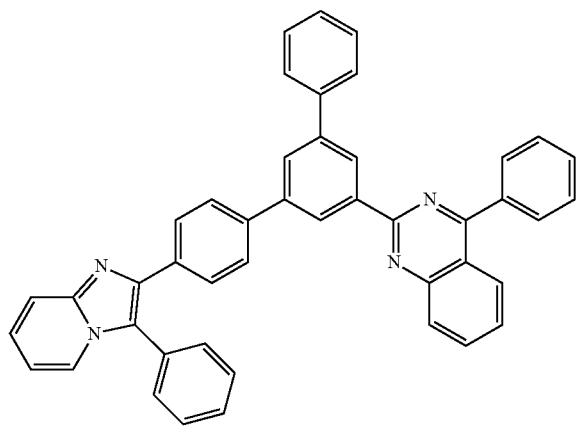
-continued
B 69
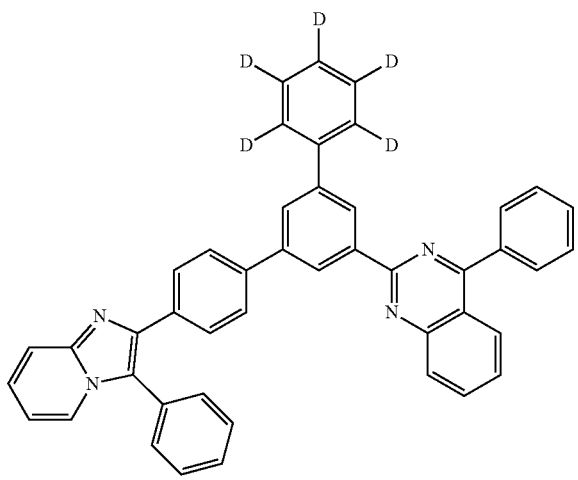
B 70
B 71

B 72
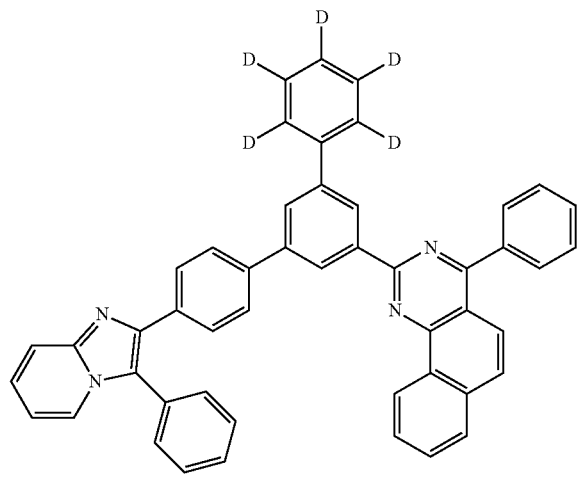
B 75
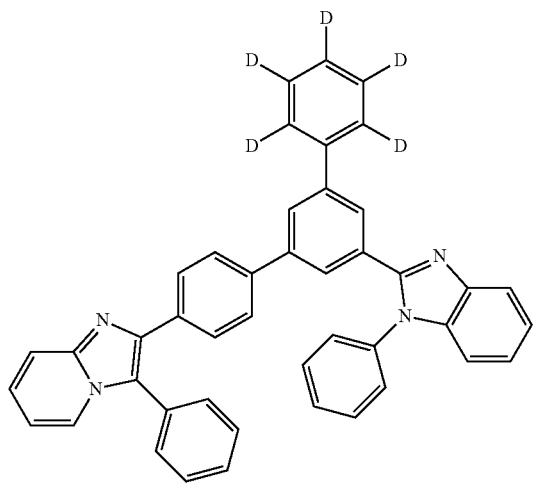
B 73
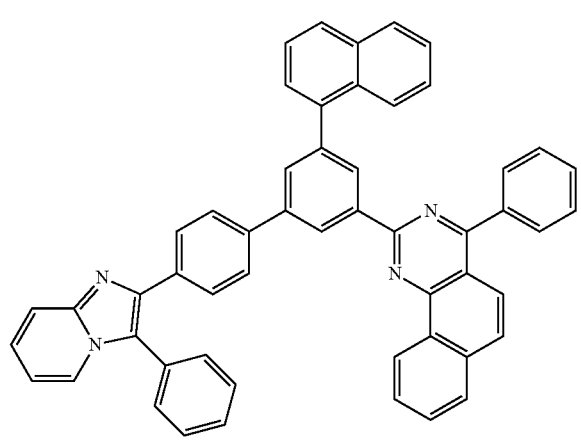
B 76
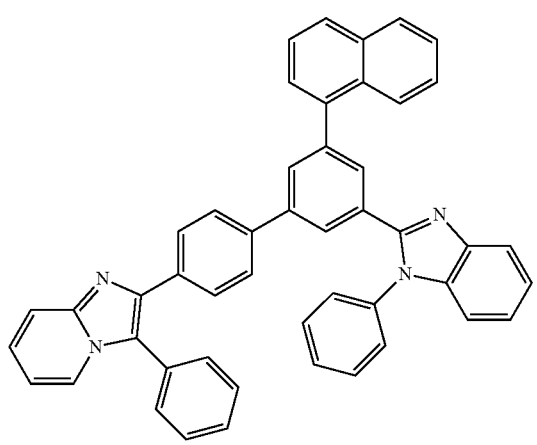
B 74
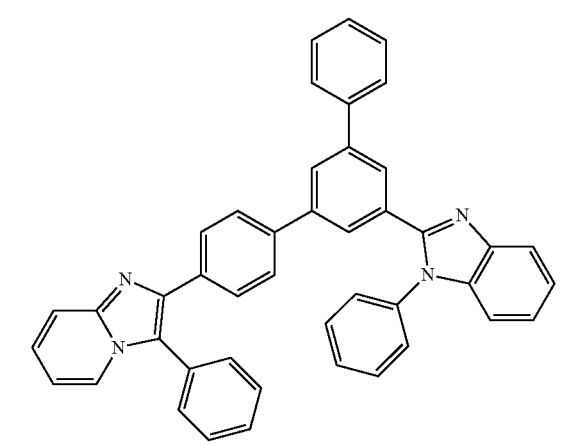
B 77
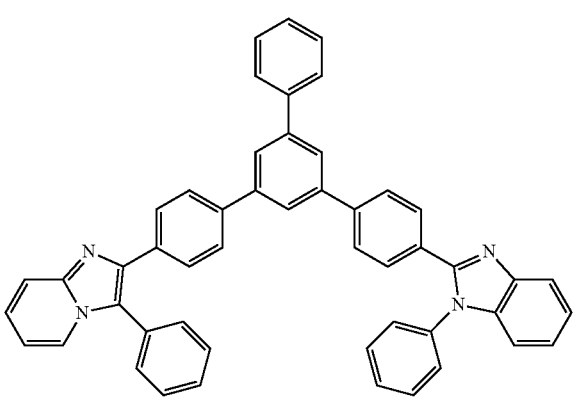

B 78
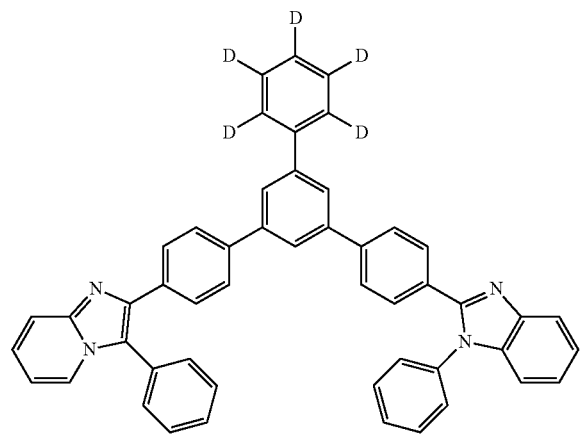
B 79
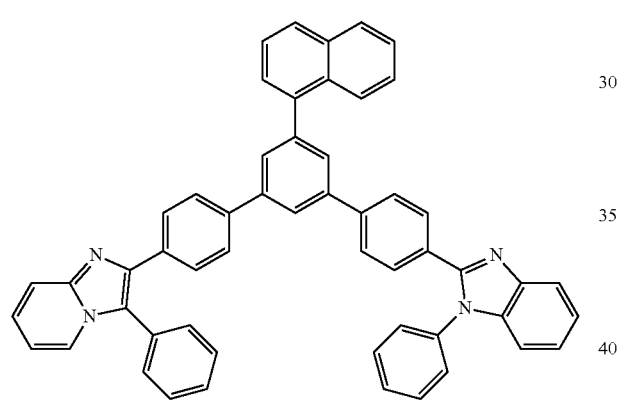
B 80
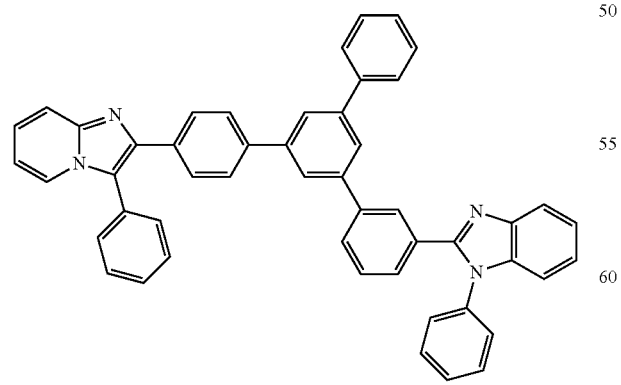
B 81
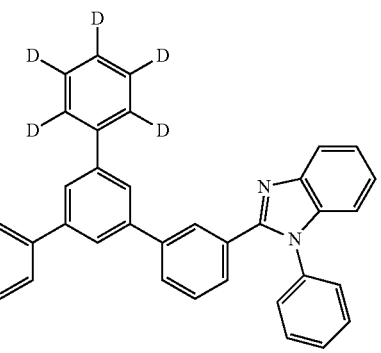
B 82
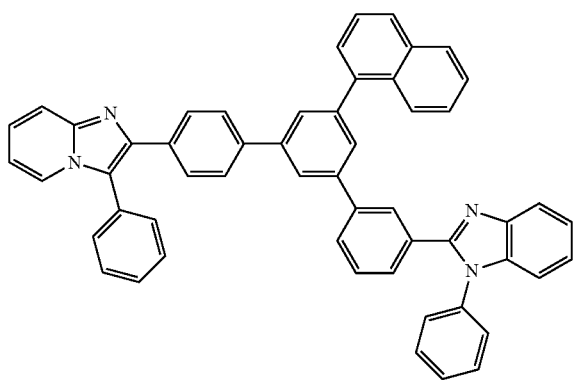
B 83
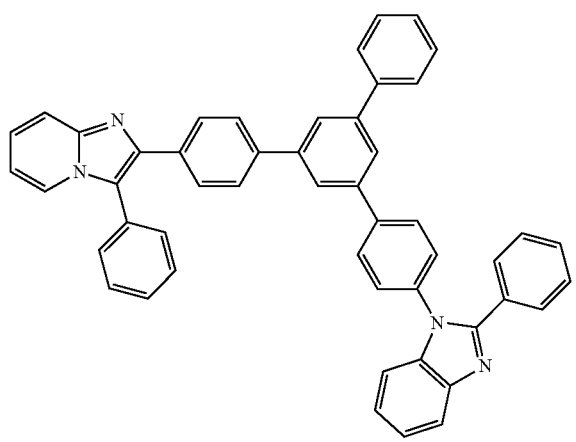

B 84
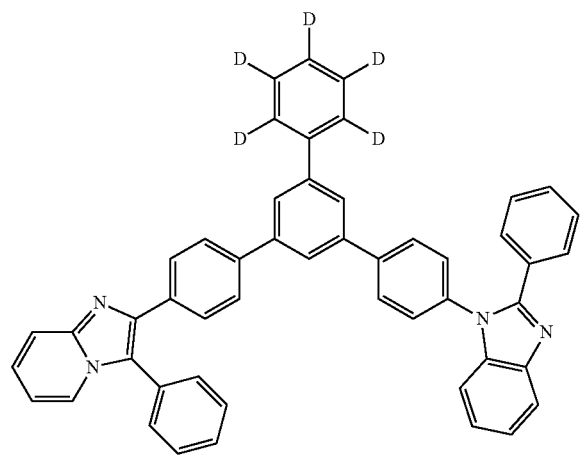
B 85
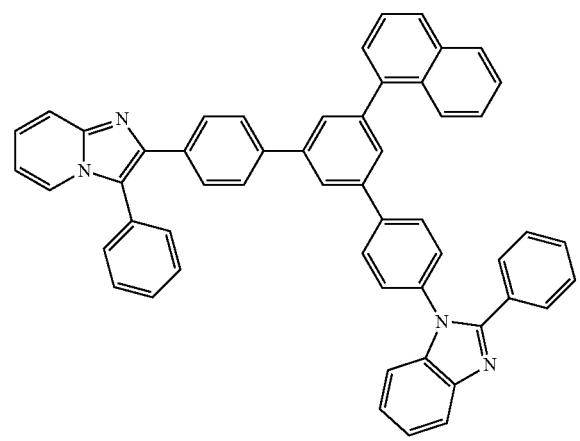
B 87
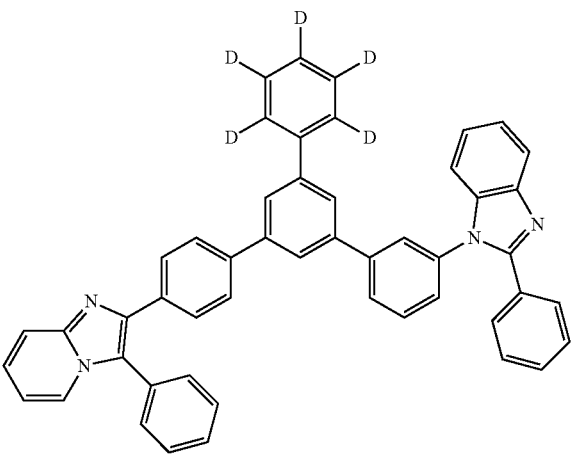
B 88
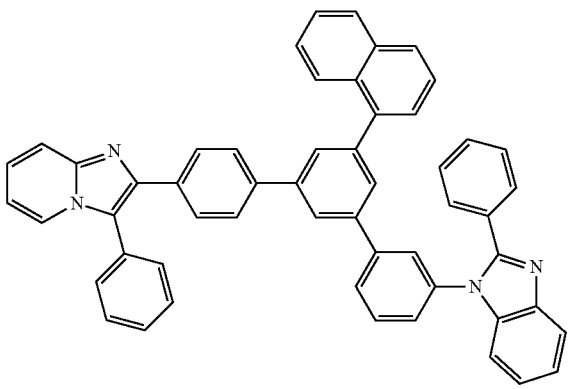
B 86
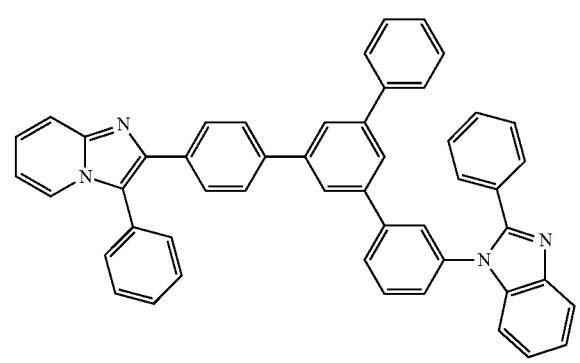
B 89

B 90
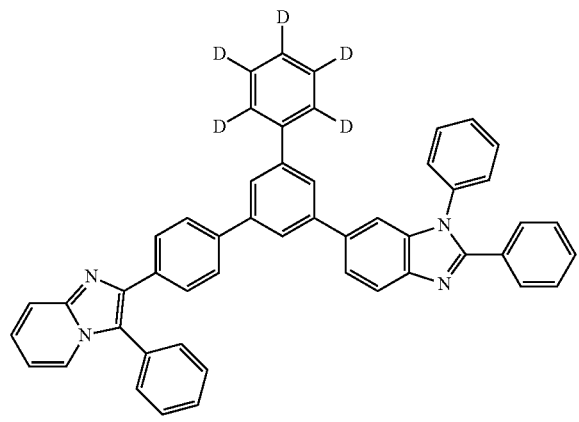
B 91
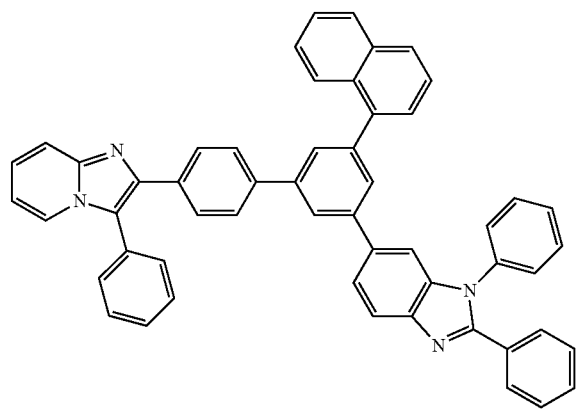
B 93
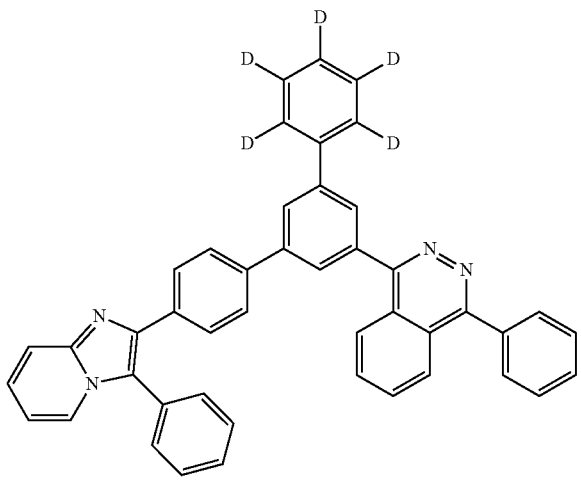
B 94
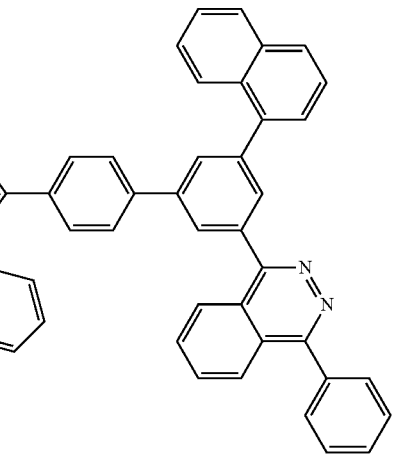
B 92
B 95
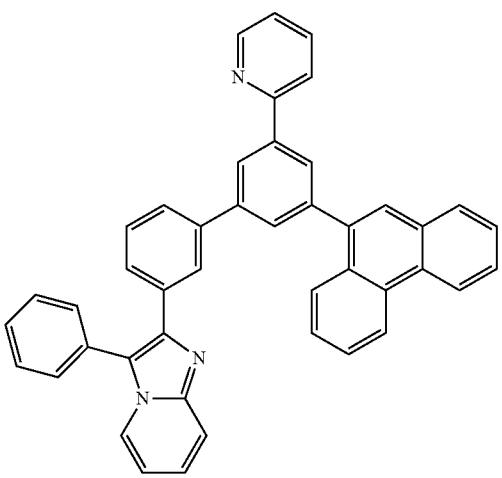

B 96
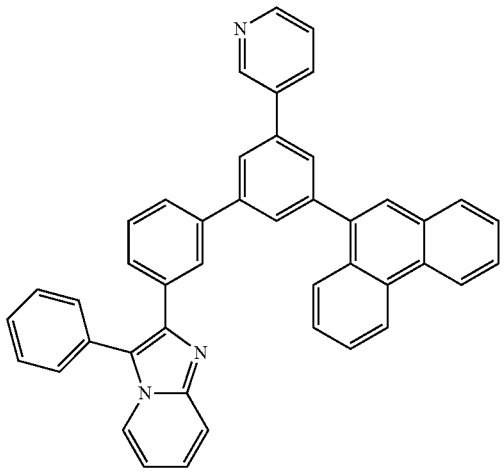
B 97
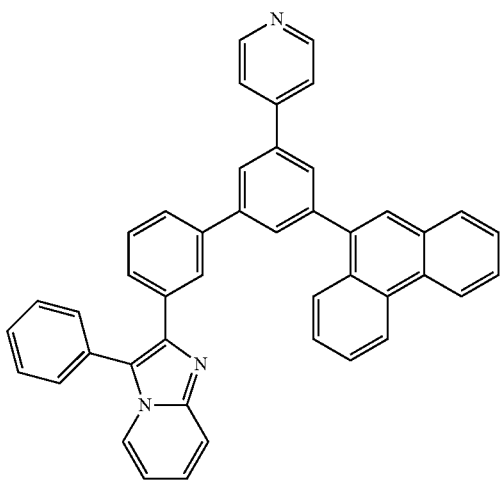
B 98
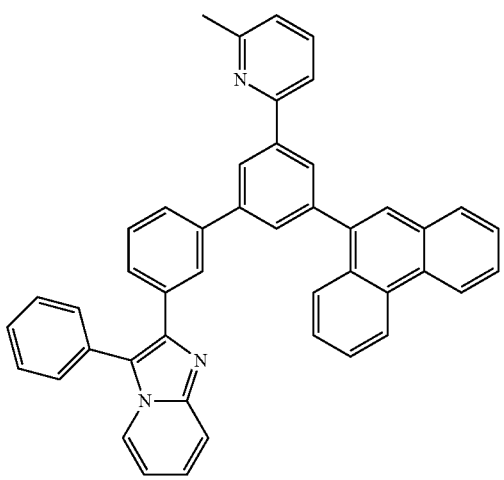
B 99
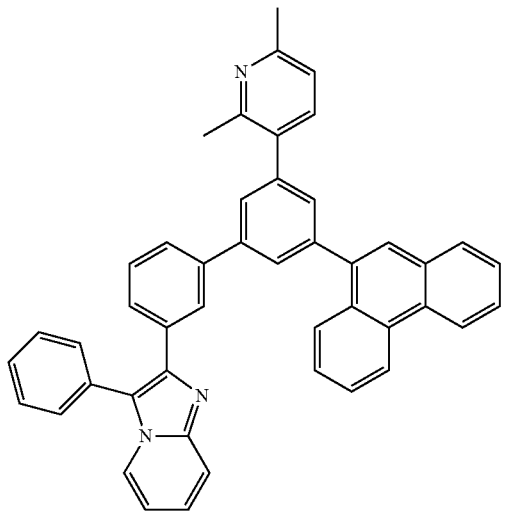
B 100
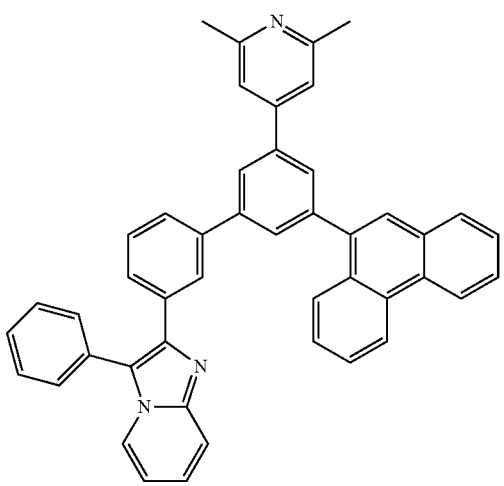
B 101
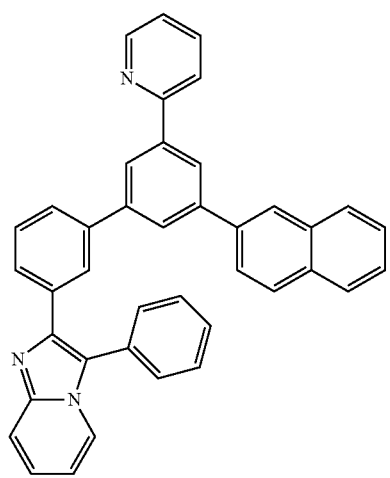

B 102
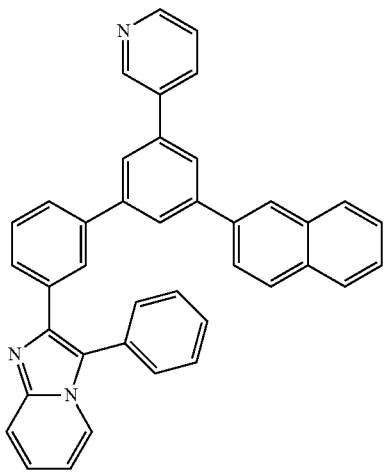
B 103
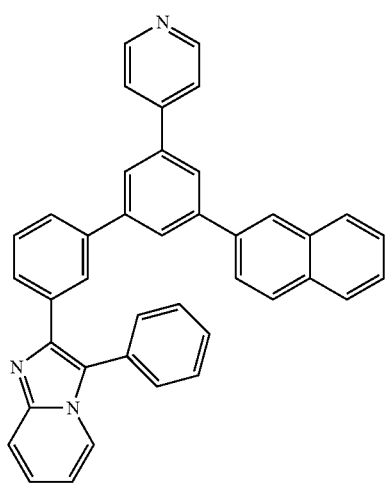
B 104
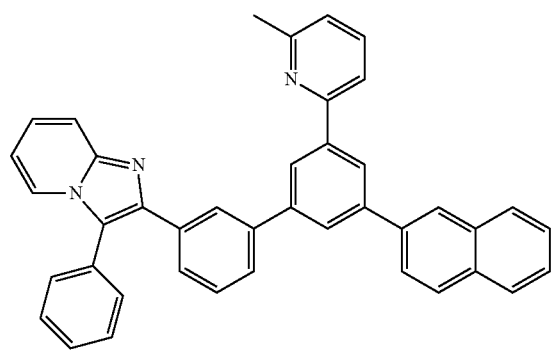
B 105
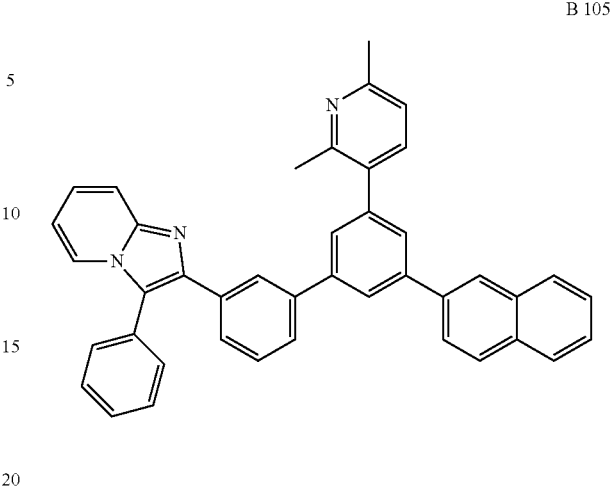
B 106
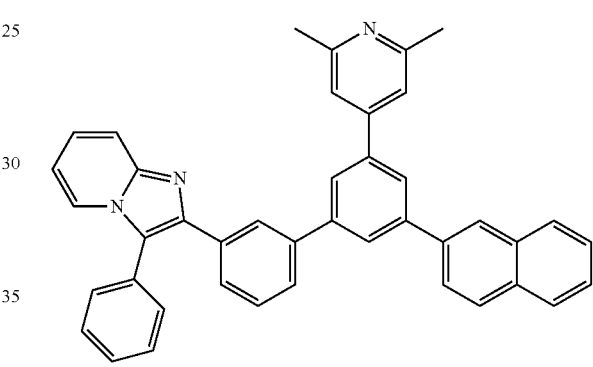
B 107
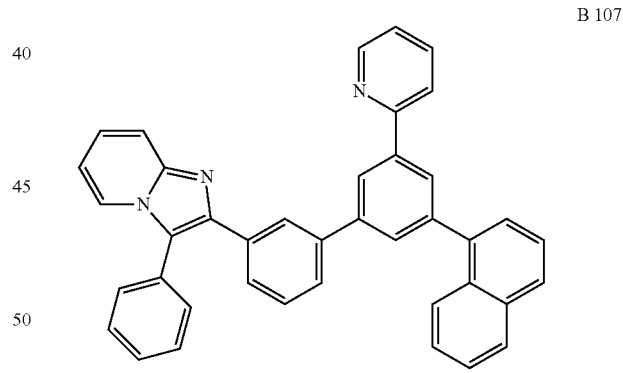
B 108
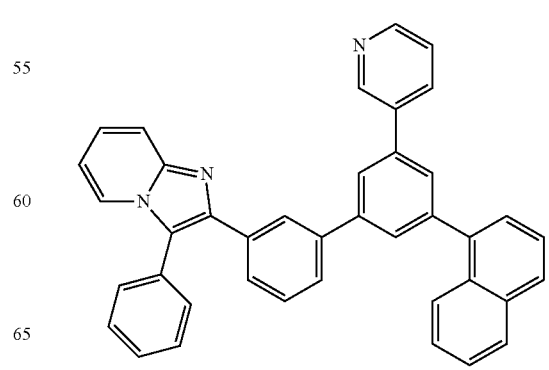

B 109
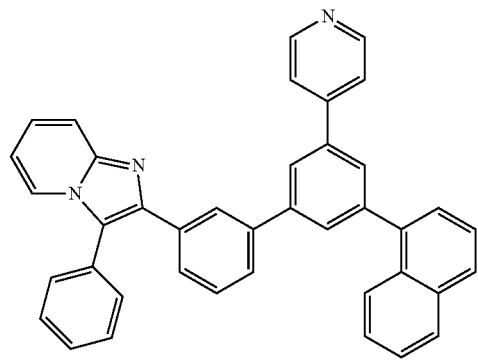
B 110
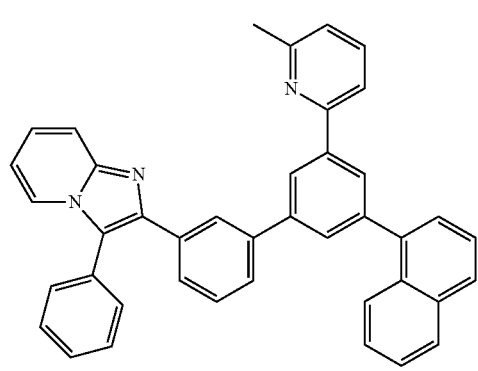
B 111
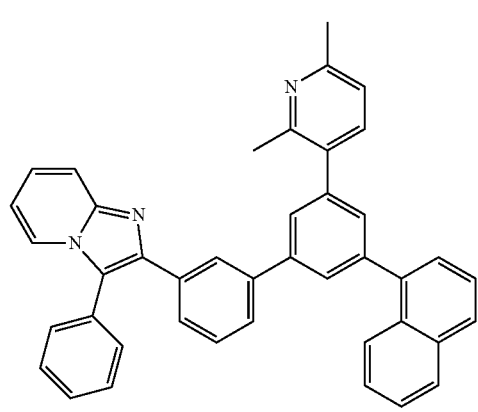
B 112
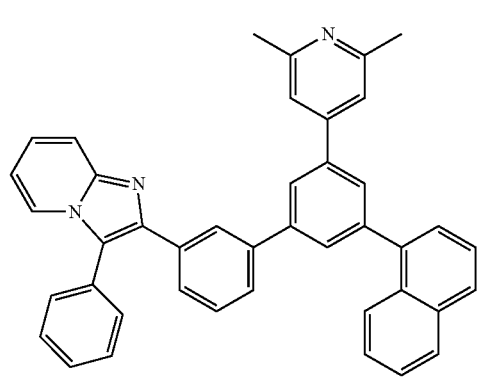
B 113
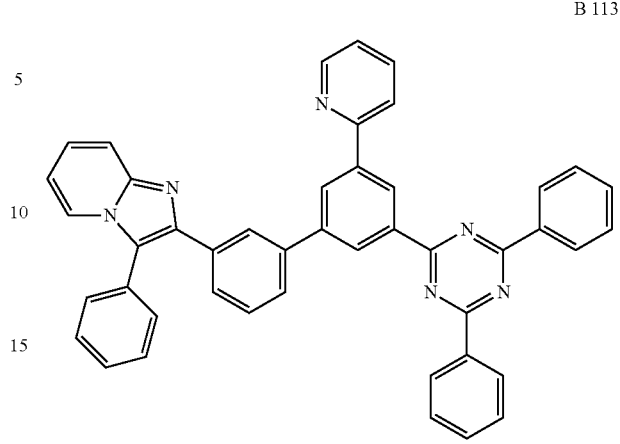
B 114
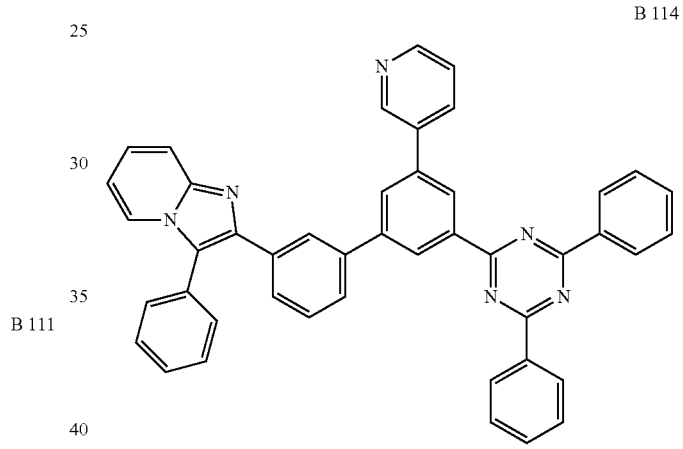
B 115
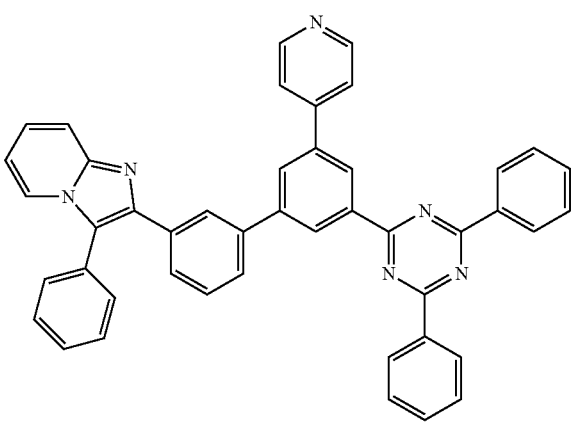

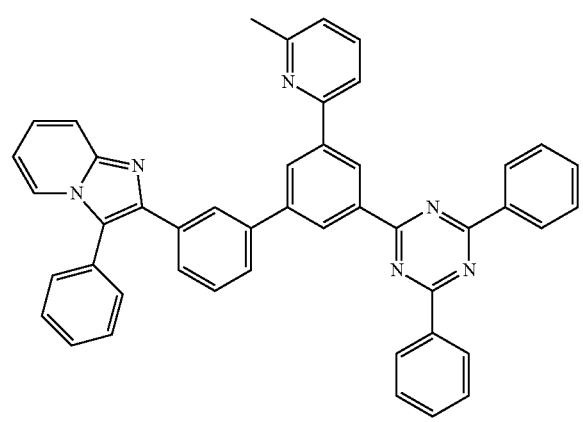
B 116
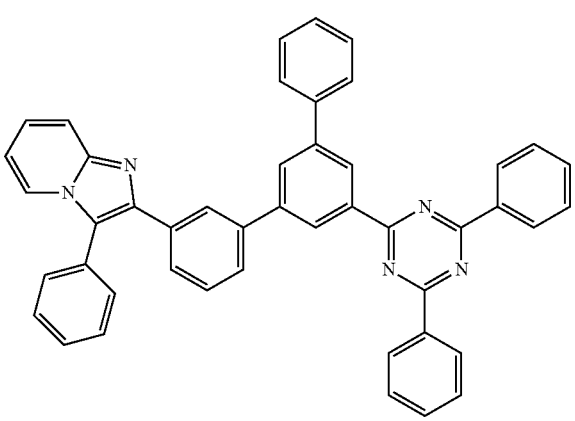
B 119
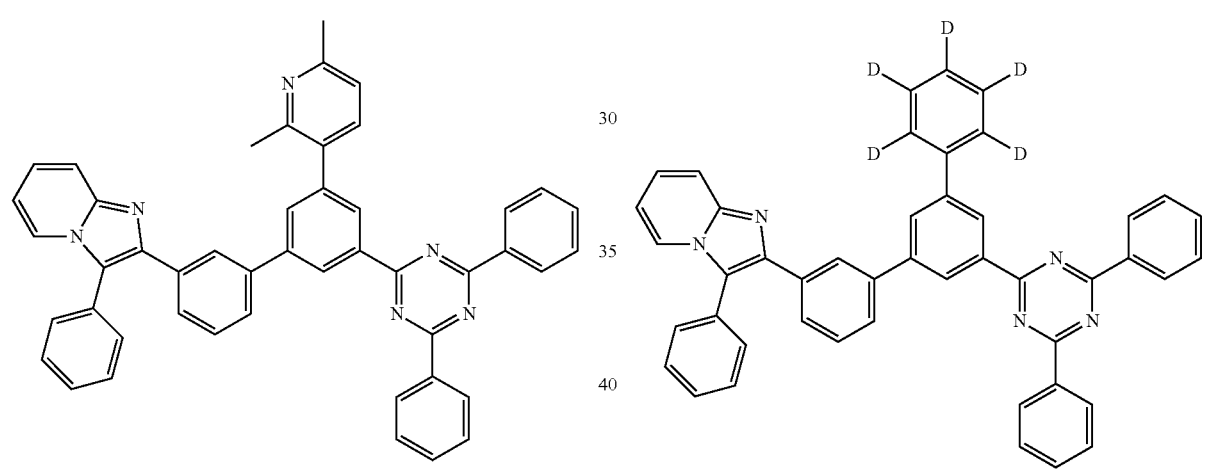
B 117
B 120
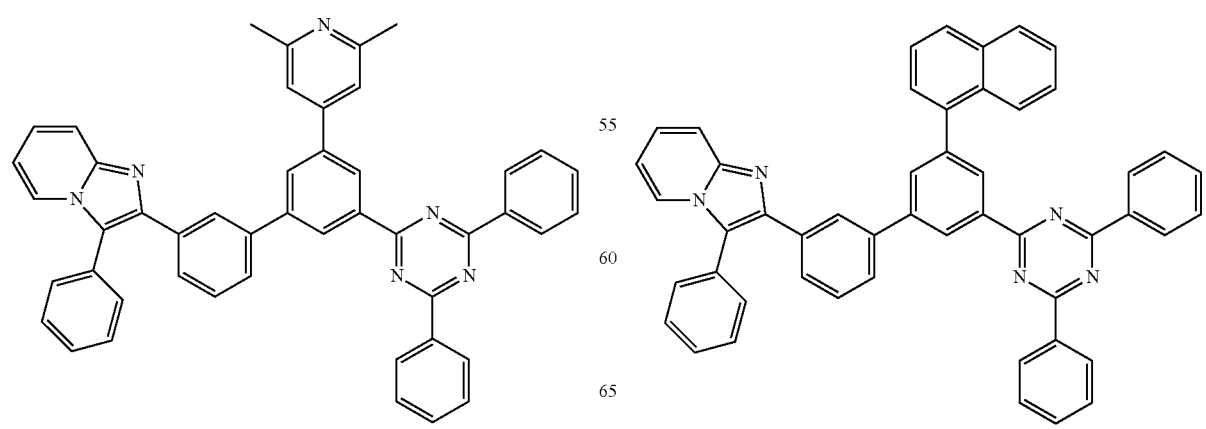
B 118
B 121

B 122
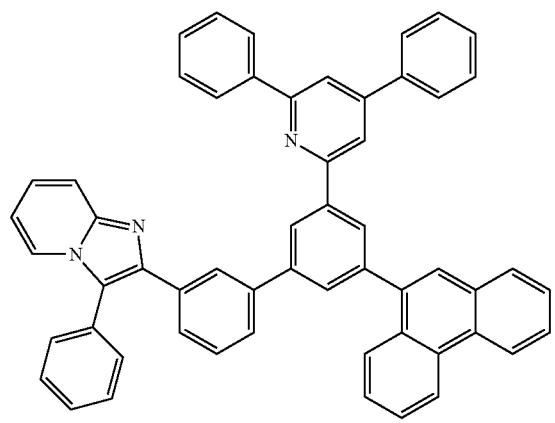
B 123
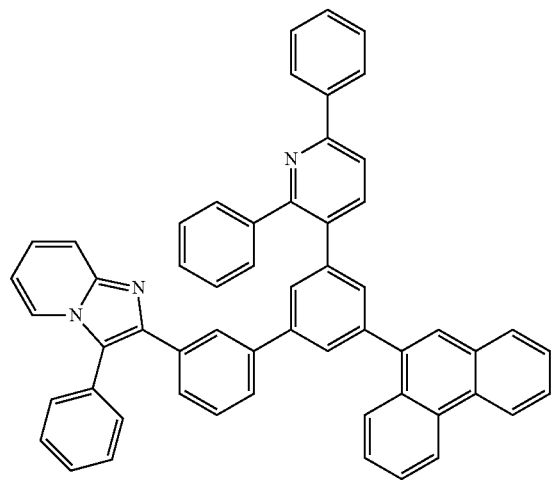
B 124
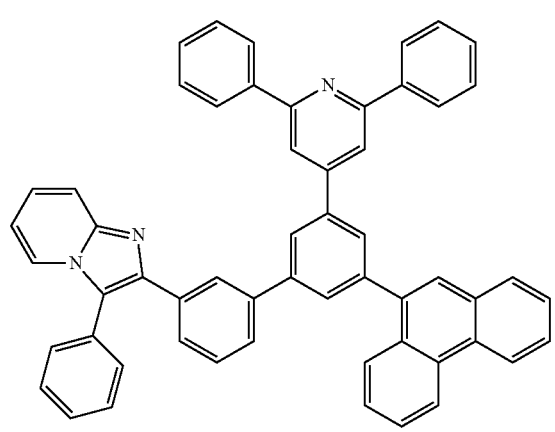
B 125
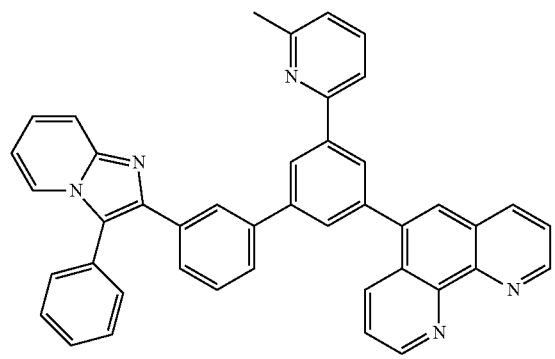
B 126
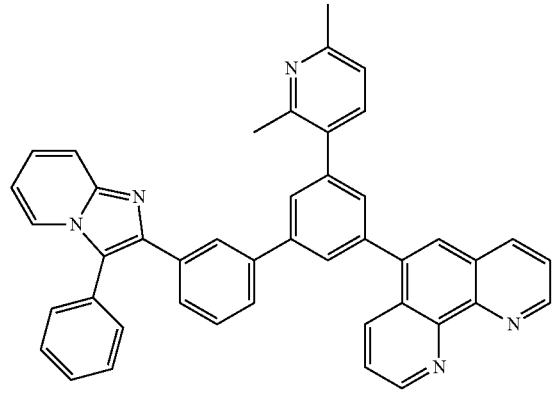
B 127
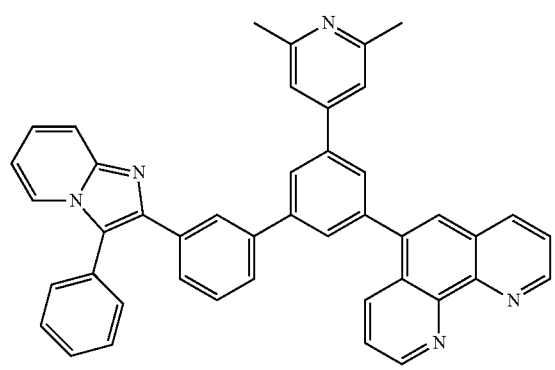
B 128
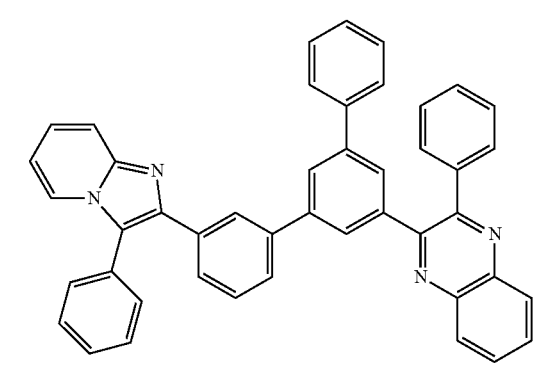

-continued
B 129
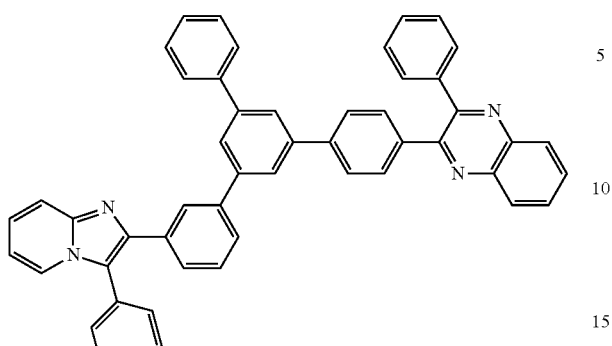
B 130
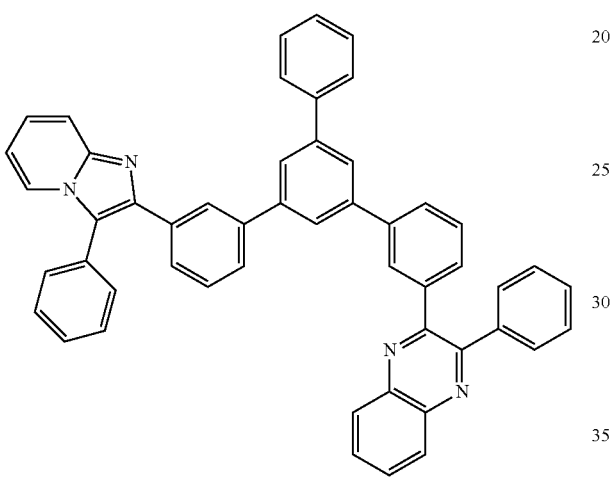
B 131
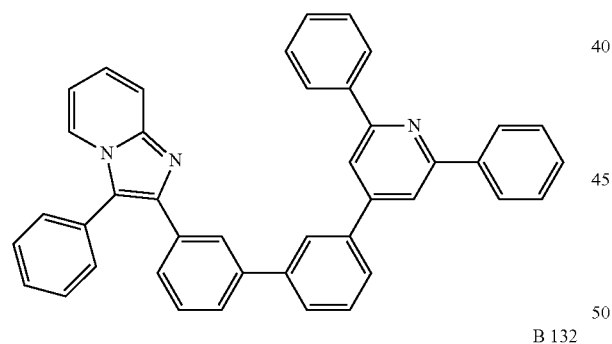
B 132
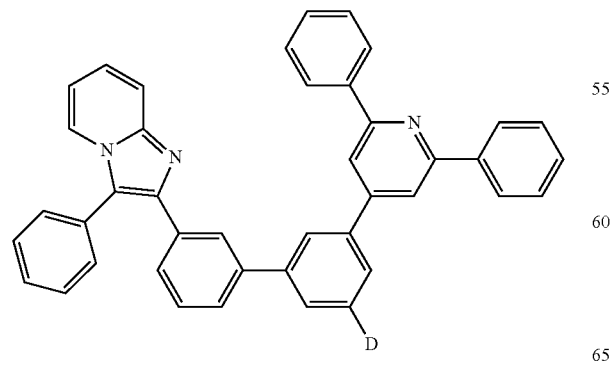
-continued
B 133
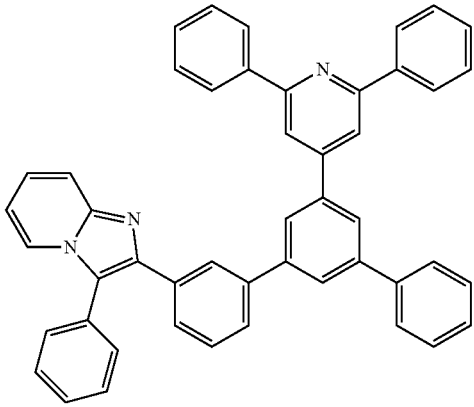
B 134
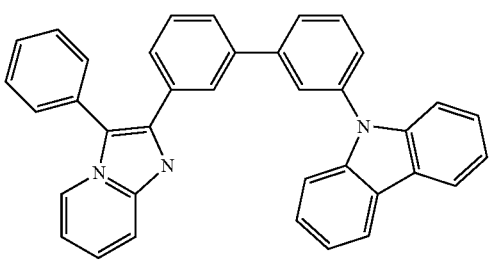
B 135
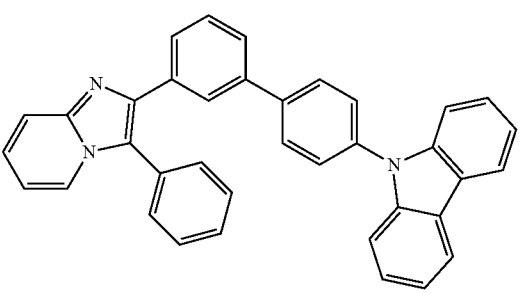
B 136
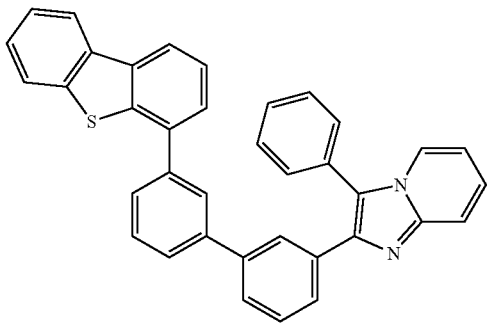

-continued
B 137
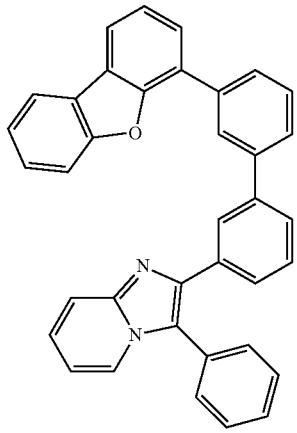
B 138
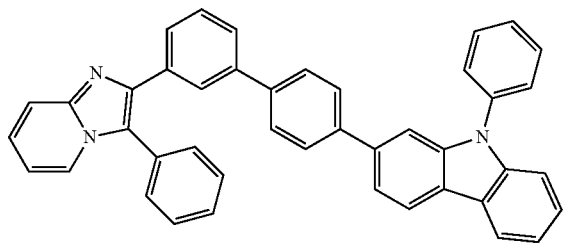
B 139
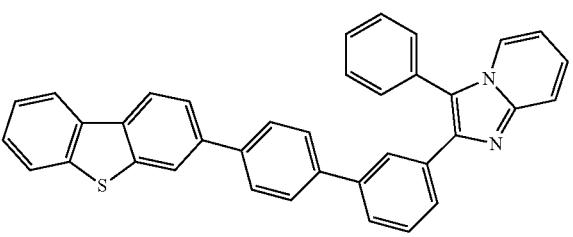
B 140
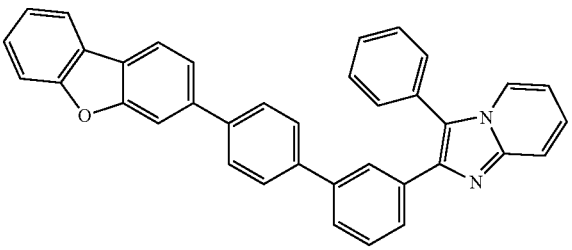
B 141
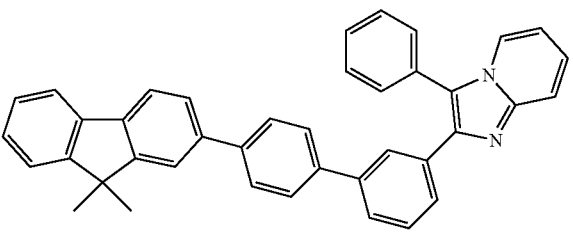
-continued
B 142

B 143
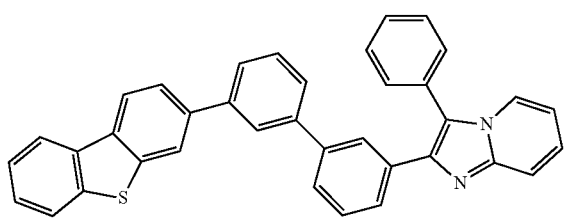
B 144
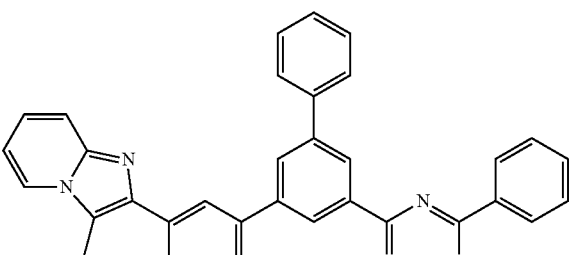
B 145
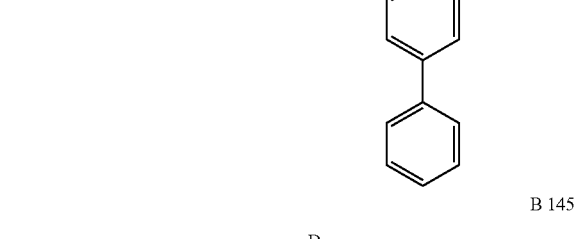
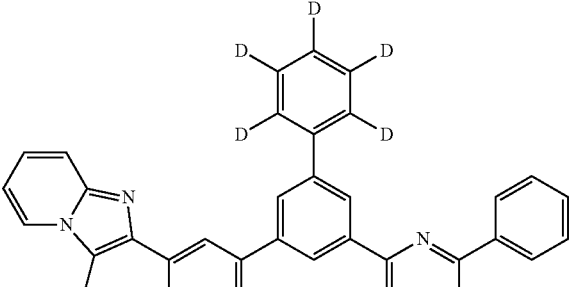

B 146
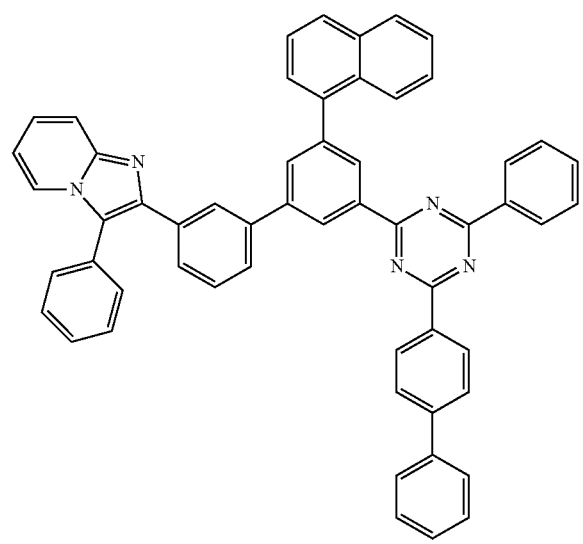
B 147
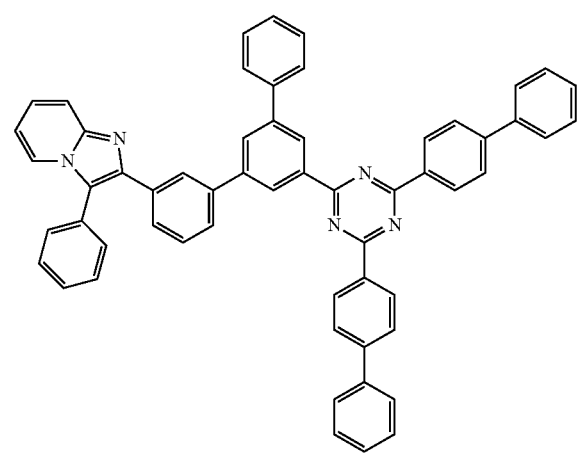
B 148
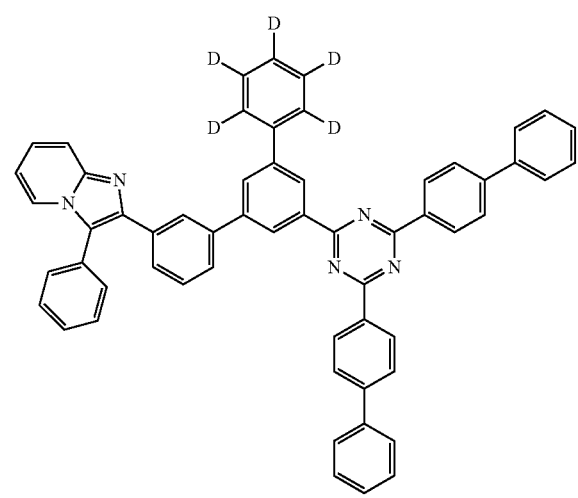
B 149
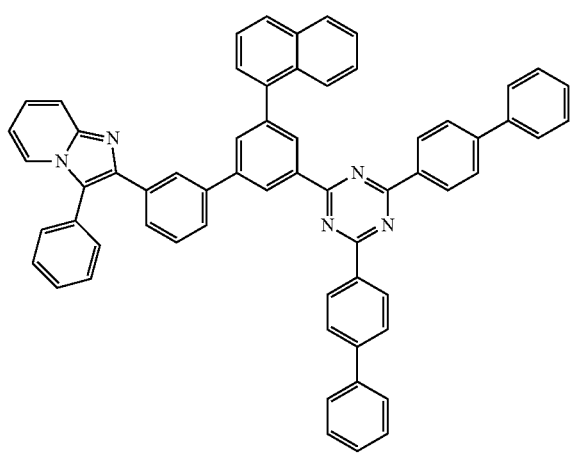
B 150
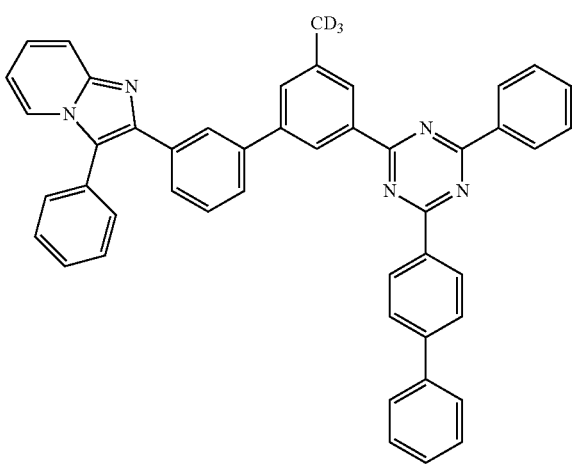
B 151

B 152
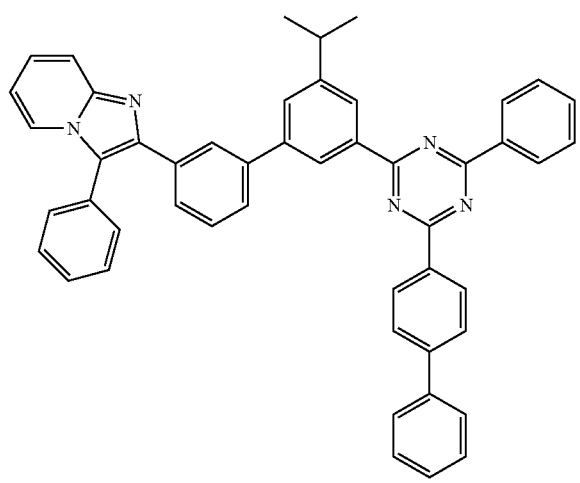
B 153
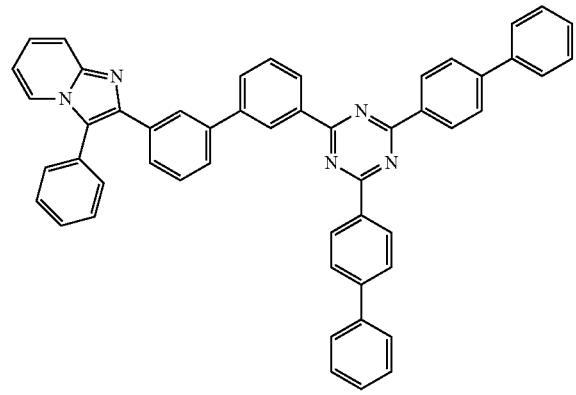
B 154
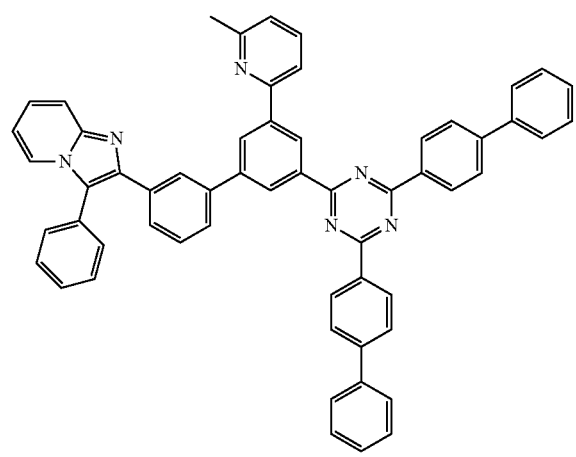
B 155
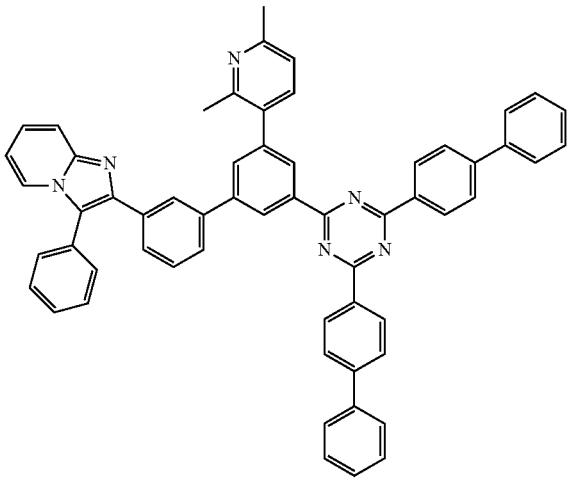
B 156
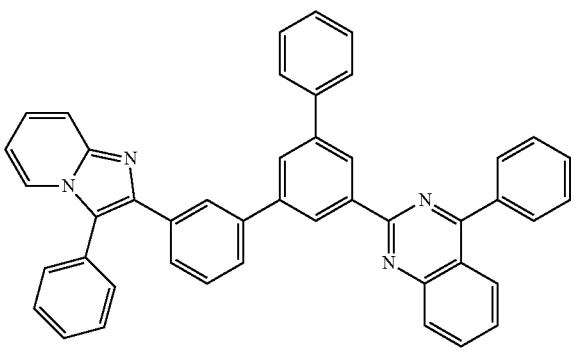
B 157
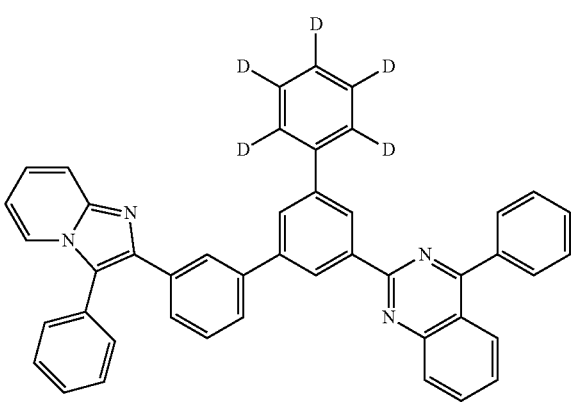
B 158
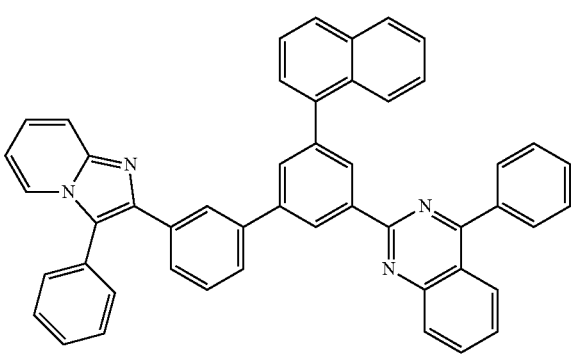

B 159
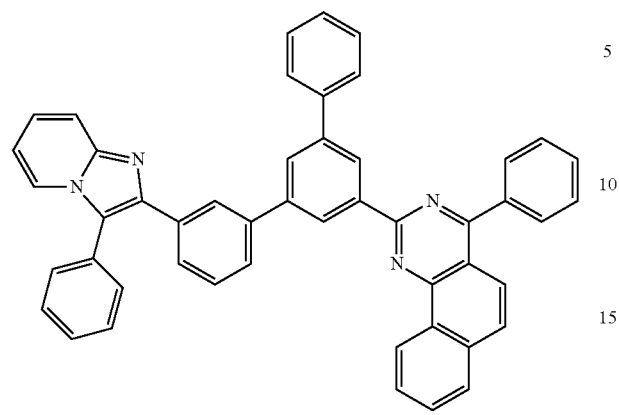
B 160
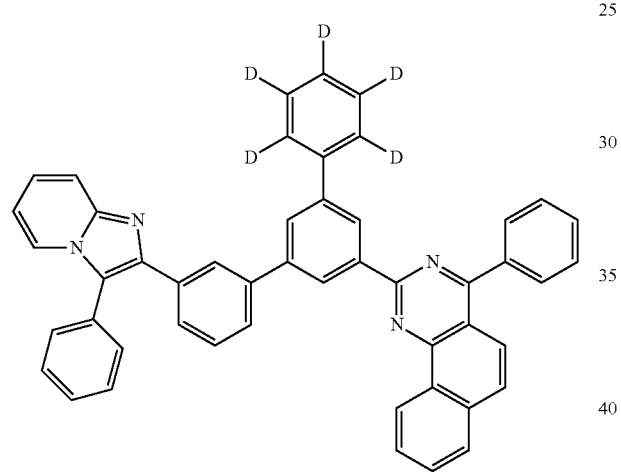
B 161
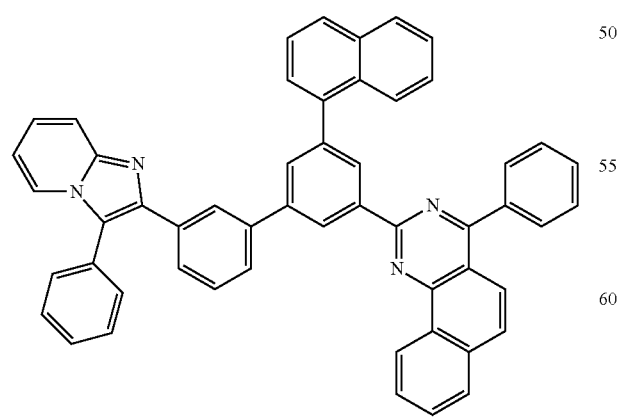
B 162
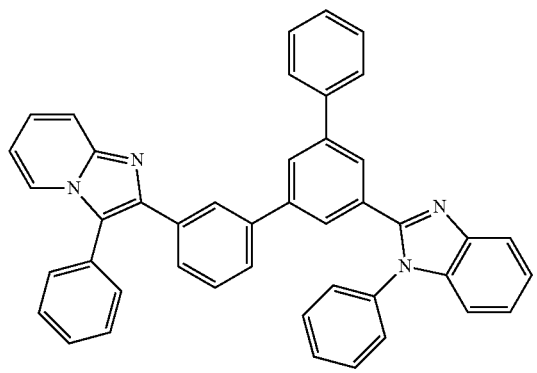
B 163
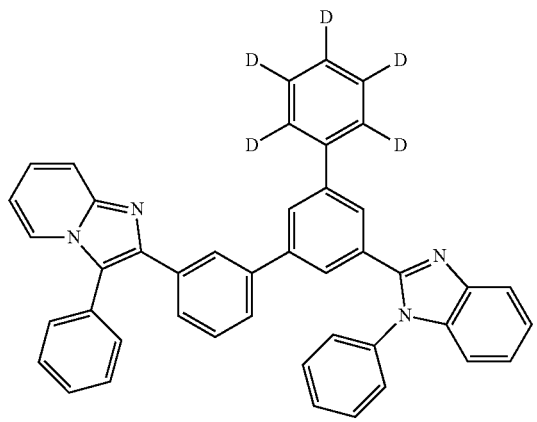
B 164
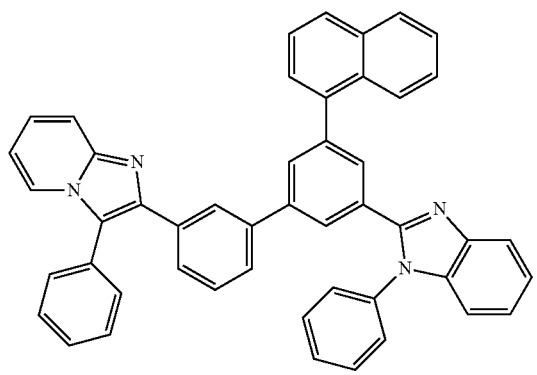
B 165
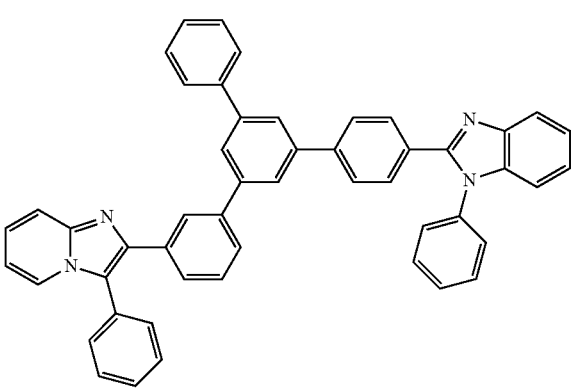

B 166
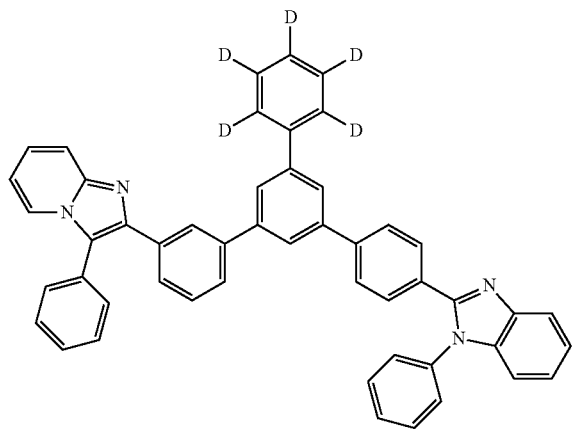
B 167
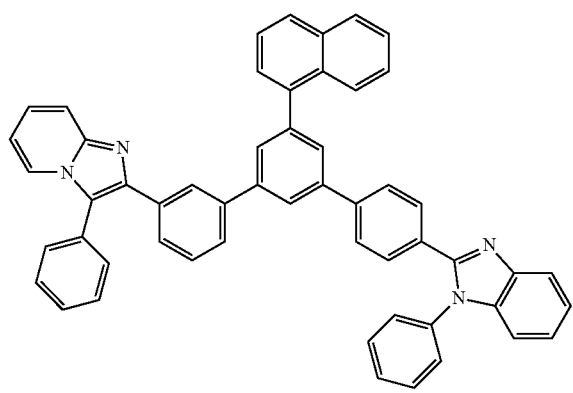
B 168
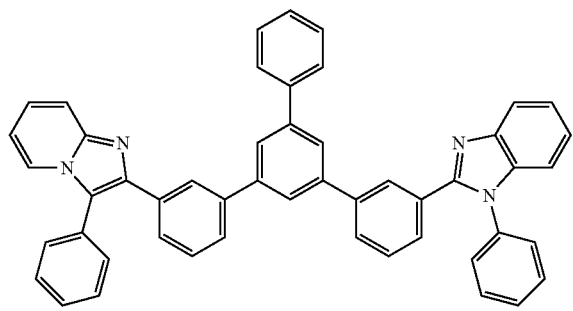
B 169
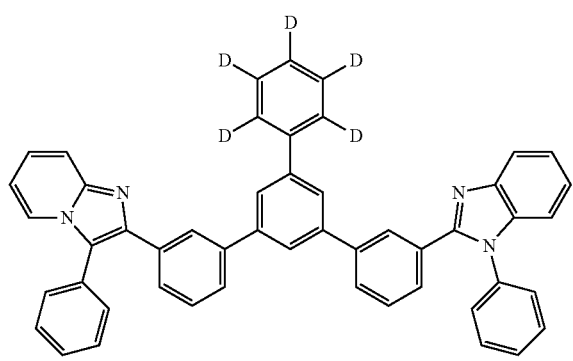
B 170
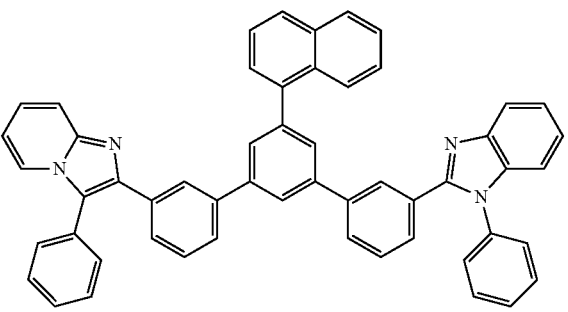
B 171
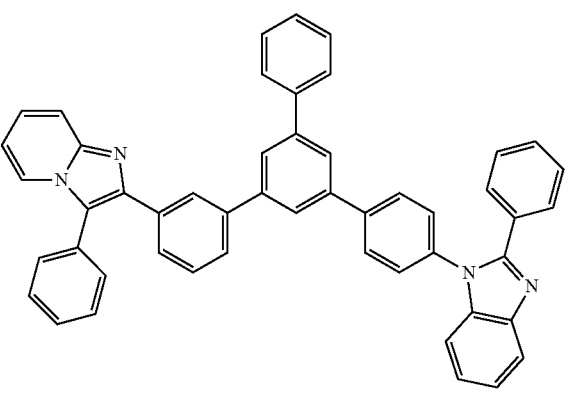
B 172
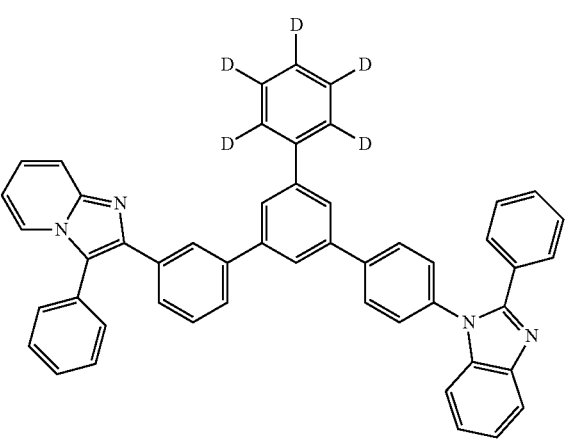
B 173
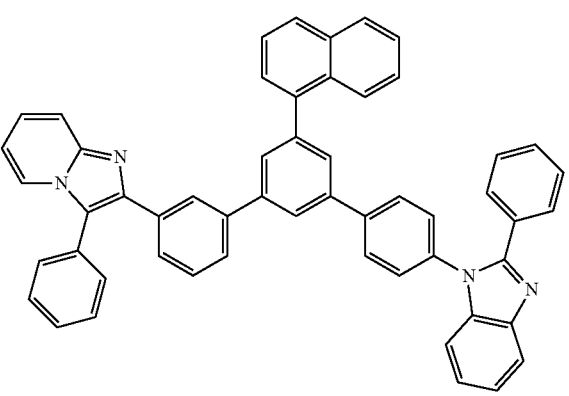

-continued
B 174
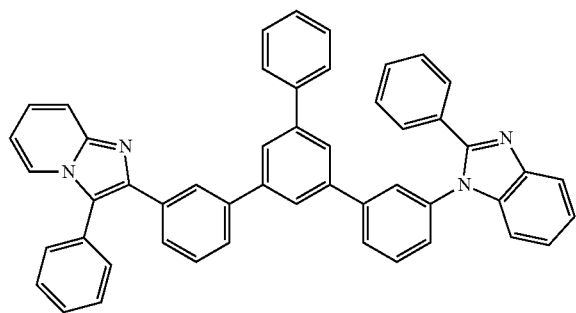
B 175
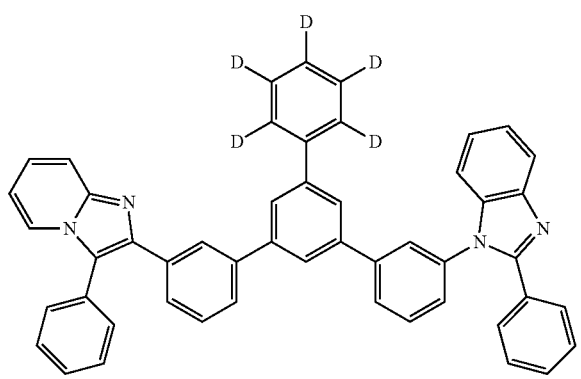
B 176
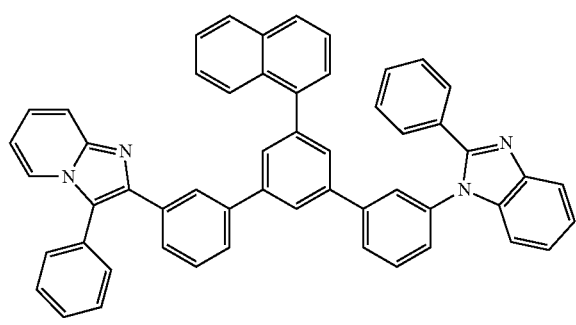
B 177
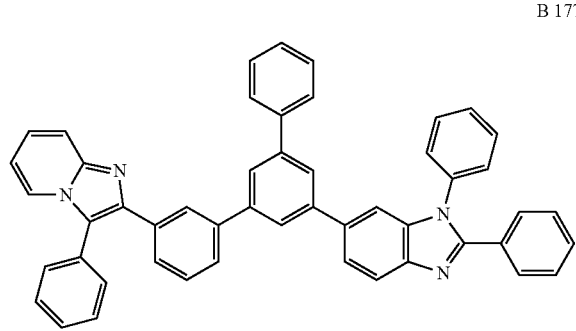
-continued
B 178
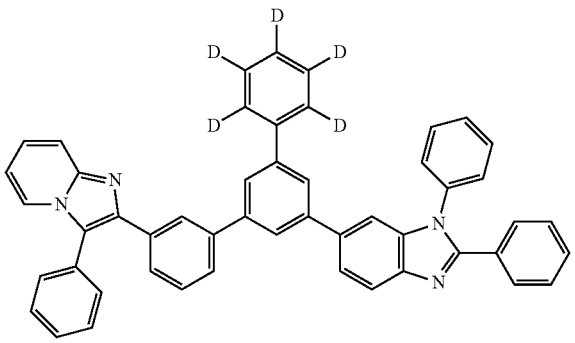
B 179
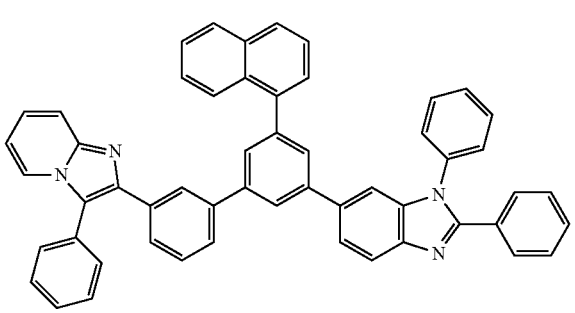
B 180
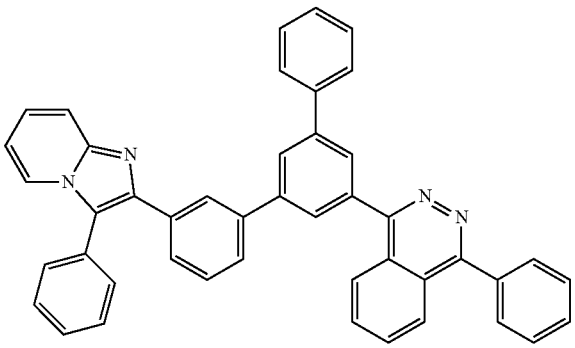
B 181
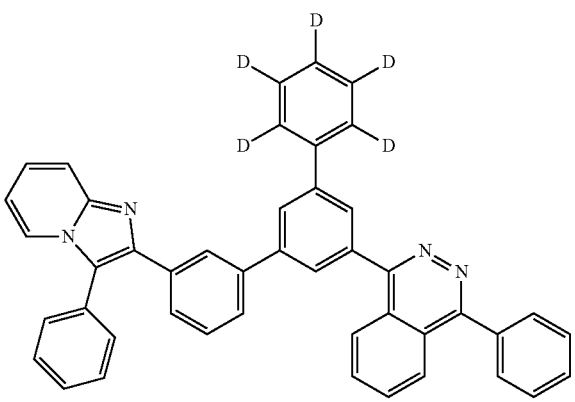

B 182
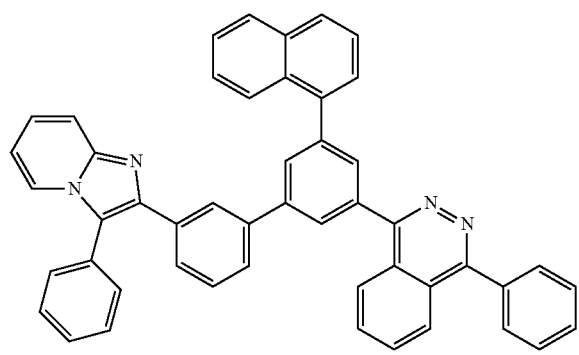
B 183
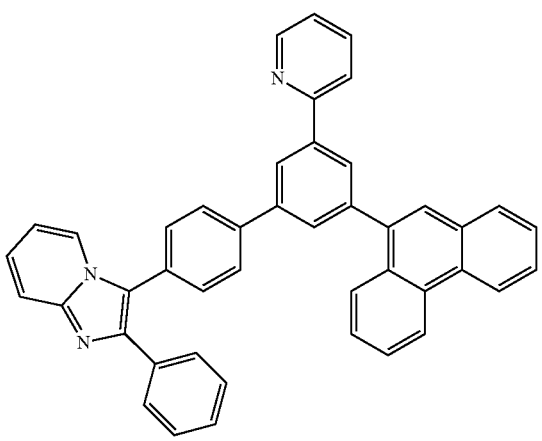
B 184
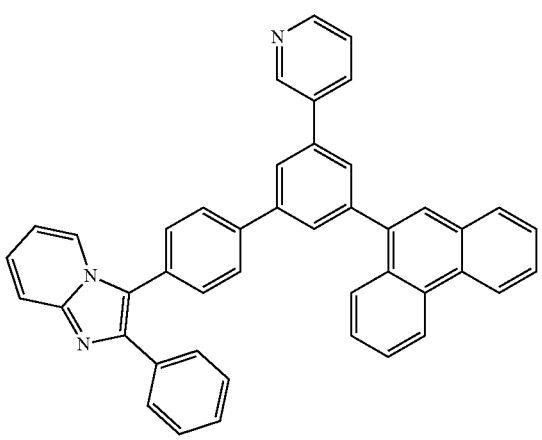
B 185
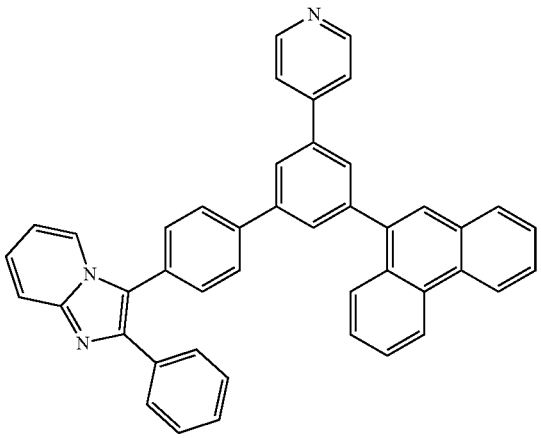
B 186
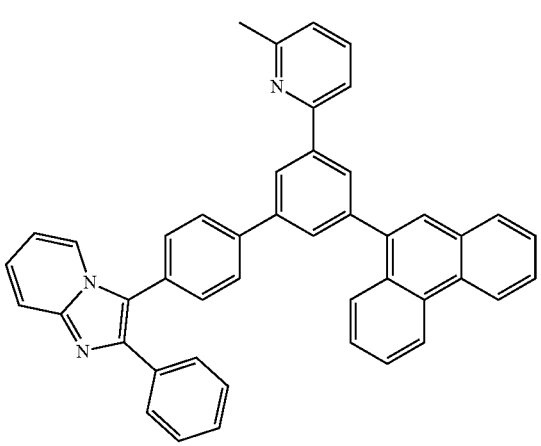
B 187
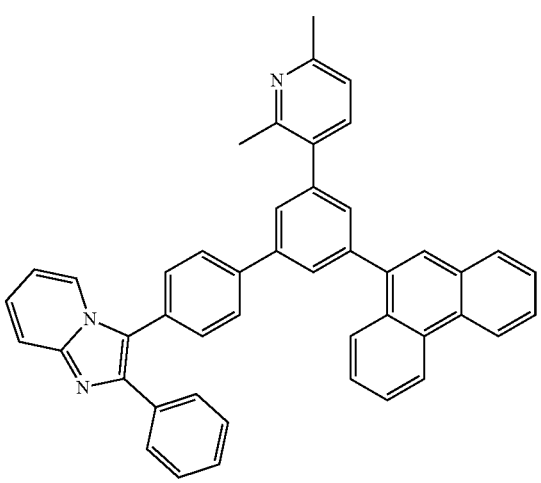

B 188
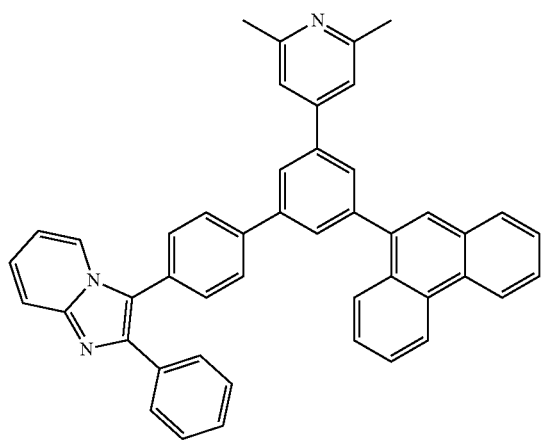
B 189
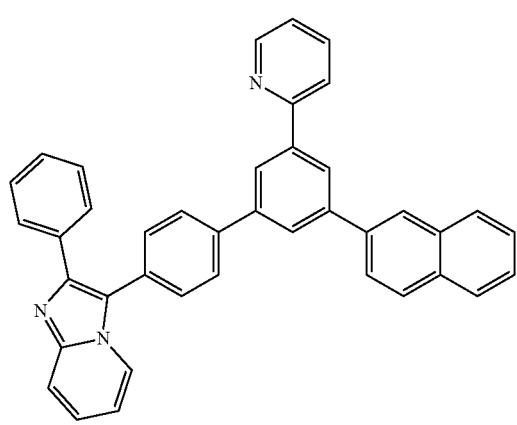
B 190
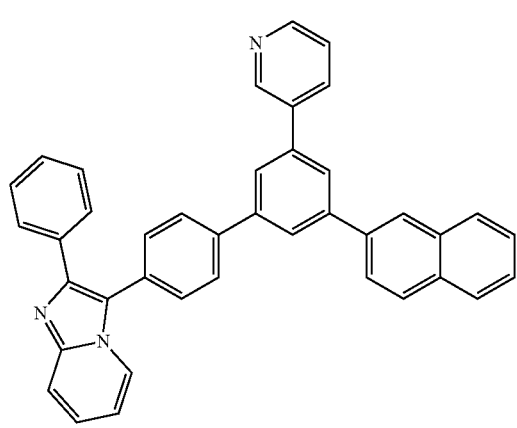
B 191
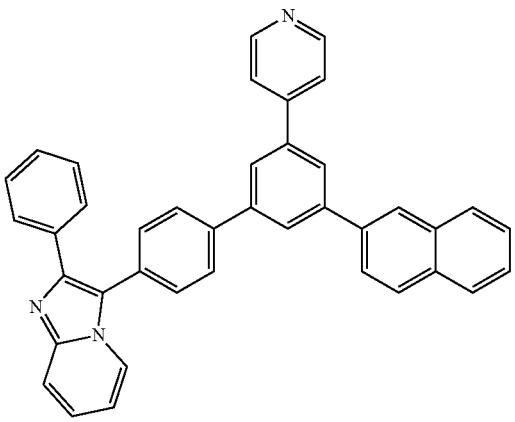
B 192
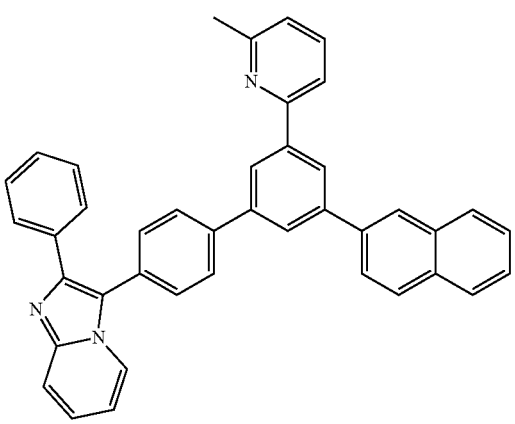
B 193
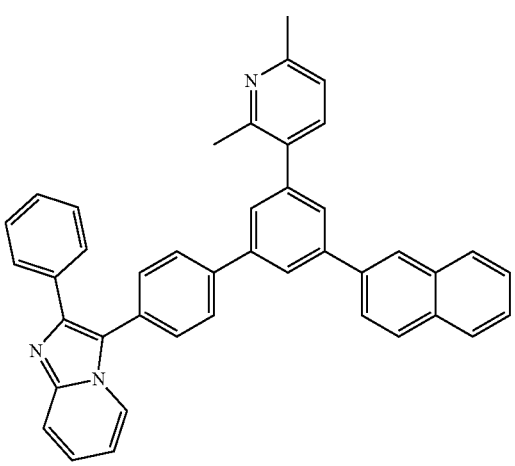

B 194
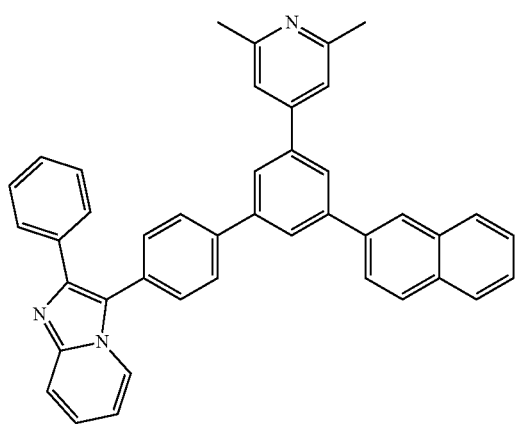
B 197
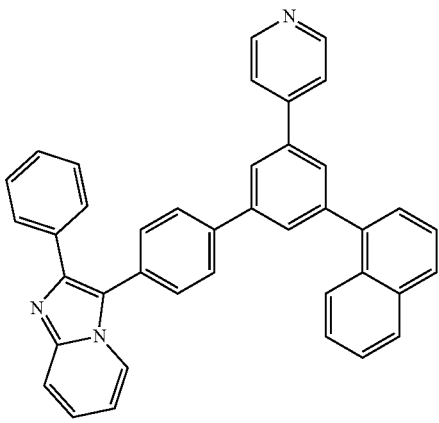
B 195
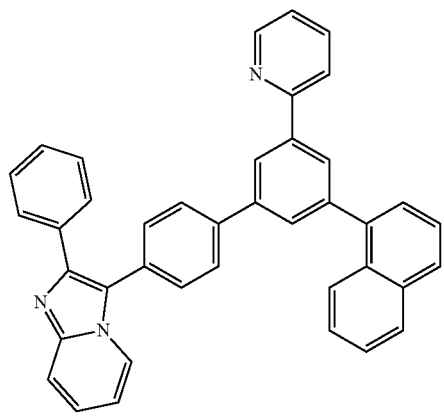
B 198
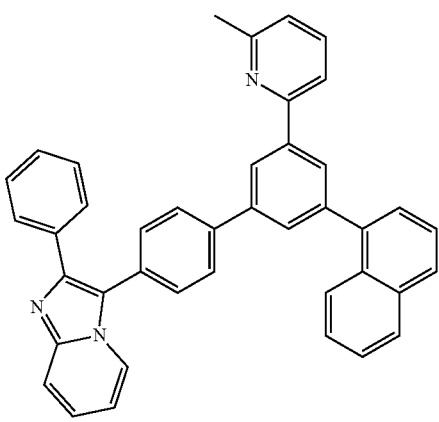
B 196
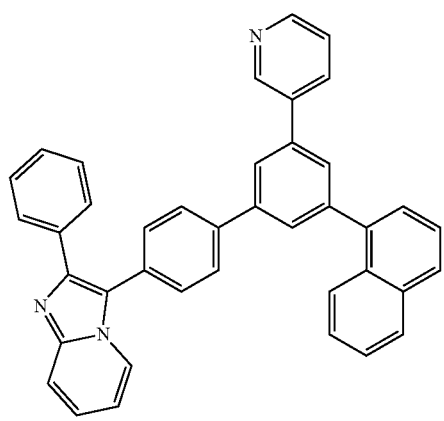
B 199
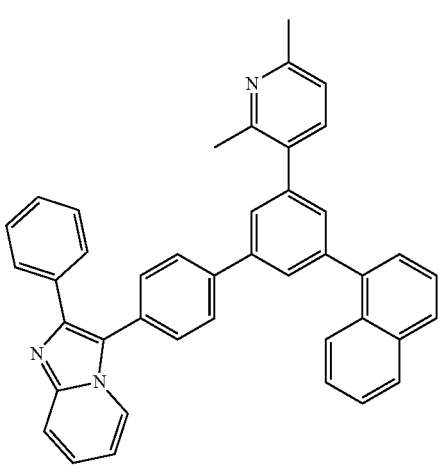

B 200
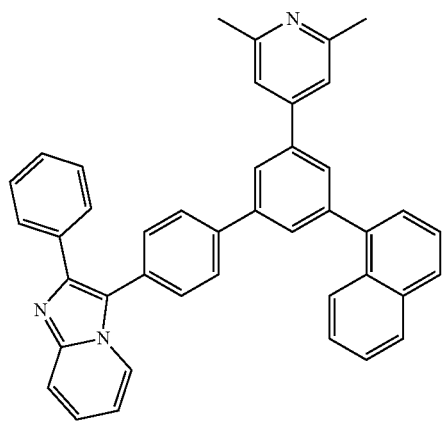
B 203
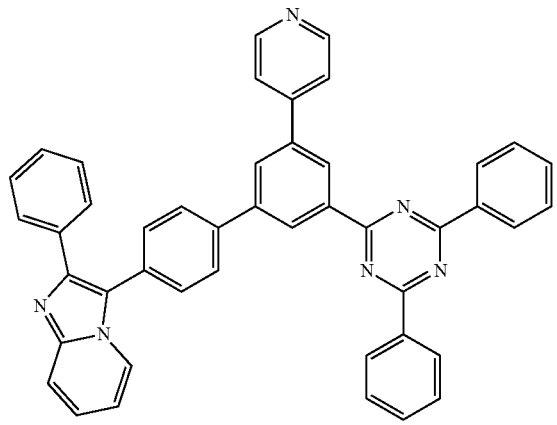
B 201
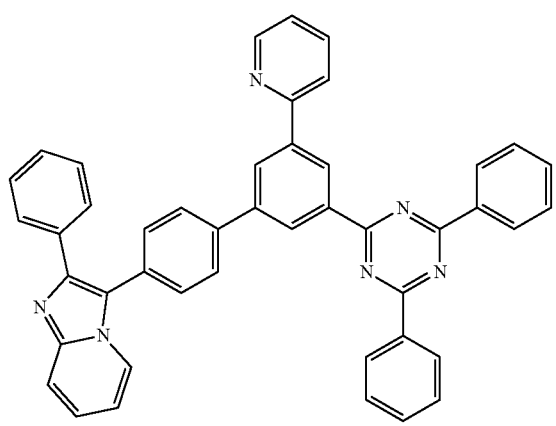
B 204
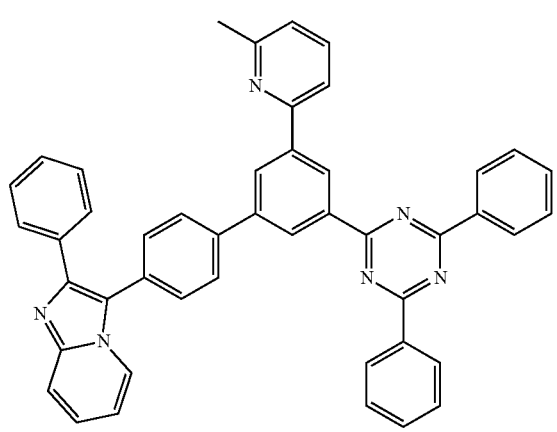
B 202
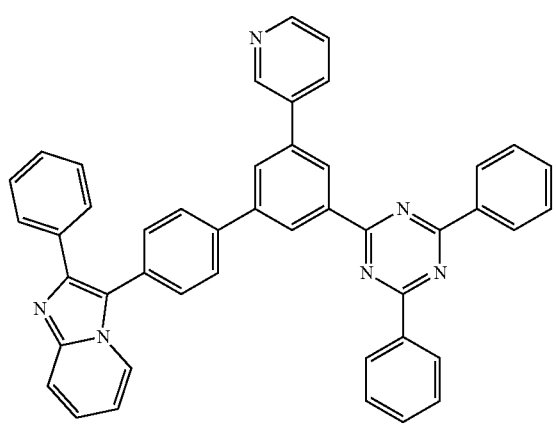
B 205
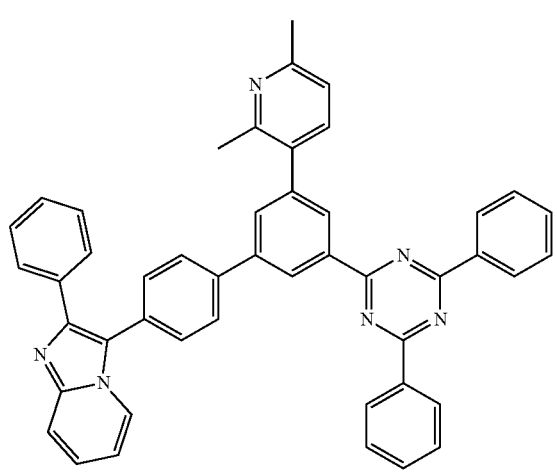

B 206
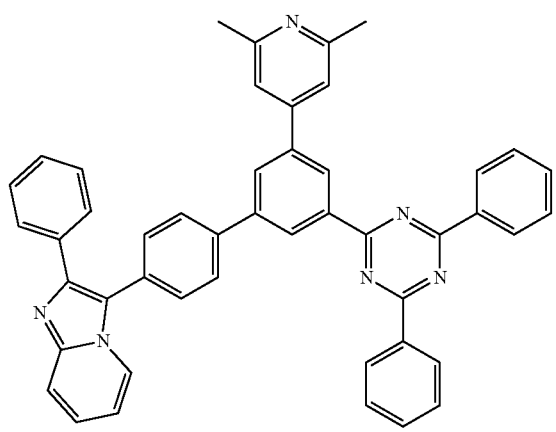
B 209
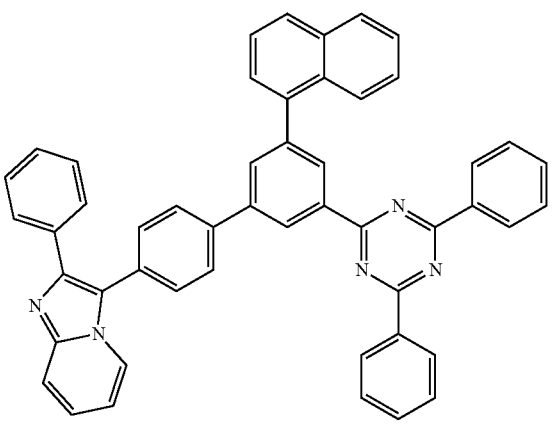
B 207
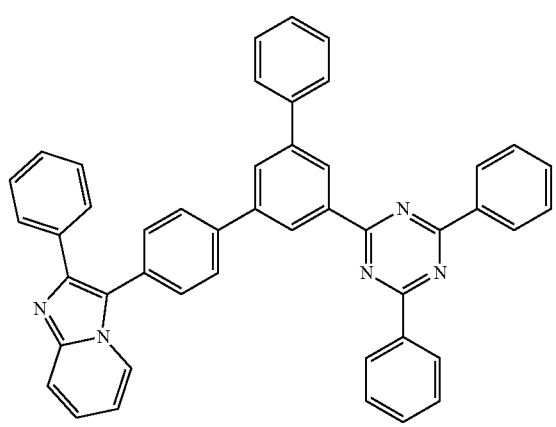
B 210
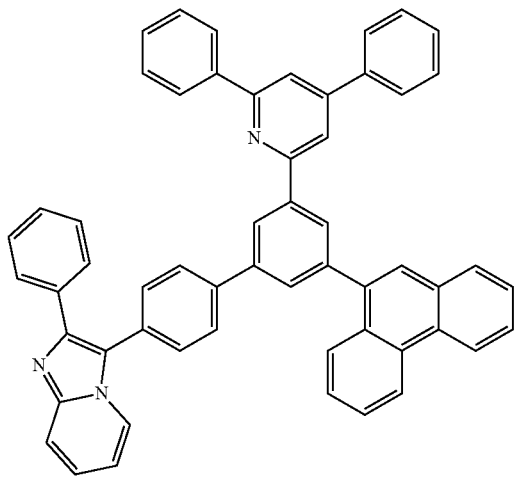
B 208
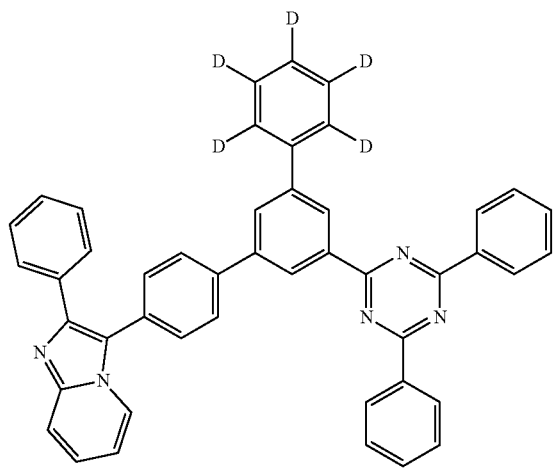
B 211
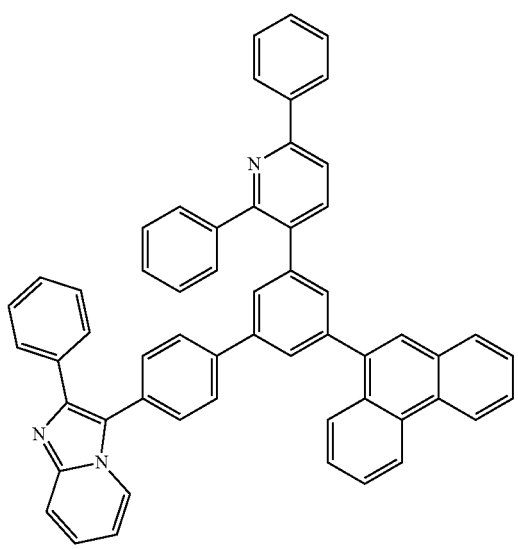

B 212
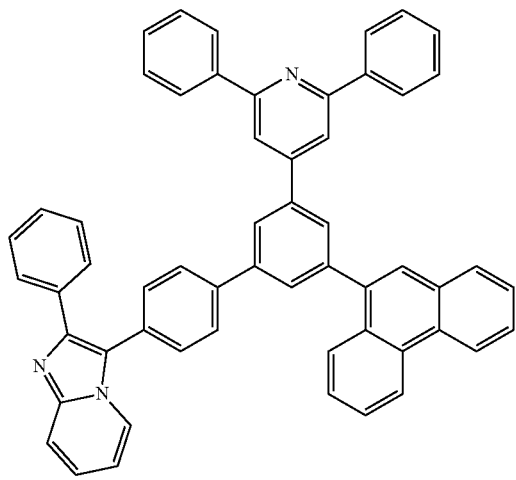
B 215
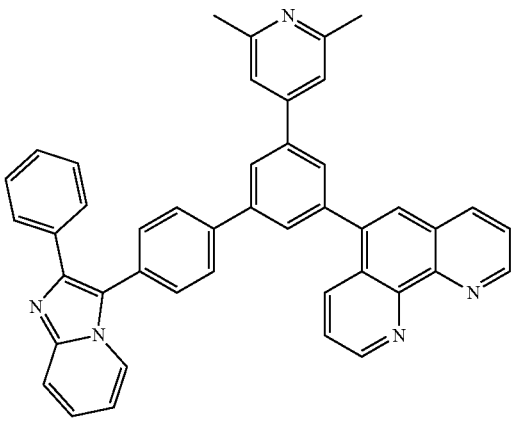
B 213
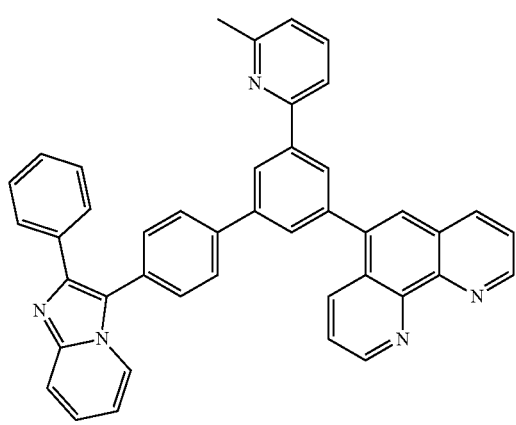
B 216
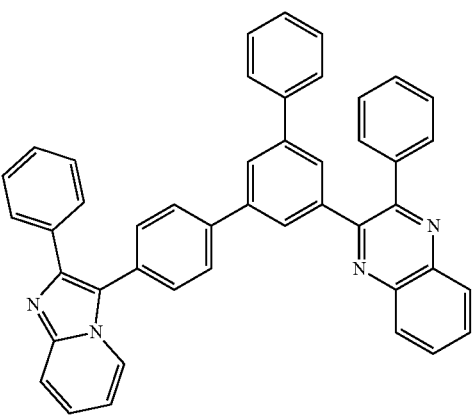
B 214
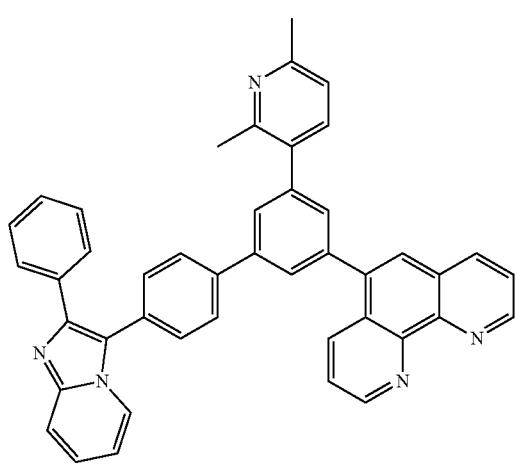
B 217
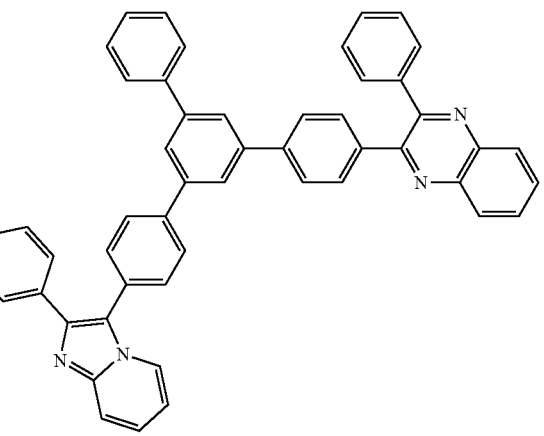

B 218
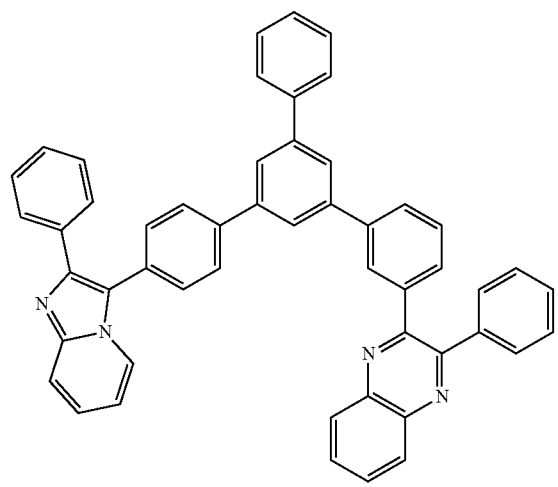
B 221
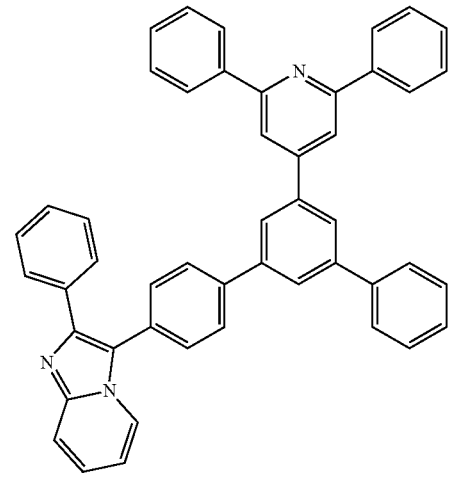
B 219
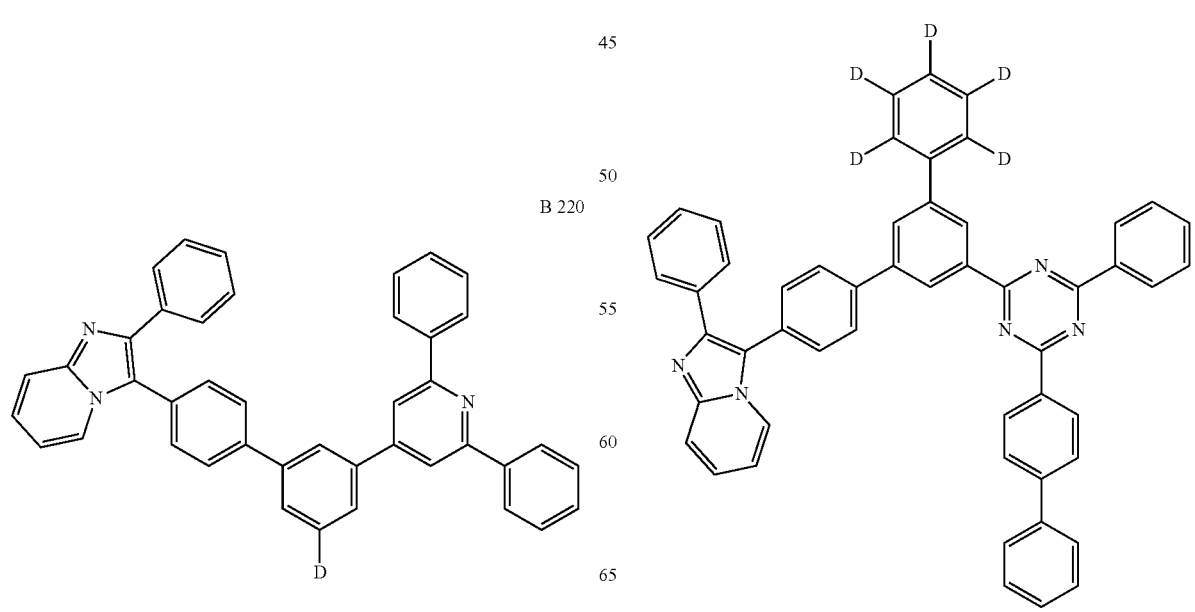
B 222
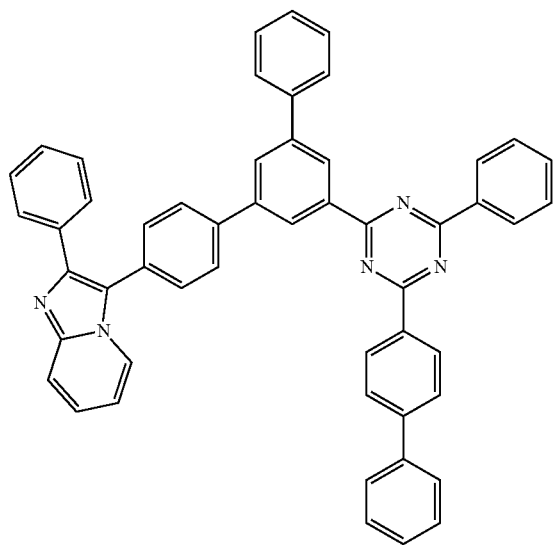
B 223
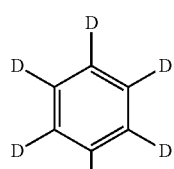
B 220

B 224
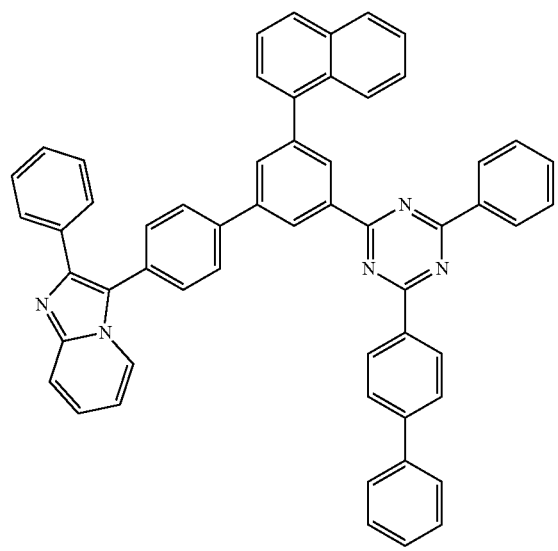
B 227
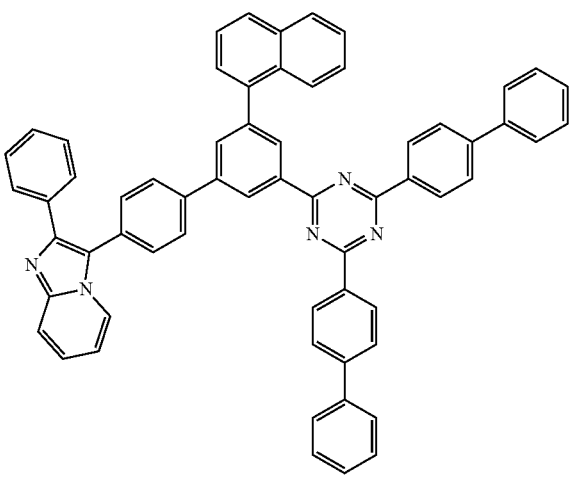
B 225
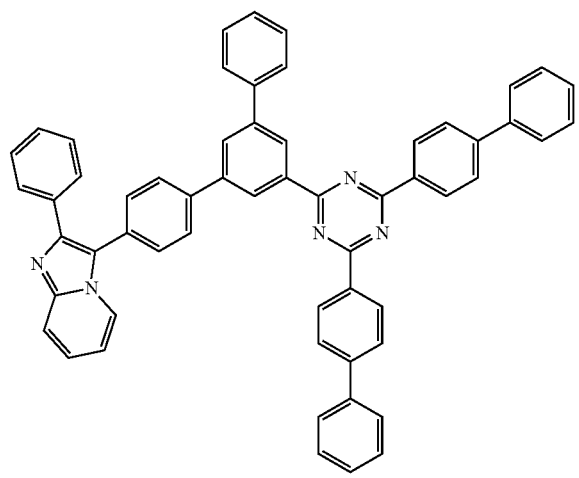
B 228
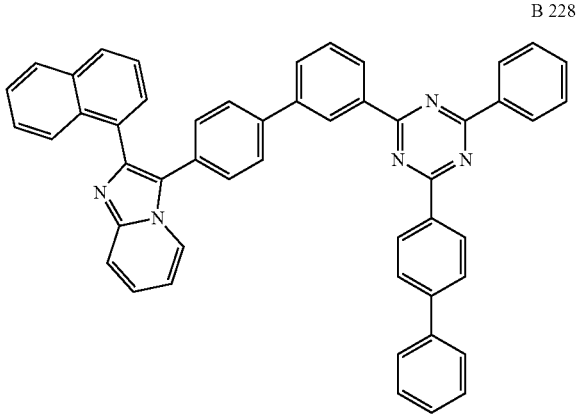
B 226
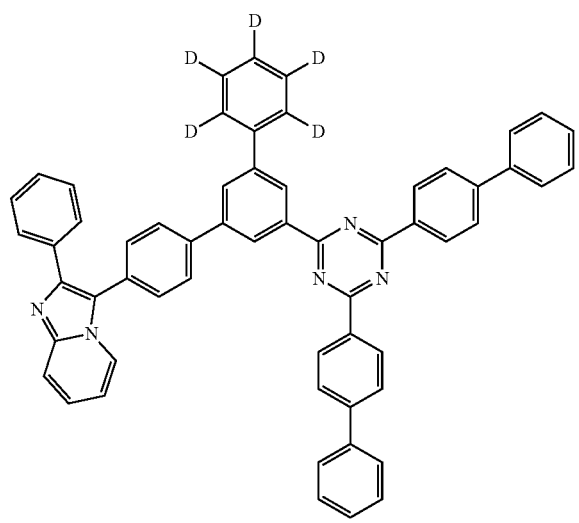
B 229
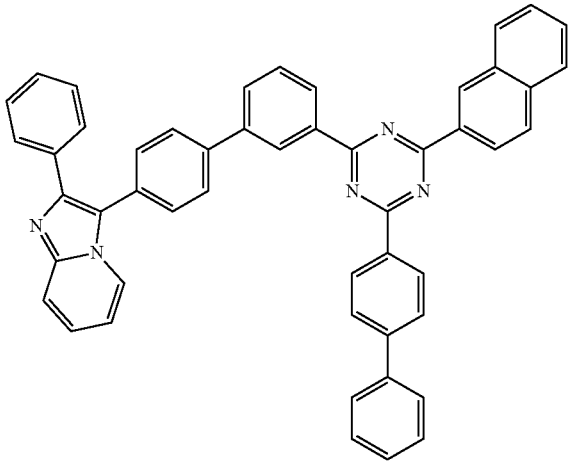

B 230
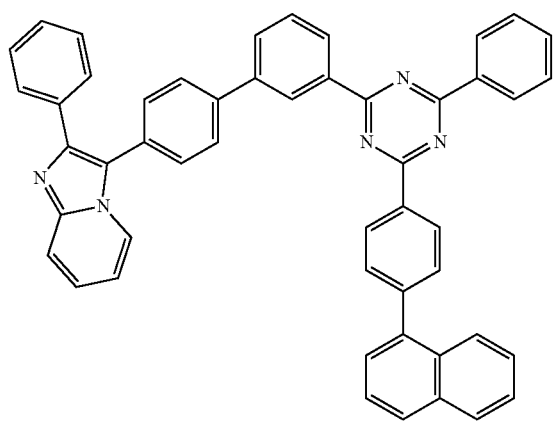
B 233
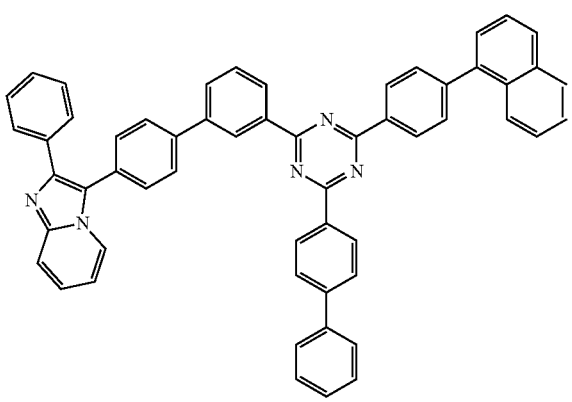
B 231
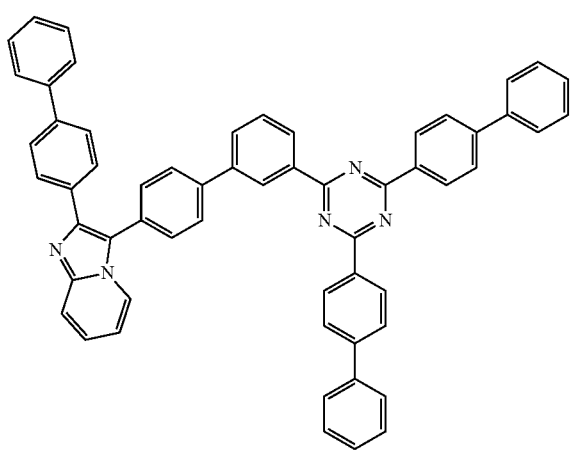
B 234
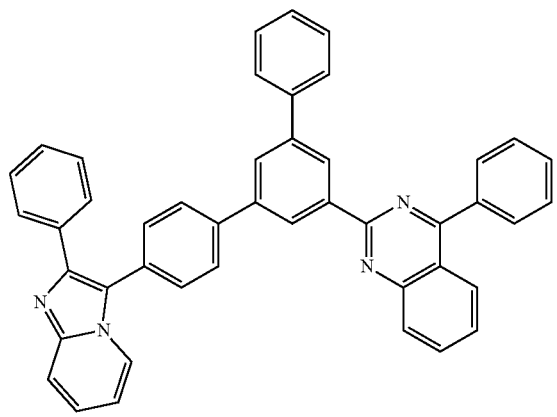
B 232
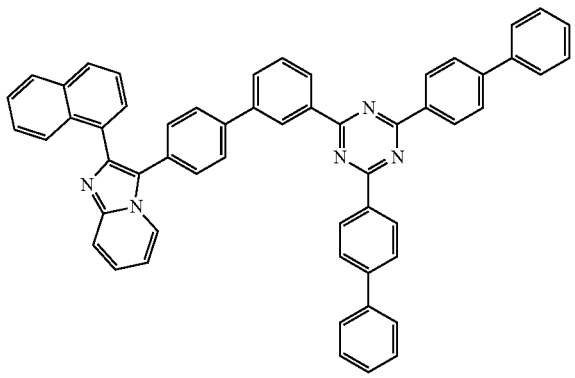
B 235
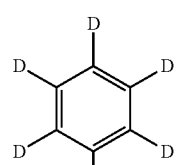
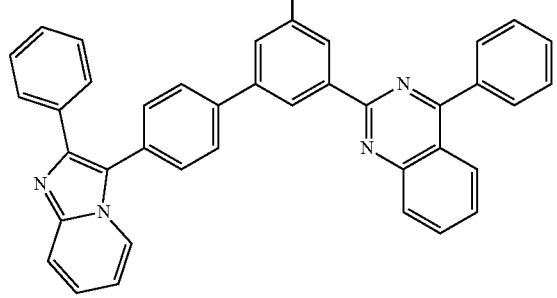

B 236
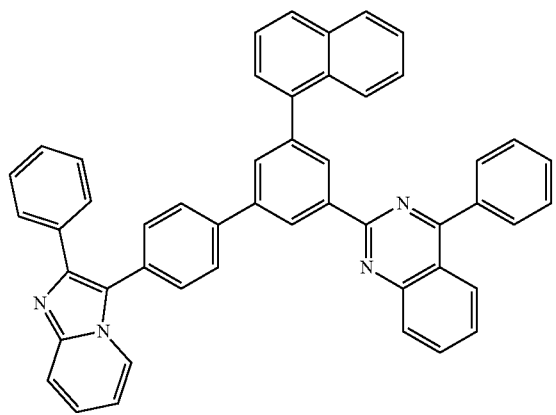
B 237
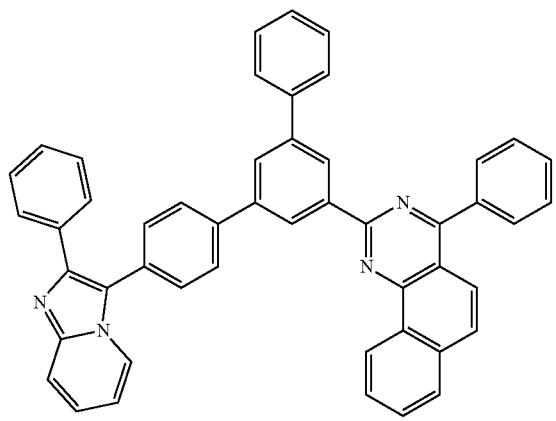
B 238
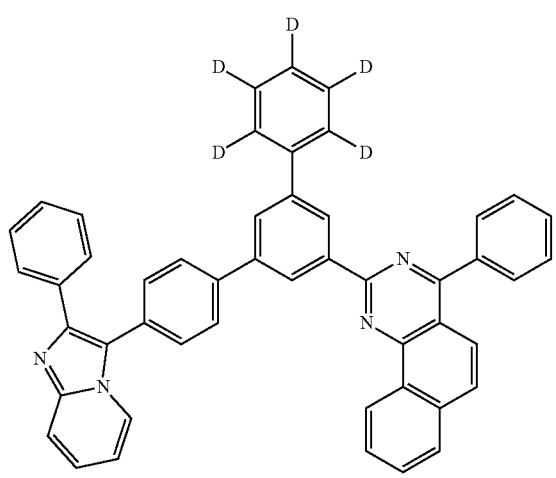
B 239
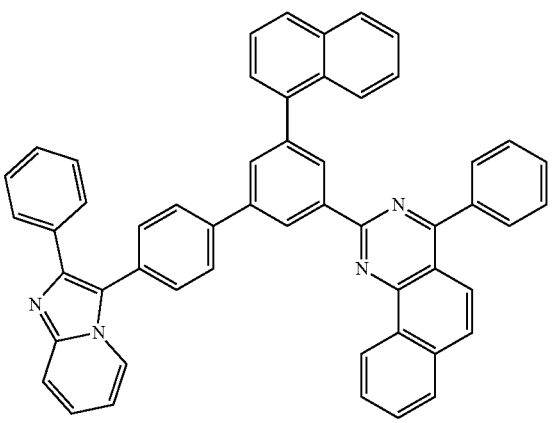
B 240
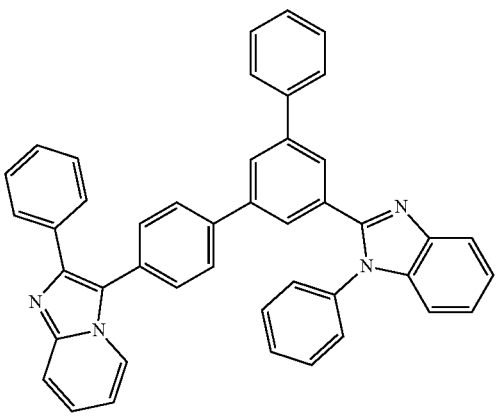
B 241
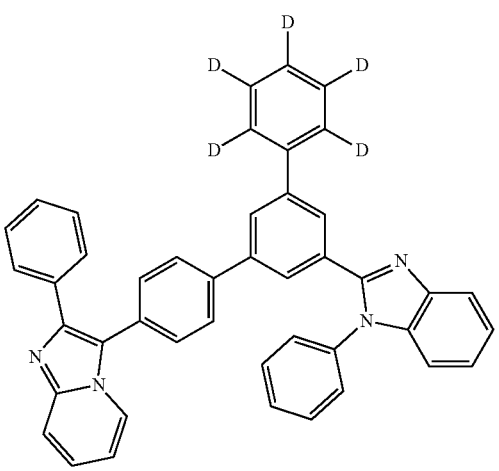

B 242
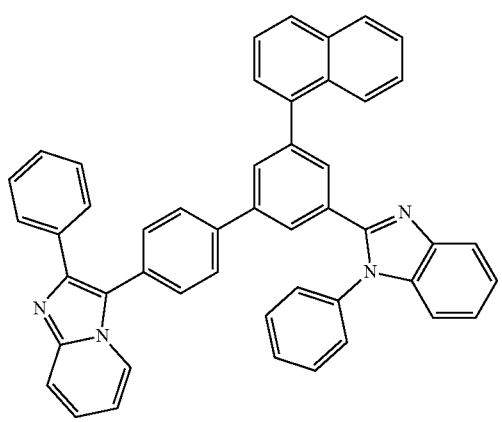
B 245
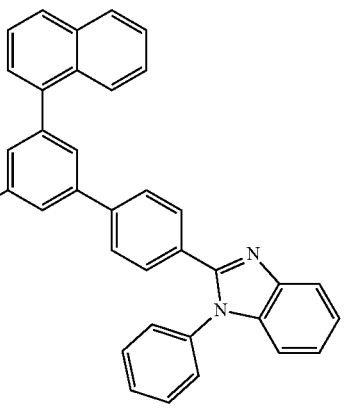
B 243
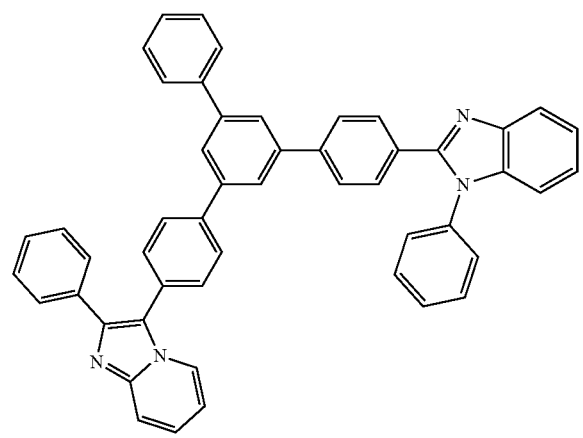
B 246
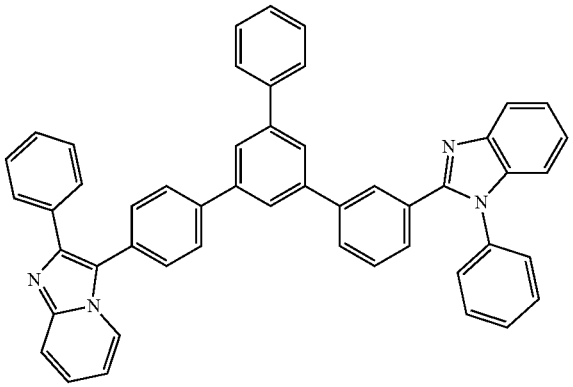
B 244
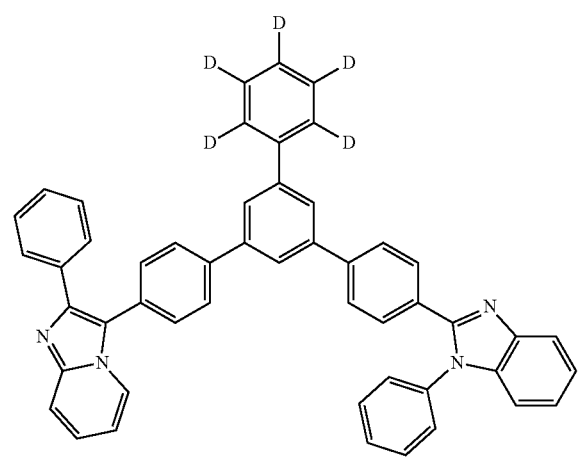
B 247
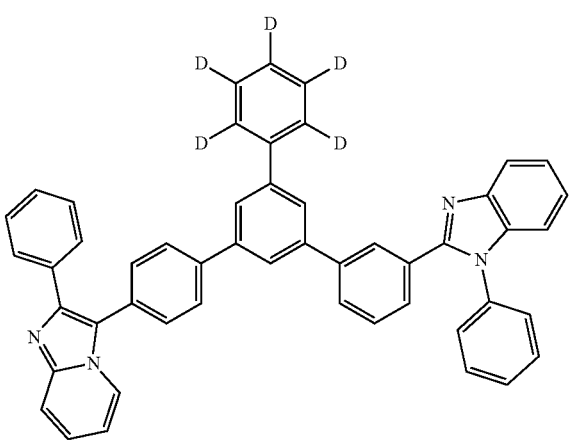

B 248
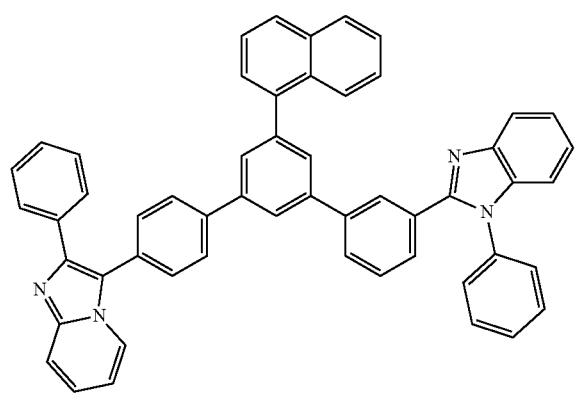
B 251
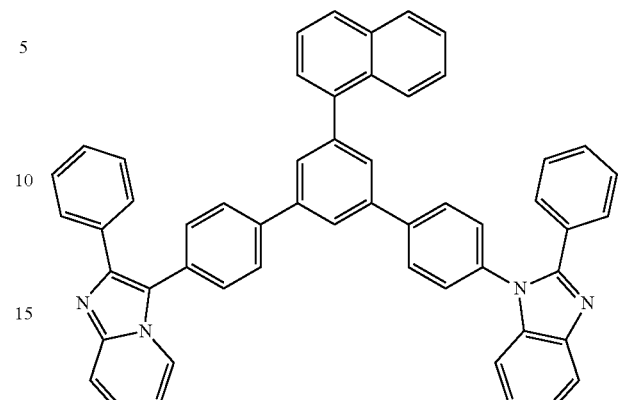
B 249
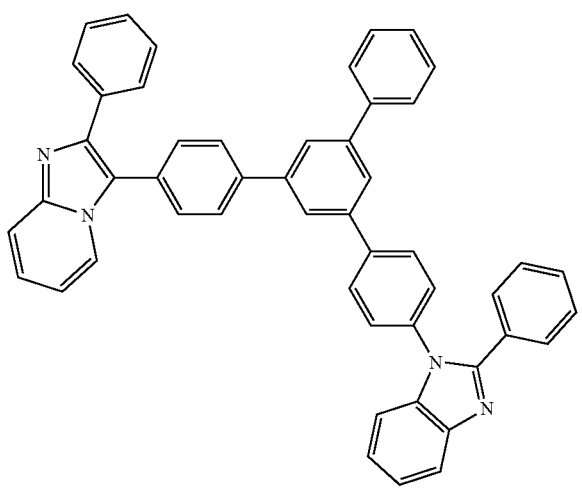
B 252
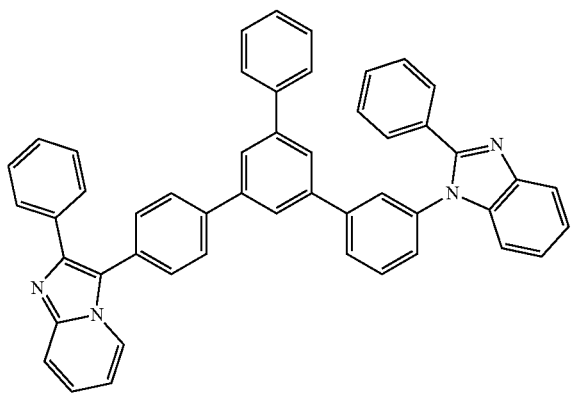
B 250
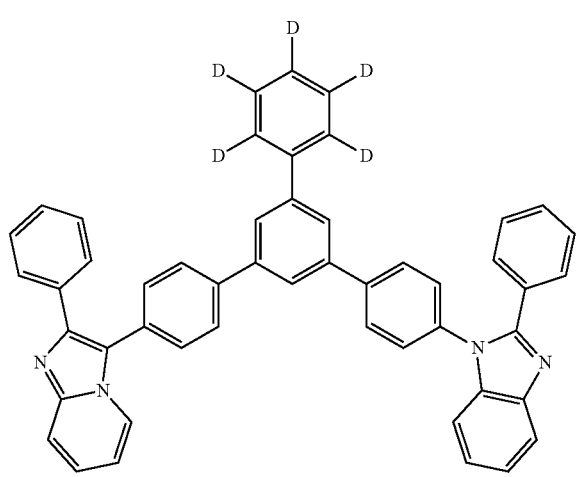
B 253
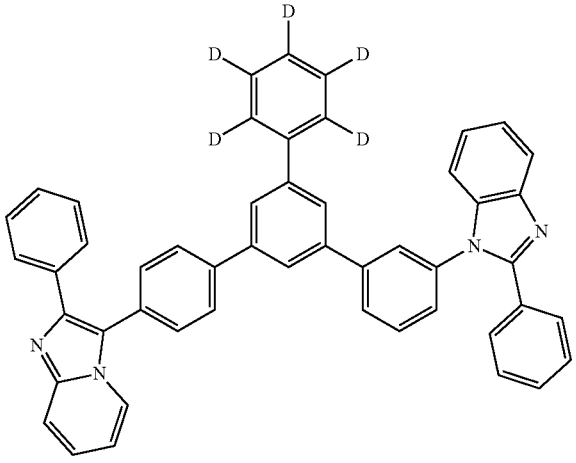

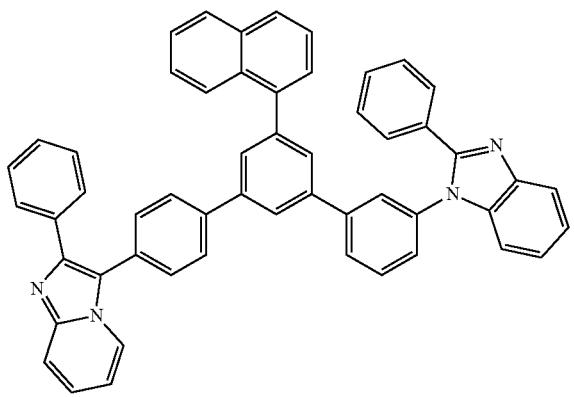
B 254
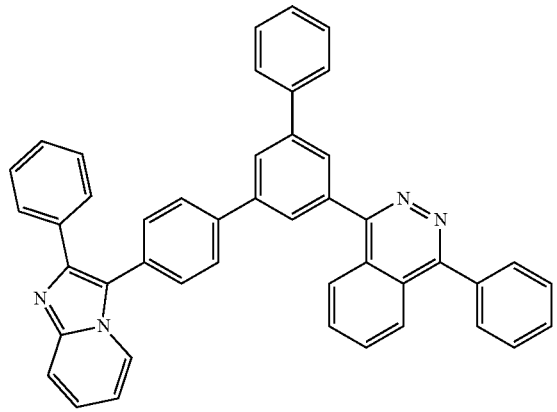
B 258
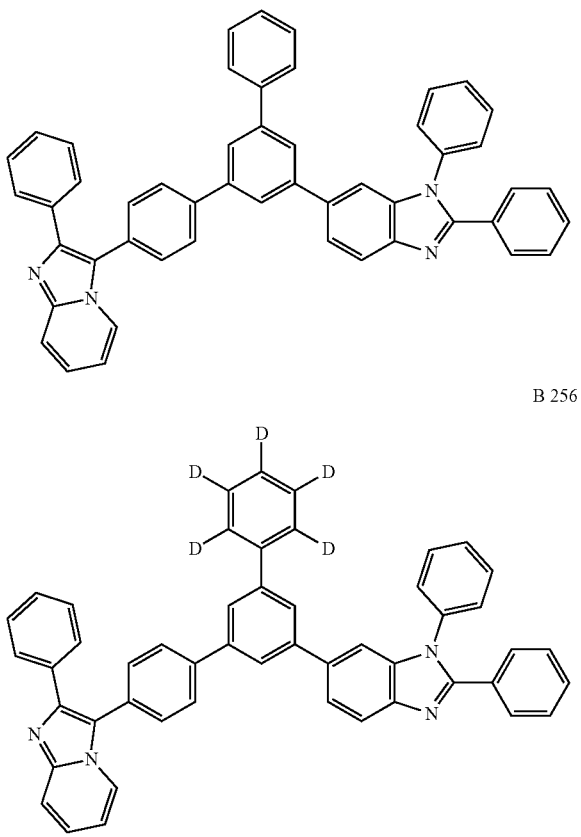
B 255
B 256
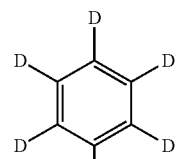
B 259
B 257
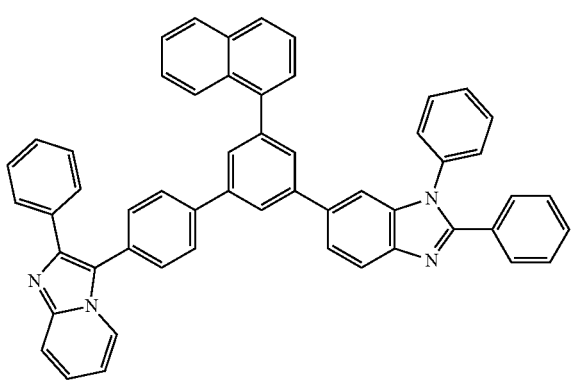
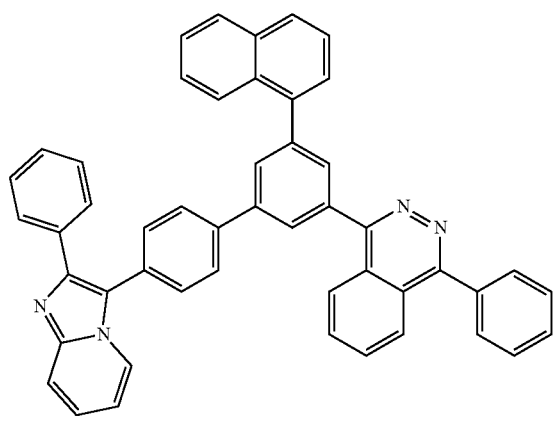
B 260

-continued
B 261
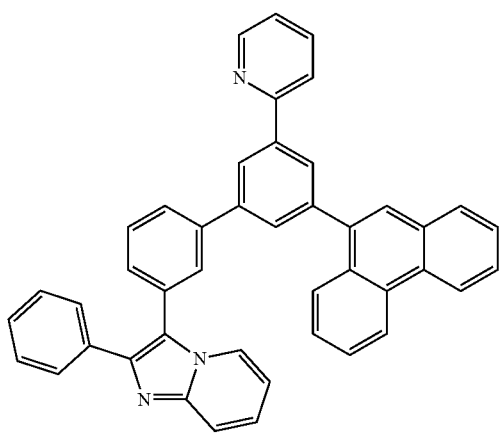
B 262
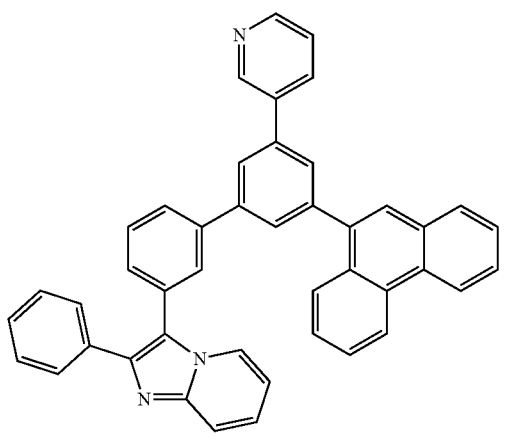
B 263
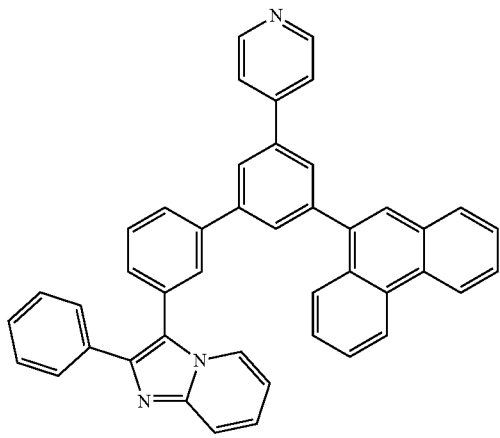
-continued
B 264
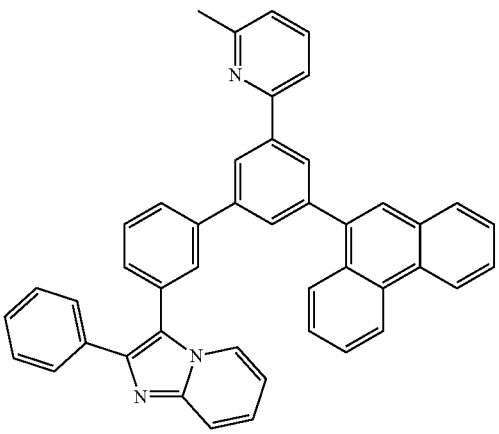
B 265
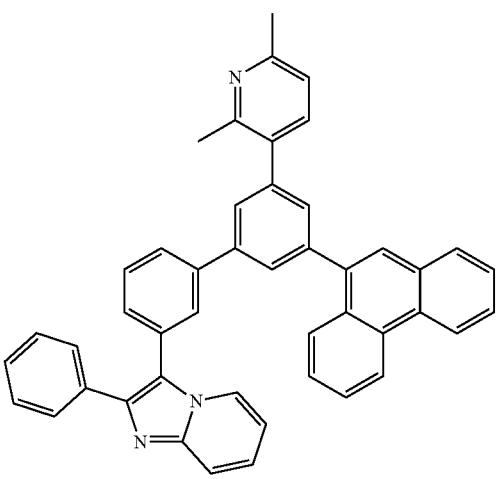
B 266
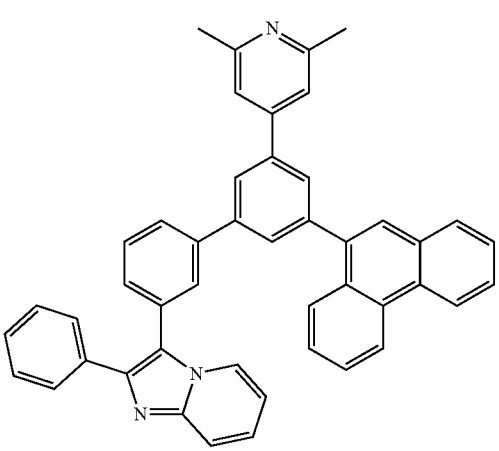

B 267
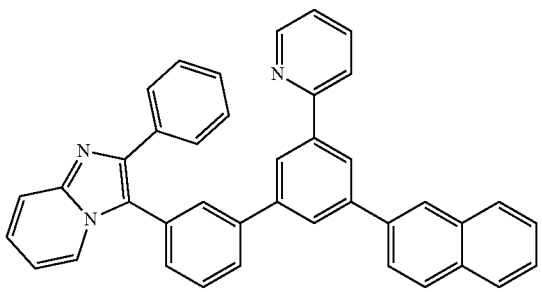
B 268
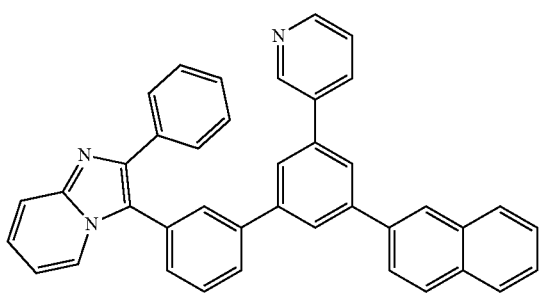
B 269
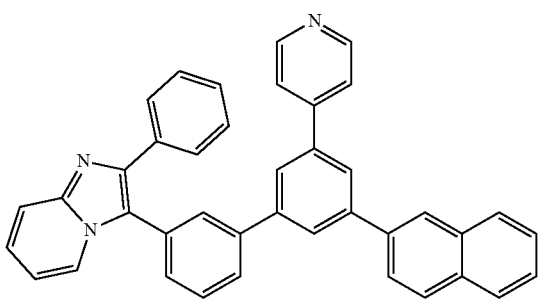
B 270
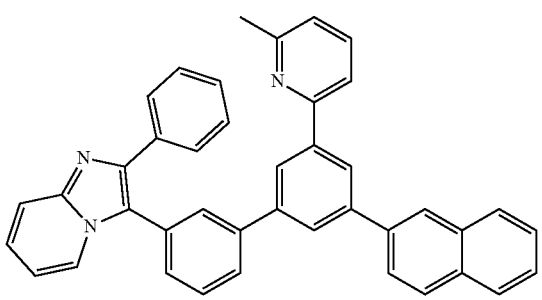
B 271
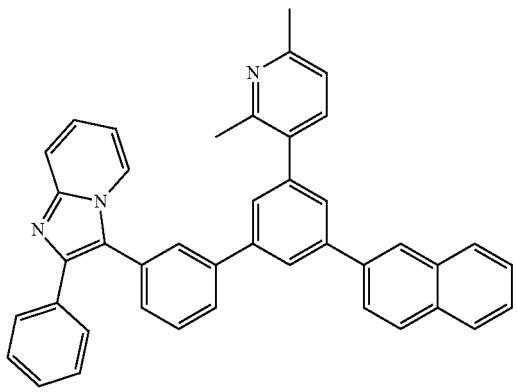
B 272
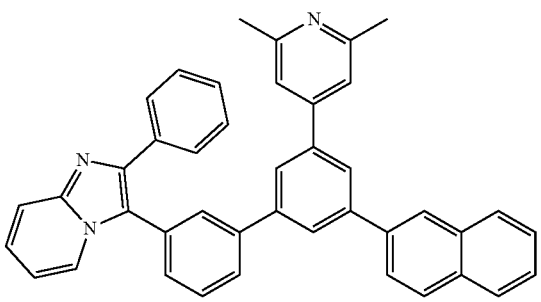
B 273
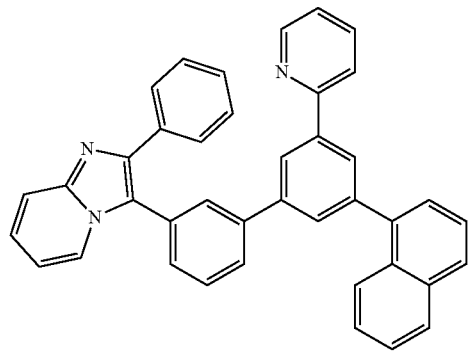
B 274
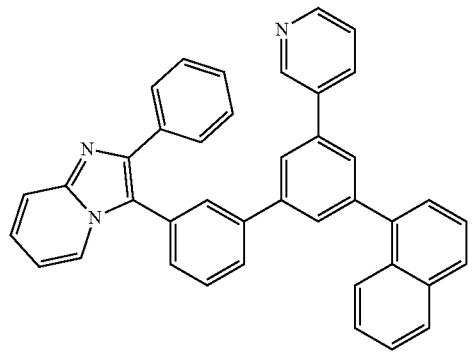

B 275
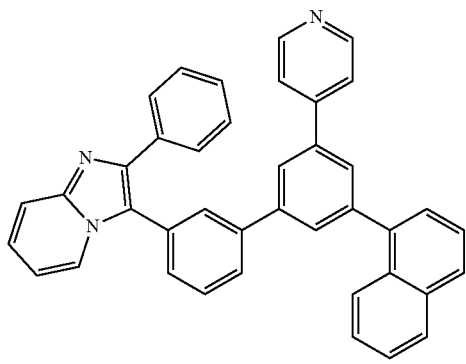
B 276
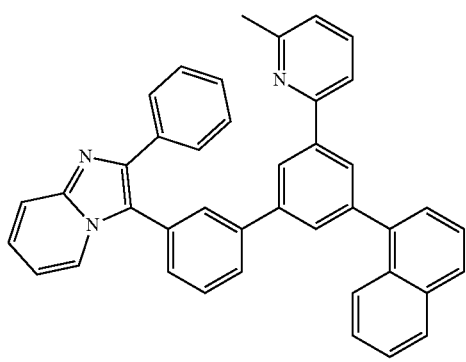
B 277
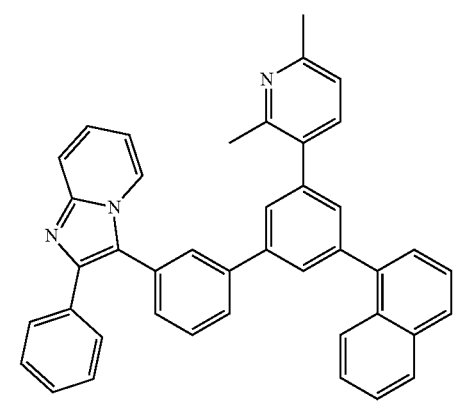
B 278
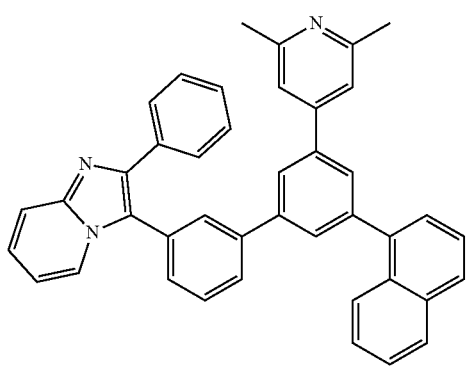
B 279
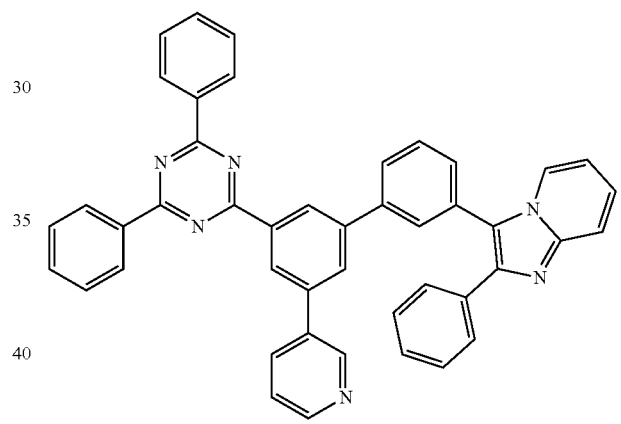
B 280
B 281
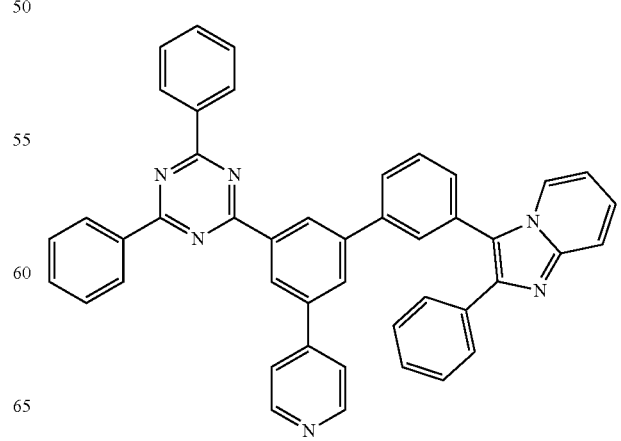

B 282
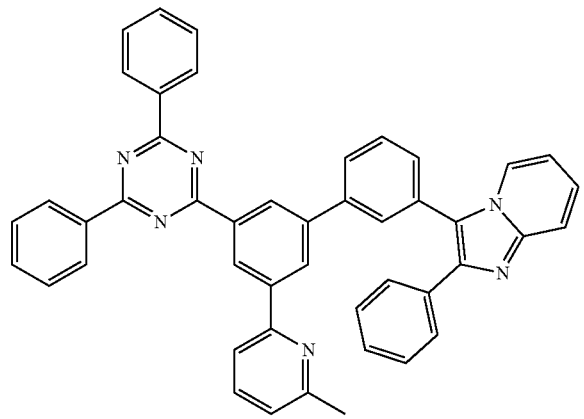
B 283
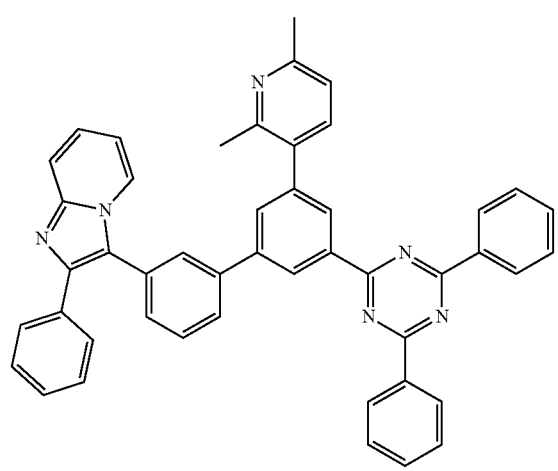
B 284
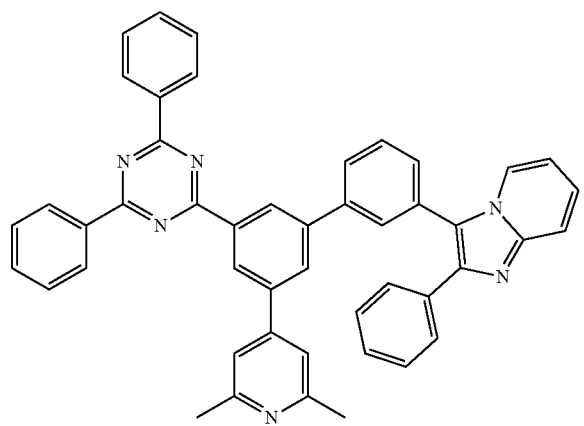
B 285
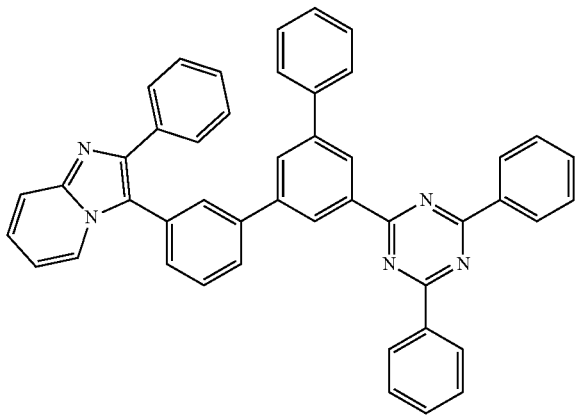
B 286
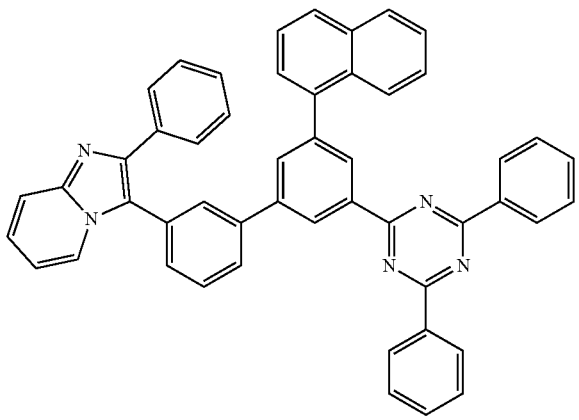
B 287

-continued
B 288
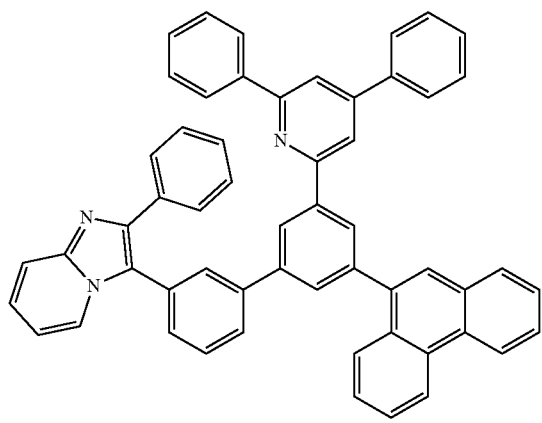
B 289
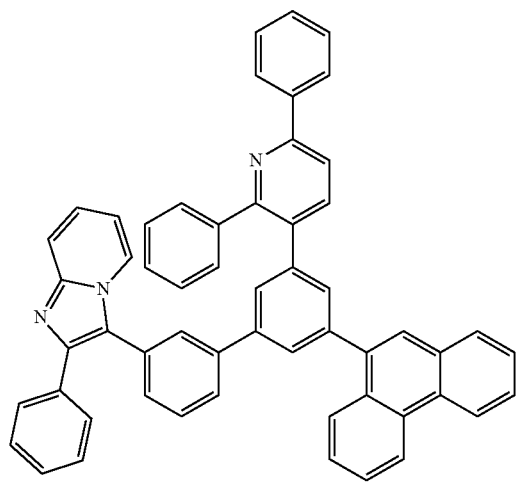
B 290
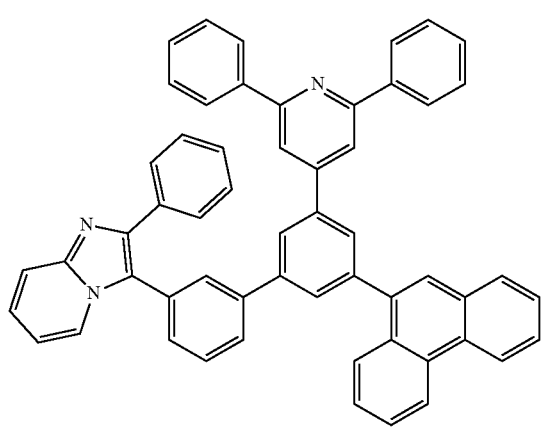
-continued
B 291
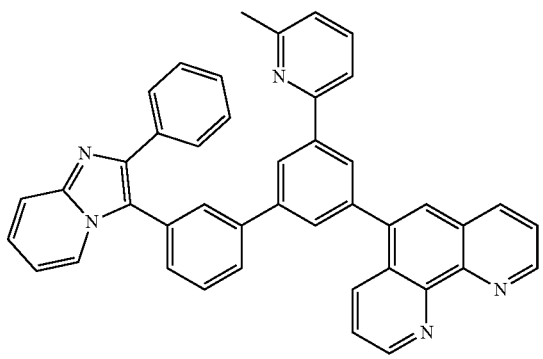
B 292
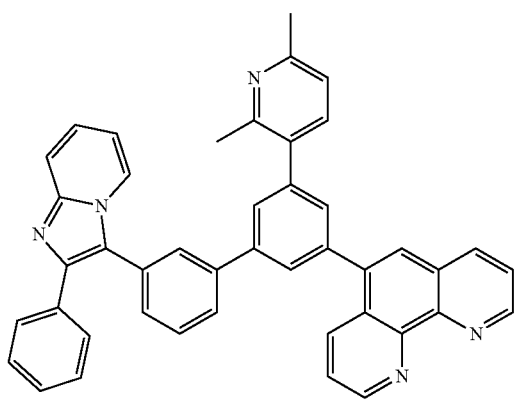
B 293
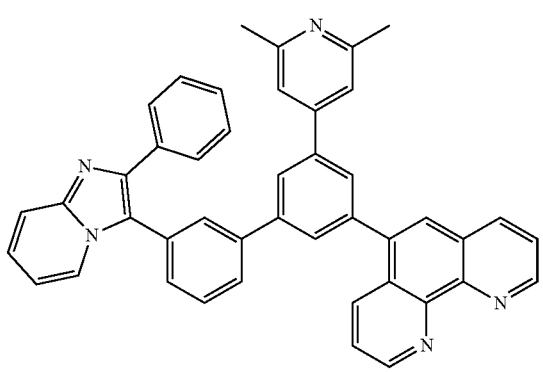
B 294
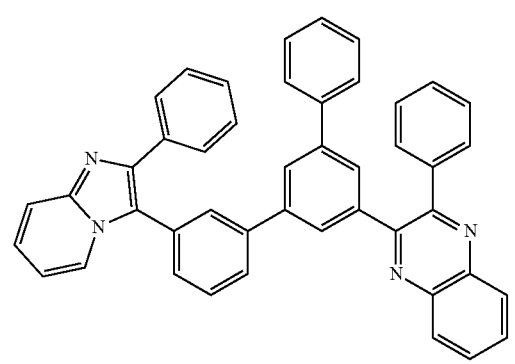

B 295
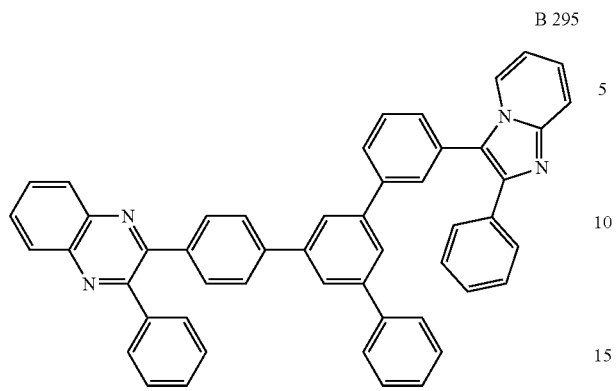
B 296
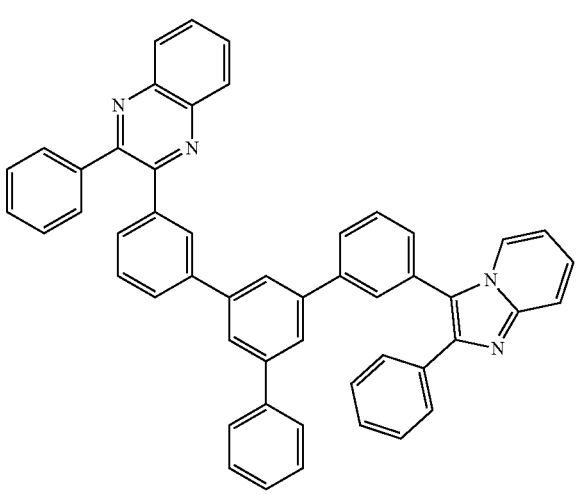
B 297
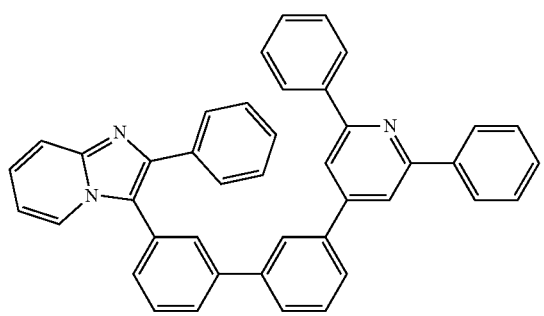
B 298
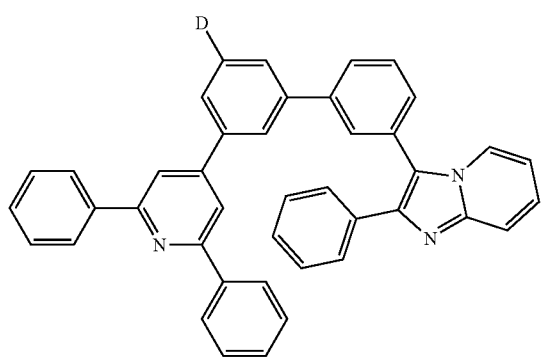
B 299
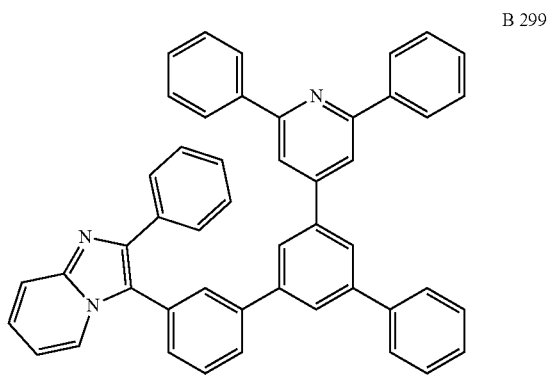
B 300
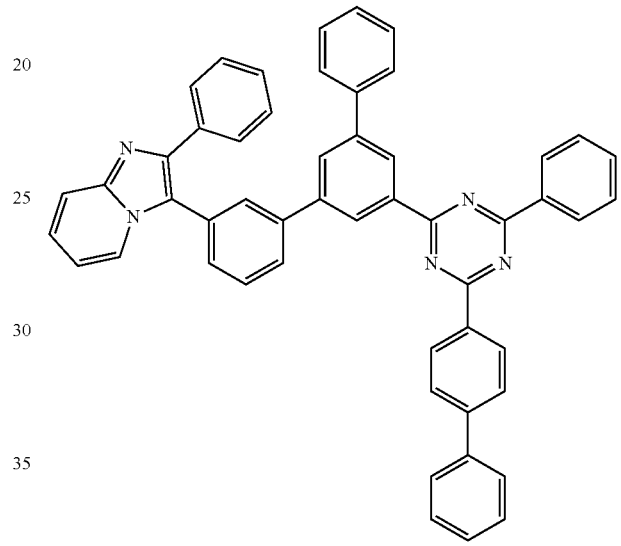
B 301
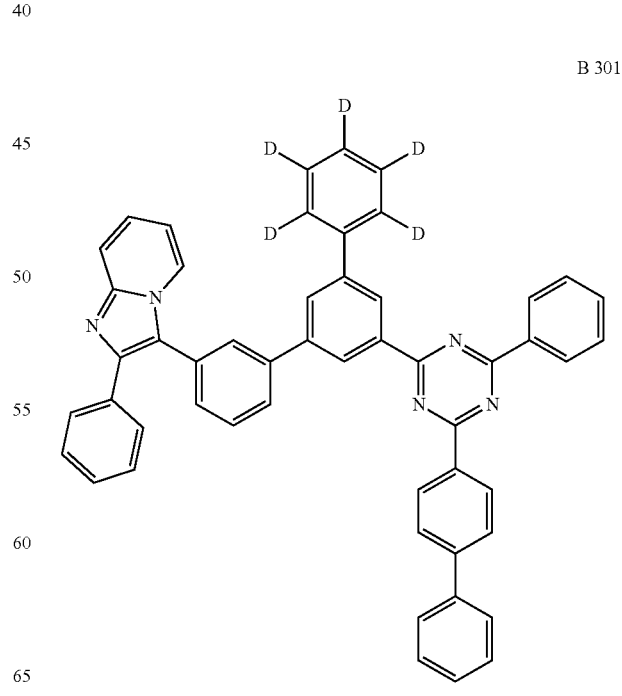

B 302
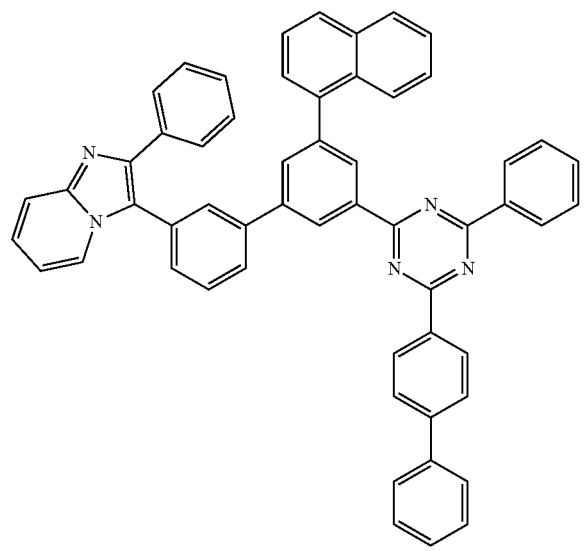
B 303
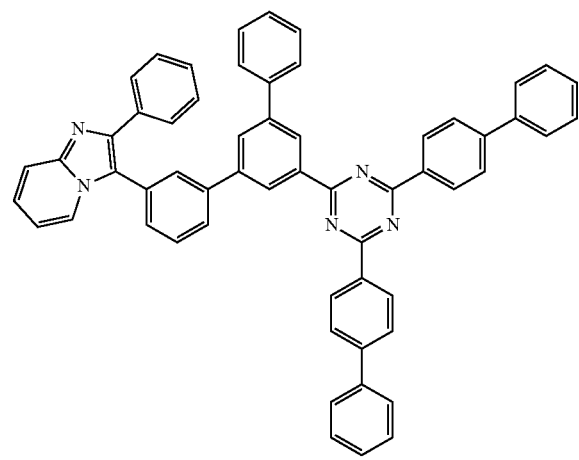
B 304
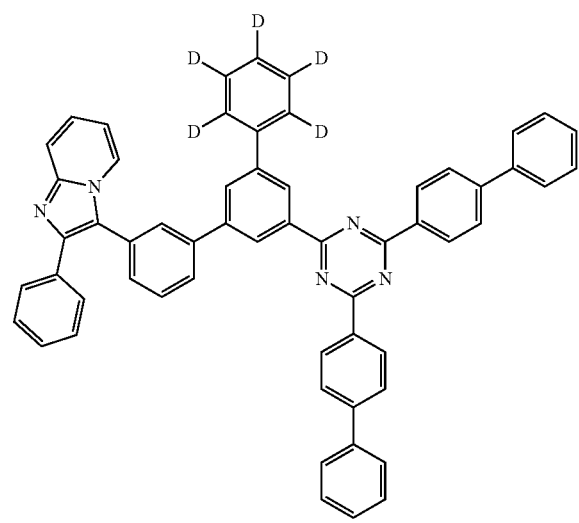
B 305
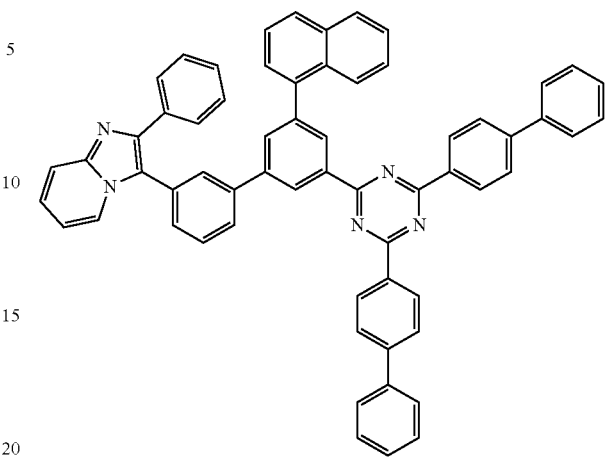
B 306
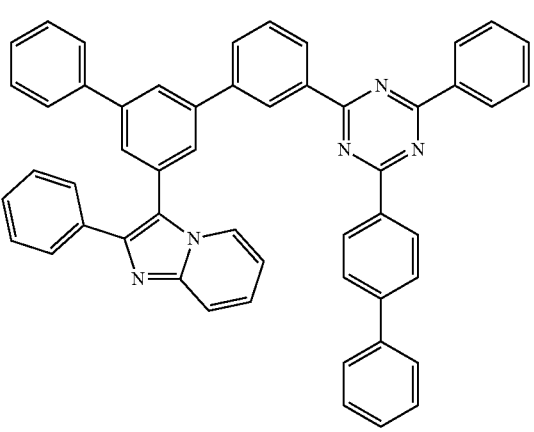
B 307
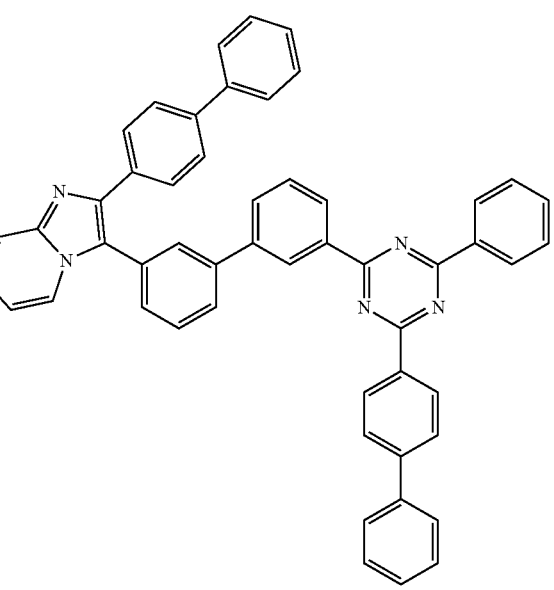

B 308
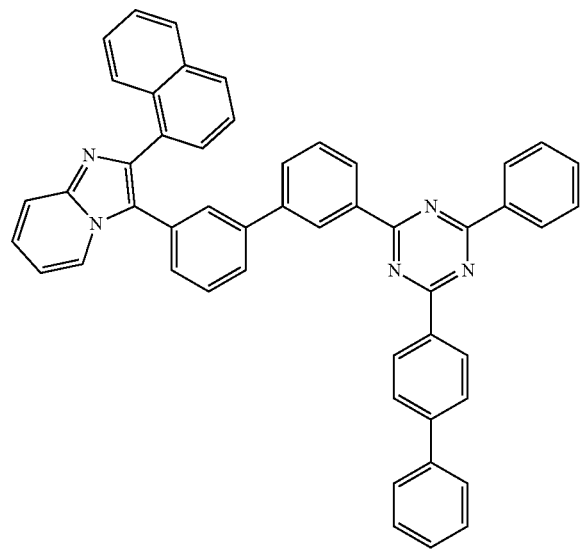
B 309
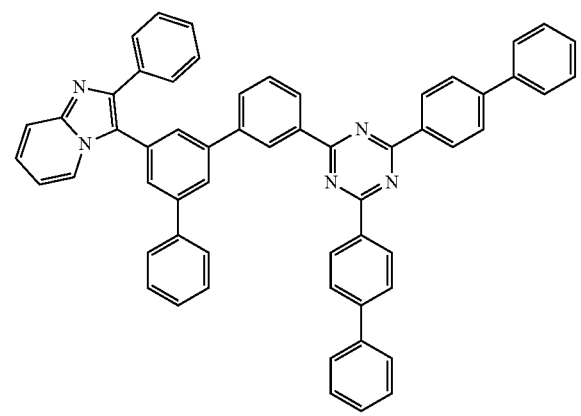
B 310
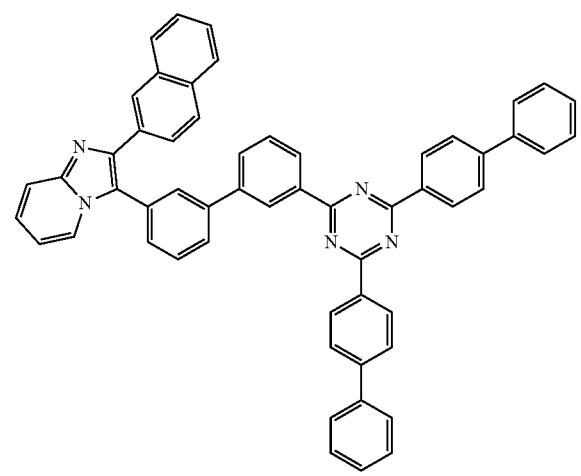
B 311
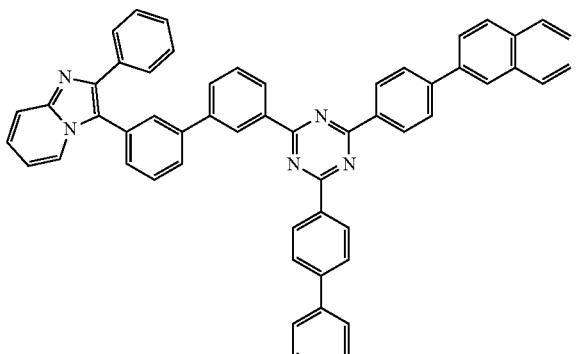
B 312
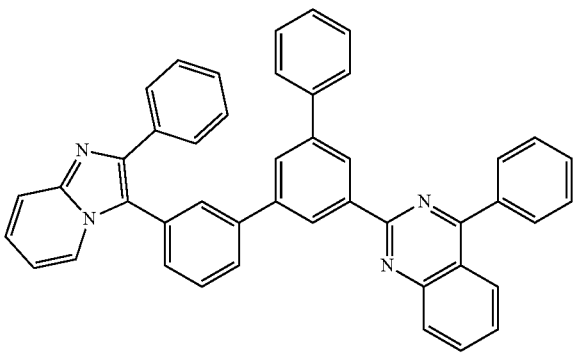
B 313
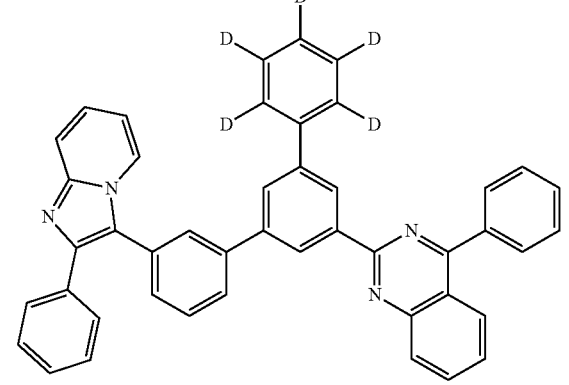
B 314
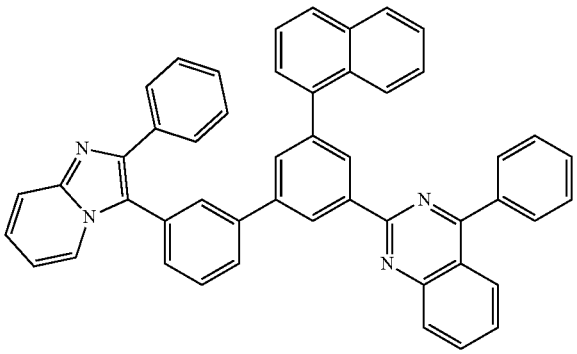

B 315
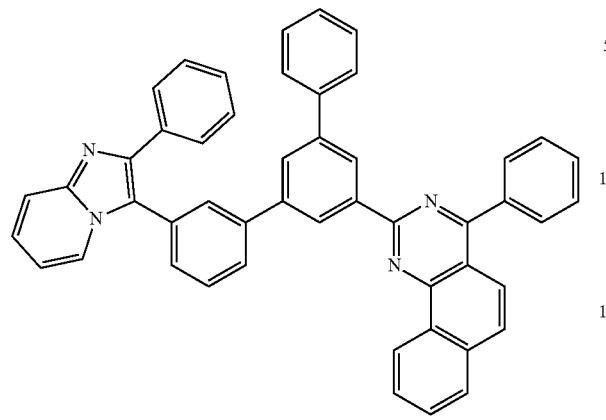
B 316
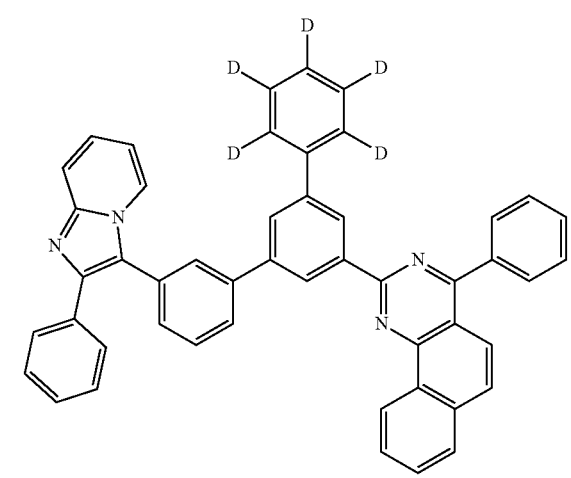
B 317
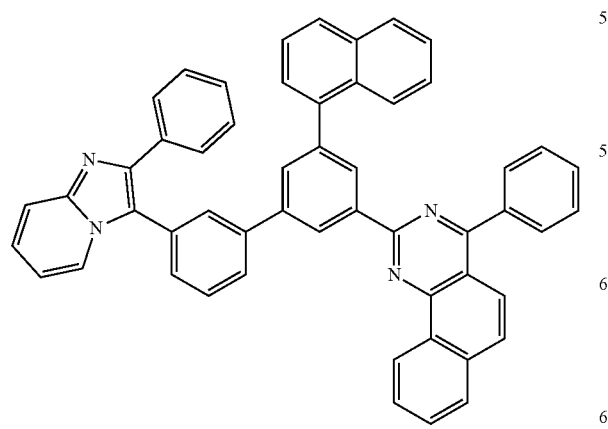
B 318
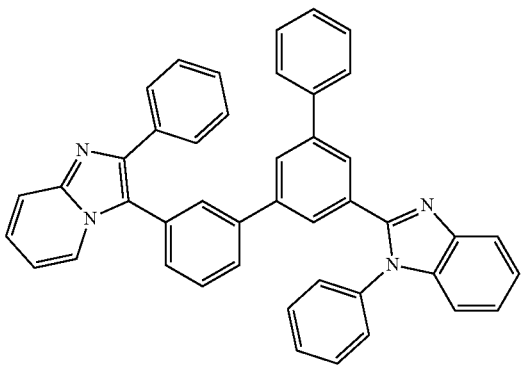
B 319
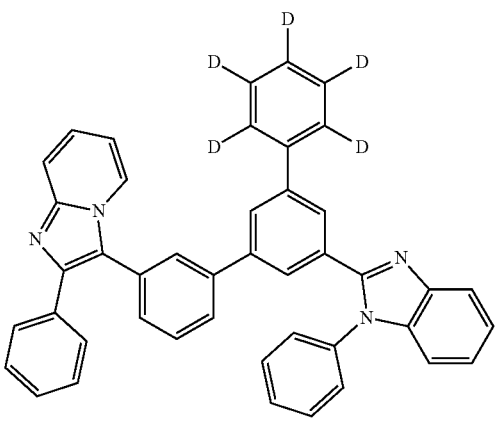
B 320
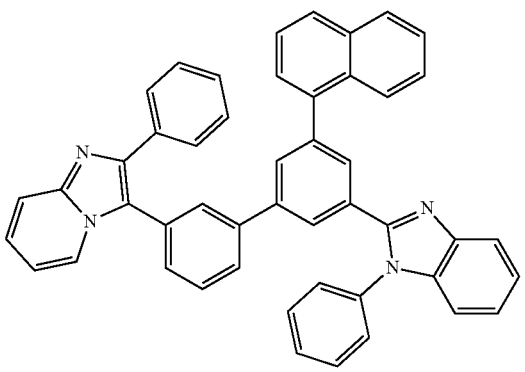
B 321
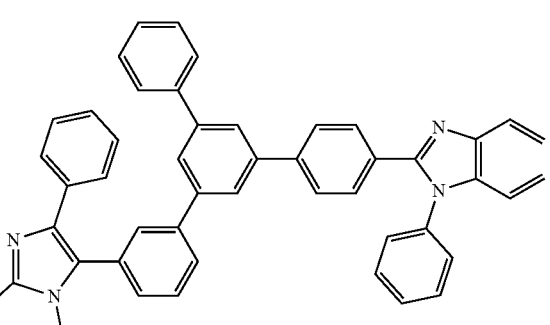

B 322
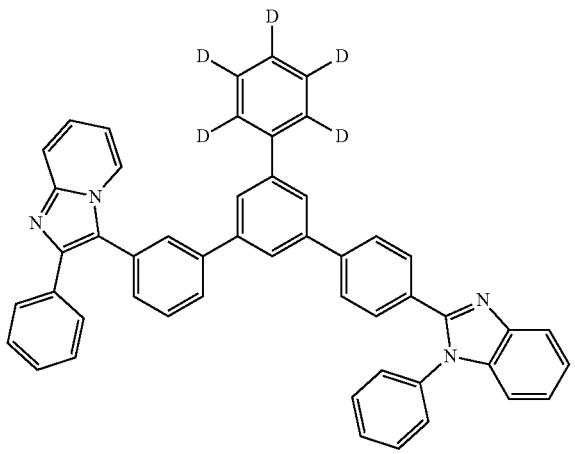
B 323
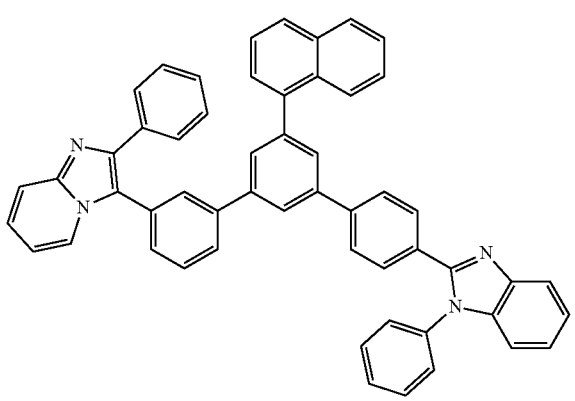
B 324
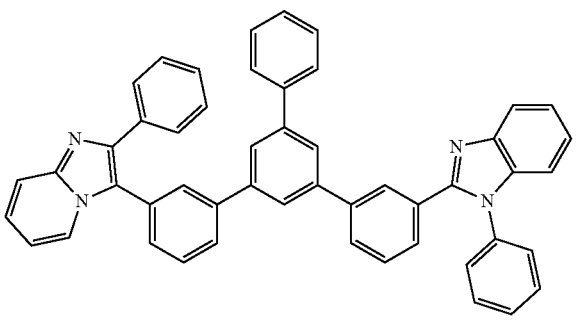
B 325
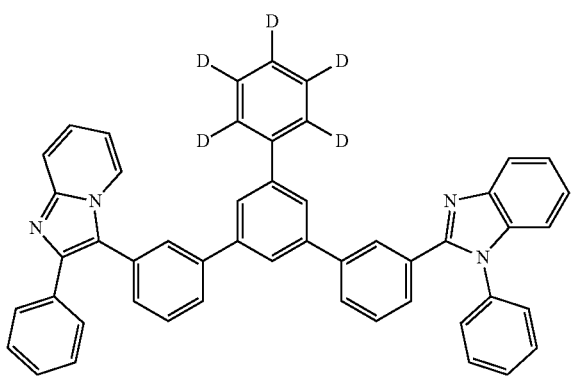
B 326
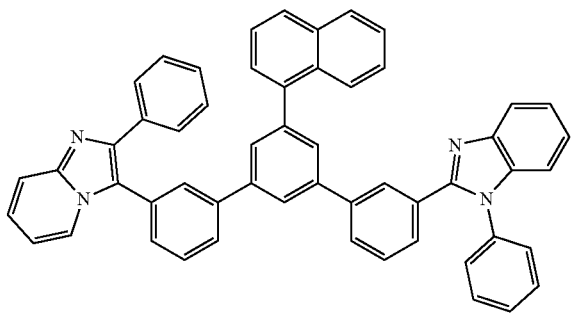
B 327
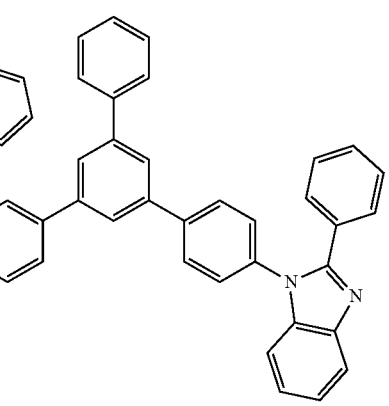
B 328
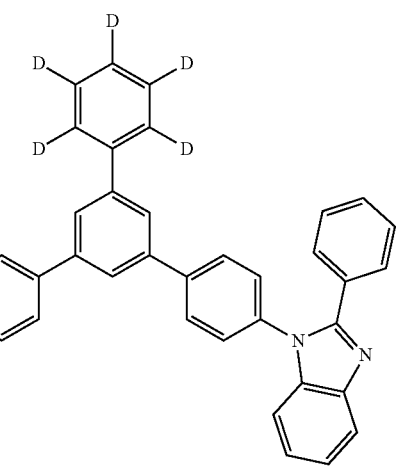
B 329
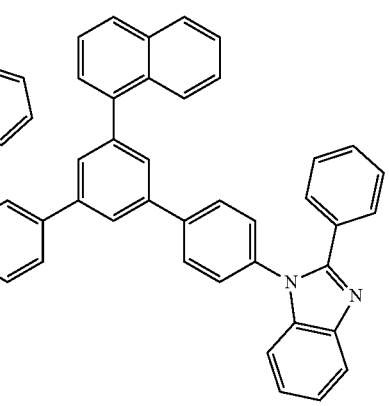

B 330
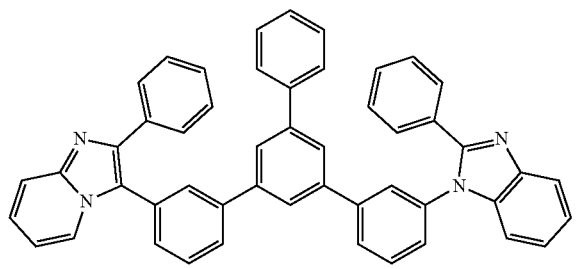
B 331
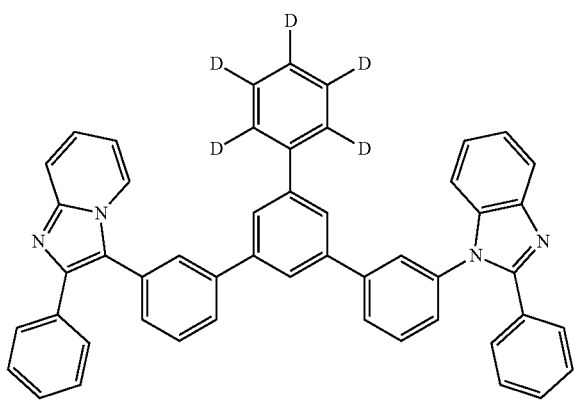
B 332
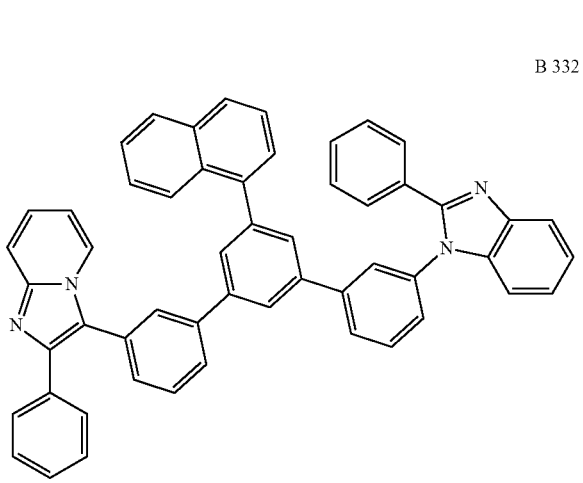
B 333
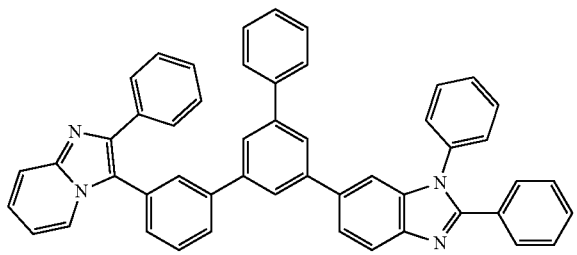
B 334
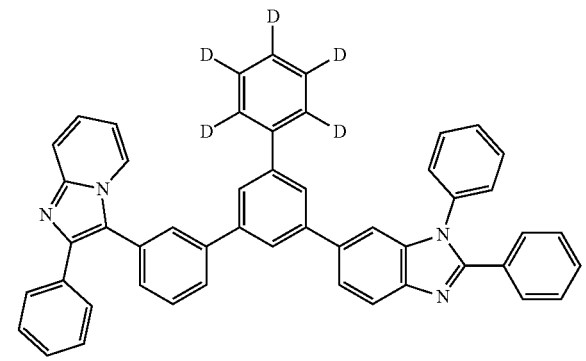
B 335
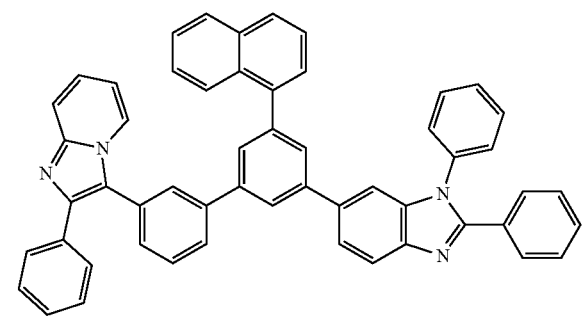
B 336
B 337
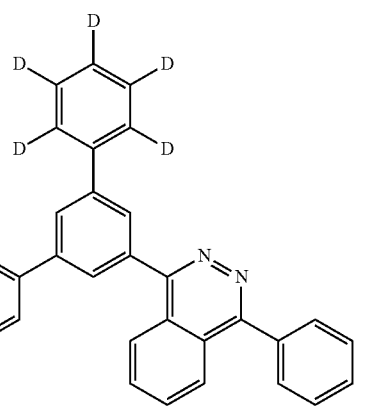

-continued
B 338
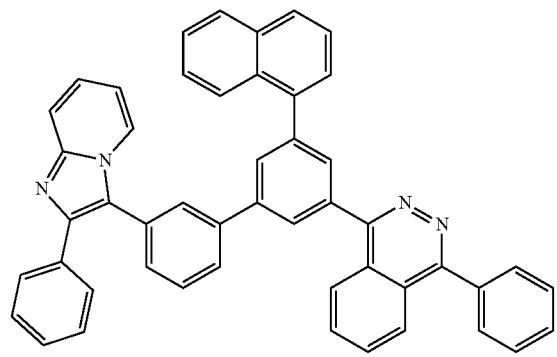
B 339
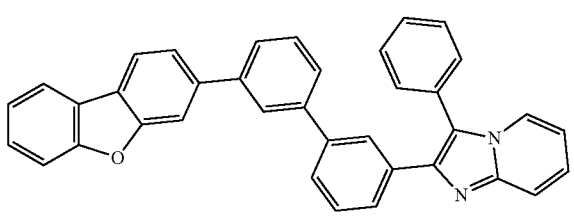
B 340
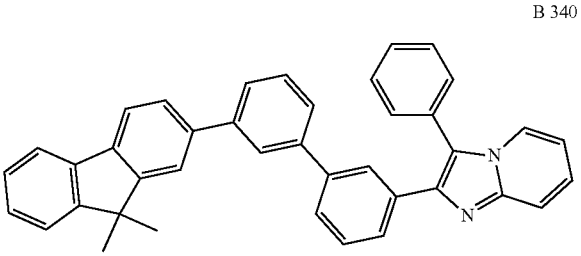
B 341
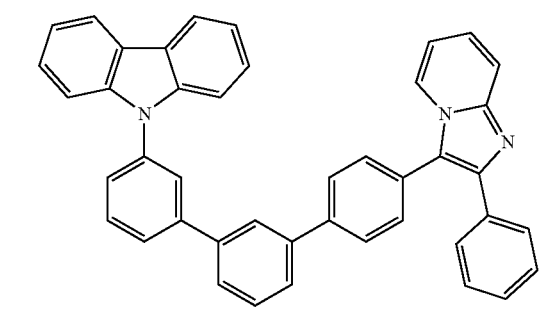
B 342
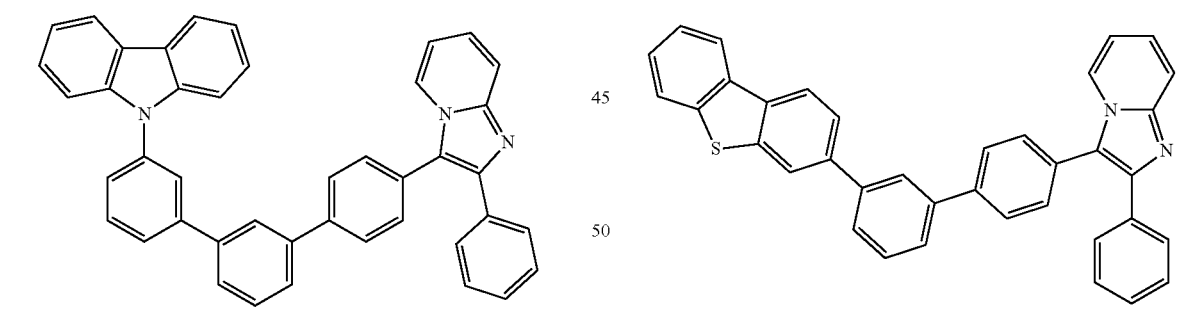
-continued
B 343
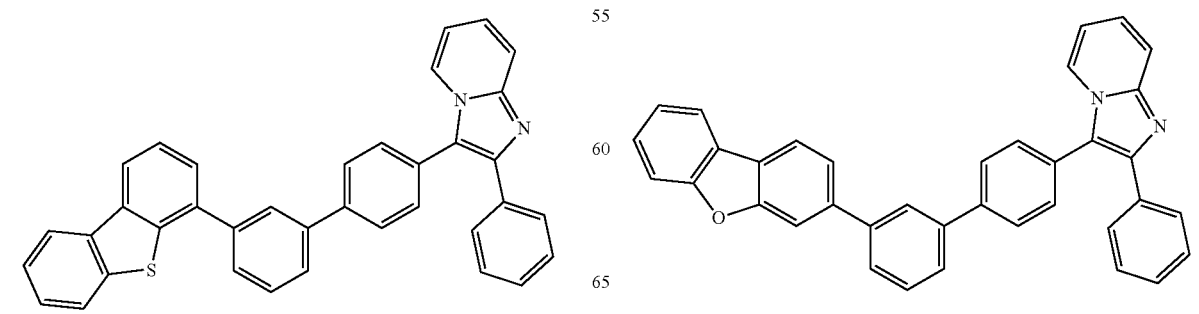
B 344
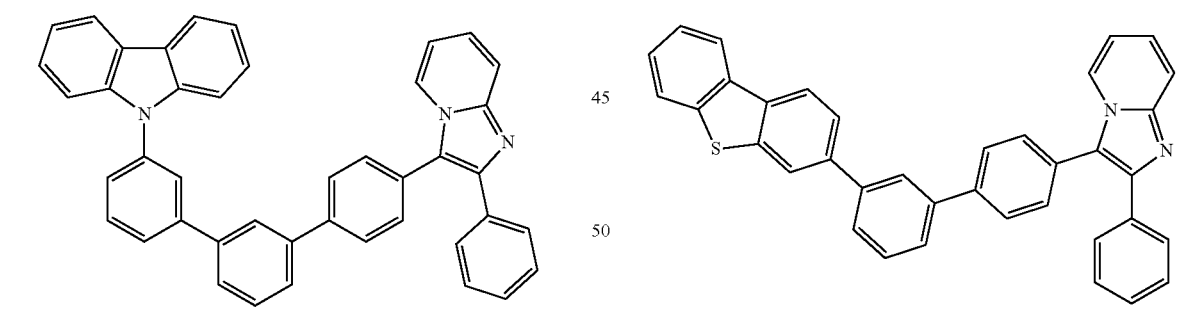
B 345
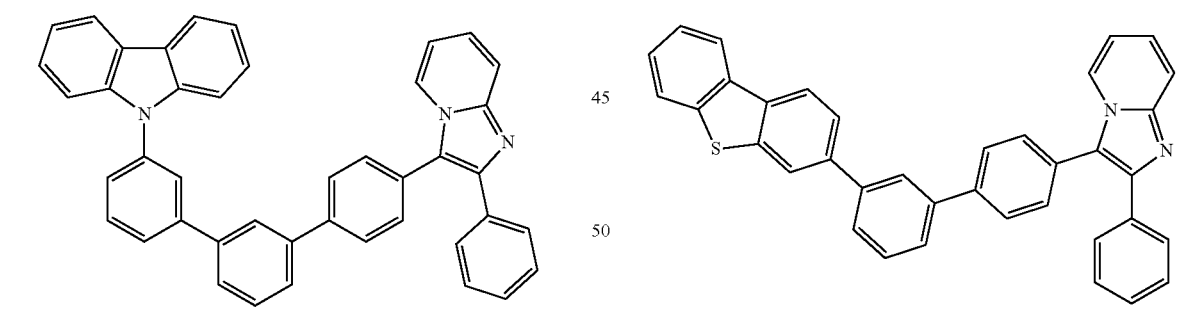
B 346
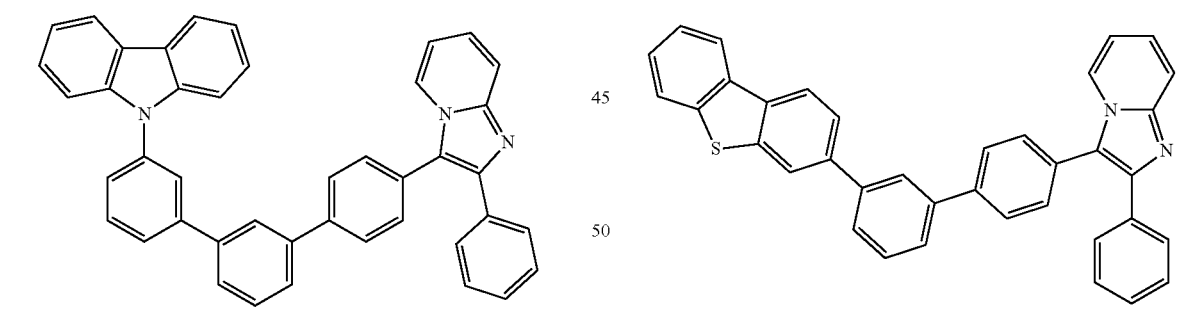
B 347
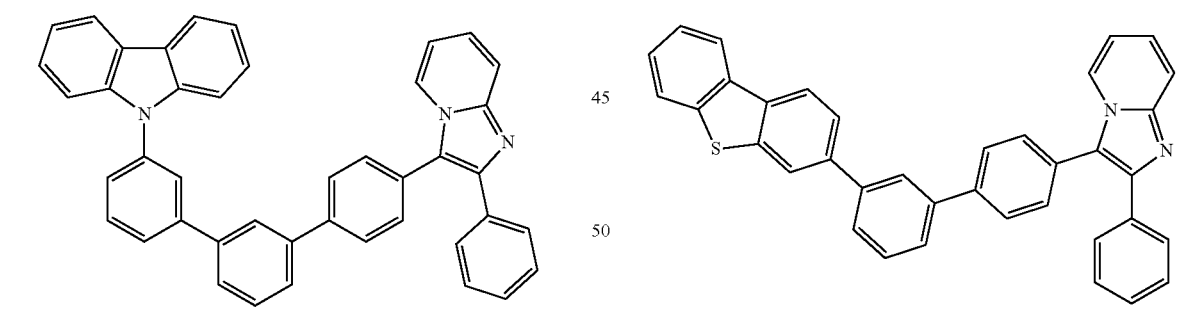

B 348
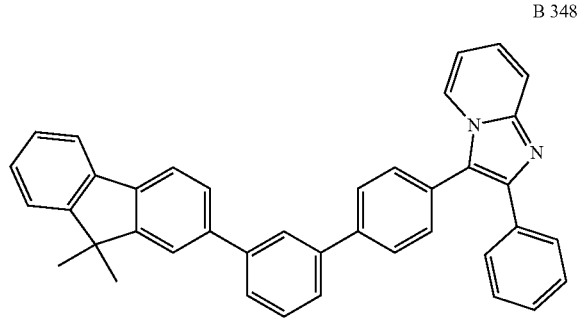
B 349
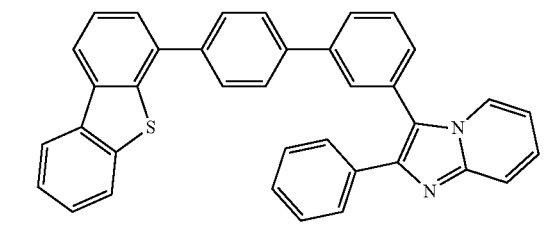
B 350
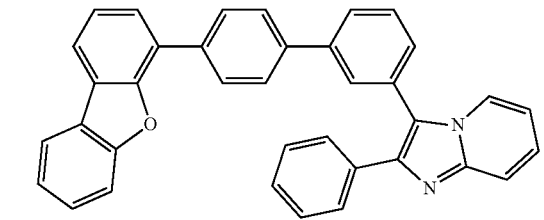
B 351
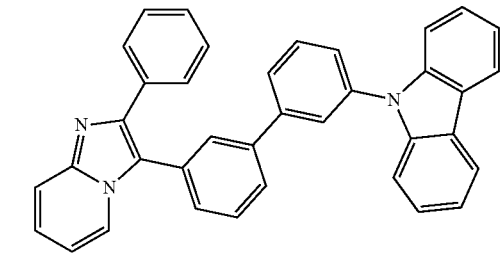
B 352
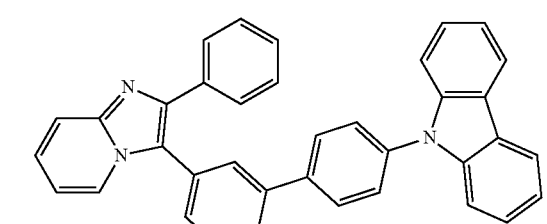
B 353
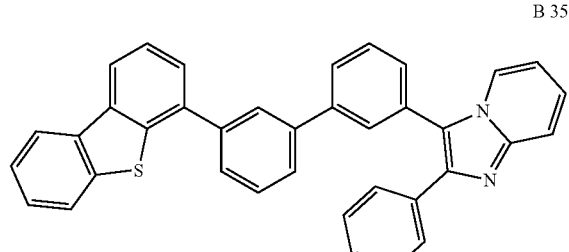
B 354
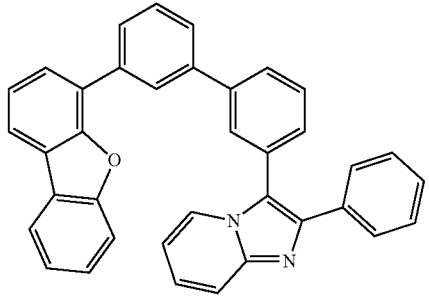
B 355
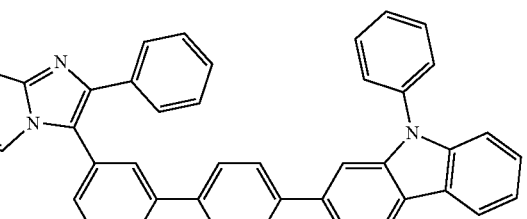
B 356
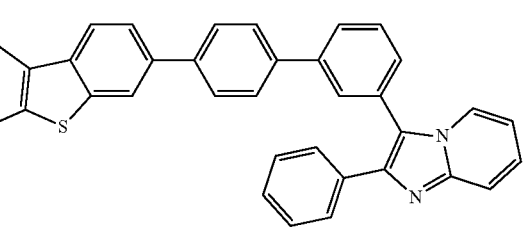
B 357
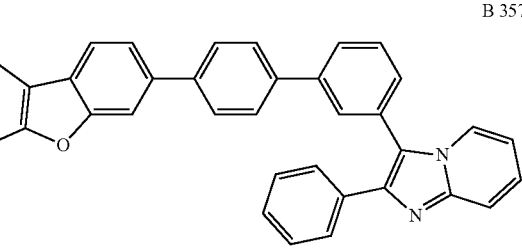
B 358
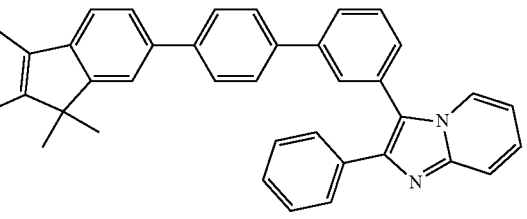
B 359
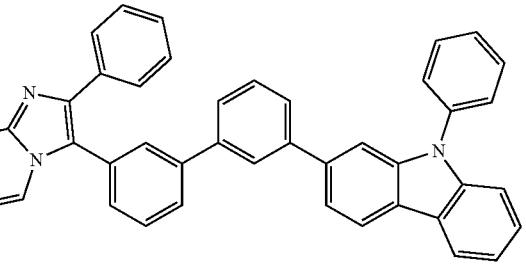

B 360

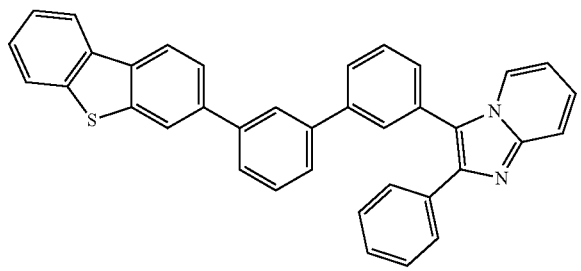

B 361

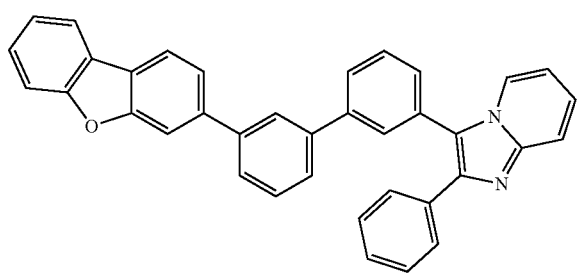

B 362

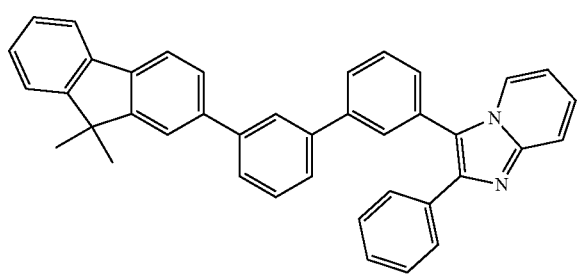

An application of the compound in an OLED apparatus.

The application of the compound as an electron transmission material, a hole barrier layer material and a light extraction layer material in the OLED apparatus.

The compound of the present invention has the advantages of low sublimation temperature, good light stability, electrical stability and thermal stability, high refractive index, small difference of refractive index in a visible light area and the like, can be used in the organic light emitting apparatus, in particular as an electron transmission material, a hole barrier layer material and a light extraction layer material, the apparatus has the advantages of low driving voltage, high luminous efficiency and long service life and has the probability of being applied to an AMOLED industry.

DETAILED DESCRIPTION (SYNTHESIS AND APPARATUS IMPLEMENTATION)

The embodiments below are merely to facilitate understanding of the present invention and are not construed as specific limitation to the present invention.

Raw materials and solvents involved in synthesis of the compound in the present invention are purchased from suppliers known by those skilled in the art such as Alfa and Acros.

EXAMPLES (1) Synthesis of the Compound A1

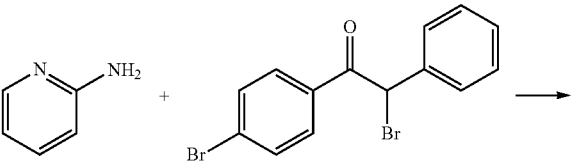

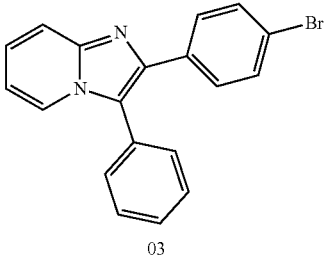

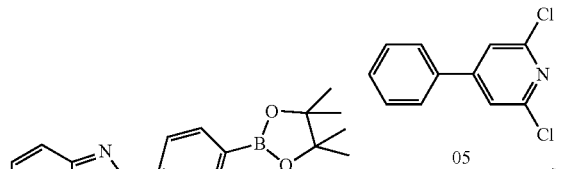

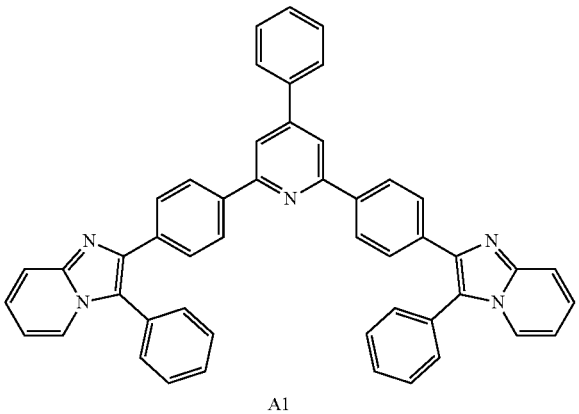

A1

Synthesis of the compound 03: the compound 01 (53.17 g, 0.57 mol and 1.0 eq), the compound 02 (200 g, 0.57 mol and 1.0 eq), NaHCO$_3$ (94.9 g, 1.14 mol and 2.0 eq) and isopropanol (1000 ml) are put into a 2 L single-mouth flask in sequence, oil bath heating is conducted to about 80 degrees centigrade, heat preservation stirring and refluxing are conducted for 7 hours, and a reaction of a raw material at a sampling point board. Cooling is conducted, deionized water is dropwise added, stirring is conducted for about 4 hours and suction filtration is conducted. A solid is pulped with ethanol, and suction filtration and drying are conducted. 157 g of white solid compound 0.3 with a yield of 79.6% is obtained. mass spectrum: 349.03 (M+H)

Synthesis of the compound 04: the compound 03 (60 g, 171.81 mol and 1.0 eq), biphenylborate (56.72 g, 223.35 mmol and 1.3 eq), Pd (dppf)Cl2 (1.26 g, 1.72 mol and 0.01 eq), CH3COOK (33.72 g, 343.62 mmol and 2.0 eq) and 600 ml of dioxane are put into a 1 L single-mouth flask in sequence, N2 replacement is conducted for three times under stirring, heating is conducted and refluxing is conducted for 3 hours. TLC monitors that the reaction is complete (EA/Hex=1:8). A reaction liquid is cooled to room temperature, dioxane is concentrated in vacuum until no solvent is distilled, 600 ml of DCM is added to dissolve the solid, the solid is washed with 200 ml of water, a water phase is extracted once with 200 ml of DCM, an organic phase is combined and is washed twice (200 ml every time) with water, and the organic phase is dried with anhydrous MgSO4. Silica gel filtration is conducted on the organic phase, the organic phase is eluted with 300 ml of DCM, the organic phase is concentrated until only about 150 ml is life, and 500 ml of normal hexane is added to reduce the room temperature to crystallize for 2 hours. Filtration is conducted, a filter cake is eluted with 100 ml of normal hexane, the filter cake is unwatered to obtain 59 g of filter cake, and vacuum drying is conducted overnight is conducted to obtain 54 g of white-like solid compound 04 with the yield of 78.2%. mass spectrum: 397.30 (M+H)

Synthesis of the compound A1: the compound 04 (45.06 g, 113.73 mmol and 2.1 eq), the compound 05 (12.62 g, 54.16 mmol and 1.0 eq), Pd132 (383.5 mg, 0.5416 mmol and 0.01 eq), K2CO3 (15.69 g, 113.73 mmol and 2.1 eq), 450 ml of methylbenzene, 150 ml of ethanol and 150 ml of water are put into a 1 L single-mouth flask in sequence, N2 replacement is conducted for three times under stirring, heating is conducted and refluxing is conducted for 20 hours. TLC monitors that the reaction is complete. Filtration is conducted after cooling the filter cake to room temperature, and the filter cake is eluted with 200 ml of water, 100 ml of ethanol, 100 ml of methylbenzene and 100 ml of methanol in sequence and are underwatered respectively to obtain 37 g of off white solid. The obtained solid is recrystallized with THF to obtain 28 g of white solid compound A1. The obtained compound is sublimated and purified to obtain 21 g of white solid compound A1 with a yield of 75%. Mass spectrum: 692.28 (M+H); 1H NMR (400 MHz, CDCl₃) δ 8.13 (d, J=8.4 Hz, 4H), 7.98 (d, J=6.9 Hz, 2H), 7.87 (s, 2H), 7.81 (d, J=8.3 Hz, 4H), 7.72 (t, J=8.4 Hz, 4H), 7.58-7.43 (m, 13H), 7.24-7.19 (m, 2H), 6.75 (t, J=6.8 Hz, 2H).

(2) Synthesis of the Compound B283

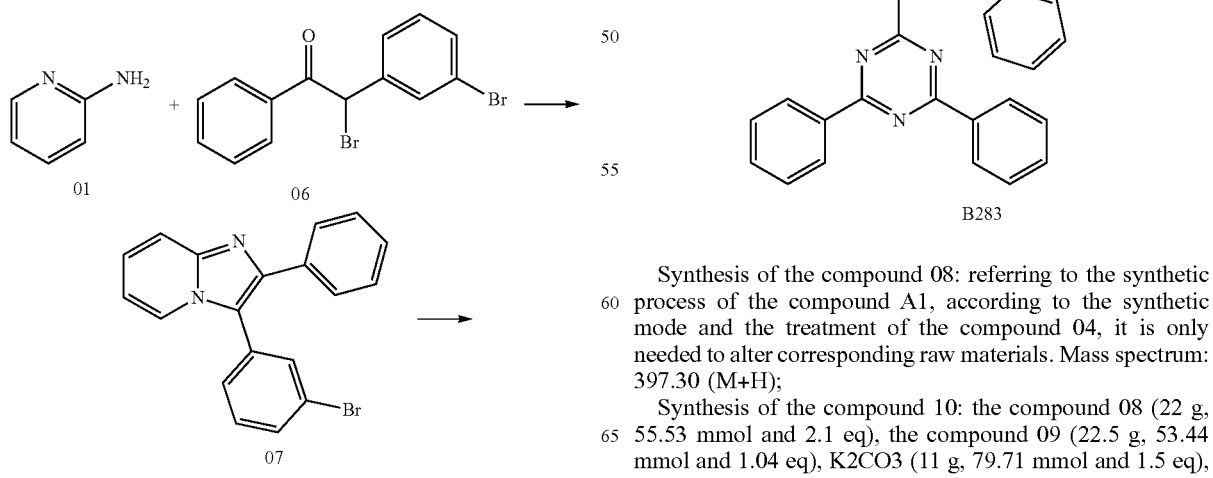

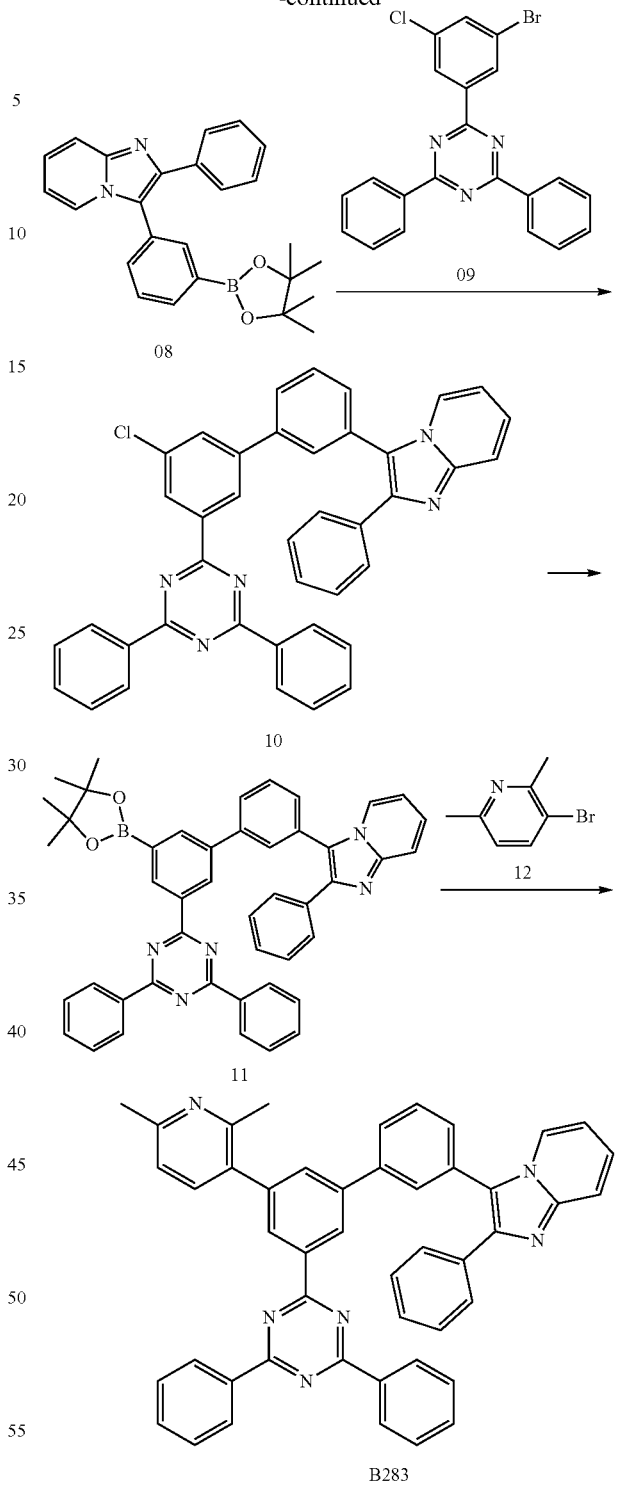

Synthesis of the compound 08: referring to the synthetic process of the compound A1, according to the synthetic mode and the treatment of the compound 04, it is only needed to alter corresponding raw materials. Mass spectrum: 397.30 (M+H);

Synthesis of the compound 10: the compound 08 (22 g, 55.53 mmol and 2.1 eq), the compound 09 (22.5 g, 53.44 mmol and 1.04 eq), K2CO3 (11 g, 79.71 mmol and 1.5 eq), Pd (PPh3)4 (1.2 g, 1.04 mmol and 0.02 eq), 400 ml of methylbenzene, 50 ml of ethanol and 50 ml of water are added into a 1 L four-mouth flask, N2 replacement is conducted for three times, the temperature is raised to 80° C., stirring is conducted for 6 hours, and TLC shows that the reaction is complete. After the reaction liquid is cooled, filtration is conducted, filter residues are pulped with ethanol/water, and suction filtration is conducted to obtain 25 g of off white solid compound 10 with a yield of 75%. Mass spectrum: 612.19 (M+H);

Synthesis of the compound 11: the compound 10 (25 g, 40.90 mmol and 1.0 eq), biphenylborate (15.5 g, 61 mmol and 1.5 eq), X-Phos (0.8 g, 1.68 mmol and 0.04 eq), CH3COOK (8 g, 81.52 mmol and 2.0 eq), 400 ml of dioxane and Pd(OAc)2 (183 mg, 0.81 mmol and 0.02 eq) are added into a 1 L four-mouth flask, N2 replacement is conducted for three times, the temperature is raised to 105° C., stirring is conducted for 3 hours, and TLC shows that the reaction is complete. After the reaction liquid is cooled, 200 ml of DCM is added, silica gel filtration is conducted, mother liquor is spin-dried water washing, and the obtained residues are recrystallized with methylbenzene/normal hexane to obtain 26 g of white solid compound 11 with a yield of 91%. Mass spectrum: 704.31 (M+H);

Synthesis of the compound B283: the compound 11 (26 g, 36.97 mmol and 1.0 eq), the compound 12 (10.3 g, 55.67 mmol and 1.5 eq), K2CO3 (10.2 g, 73.91 mmol and 2.0 eq), Pd-132 (0.5 g, 0.7061 mmol and 0.02 eq), 300 ml of methylbenzene, 50 ml of ethanol and 50 ml of water are added into a 1 L four-mouth flask, N2 replacement is conducted for three times, the temperature is raised to 85° C., stirring is conducted for 5 hours, and TLC shows that the reaction is complete. After the reaction liquid is cooled, 500 ml of DCM is added, silica gel filtration is conducted, mother liquor is spin-dried water washing to obtain 25 g of crude product, and the residues are recrystallized with Tol/hex to obtain 12 g of white solid compound B283 with a yield of 48%. The obtained compound is sublimated and purified to obtain 7.56 g of white solid compound B283 with a yield of 63%. Mass spectrum: 683.28 (M+H); 1H NMR (400 MHz, CDCl$_3$) δ 8.99 (s, 1H), 8.77-8.73 (m, 5H), 8.13-8.11 (d, 2H), 7.99-7.87 (m, 2H), 7.78-7.69 (m, 5H), 7.64-7.52 (m, 8H), 7.34-7.29 (t, 2H), 7.24-7.21 (t, 2H), 7.14-7.12 (d, 1H), 2.64 (s, 3H), 2.60 (s, 3H).

(3) Synthesis of the Compound A3

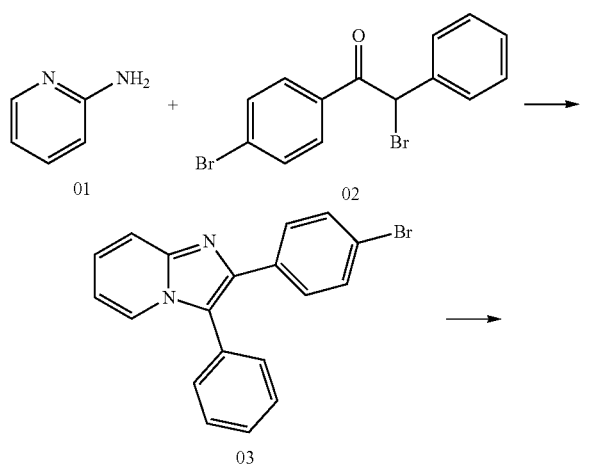

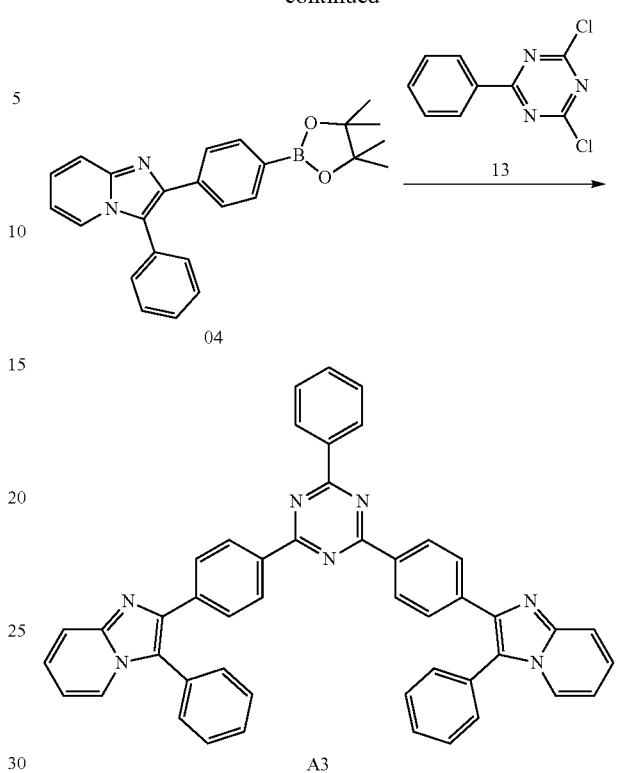

Synthesis of the compound A3: corresponding materials are selected to obtain the yellow solid compound A3 referring to synthesis and sublimation of the compound A1.

(4) Synthesis of the Compound B19

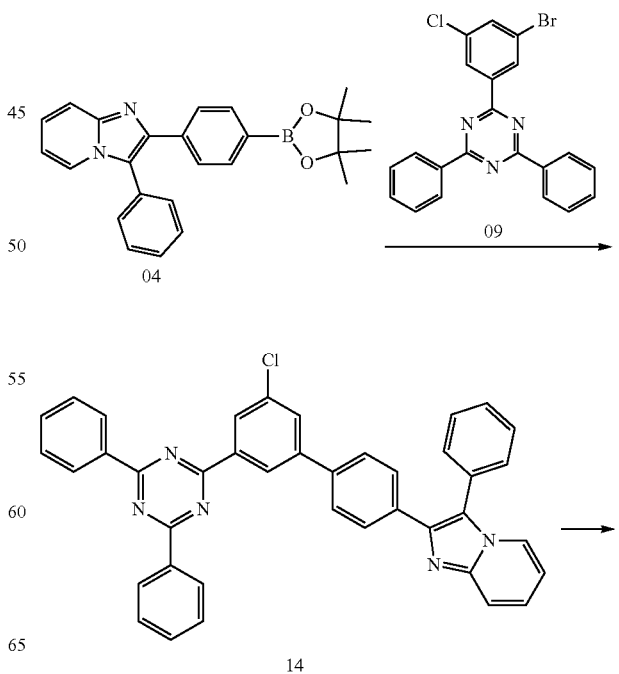

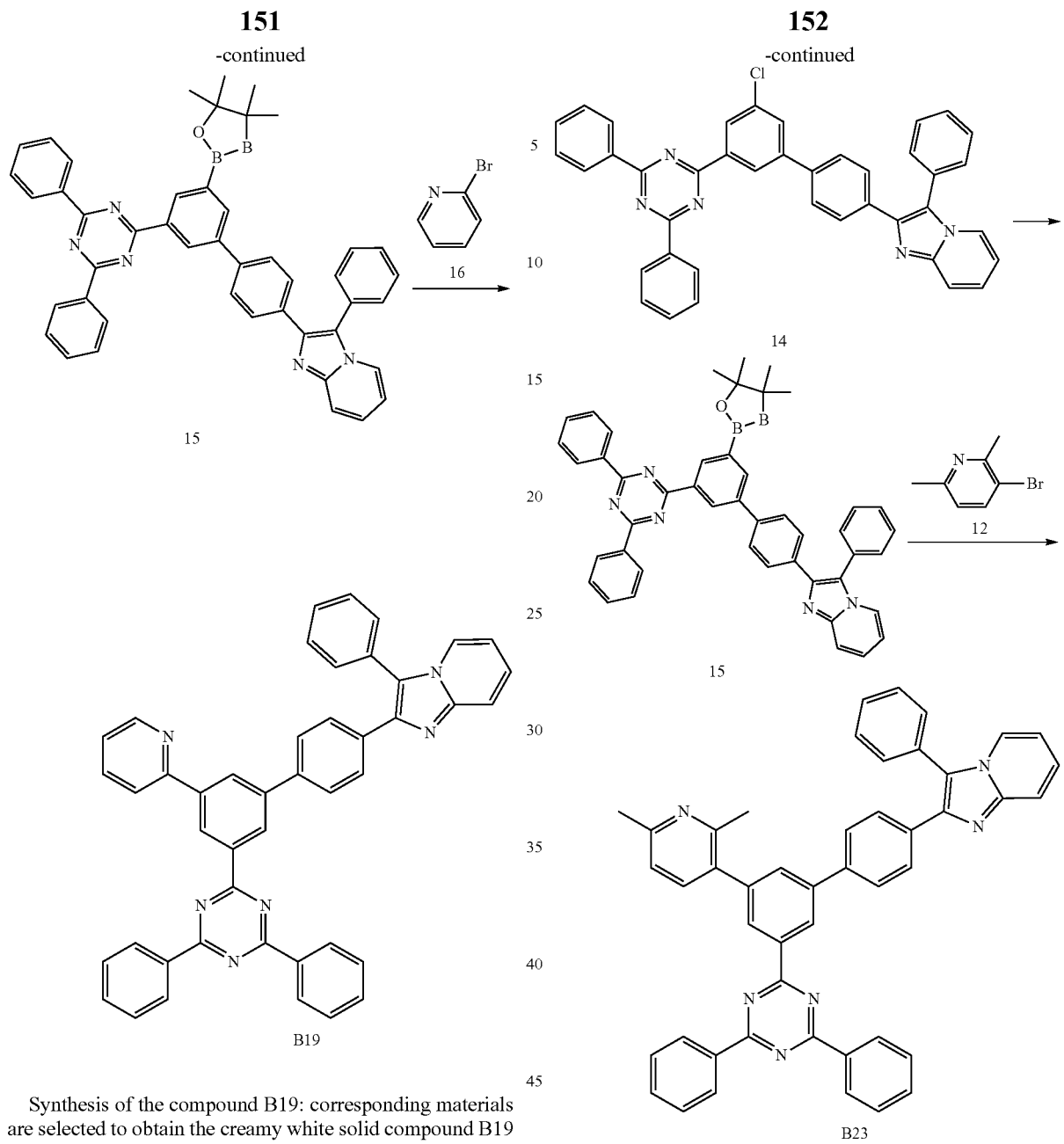

Synthesis of the compound B19: corresponding materials are selected to obtain the creamy white solid compound B19 referring to synthesis and sublimation of the compound B283.

(5) Synthesis of the Compound B23

Synthesis of the compound B23: corresponding materials are selected to obtain the creamy white solid compound B23 referring to synthesis and sublimation of the compound B283.

(6) Synthesis of the Compound A46

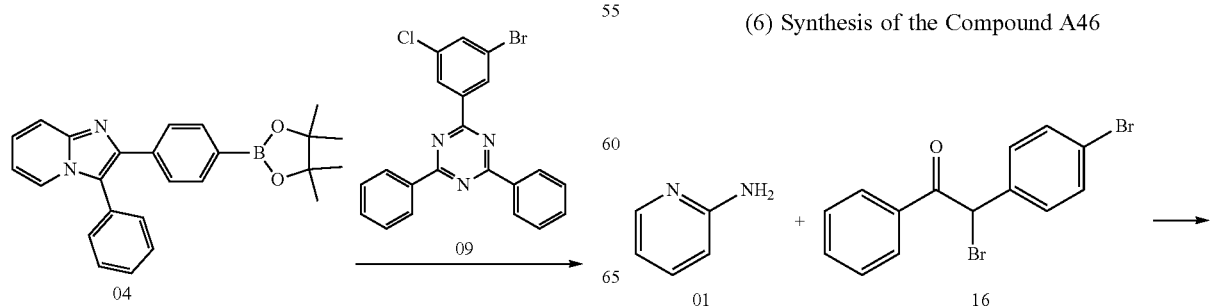

153

-continued

154

-continued

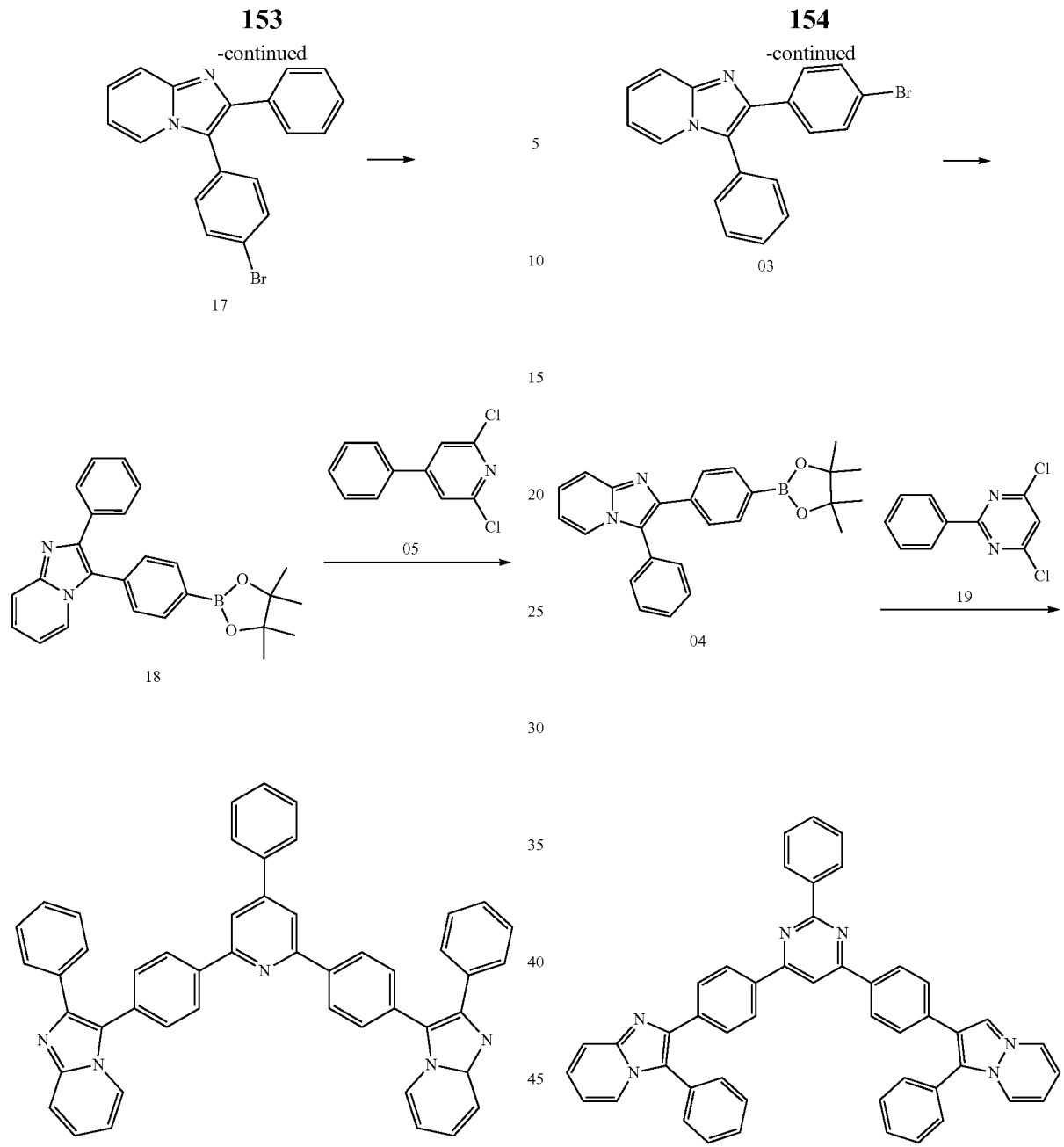

Synthesis of the compound A46: corresponding materials are selected to obtain the yellow solid compound A46 referring to synthesis and sublimation of the compound A1.

(7) Synthesis of the Compound A2

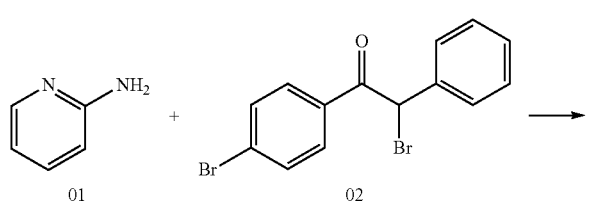

Synthesis of the compound A2: corresponding materials are selected to obtain the yellow solid compound A2 referring to synthesis and sublimation of the compound A1.

Corresponding materials are selected and can be used for synthesis and sublimation to obtain other compounds by similar methods.

APPLICATION EXAMPLES (1) compound performance comparison: the compound of the present invention can be taken as the light extraction layer material in the OLED apparatus and has relatively high glass-transition temperature, relatively high refractive index and relatively small refractive index difference value in the visible light region. Basic performance is limited in the follow table 1.

TABLE 1

| | Glass-transition temperature | Refractive index | | | Refractive index difference value | | |
|---|---|---|---|---|---|---|---|
| | | @450 nm | @520 nm | @630 nm | ΔB-G | ΔB-R | ΔB-R |
| Compound A1: | 150 | 2.14 | 2.05 | 2.00 | 0.09 | 0.14 | 0.05 |
| Compound B283: | 128 | 2.02 | 1.96 | 1.94 | 0.06 | 0.08 | 0.02 |
| Compound A3: | 156 | 2.21 | 2.16 | 2.06 | 0.05 | 0.15 | 0.1 |
| Compound B19: | 134 | 2.09 | 2.03 | 1.98 | 0.06 | 0.11 | 0.05 |
| Compound B23: | 133 | 2.06 | 1.99 | 1.94 | 0.07 | 0.12 | 0.05 |
| Compound A46: | 158 | 2.03 | 1.95 | 1.91 | 0.08 | 0.12 | 0.04 |
| Compound A2: | 155 | 2.24 | 2.12 | 2.06 | 0.12 | 0.18 | 0.06 |
| HTM1 | 134 | 1.99 | 1.91 | 1.85 | 0.08 | 0.14 | 0.06 |
| Comparative compound 3 | 132 | 1.99 | 1.89 | 1.84 | 0.1 | 0.15 | 0.05 |

(2) manufacturing of the organic electroluminescent apparatus

A 50 mm*50 mm*1.0 mm glass substrate with an ITO (100 nm) transparent electrode is ultrasonically cleaned for 10 minutes in ethanol, dried at 150 degrees centigrade and N2 plasma treatment is conducted for 30 minutes. The washed glass substrata is mounted on a substrate bracket of a vacuum evaporation device, a compound HATCN is evaporated on a surface of one side of the transparent electrode by way of covering the transparent electrode to form a 5 nm thick film, then a layer of HTM1 is evaporated to form a 60 nm thick film, then a layer of HTM2 is evaporated on the HTM1 film to form a 10 nm thick film, and then a main body material CBP and a doping material are evaporated on the HTM2 film layer by way of co-evaporation, the film thickness is 30 nm and the ratio of the main body material to the doping material is 90%:10%. HBL (5 nm) is evaporated on the luminous layer as the hole barrier layer material and ETL (30 nm) as the electron transmission material in sequence according to match in the following table, then LiF (1 nm) is evaporated on the electron transmission material layer as the electron injection material, then Mg/Ag (18 nm, 1:9) is evaporated by a co-evaporation mode) as an anode material, and finally, CPL (50 nm) is evaporated on the anode material according to the table below as the light extraction layer material.

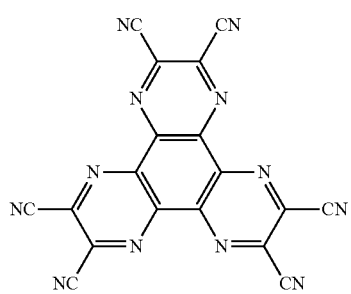

HATCN

-continued

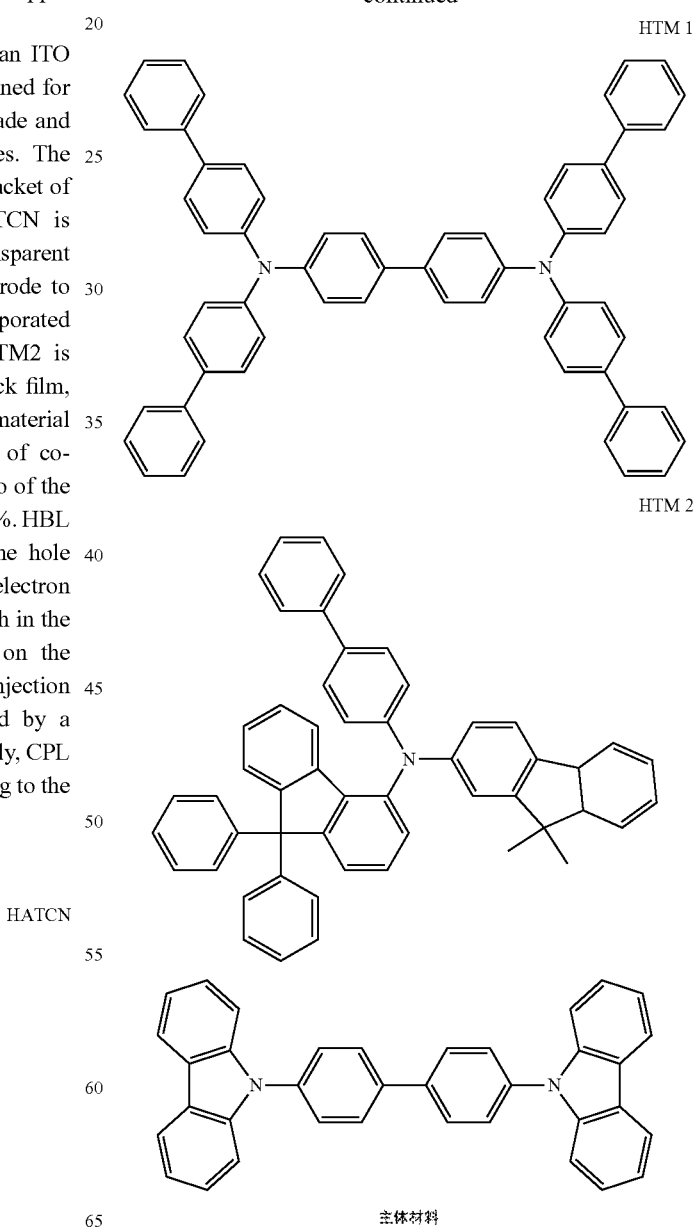

-continued

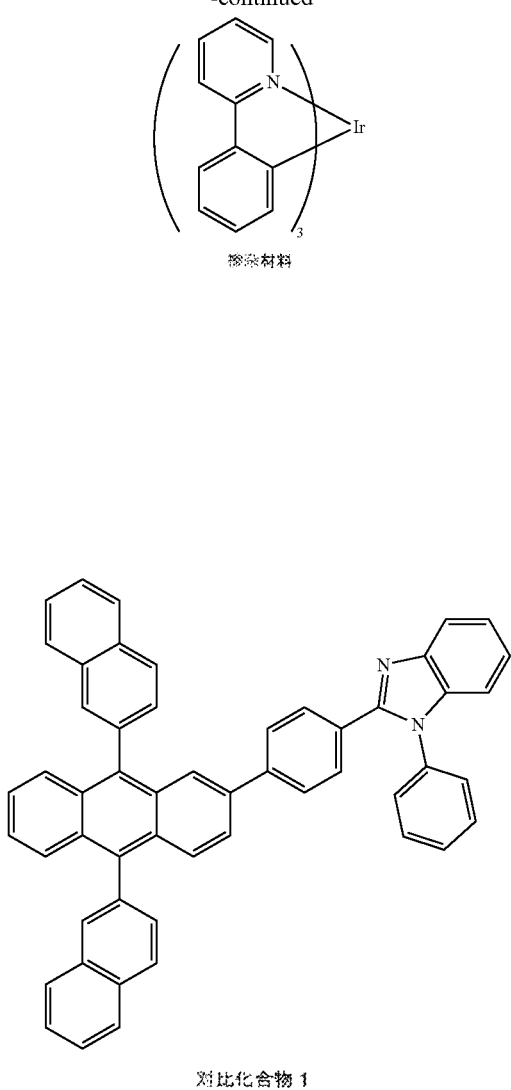

对比化合物 1

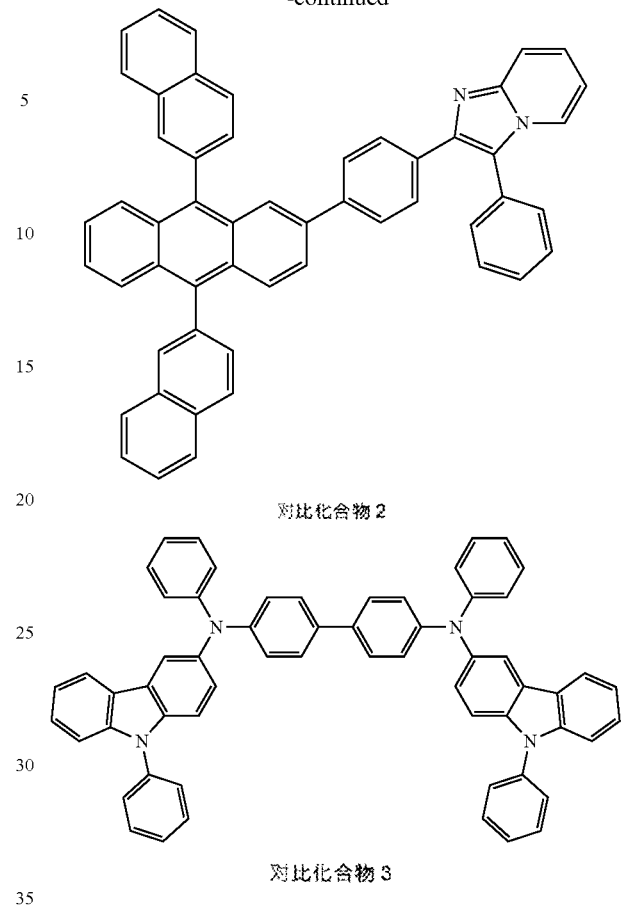

对比化合物 2

对比化合物 3

Apparatus Performance Evaluation

Apparatus performance test of the apparatus is conducted. In various embodiments and comparative examples, a constant current power supply (Keithley 2400) is used, a fixed current density flows through the luminous element, and a spectral radiation series (CS 2000) is used to test a luminous spectrum. A voltage value is tested and a time (LT90) with a brightness being 90% of an initial brightness is tested simultaneously. A result is following shown in a table 2:

TABLE 2:

|  | HBL | ETL | CPL | Starting voltage V @3000 nits | Current efficiency Cd/A @3000 nits | LT90@ 3000 nits |
|---|---|---|---|---|---|---|
| Example 1 | Compound A1: | Compound A1: | HTM1 | 4.6 | 61 | 186 |
| Example 2 | Compound B283: | Compound B283: | HTM1 | 4.5 | 63 | 175 |
| Example 3 | Compound A3: | Compound A3: | HTM1 | 4.6 | 64 | 192 |
| Example 4 | Compound B19: | Compound B19: | HTM1 | 4.4 | 62 | 169 |
| Example 5 | Compound B23: | Compound B23: | HTM1 | 4.3 | 63 | 173 |
| Example 6 | Compound A46: | Compound A46: | HTM1 | 4.5 | 61 | 181 |
| Example 7 | Compound A2: | Compound A2: | HTM1 | 4.5 | 60 | 156 |
| Example 8 | Compound B340: | Compound B283: | Compound A3: | 4.2 | 68 | 216 |
| Example 9 | Comparative compound 1 | Comparative compound 1 | Compound A3: | 4.7 | 53 | 96 |

TABLE 2:-continued

|  | HBL | ETL | CPL | Starting voltage V @3000 nits | Current efficiency Cd/A @3000 nits | LT90@ 3000 nits |
|---|---|---|---|---|---|---|
| Example 10 | Comparative compound 2 | Comparative compound 2 | Compound A3: | 4.7 | 55 | 130 |
| Example 11 | Compound B340: | Compound B23: | Compound A3: | 4.6 | 69 | 256 |
| Example 12 | Compound B340: | Compound B9: | Compound A2: | 4.7 | 67 | 234 |
| Comparative example 1 | Comparative compound 1 | Comparative compound 1 | HTM1 | 5.2 | 48 | 92 |
| Comparative example 2 | Comparative compound 2 | Comparative compound 2 | HTM1 | 4.9 | 50 | 125 |

It can be known from comparison of data in the table above, compared with the comparative compounds, the compound of the present invention applied as the hole transmission layer or the electron transmission layer of the light extraction layer material in the organic electroluminescent apparatus shows more excellent performance in driving voltage, luminous efficiency and service life.

The result shows that the compound of the present invention has the advantages of low sublimation temperature, good light stability, electrical stability and thermal stability, high refractive index, small difference of refractive index in a visible light area and the like, and an apparatus prepared by the compound has the advantages of low voltage, long service life, high luminous efficiency and the like and can be used in an organic luminescent apparatus. In particular, as an electron transmission material, a hole barrier layer material and a light extraction layer material, the imidazoazacyclo compound has the probability of being applied to an AMO-LED industry.

The invention claimed is:

1. A compound, a structural formula (I) thereof being as shown in:

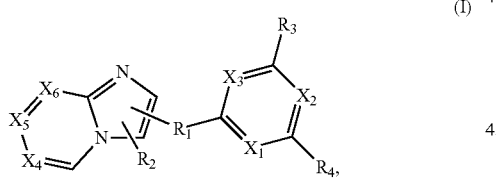

(I)

wherein R1 is a single bond, alkyl, heteroalkyl, cycloalkyl, substituted or unsubstituted C6-C30 non-fused ring aryl or substituted or unsubstituted C3-C27 non-fused ring aryl;

R2, R3 and R4 are independently selected from hydrogen, deuterium, halogen, alkyl, heteroalkyl, cycloalkyl, alkoxyl, aryloxy, amino, silicyl, nitrile, isonitrile, phosphino, substituted or unsubstituted C6-C60 aryl, substituted or unsubstituted C1-C60 heteroaryl, substituted or unsubstituted monocyclic or polycyclic C3-C60 aliphatic ring or aromatic ring and at least one of R3 and R4 is substituted or unsubstituted C6-C60 aryl, substituted or unsubstituted C1-C60 heteroaryl, substituted or unsubstituted monocyclic or polycyclic C3-C60 aliphatic ring or aromatic ring, where one or more carbon atoms in the heteroalkyl or heteroaryl can be substituted by at least one heteroatom selected from O, S, N, Se, Si and Ge; the being substituted is being substituted by deuterium, halogen, C1-C30 alkyl, C1-C30 heteroalkyl, C3-C30 cycloalkyl, amino, silicyl, nitrile, isonitrile, phosphino, C6-C60 aryl or C1-C60 heteroaryl; and X1, X2 and X3 independently represent CH or N; X4, X5 and X6 independently represent CR0 or N, R0 is independently selected from hydrogen, deuterium, halogen, alkyl, heteroalkyl, aralkyl, alkoxyl, aryloxy, amino, silicyl, aryl, heteroaryl, nitrile, isonitrile or phosphino.

2. The compound according to claim 1, wherein R1 is a single bond, C1-C30 alkyl, C1-C30 heteroalkyl, C3-C30 cycloalkyl, substituted or unsubstituted C6-C30 non-fused ring aryl or substituted or unsubstituted C3-C27 non-fused ring aryl;

R2, R3 and R4 are independently selected from hydrogen, deuterium, halogen, C1-C30 alkyl, C1-C30 heteroalkyl, C3-C30 cycloalkyl, amino, silicyl, nitrile, isonitrile, phosphino, substituted or unsubstituted C6-C60 aryl, substituted or unsubstituted C1-C60 heteroaryl, substituted or unsubstituted monocyclic or polycyclic C3-C60 aliphatic ring or aromatic ring and at least one of R3 and R4 is substituted or unsubstituted C6-C60 aryl, substituted or unsubstituted C1-C60 heteroaryl, substituted or unsubstituted monocyclic or polycyclic C3-C60 aliphatic ring or aromatic ring, where one or more carbon atoms in the heteroalkyl or heteroaryl can be substituted by at least one heteroatom selected from O, S and N; the being substituted is being substituted by deuterium, halogen, C1-C30 alkyl, C1-C30 heteroalkyl, C3-C30 cycloalkyl, amino, silicyl, nitrile, isonitrile, phosphino, C6-C60 aryl or C1-C60 heteroaryl;

X1, X2 and X3 independently represent CH or N; X4, X5 and X6 independently represent CR0 or N, R0 is independently selected from hydrogen, deuterium, halogen, C1-C30 alkyl, C1-C30 heteroalkyl, aralkyl, amino, silicyl, aryl, heteroaryl, nitrile, isonitrile or phosphino.

3. The compound according to claim 1, wherein at least one of X1, X2 and X3 is N.

4. The compound according to claim 3, at least one of R3 or R4 comprising a structural formula (II), wherein R1 is a single bond, alkyl, heteroalkyl, cycloalkyl, C1-C30 alkyl substituted or unsubstituted C6-C30 non-fused ring aryl or C1-C30 alkyl substituted or unsubstituted C3-C27 non-fused ring heteroaryl, wherein R2 is hydrogen, deuterium, halogen, alkyl, heteroalkyl, cycloaryl, C1-C30 alkyl substituted or unsubstituted C6-C30 aryl or C1-C30 alkyl substituted or unsubstituted C1-C60 heteroaryl,

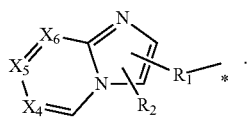

Formula (II)

5. The compound according to claim 4, wherein one of R3 and R4 is a structure shown in the formula (II) and the other one is C1-C4 alkyl substituted or unsubstituted C6-C18 aryl, C1-C4 alkyl substituted or unsubstituted C3-C15 heteroaryl; R1 is C1-C4 alkyl substituted or unsubstituted C6-C18 non-fused ring aryl, C1-C4 alkyl substituted or unsubstituted C3-C15 non-fused ring heteroaryl; and R2 is C1-C4 alkyl substituted or unsubstituted C6-C18 aryl or C1-C4 alkyl substituted or unsubstituted C3-C15 heteroaryl.

6. The compound according to claim 5, wherein R1 is C6-C18 non-fused ring aryl or C5C-15 non-fused ring heteroaryl; and R2 is C6-C18 aryl or C5-C15 heteroaryl.

7. The compound according to claim 6, being one of the following compounds:

A1

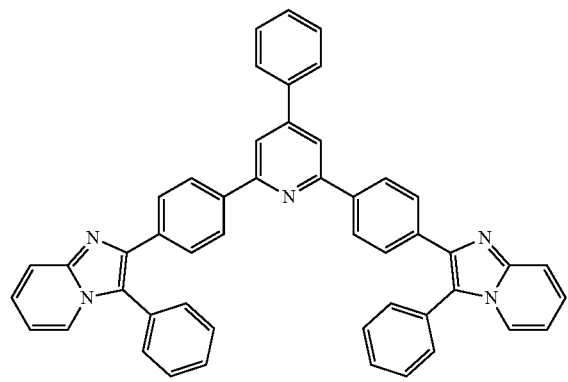

A2

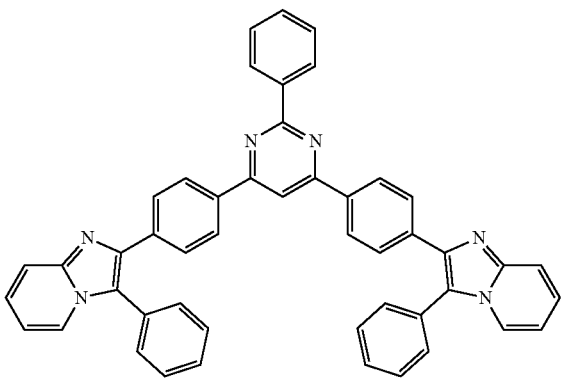

A3

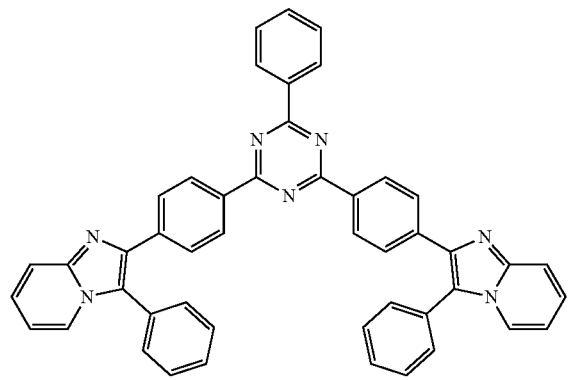

A4

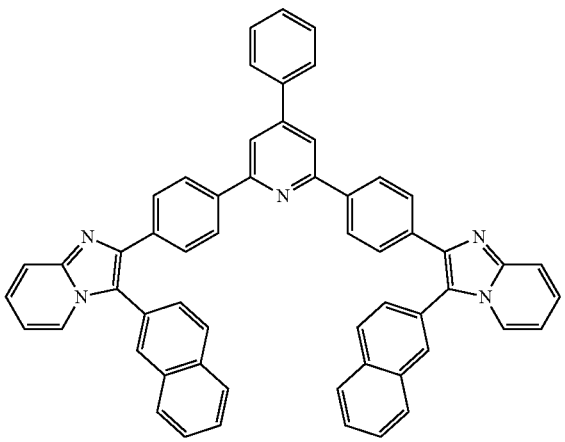

A5

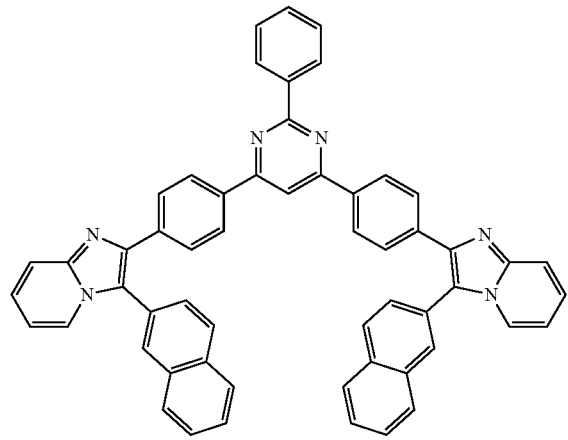

A6

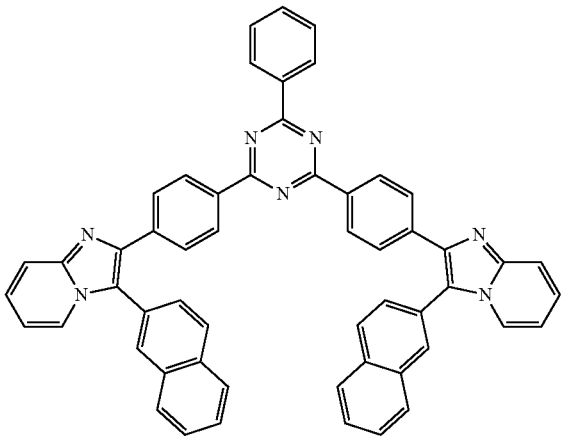

-continued
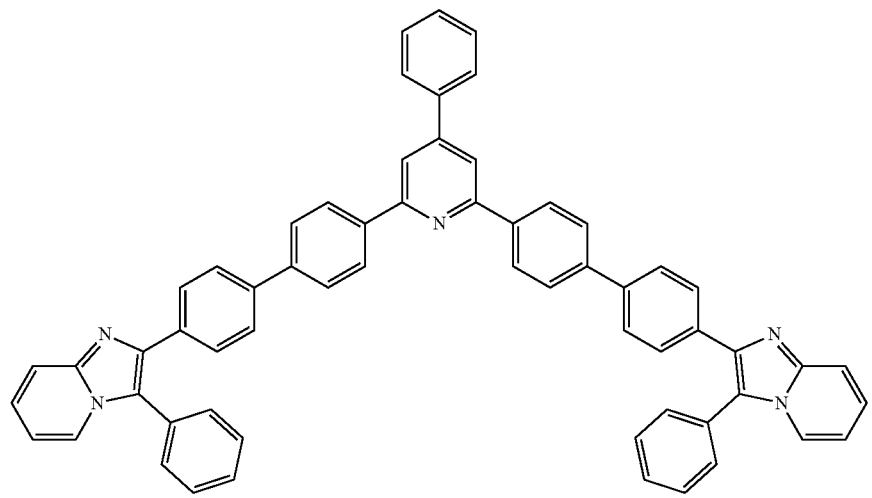
A7
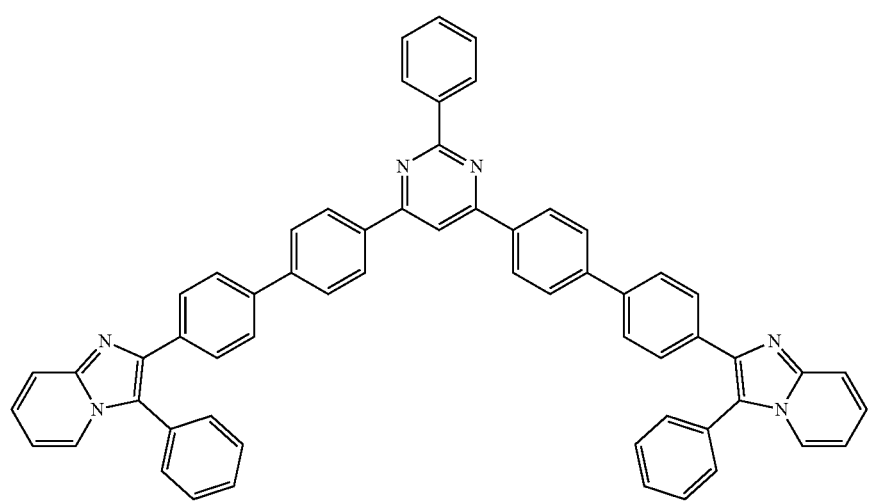
A8
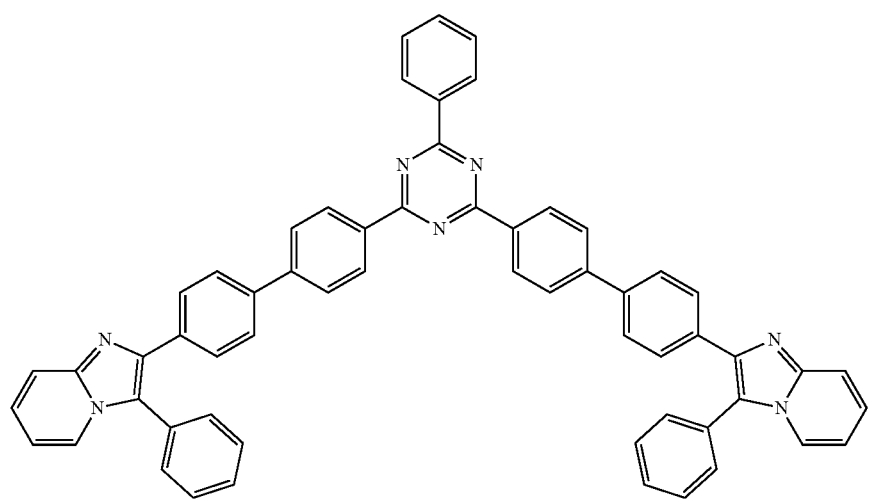
A9

-continued
A10
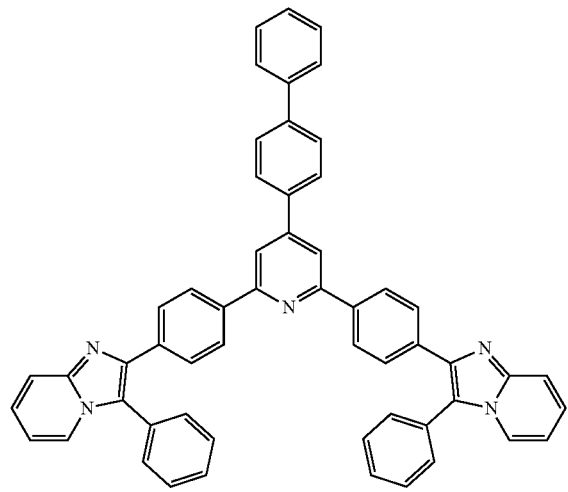
A11
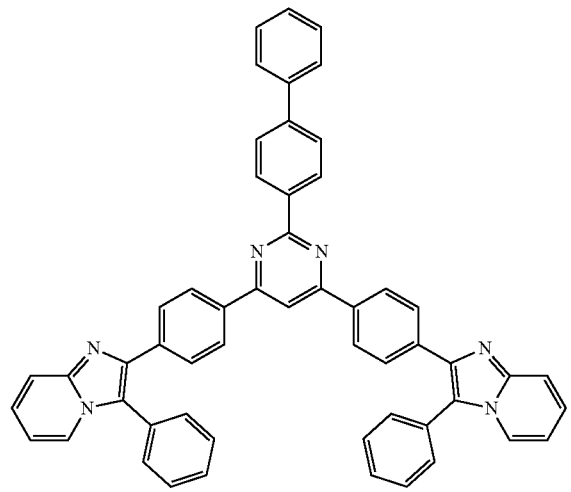
A12
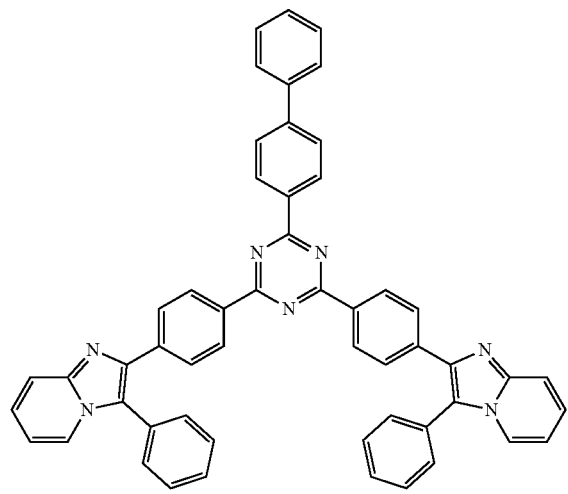
A13
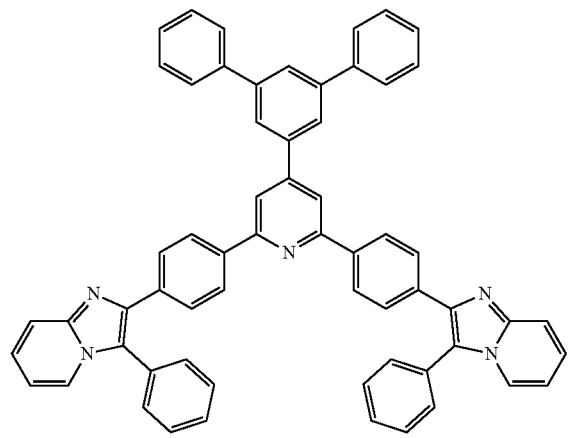
A14
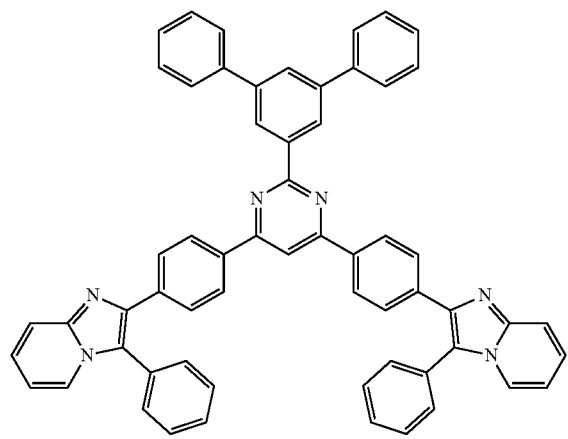
A15
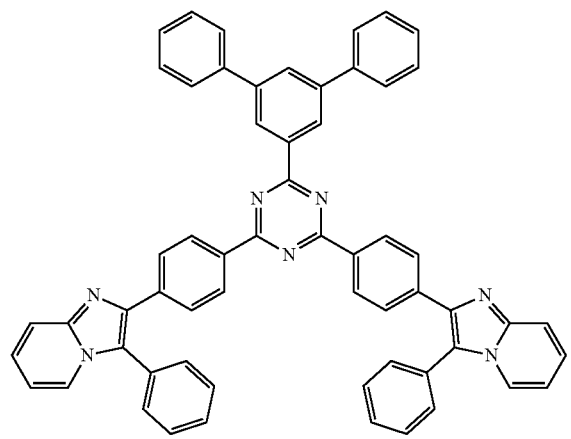

-continued
A16
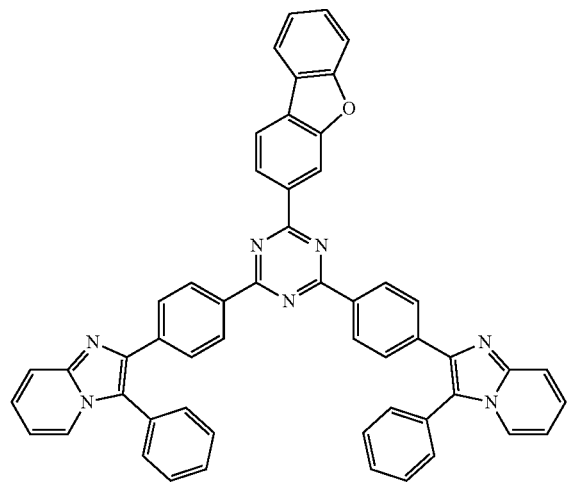
A17
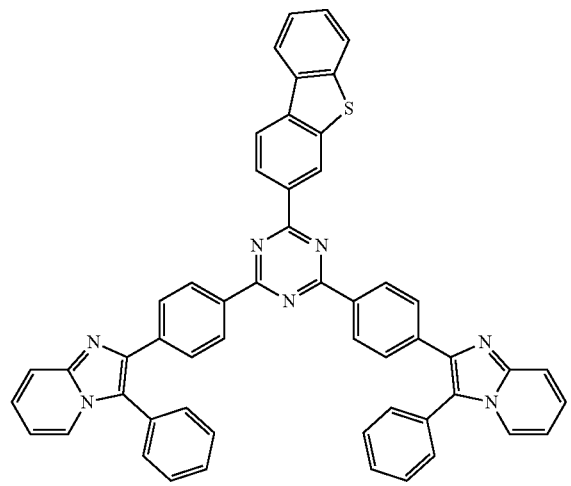
A18
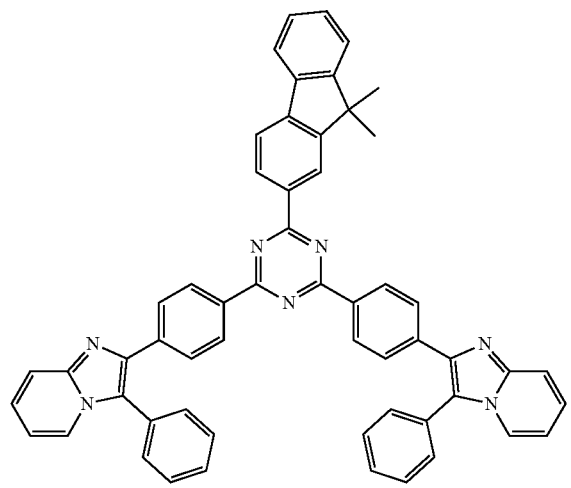
A19
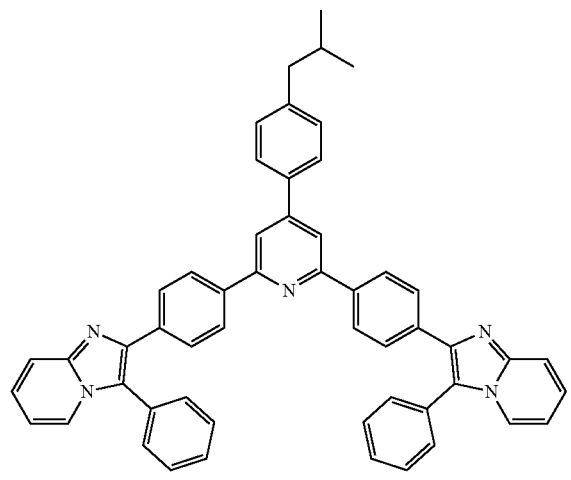
A20
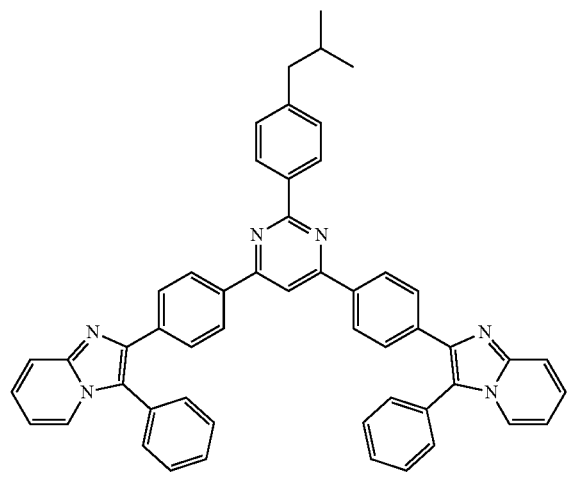
A21
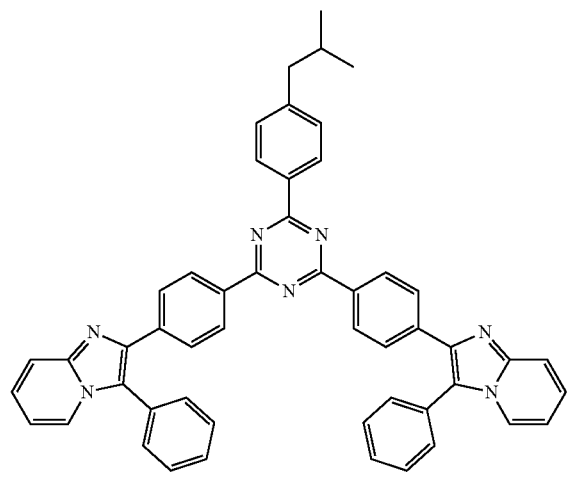

-continued
A22
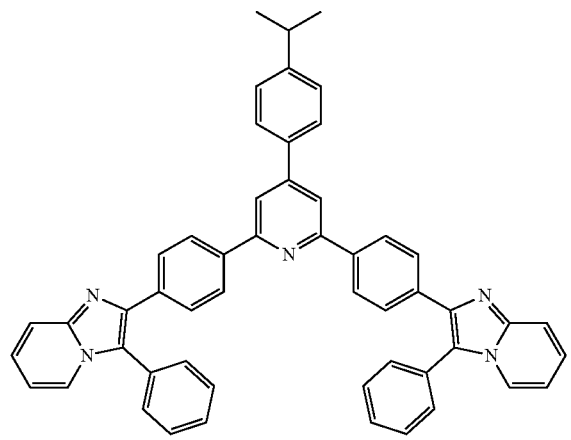
A23
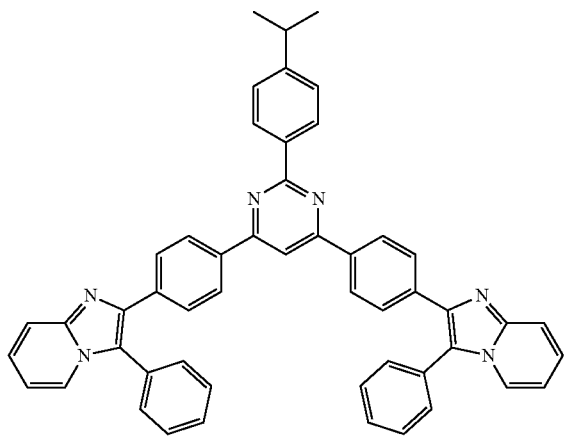
A24
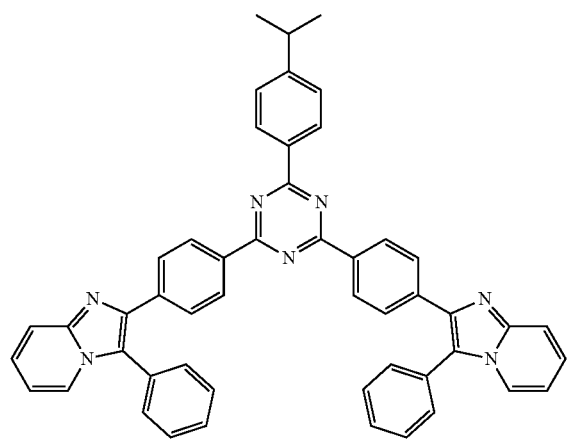
A25
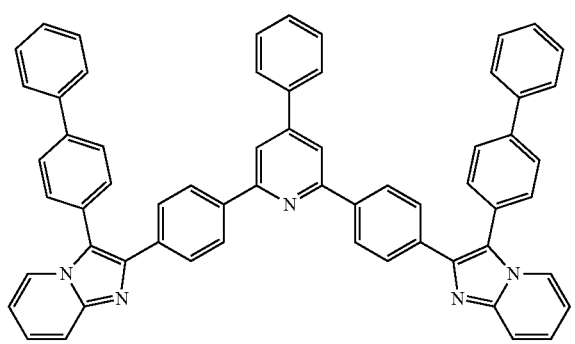
A26
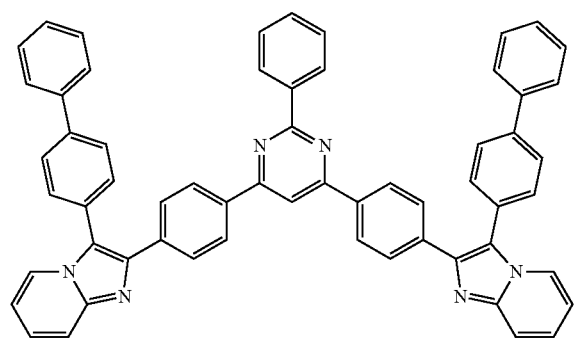
A27
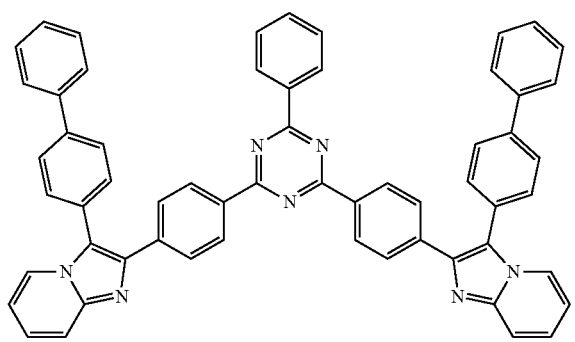

-continued
A28
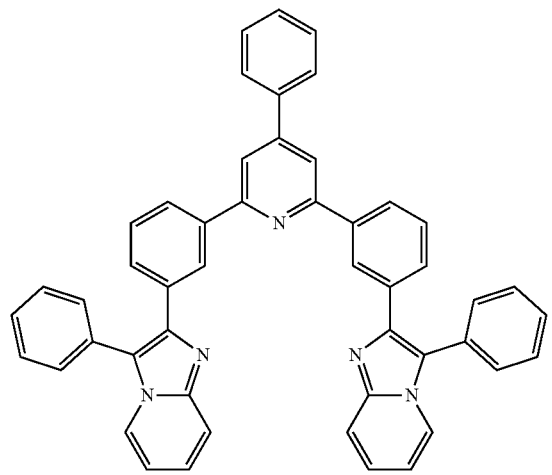
A29
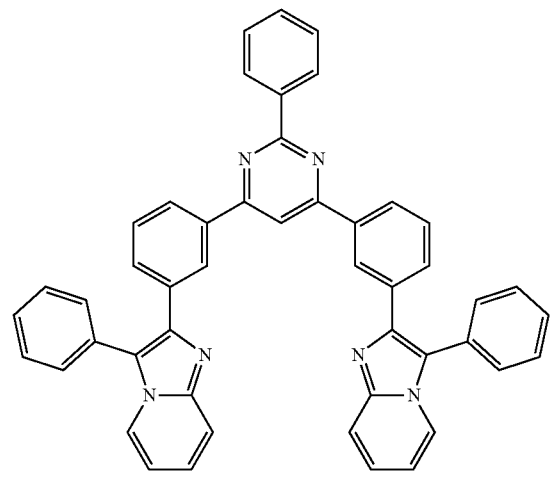
A30
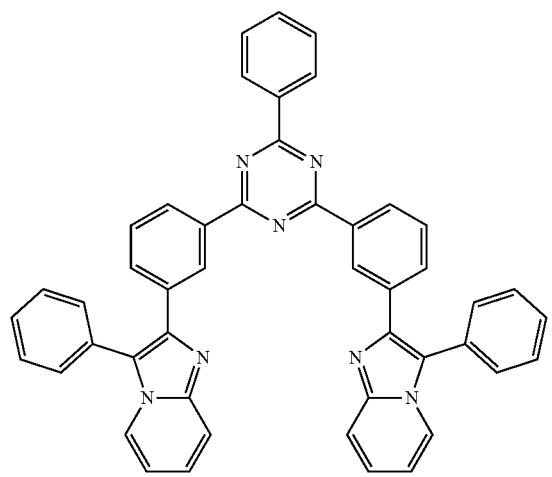
A31
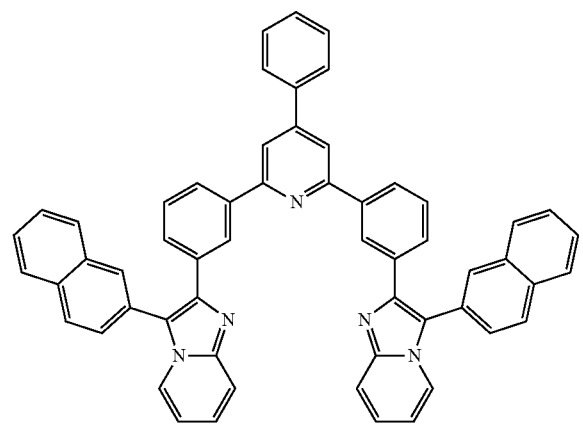
A32
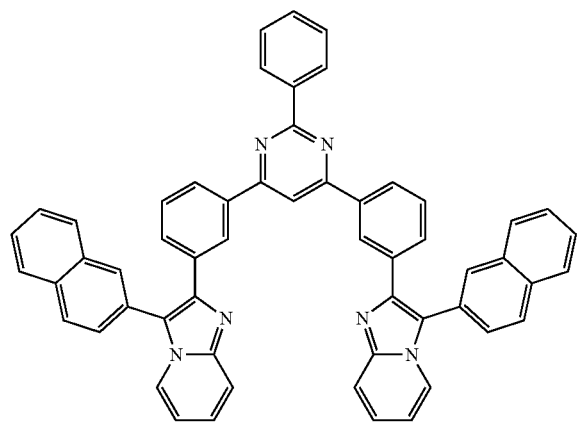
A33
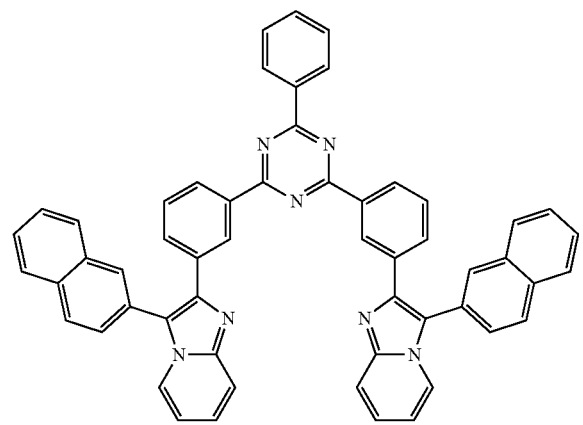

-continued
A34
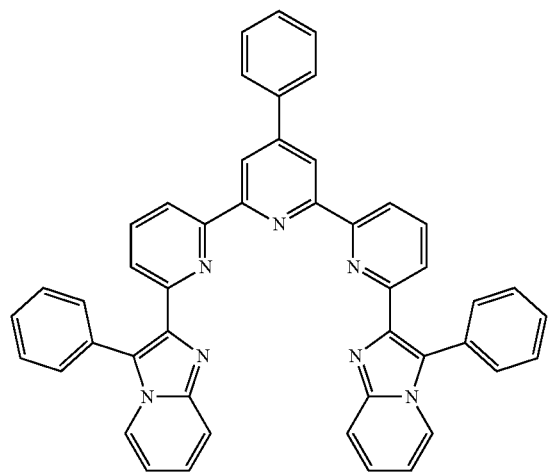
A35
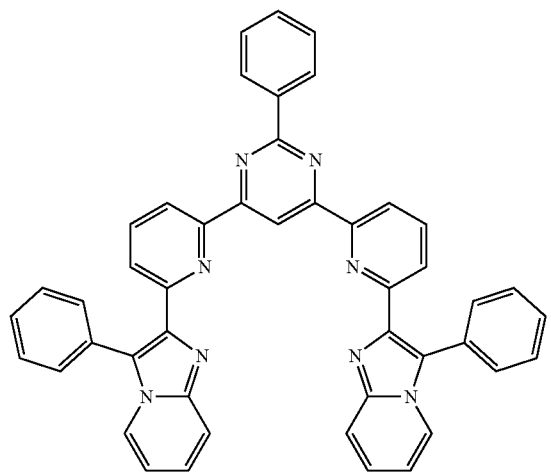
A36
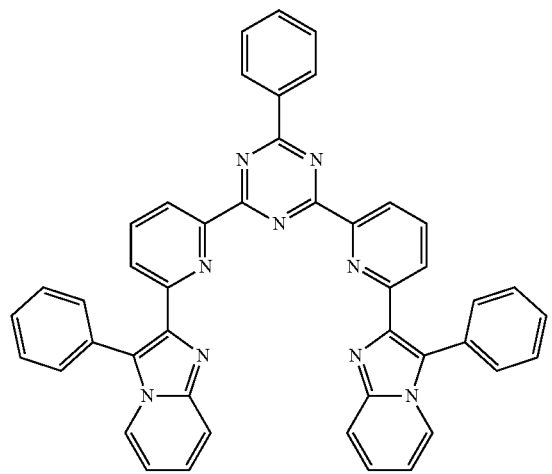
A37
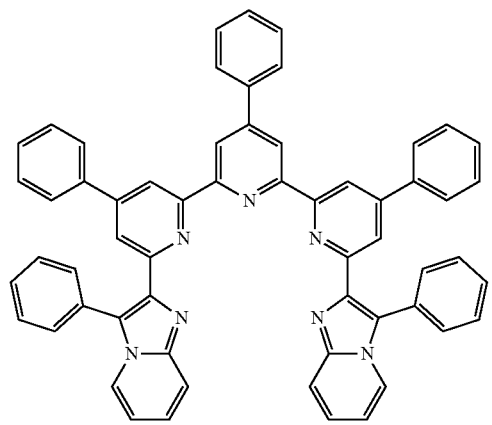
A38
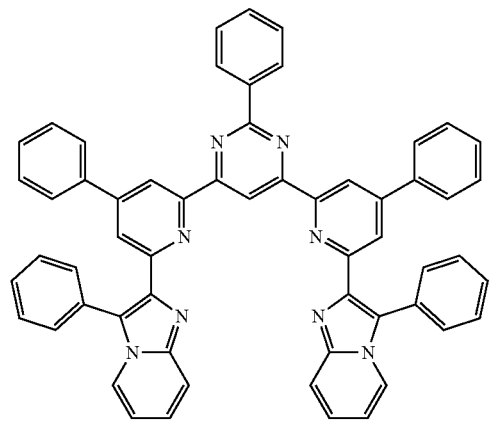
A39
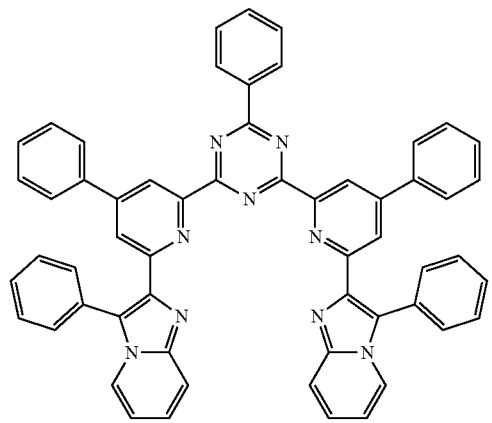

-continued
A40
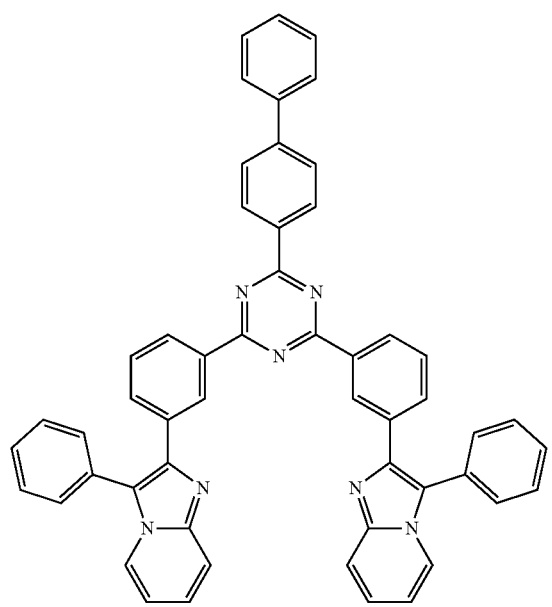
A41
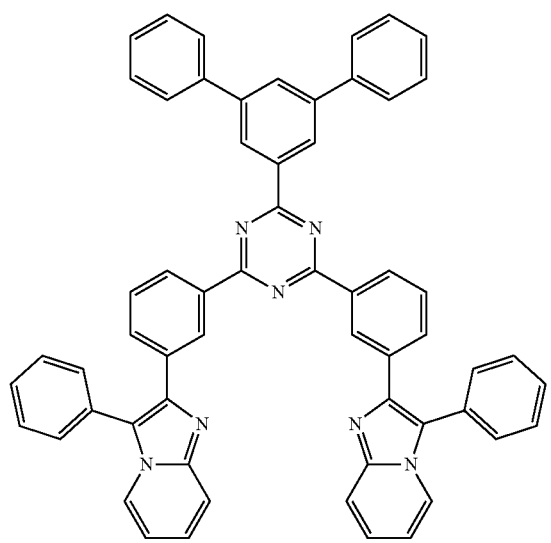
A42
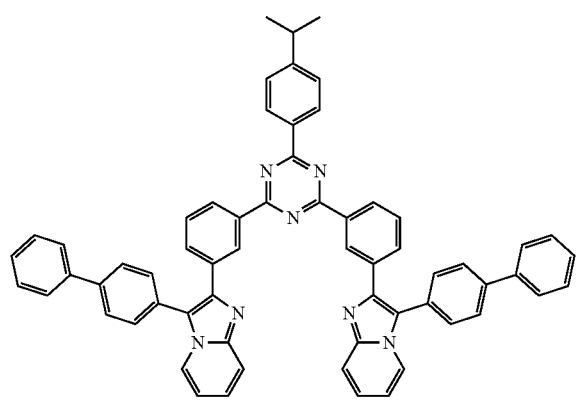
A43
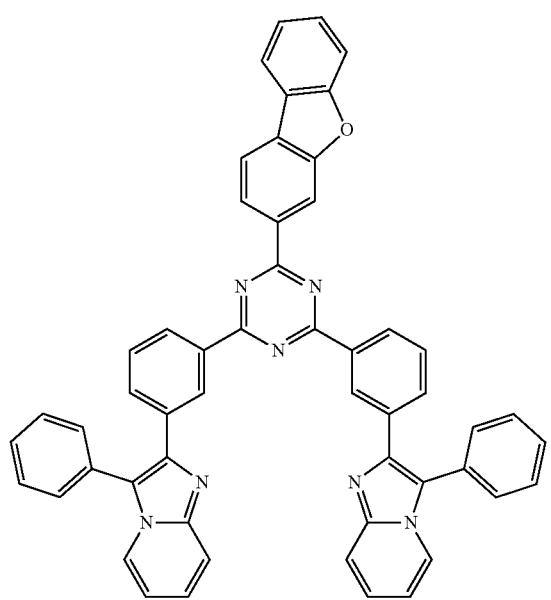

-continued
A44
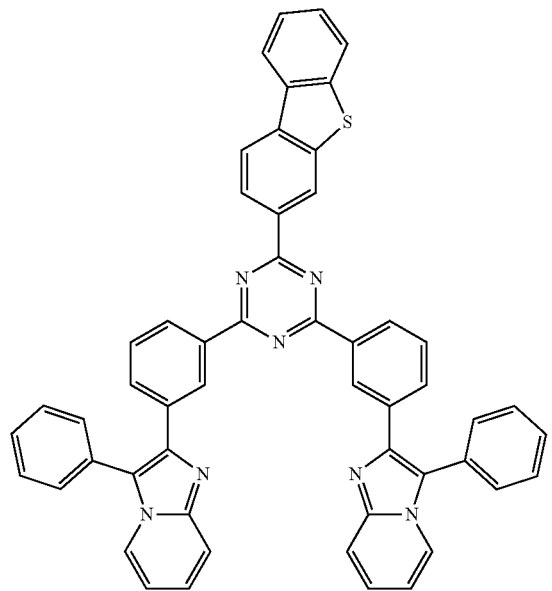
A45
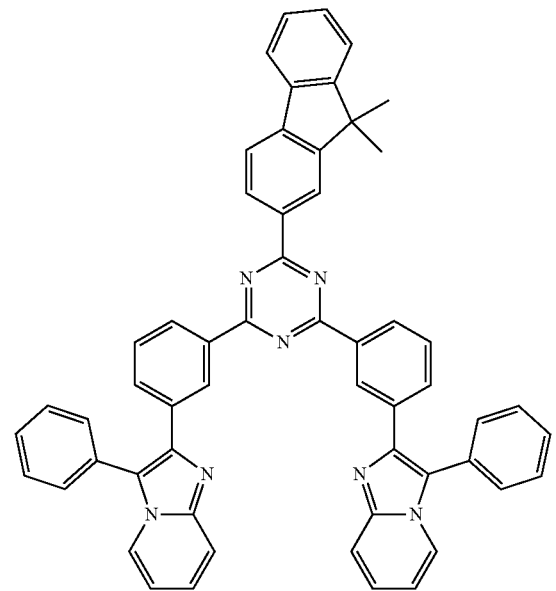
A46
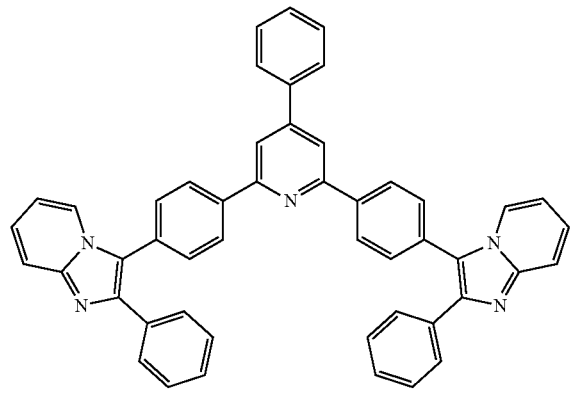
A47
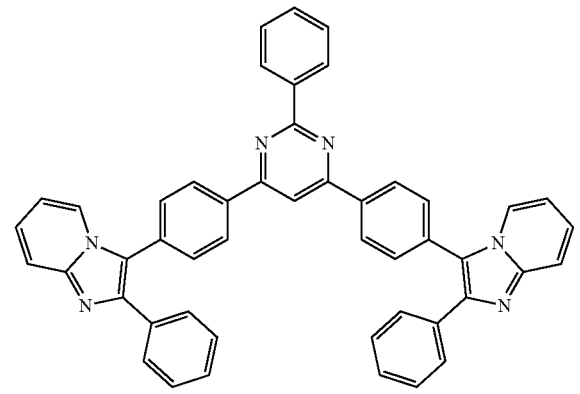
A48
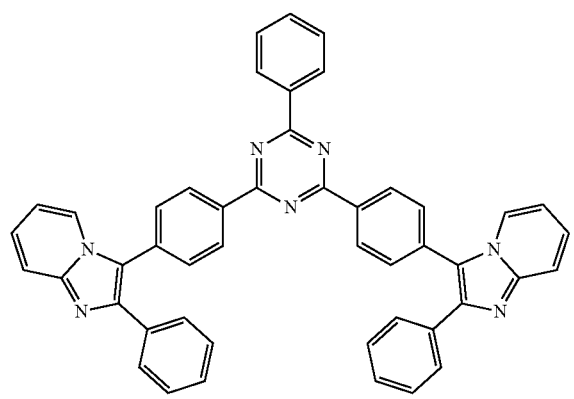
A49
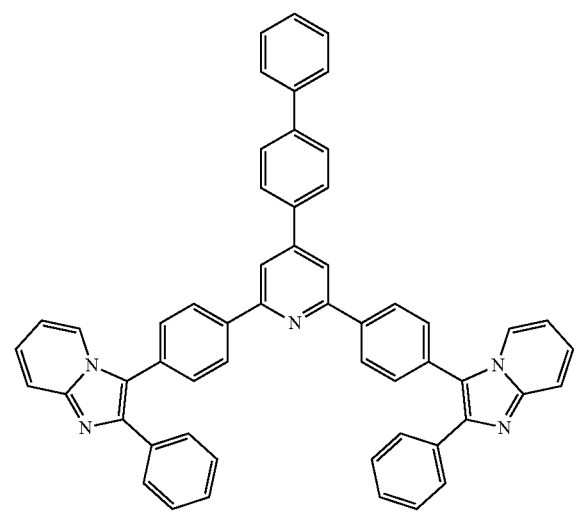

-continued
A50
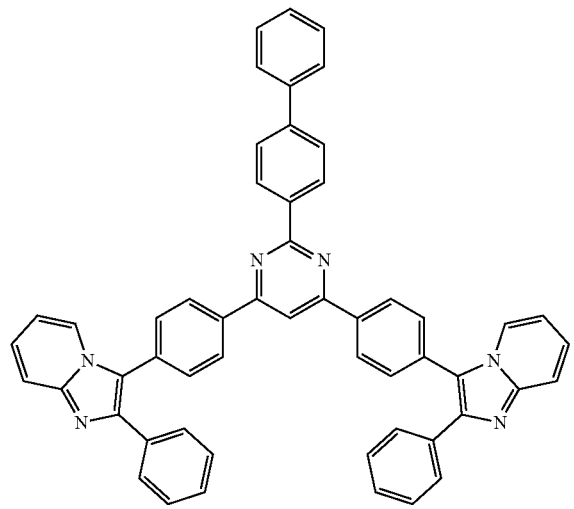
A51
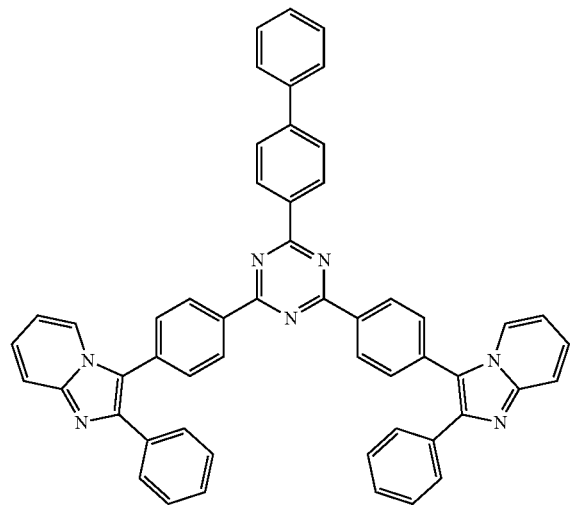
A52
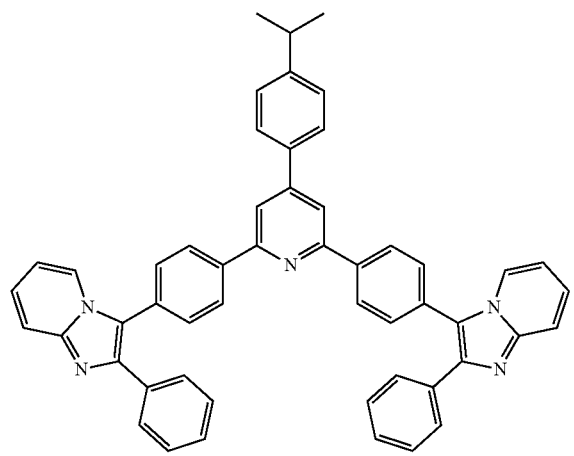
A53
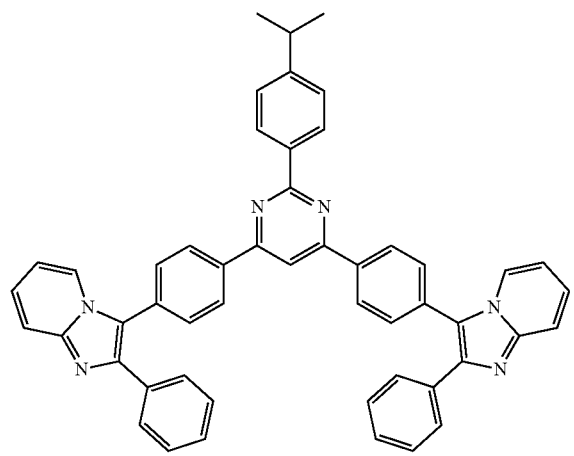
A54
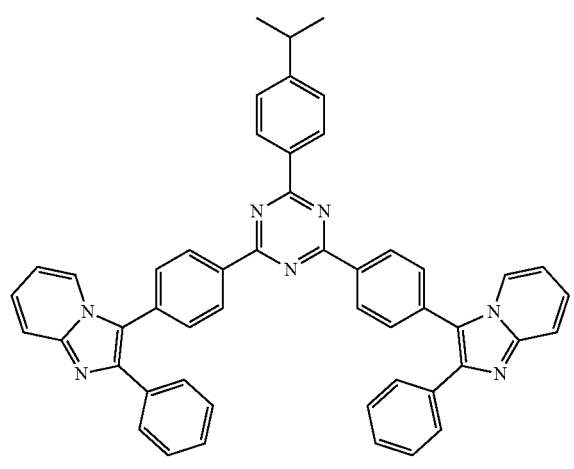
A55
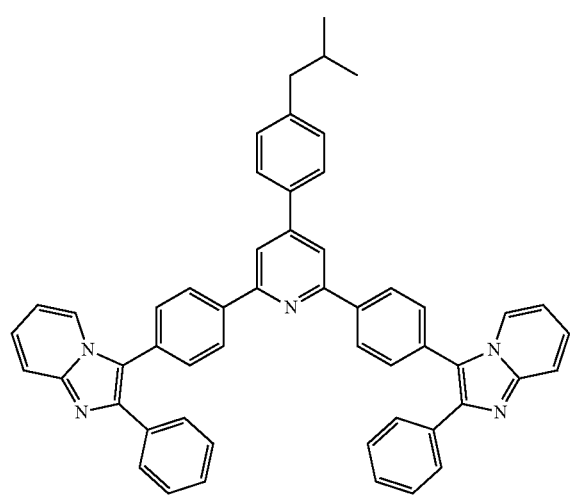

-continued
A56
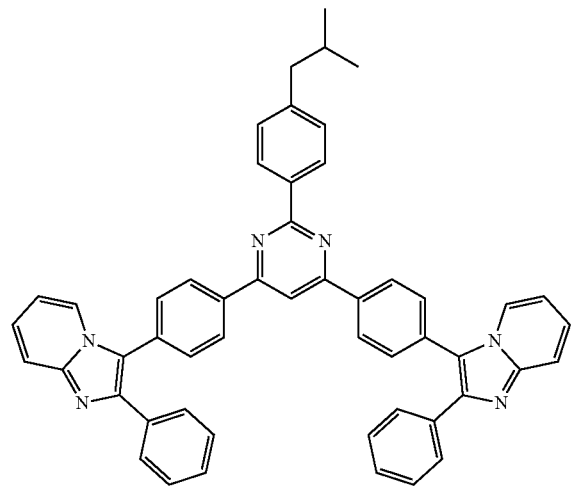
A57
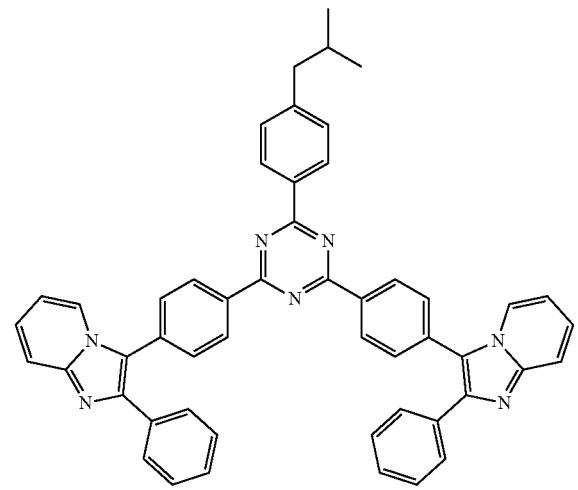
A58
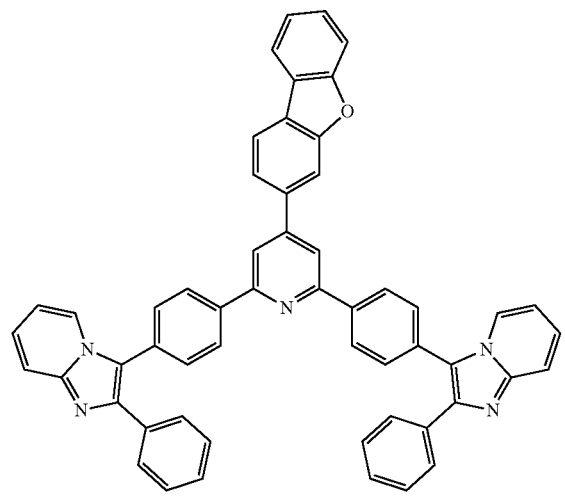
A59
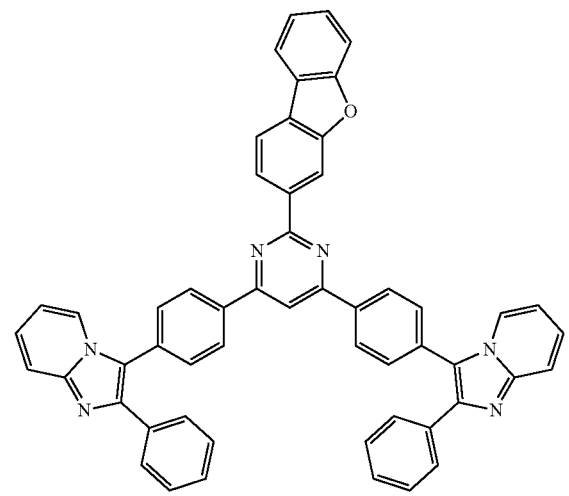
A60
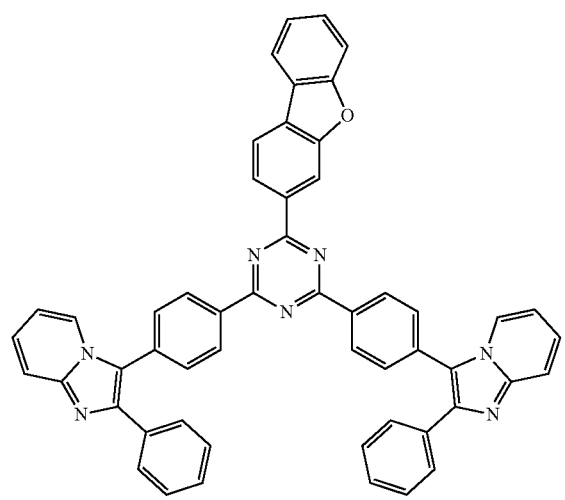
A61
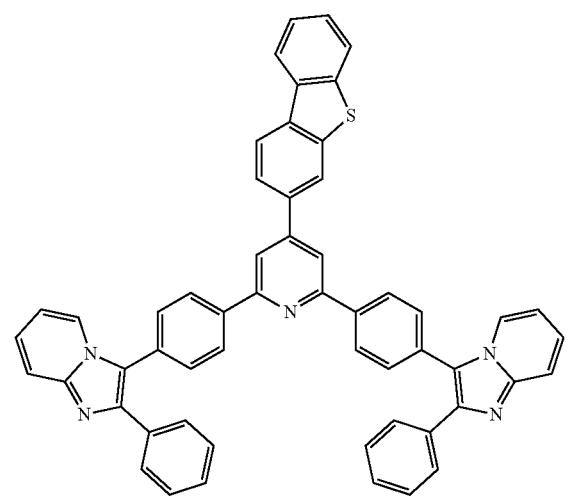

-continued
A62
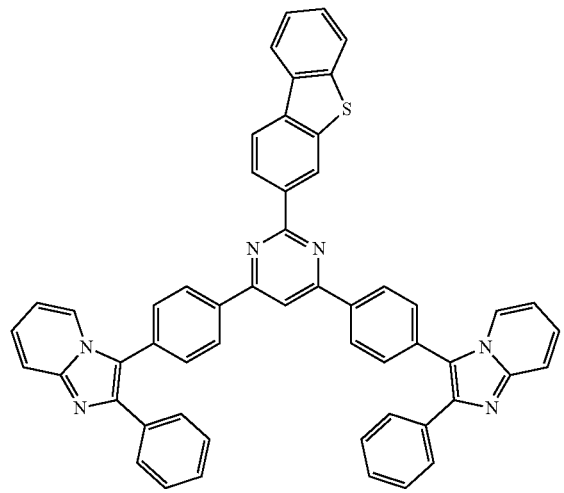
A63
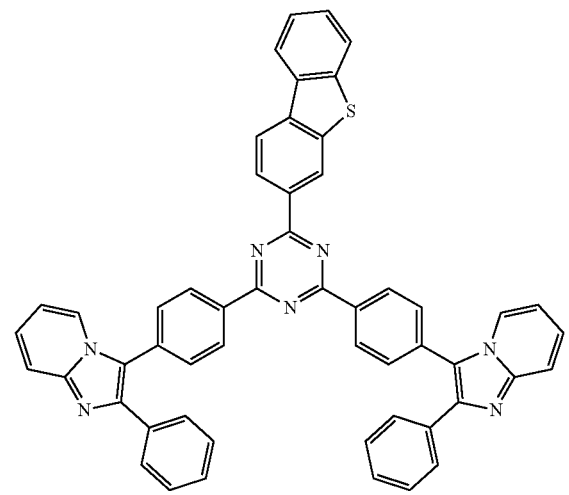
A64
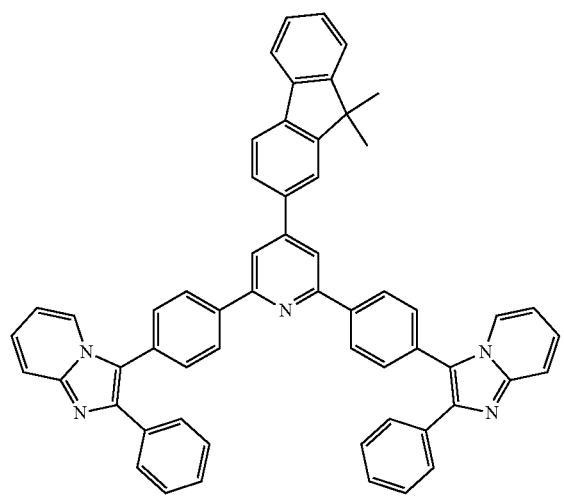
A65
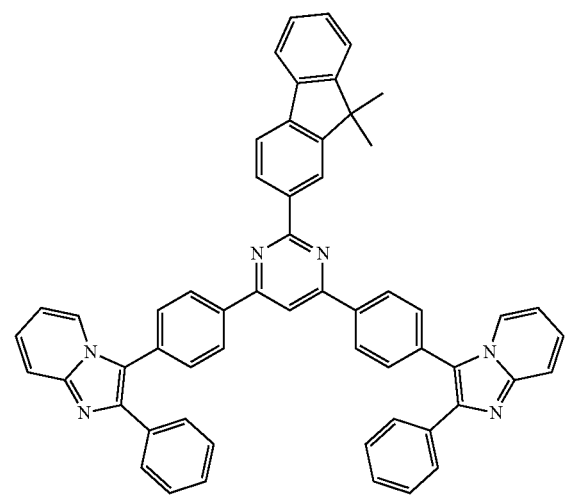
A66
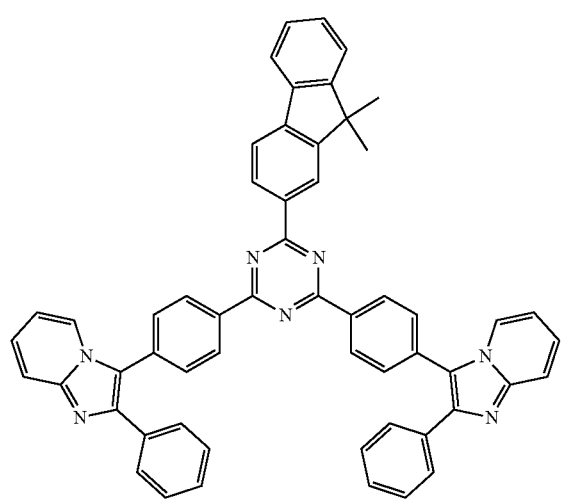
A67
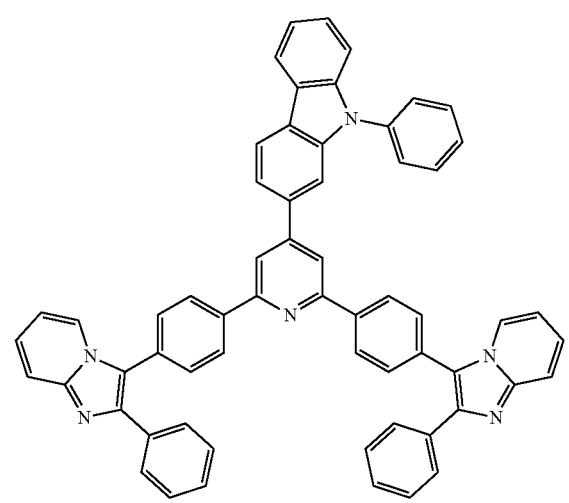

-continued
A68
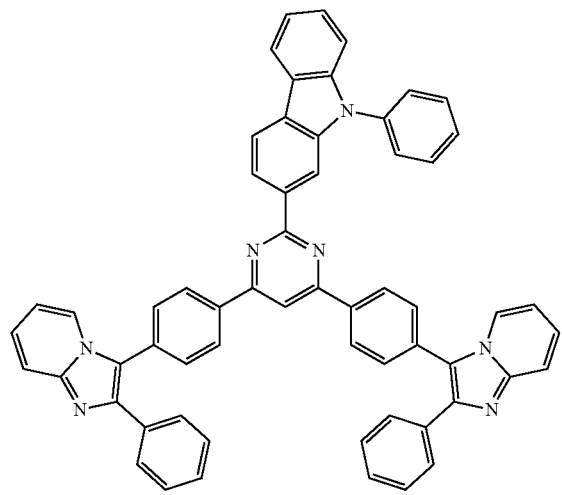
A69
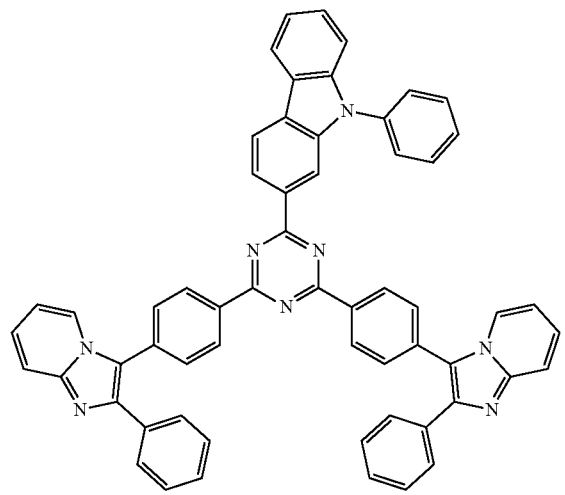
A70
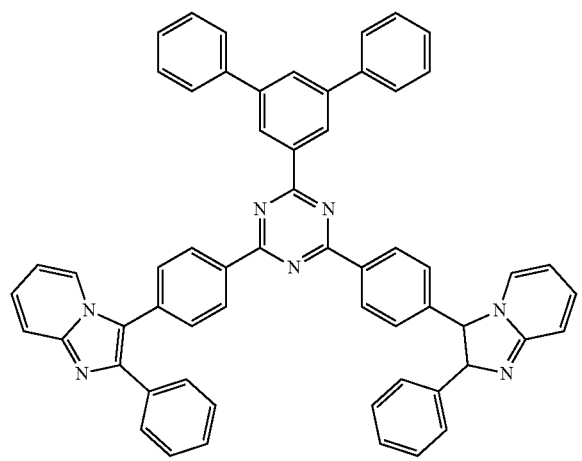
A71
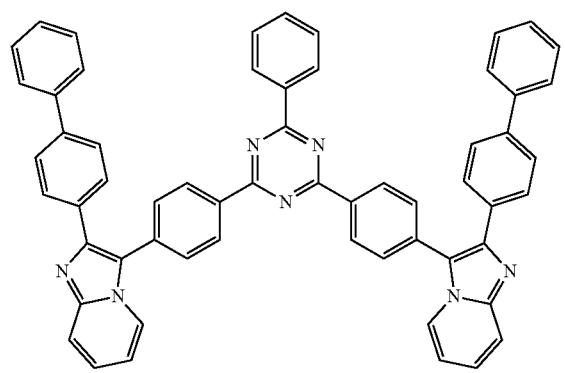
A72
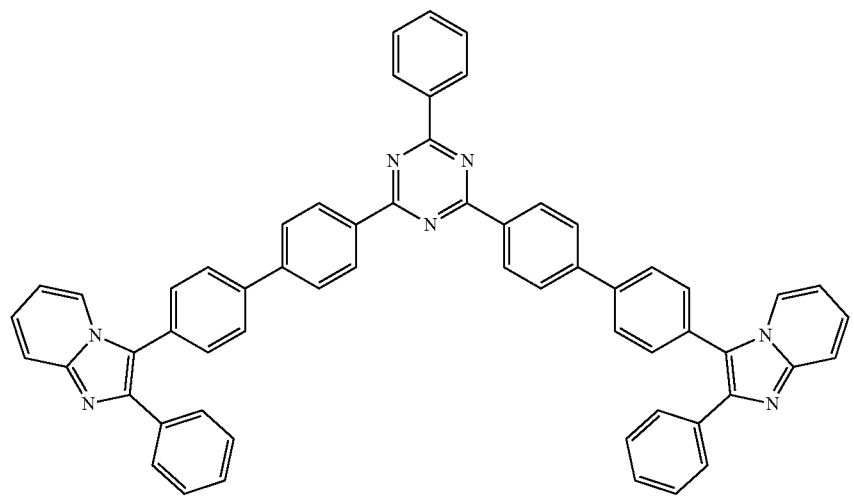

-continued
A73
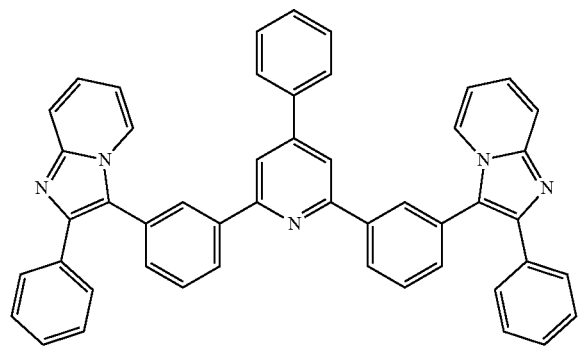
A74
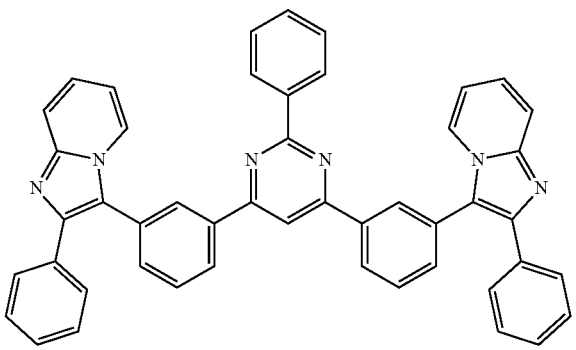
A75
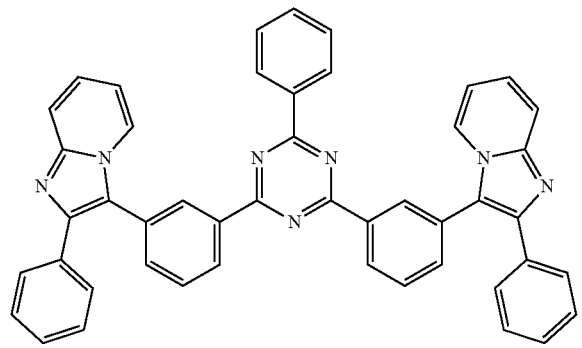
A76
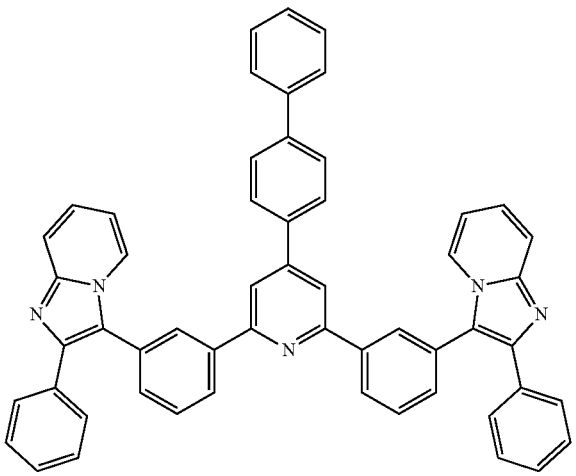
A77
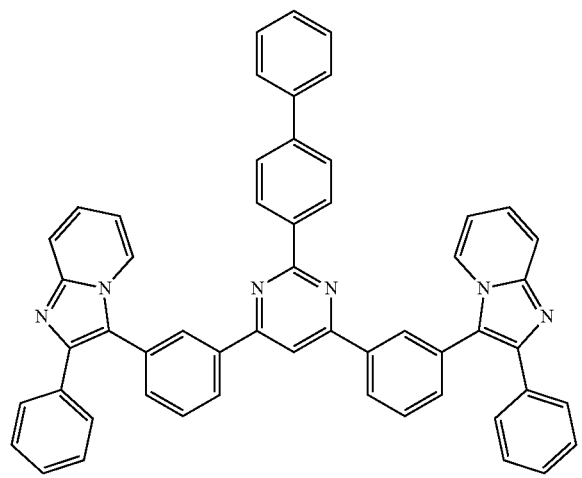
A78
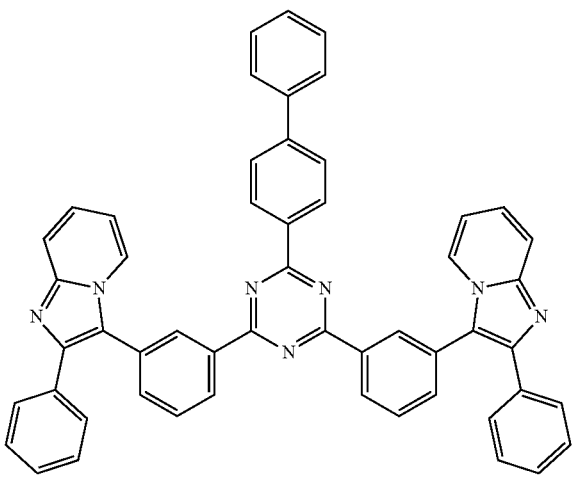

-continued
A79
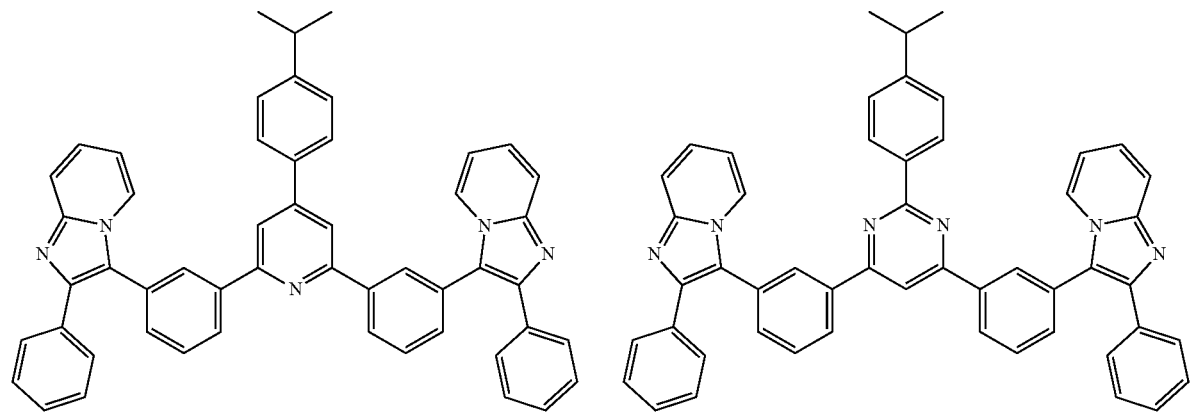
A80
A81
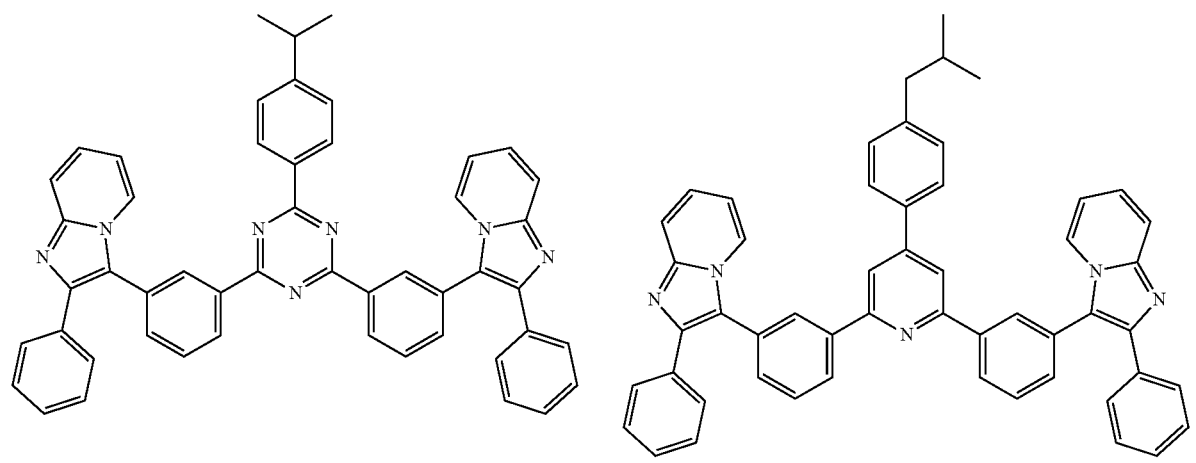
A82
A83
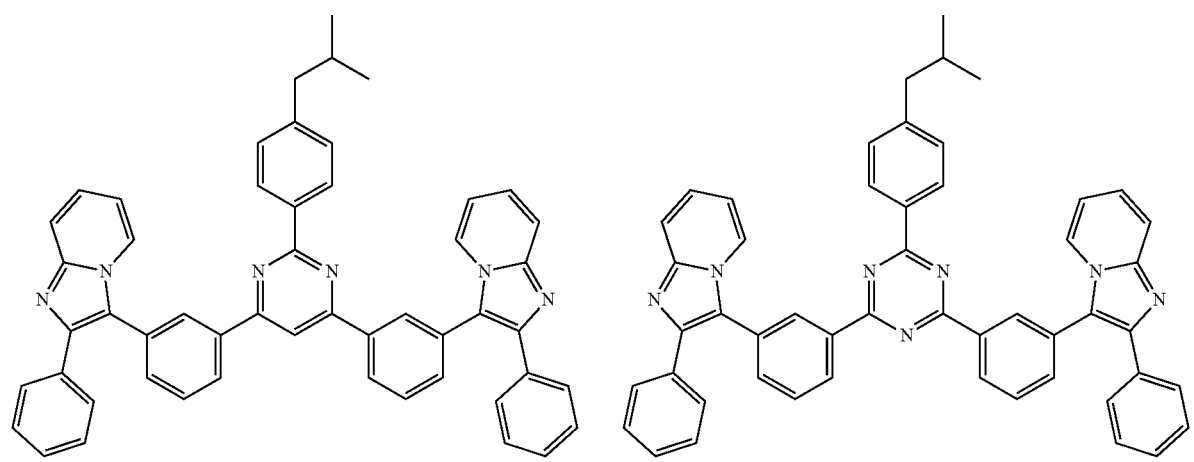
A84

-continued
A85 A86
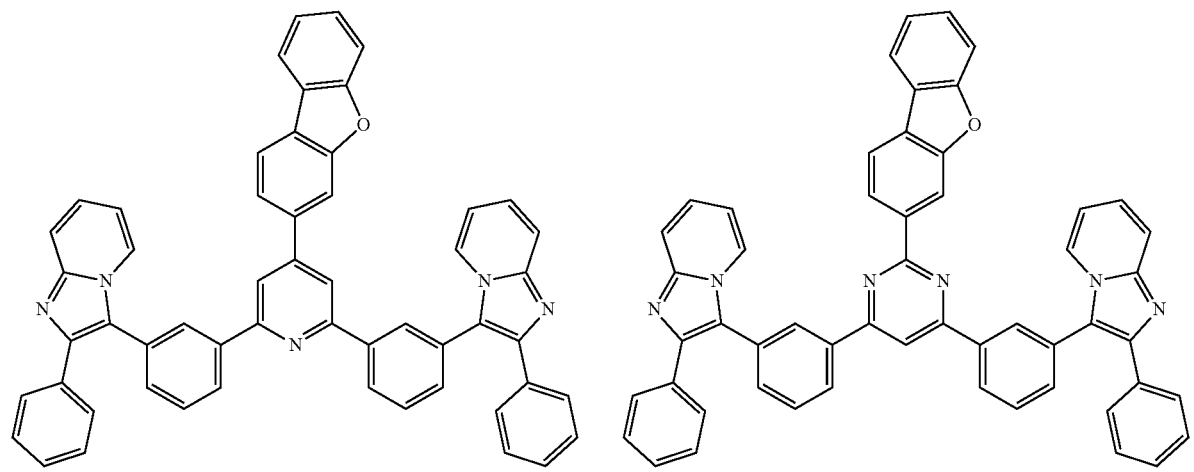
A87 A88
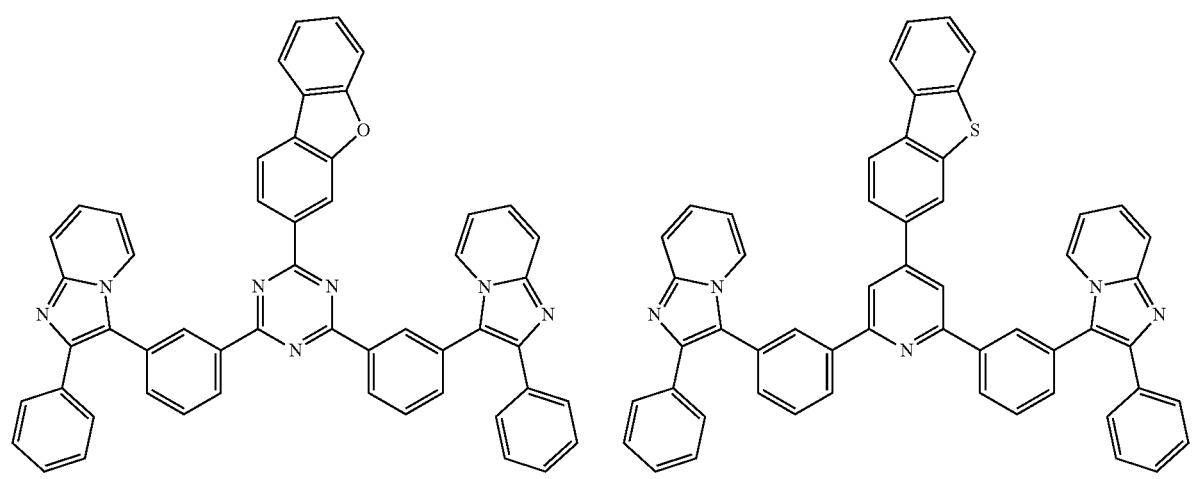
A89 A90
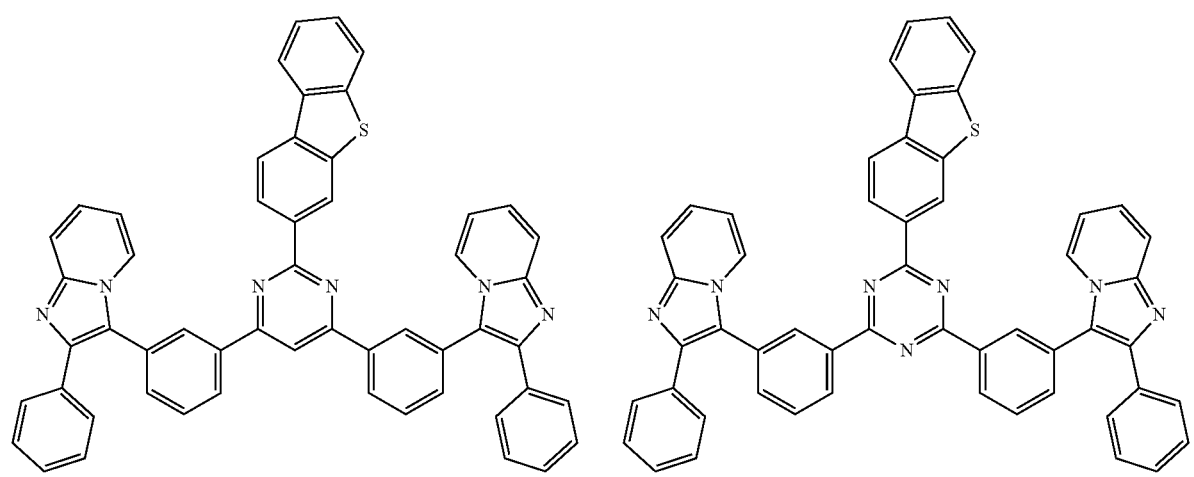

-continued
A91
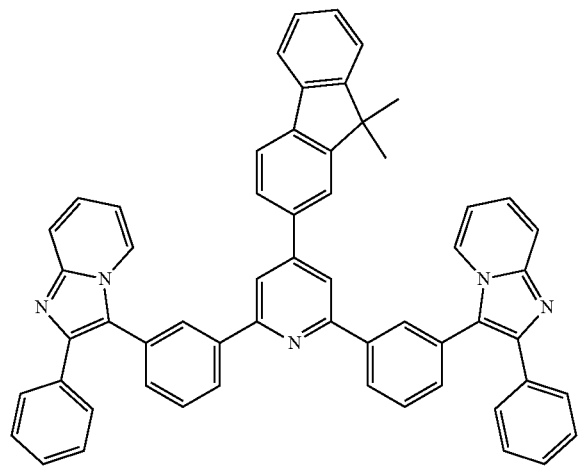
A92
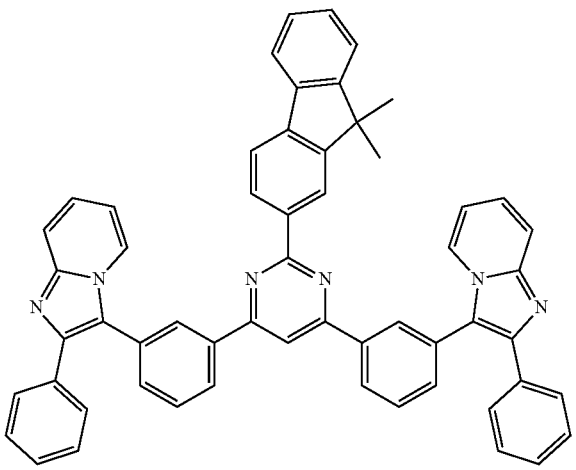
A93
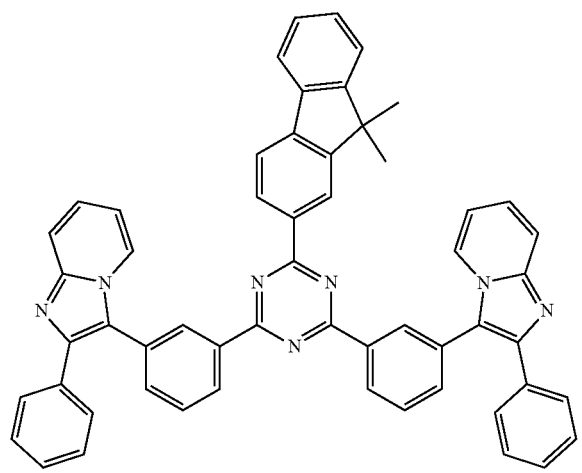
A94
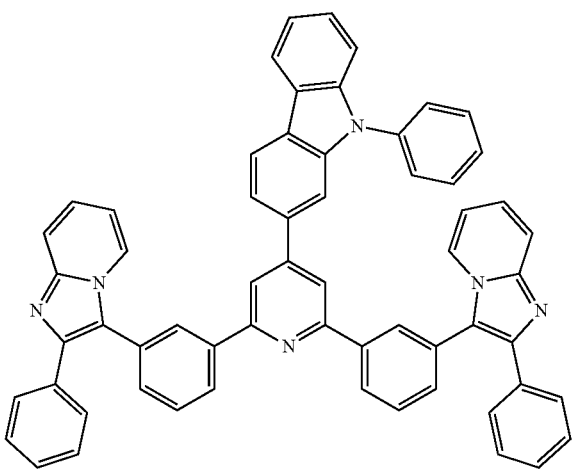
A95
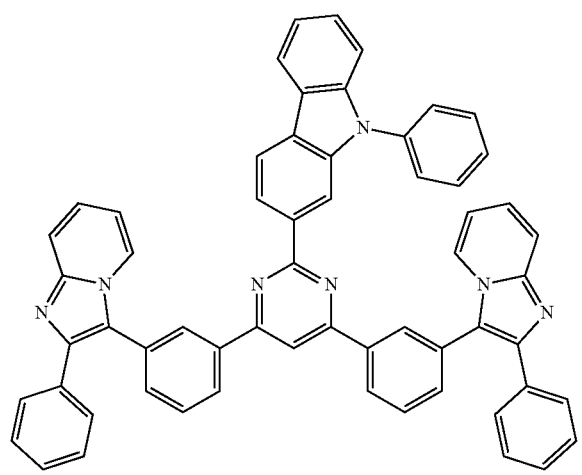
A96
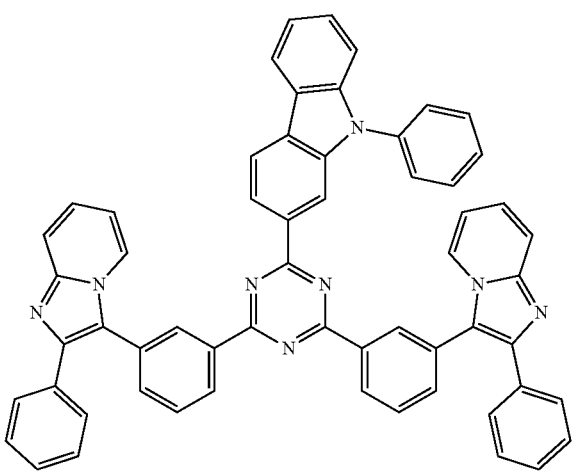

-continued

A97

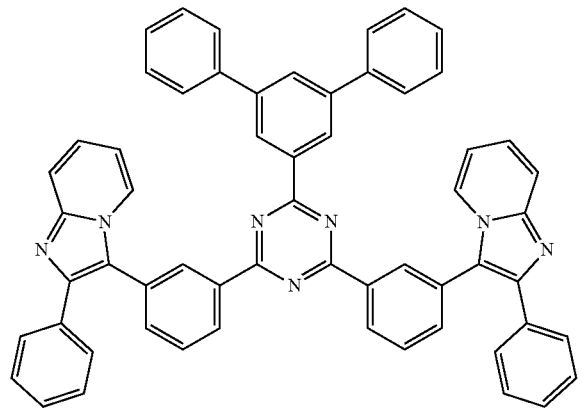

A98

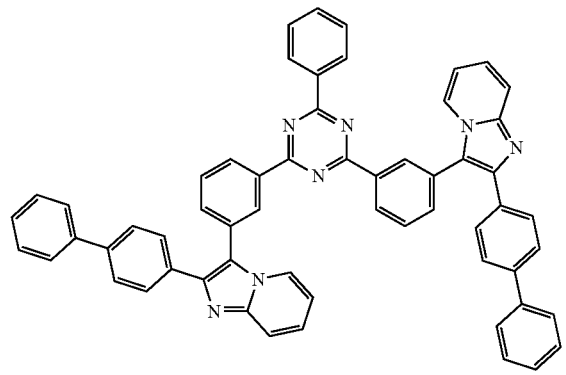

A99

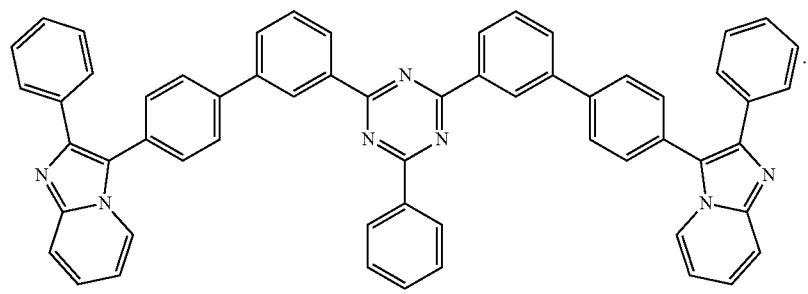

8. The compound according to claim 1, wherein X1, X2 and X3 are represented as N.

9. The compound according to claim 8, wherein R1 is a single bond, C1-C30 alkyl substituted or non-substituted C6-C30 non-fused ring aryl, C1-C30 substituted or non-substituted C3-C27 non-fused ring heteroaryl; R2 is C1-C30 substituted or non-substituted C6-C60 aryl, C1-C30 substituted or non-substituted C1-C60 heteroaryl; R3 and R4 are hydrogen, deuterium, halogen, alkyl, heteroalkyl, cycloalkyl, C1-C30 substituted or non-substituted C6-C60 aryl, C1-C30 substituted or non-substituted C1-C60 heteroaryl, substituted or non-substituted monocyclic or polycyclic C3-C60 aliphatic ring or aromatic ring, and at least one of R3 and R4 is C1-C30 substituted or non-substituted C6-C60 aryl, C1-C30 substituted or non-substitute C1-C60 heteroaryl or substituted or non-substitute monocyclic or polycyclic C3-C60 aliphatic ring or aromatic ring.

10. The compound according to claim 9, wherein R1 is a single bond, C1-C4 alkyl substituted or non-substituted C6-C18 non-fused ring aryl, C1-C4 substituted or non-substituted C3-C15 non-fused ring heteroaryl; R2 is C1-C4 substituted or non-substituted C6-C18 aryl, C1-C4 substituted or non-substituted C3-C15 heteroaryl; R3 and R4 are hydrogen, deuterium, halogen, alkyl, C1-C4 substituted or non-substituted C6-C18 aryl, C1-C4 substituted or non-substituted C3-C15 heteroaryl, substituted or non-substituted monocyclic or polycyclic C3-C18 aliphatic ring or aromatic ring, and R3 and R4 are different.

11. The compound according to claim 10, wherein R1 is a single bond, C6-C18 non-fused ring aryl or C3-C15 non-fused ring heteroaryl; and R2 is C6-C18 aryl or C3-C15 heteroaryl.

12. The compound according to claim 11, being one of the following compounds:

B 1

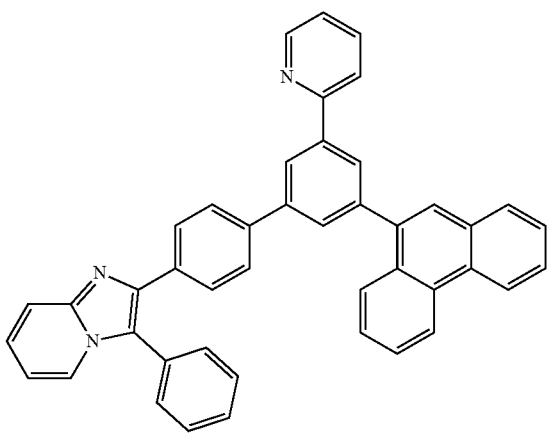 [SMILES: c1ccc(-c2c(-c3ccc(-c4cc(-c5ccccn5)cc(-c5cc6ccccc6c6ccccc56)c4)cc3)nc3ccccn23)cc1]

B 2
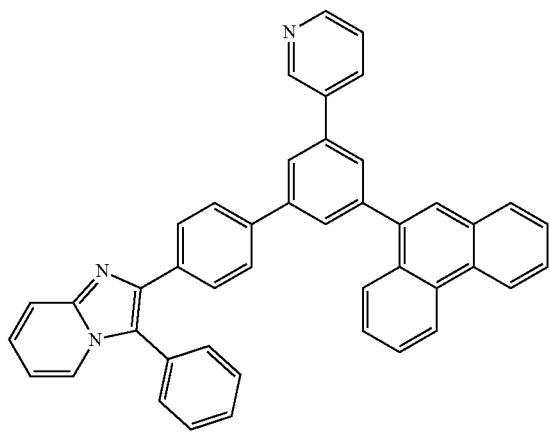 [SMILES: c1ccc(-c2c(-c3ccc(-c4cc(-c5cccnc5)cc(-c5cc6ccccc6c6ccccc56)c4)cc3)nc3ccccn23)cc1]
B 3
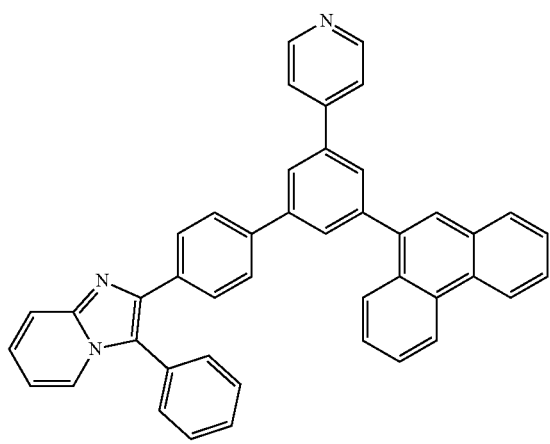 [SMILES: c1ccc(-c2c(-c3ccc(-c4cc(-c5ccncc5)cc(-c5cc6ccccc6c6ccccc56)c4)cc3)nc3ccccn23)cc1]
B 4
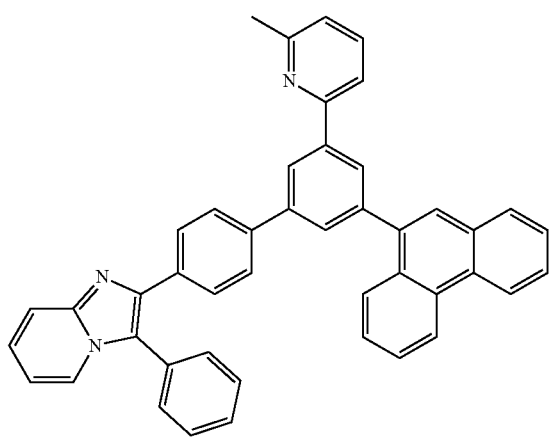 [SMILES: Cc1cccc(-c2cc(-c3ccc(-c4nc5ccccn5c4-c4ccccc4)cc3)cc(-c3cc4ccccc4c4ccccc34)c2)n1]

-continued
B 5
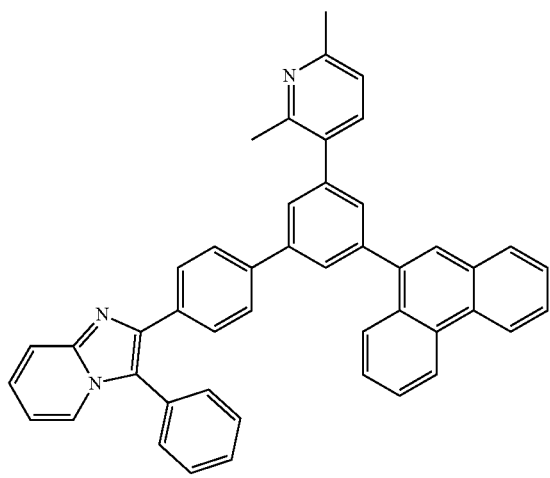 [SMILES: Cc1ccc(-c2cc(-c3ccc(-c4nc5ccccn5c4-c4ccccc4)cc3)cc(-c3cc4ccccc4c4ccccc34)c2)c(C)n1]
B 6
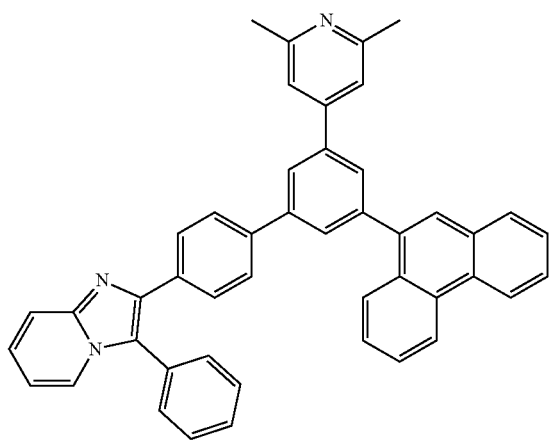 [SMILES: Cc1cc(-c2cc(-c3ccc(-c4nc5ccccn5c4-c4ccccc4)cc3)cc(-c3cc4ccccc4c4ccccc34)c2)cc(C)n1]
B 7
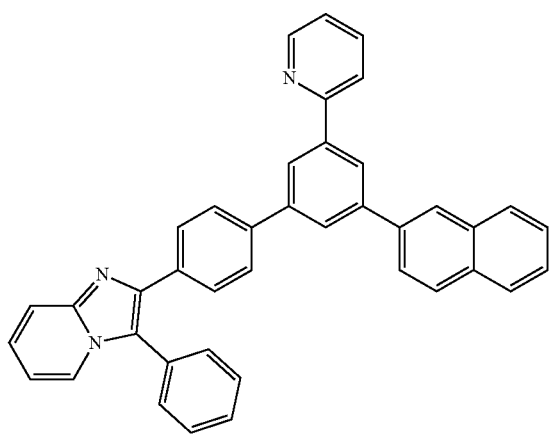 [SMILES: c1ccc(-c2c(-c3ccc(-c4cc(-c5ccc6ccccc6c5)cc(-c5ccccn5)c4)cc3)nc3ccccn23)cc1]

B 8
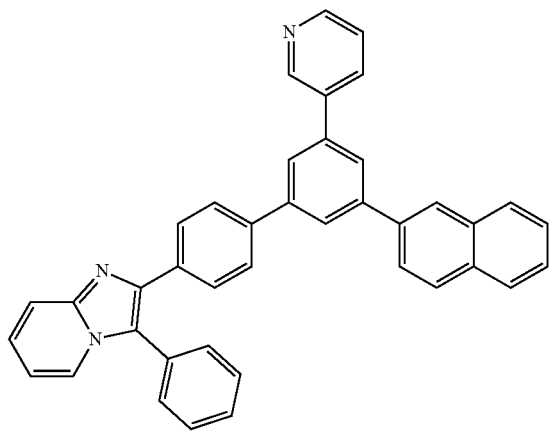 [SMILES: c1ccc(-c2c(-c3ccc(-c4cc(-c5cccnc5)cc(-c5ccc6ccccc6c5)c4)cc3)nc3ccccn23)cc1]
B 9
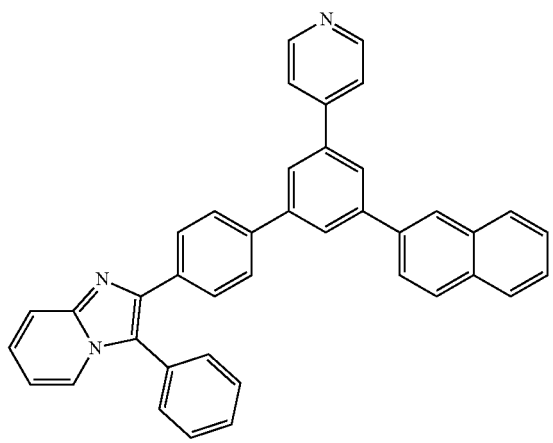 [SMILES: c1ccc(-c2c(-c3ccc(-c4cc(-c5ccncc5)cc(-c5ccc6ccccc6c5)c4)cc3)nc3ccccn23)cc1]
B 10
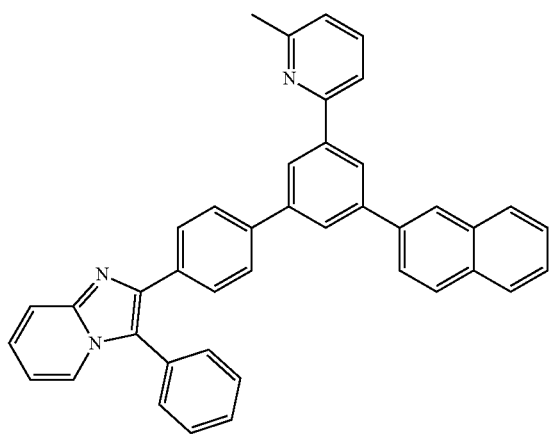 [SMILES: Cc1cccc(-c2cc(-c3ccc(-c4nc5ccccn5c4-c4ccccc4)cc3)cc(-c3ccc4ccccc4c3)c2)n1]

-continued
B 11
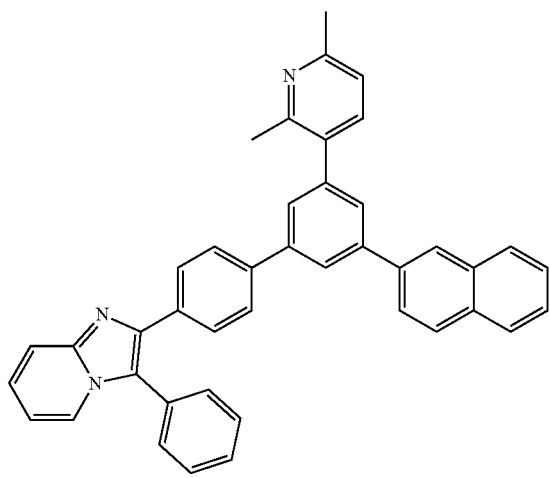 [SMILES: Cc1ccc(-c2cc(-c3ccc(-c4nc5ccccn5c4-c4ccccc4)cc3)cc(-c3ccc4ccccc4c3)c2)c(C)n1]
B 12
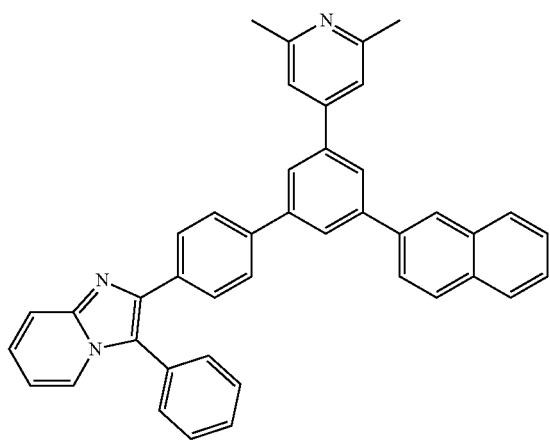 [SMILES: Cc1cc(-c2cc(-c3ccc(-c4nc5ccccn5c4-c4ccccc4)cc3)cc(-c3ccc4ccccc4c3)c2)cc(C)n1]
B 13
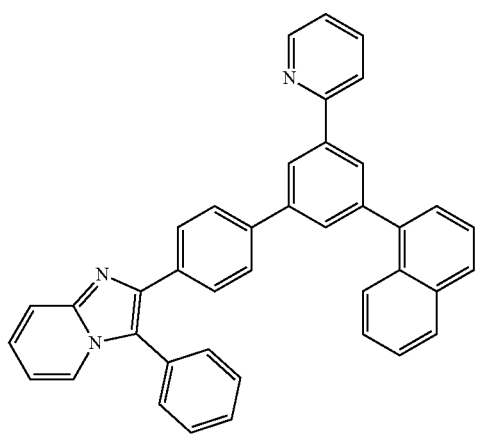 [SMILES: c1ccc(-c2c(-c3ccc(-c4cc(-c5ccccn5)cc(-c5cccc6ccccc56)c4)cc3)nc3ccccn23)cc1]

B 14
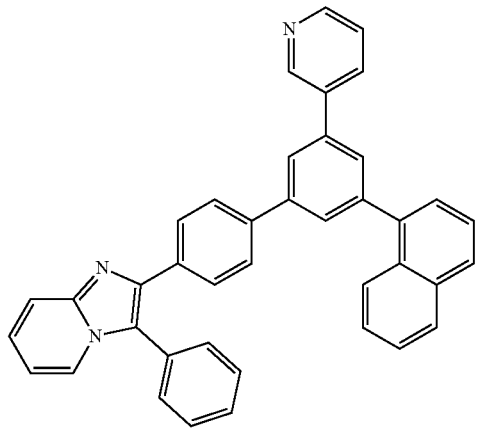 [SMILES: c1ccc(-c2c(-c3ccc(-c4cc(-c5cccnc5)cc(-c5cccc6ccccc56)c4)cc3)nc3ccccn23)cc1]
B 15
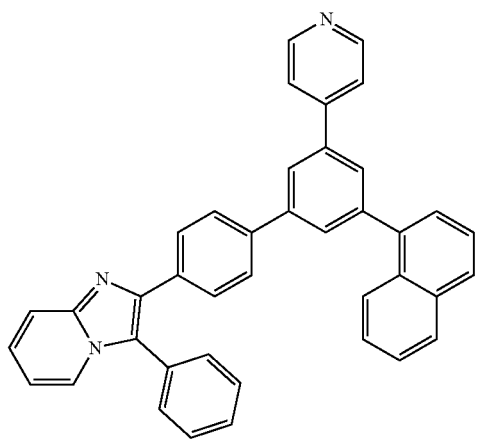 [SMILES: c1ccc(-c2c(-c3ccc(-c4cc(-c5ccncc5)cc(-c5cccc6ccccc56)c4)cc3)nc3ccccn23)cc1]
B 16
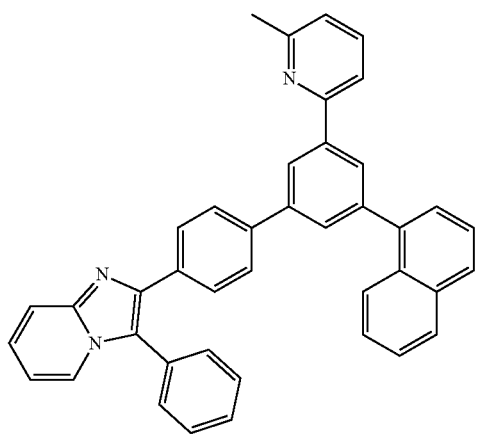 [SMILES: Cc1cccc(-c2cc(-c3ccc(-c4nc5ccccn5c4-c4ccccc4)cc3)cc(-c3cccc4ccccc34)c2)n1]

-continued
B 17
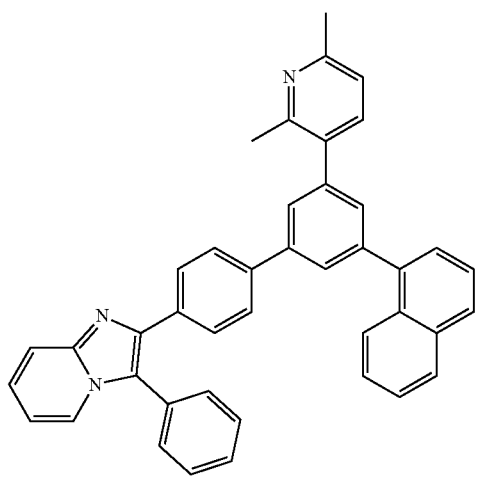 [SMILES: Cc1ccc(-c2cc(-c3ccc(-c4nc5ccccn5c4-c4ccccc4)cc3)cc(-c3cccc4ccccc34)c2)c(C)n1]
B 18
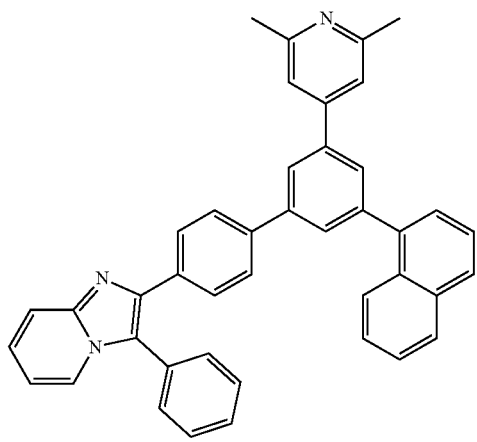 [SMILES: Cc1cc(-c2cc(-c3ccc(-c4nc5ccccn5c4-c4ccccc4)cc3)cc(-c3cccc4ccccc34)c2)cc(C)n1]
B 19
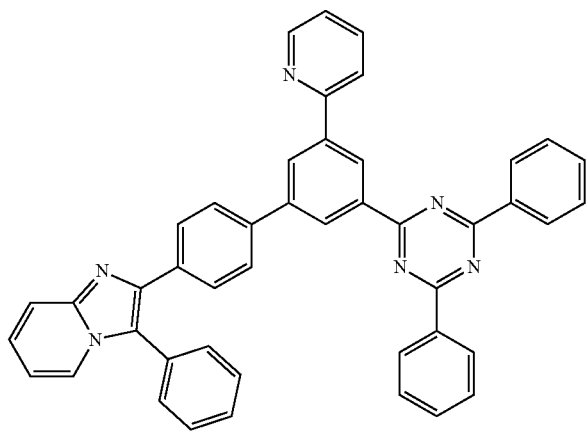 [SMILES: c1ccc(-c2nc(-c3ccccc3)nc(-c3cc(-c4ccc(-c5nc6ccccn6c5-c5ccccc5)cc4)cc(-c4ccccn4)c3)n2)cc1]

-continued
B 20
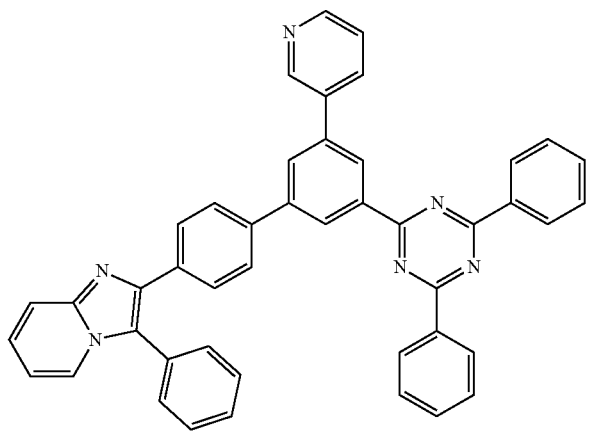 [SMILES: c1ccc(-c2nc(-c3ccccc3)nc(-c3cc(-c4ccc(-c5nc6ccccn6c5-c5ccccc5)cc4)cc(-c4cccnc4)c3)n2)cc1]
B 21
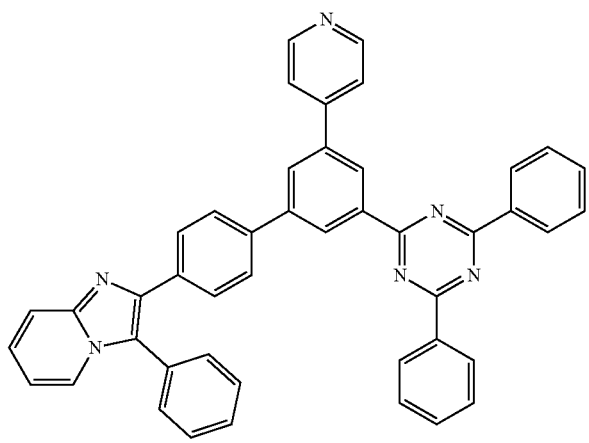 [SMILES: c1ccc(-c2nc(-c3ccccc3)nc(-c3cc(-c4ccncc4)cc(-c4ccc(-c5nc6ccccn6c5-c5ccccc5)cc4)c3)n2)cc1]
B 22
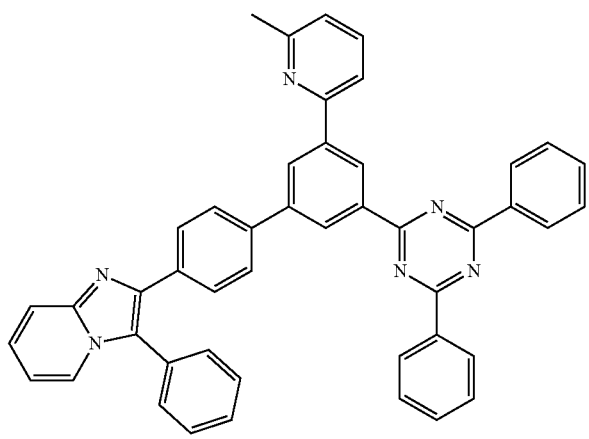 [SMILES: Cc1cccc(-c2cc(-c3ccc(-c4nc5ccccn5c4-c4ccccc4)cc3)cc(-c3nc(-c4ccccc4)nc(-c4ccccc4)n3)c2)n1]

-continued
B 23
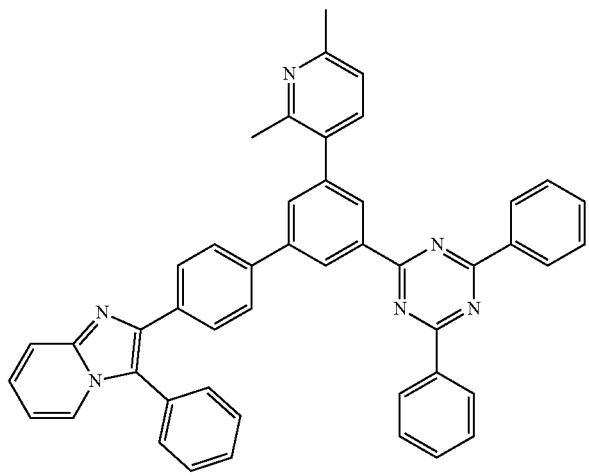 [SMILES: Cc1ccc(-c2cc(-c3ccc(-c4nc5ccccn5c4-c4ccccc4)cc3)cc(-c3nc(-c4ccccc4)nc(-c4ccccc4)n3)c2)c(C)n1]
B 24
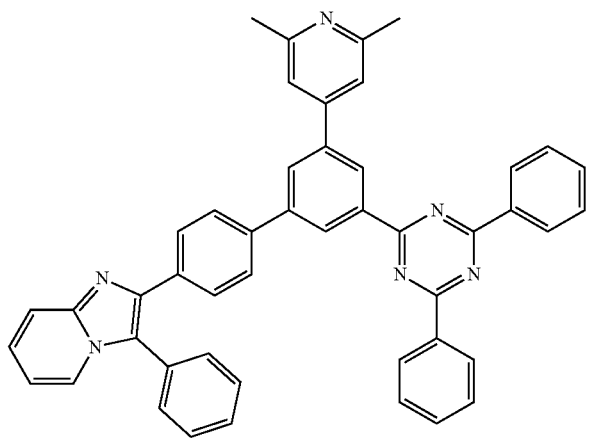 [SMILES: Cc1cc(-c2cc(-c3ccc(-c4nc5ccccn5c4-c4ccccc4)cc3)cc(-c3nc(-c4ccccc4)nc(-c4ccccc4)n3)c2)cc(C)n1]
B 25
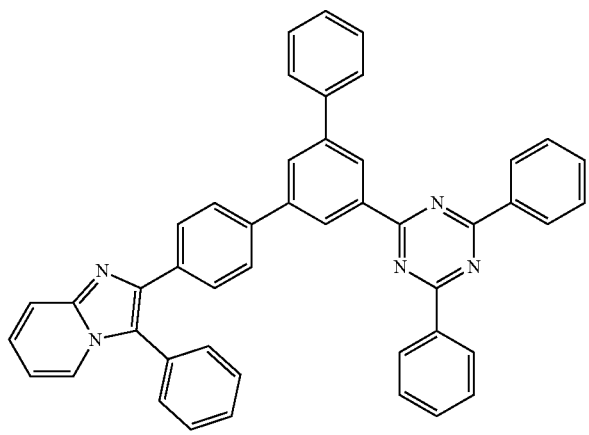 [SMILES: c1ccc(-c2cc(-c3ccc(-c4nc5ccccn5c4-c4ccccc4)cc3)cc(-c3nc(-c4ccccc4)nc(-c4ccccc4)n3)c2)cc1]

B 26
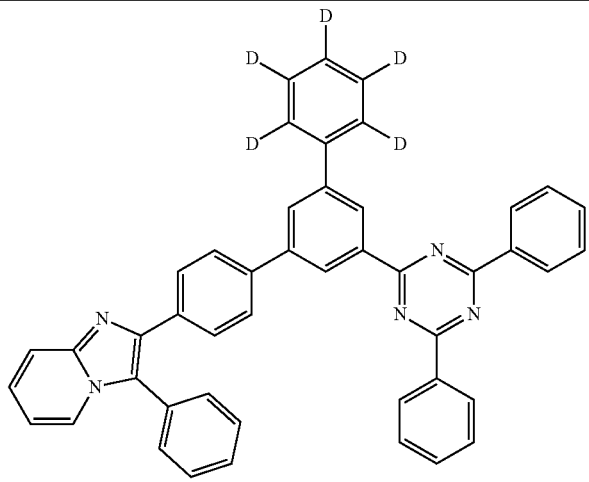
B 27
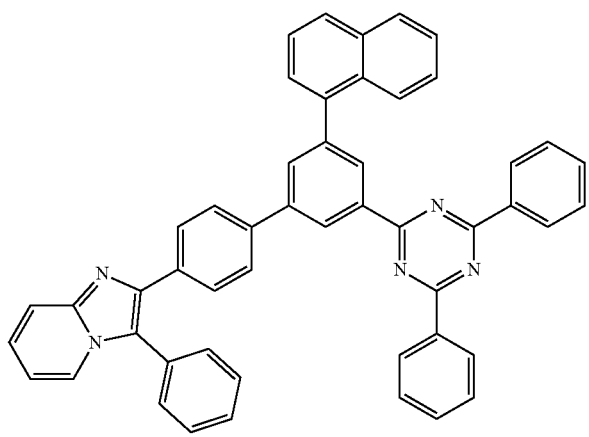 [SMILES: c1ccc(-c2nc(-c3ccccc3)nc(-c3cc(-c4ccc(-c5nc6ccccn6c5-c5ccccc5)cc4)cc(-c4cccc5ccccc45)c3)n2)cc1]
B 28
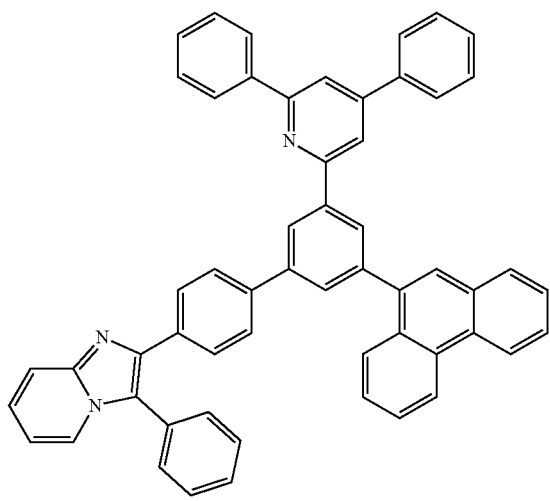 [SMILES: c1ccc(-c2cc(-c3ccccc3)nc(-c3cc(-c4ccc(-c5nc6ccccn6c5-c5ccccc5)cc4)cc(-c4cc5ccccc5c5ccccc45)c3)c2)cc1]

-continued
B 29
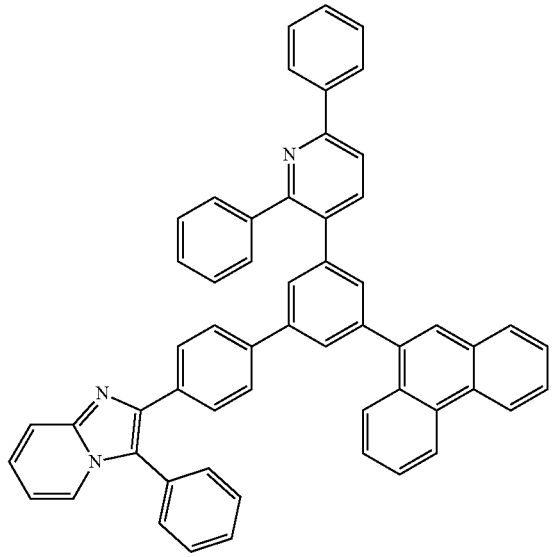 [SMILES: c1ccc(-c2ccc(-c3cc(-c4ccc(-c5nc6ccccn6c5-c5ccccc5)cc4)cc(-c4cc5ccccc5c5ccccc45)c3)c(-c3ccccc3)n2)cc1]
B 30
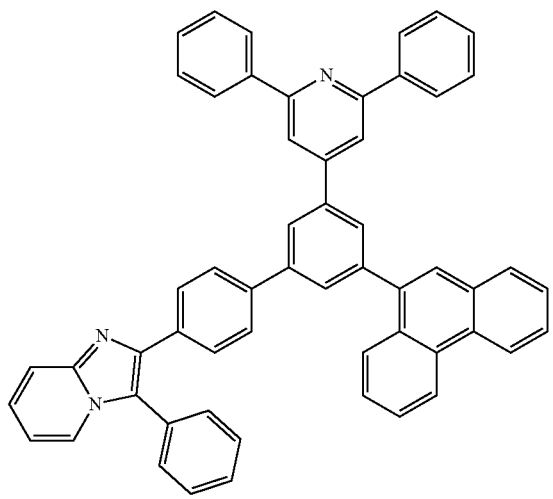 [SMILES: c1ccc(-c2cc(-c3cc(-c4ccc(-c5nc6ccccn6c5-c5ccccc5)cc4)cc(-c4cc5ccccc5c5ccccc45)c3)cc(-c3ccccc3)n2)cc1]
B 31
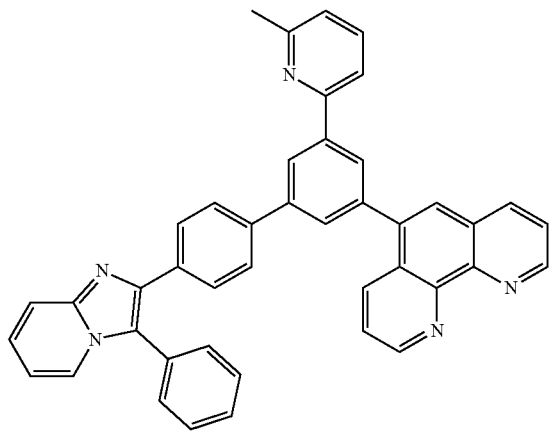 [SMILES: Cc1cccc(-c2cc(-c3ccc(-c4nc5ccccn5c4-c4ccccc4)cc3)cc(-c3cc4cccnc4c4ncccc34)c2)n1]

-continued
B 32
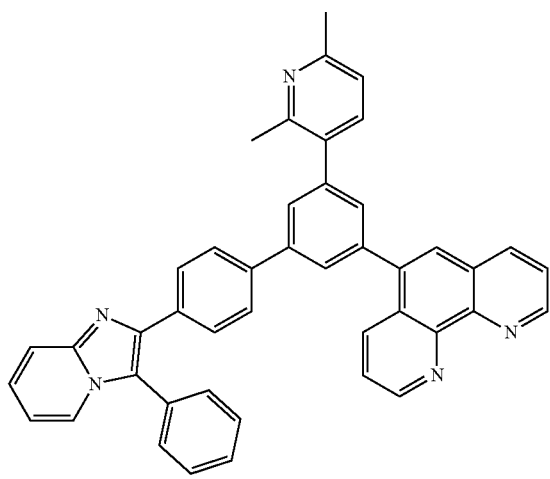
B 33
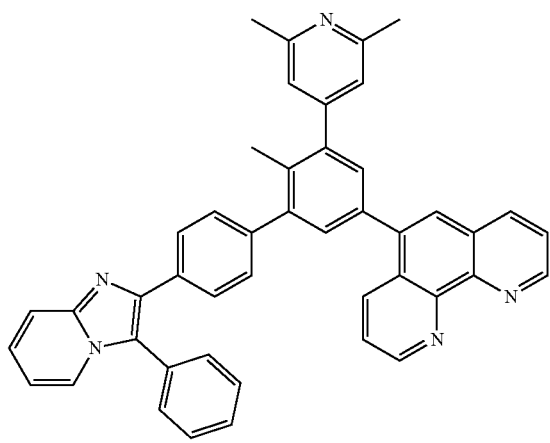 [SMILES: Cc1cc(-c2cc(-c3cc4cccnc4c4ncccc34)cc(-c3ccc(-c4nc5ccccn5c4-c4ccccc4)cc3)c2C)cc(C)n1]
B 34
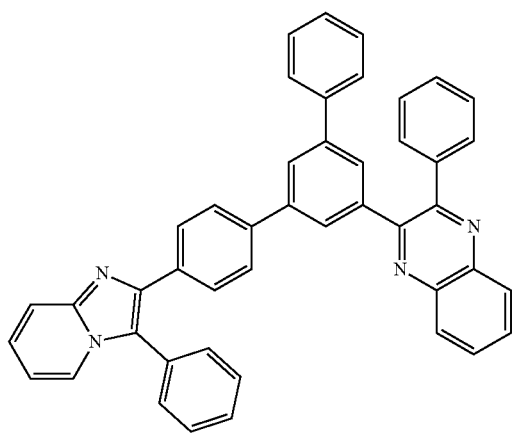 [SMILES: c1ccc(-c2cc(-c3ccc(-c4nc5ccccn5c4-c4ccccc4)cc3)cc(-c3nc4ccccc4nc3-c3ccccc3)c2)cc1]

-continued
B 35
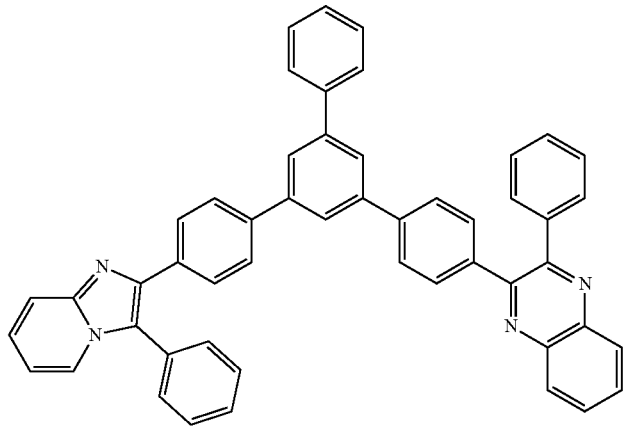 [SMILES: c1ccc(-c2cc(-c3ccc(-c4nc5ccccc5nc4-c4ccccc4)cc3)cc(-c3ccc(-c4nc5ccccn5c4-c4ccccc4)cc3)c2)cc1]
B 36
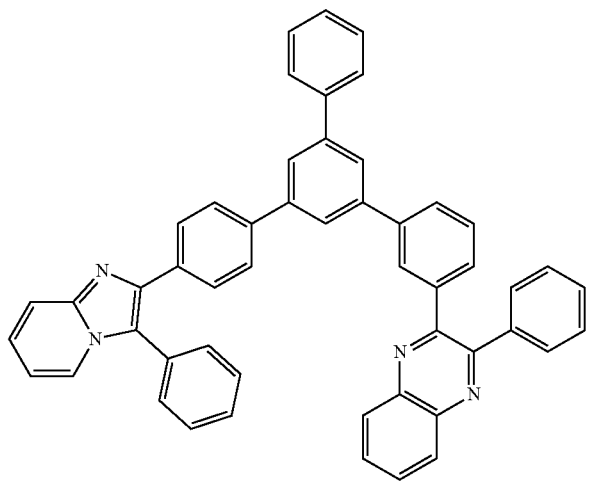 [SMILES: c1ccc(-c2cc(-c3ccc(-c4nc5ccccn5c4-c4ccccc4)cc3)cc(-c3cccc(-c4nc5ccccc5nc4-c4ccccc4)c3)c2)cc1]
B 37
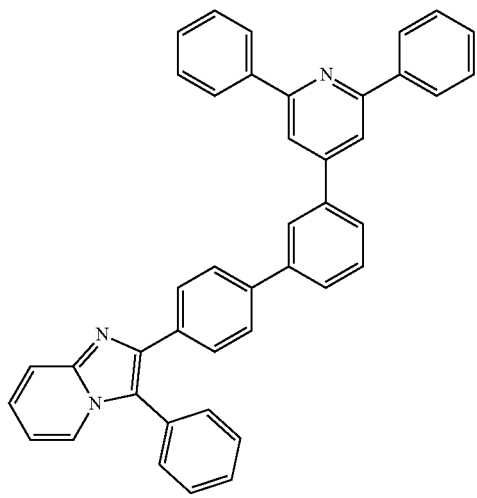 [SMILES: c1ccc(-c2cc(-c3cccc(-c4ccc(-c5nc6ccccn6c5-c5ccccc5)cc4)c3)cc(-c3ccccc3)n2)cc1]

-continued
B 38
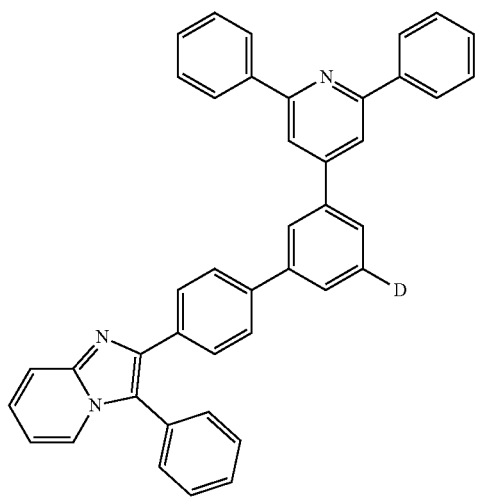 [SMILES: [2H]c1cc(-c2ccc(-c3nc4ccccn4c3-c3ccccc3)cc2)cc(-c2cc(-c3ccccc3)nc(-c3ccccc3)c2)c1]
B 39
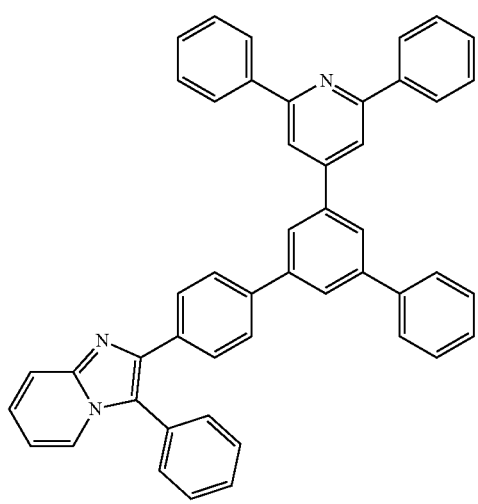 [SMILES: c1ccc(-c2cc(-c3ccc(-c4nc5ccccn5c4-c4ccccc4)cc3)cc(-c3cc(-c4ccccc4)nc(-c4ccccc4)c3)c2)cc1]
B 40
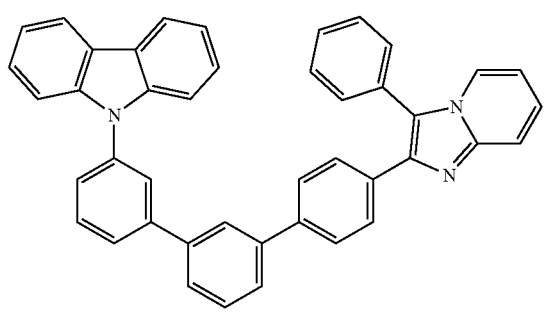 [SMILES: c1ccc(-c2c(-c3ccc(-c4cccc(-c5cccc(-n6c7ccccc7c7ccccc76)c5)c4)cc3)nc3ccccn23)cc1]
B 41
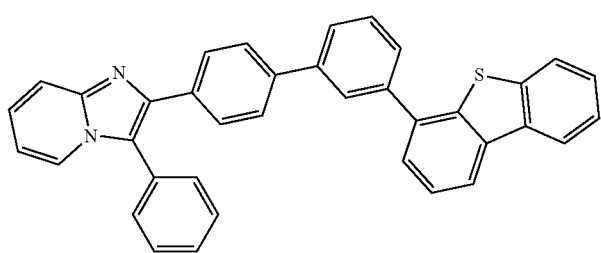 [SMILES: c1ccc(-c2c(-c3ccc(-c4cccc(-c5cccc6c5sc5ccccc56)c4)cc3)nc3ccccn23)cc1]

B 42
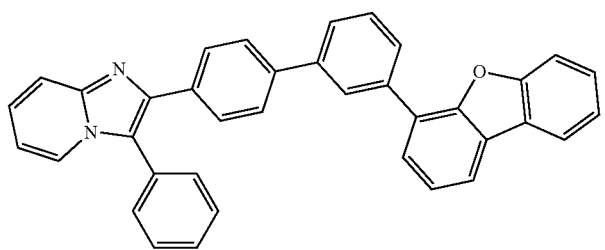 [SMILES: c1ccc(-c2c(-c3ccc(-c4cccc(-c5cccc6c5oc5ccccc56)c4)cc3)nc3ccccn23)cc1]
B 43
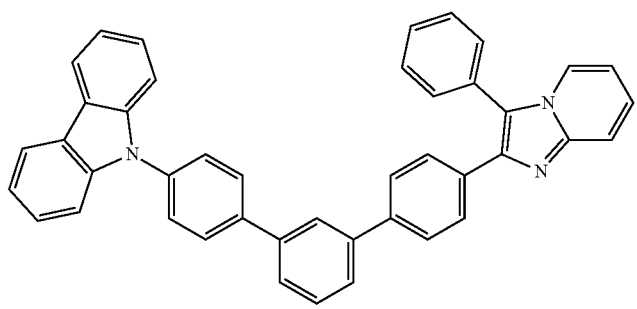 [SMILES: c1ccc(-c2c(-c3ccc(-c4cccc(-c5ccc(-n6c7ccccc7c7ccccc76)cc5)c4)cc3)nc3ccccn23)cc1]
B 44
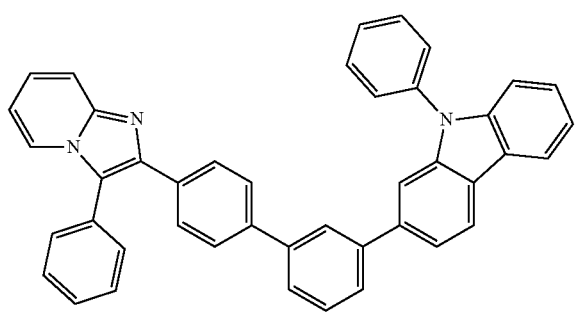 [SMILES: c1ccc(-c2c(-c3ccc(-c4cccc(-c5ccc6c7ccccc7n(-c7ccccc7)c6c5)c4)cc3)nc3ccccn23)cc1]
B 45
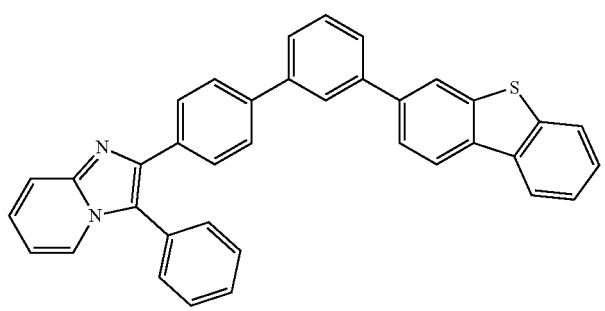 [SMILES: c1ccc(-c2c(-c3ccc(-c4cccc(-c5ccc6c(c5)sc5ccccc56)c4)cc3)nc3ccccn23)cc1]
B 46
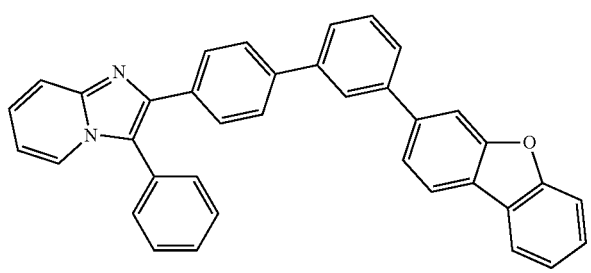 [SMILES: c1ccc(-c2c(-c3ccc(-c4cccc(-c5ccc6c(c5)oc5ccccc56)c4)cc3)nc3ccccn23)cc1]

-continued
B 47
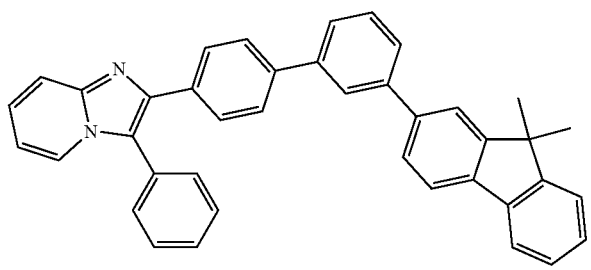 [SMILES: CC1(C)c2ccccc2-c2ccc(-c3cccc(-c4ccc(-c5nc6ccccn6c5-c5ccccc5)cc4)c3)cc21]
B 48
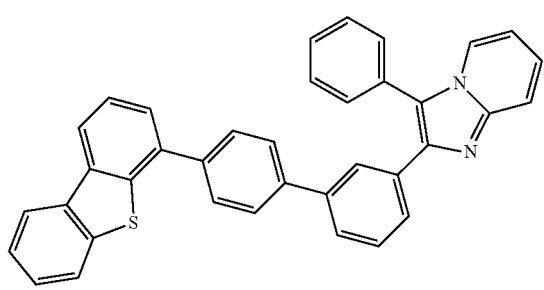 [SMILES: c1ccc(-c2c(-c3cccc(-c4ccc(-c5cccc6c5sc5ccccc56)cc4)c3)nc3ccccn23)cc1]
B 49
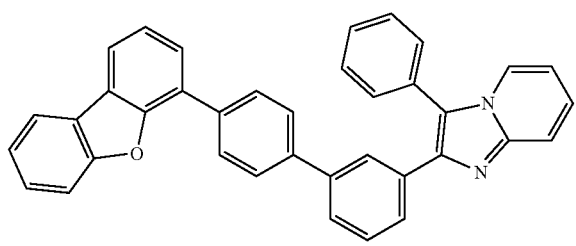 [SMILES: c1ccc(-c2c(-c3cccc(-c4ccc(-c5cccc6c5oc5ccccc56)cc4)c3)nc3ccccn23)cc1]
B 50
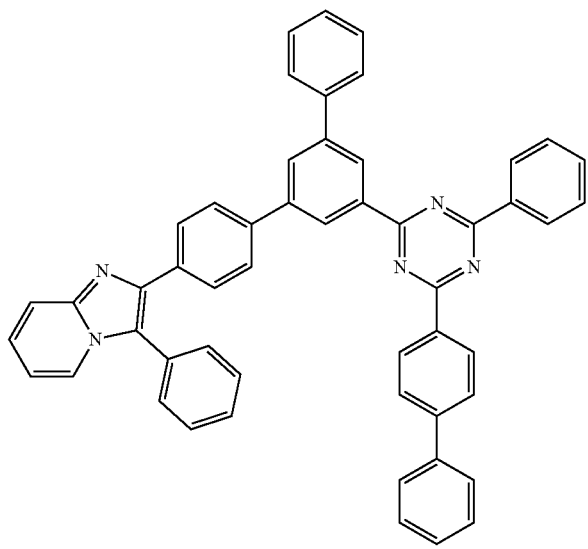 [SMILES: c1ccc(-c2ccc(-c3nc(-c4ccccc4)nc(-c4cc(-c5ccccc5)cc(-c5ccc(-c6nc7ccccn7c6-c6ccccc6)cc5)c4)n3)cc2)cc1]

B 51
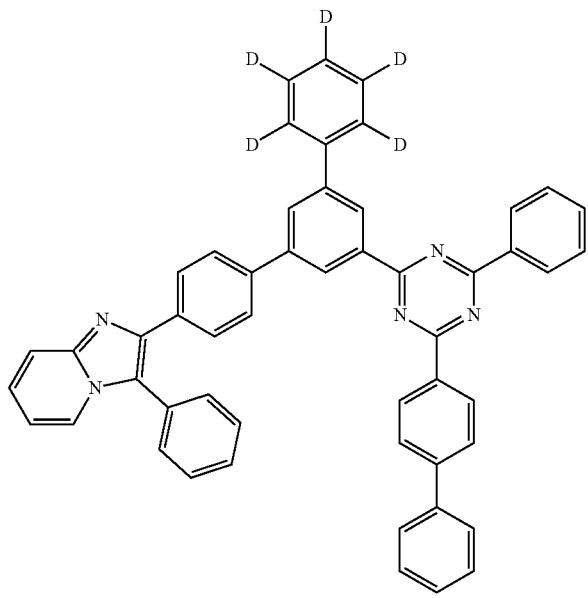 [SMILES: [2H]c1c([2H])c([2H])c(-c2cc(-c3ccc(-c4nc5ccccn5c4-c4ccccc4)cc3)cc(-c3nc(-c4ccccc4)nc(-c4ccc(-c5ccccc5)cc4)n3)c2)c([2H])c1[2H]]
B 52
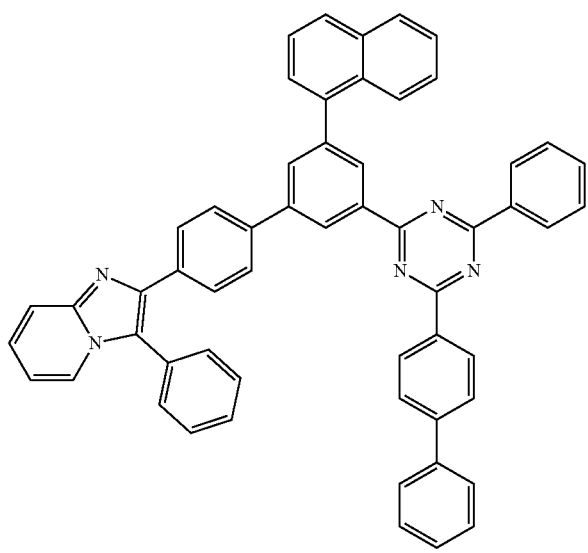 [SMILES: c1ccc(-c2ccc(-c3nc(-c4ccccc4)nc(-c4cc(-c5ccc(-c6nc7ccccn7c6-c6ccccc6)cc5)cc(-c5cccc6ccccc56)c4)n3)cc2)cc1]

B 53
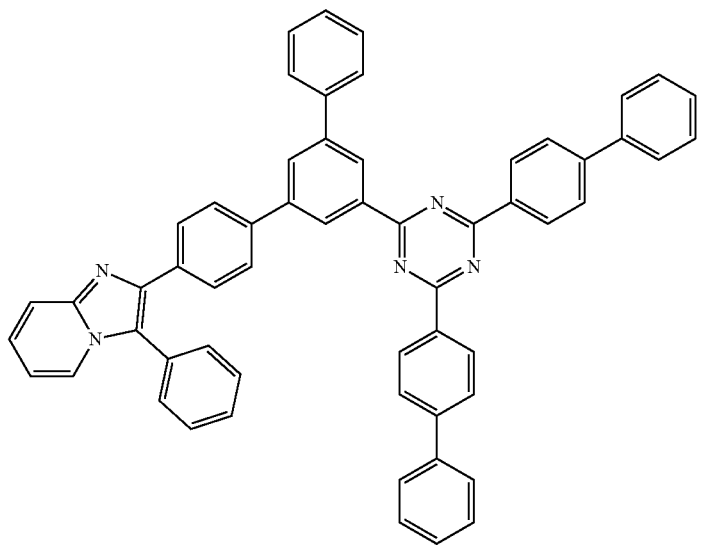 [SMILES: c1ccc(-c2ccc(-c3nc(-c4ccc(-c5ccccc5)cc4)nc(-c4cc(-c5ccccc5)cc(-c5ccc(-c6nc7ccccn7c6-c6ccccc6)cc5)c4)n3)cc2)cc1]
B 54
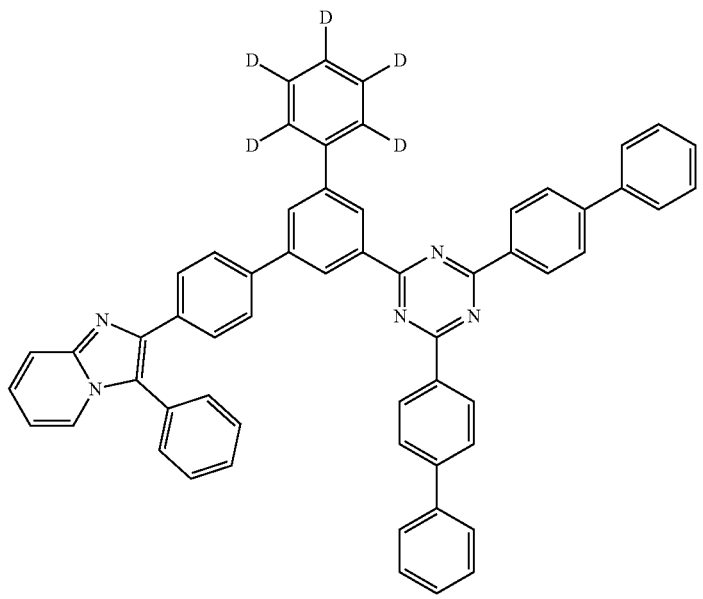 [SMILES: [2H]c1c([2H])c([2H])c(-c2cc(-c3ccc(-c4nc5ccccn5c4-c4ccccc4)cc3)cc(-c3nc(-c4ccc(-c5ccccc5)cc4)nc(-c4ccc(-c5ccccc5)cc4)n3)c2)c([2H])c1[2H]]

B 55
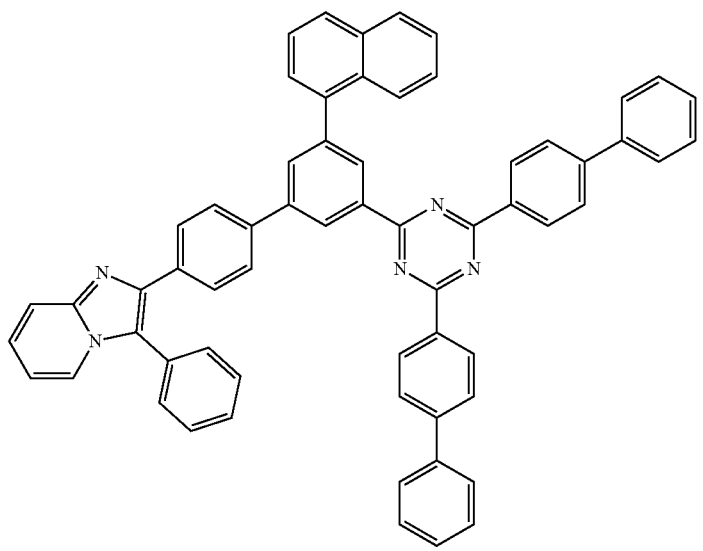 [SMILES: c1ccc(-c2ccc(-c3nc(-c4ccc(-c5ccccc5)cc4)nc(-c4cc(-c5ccc(-c6nc7ccccn7c6-c6ccccc6)cc5)cc(-c5cccc6ccccc56)c4)n3)cc2)cc1]
B 56
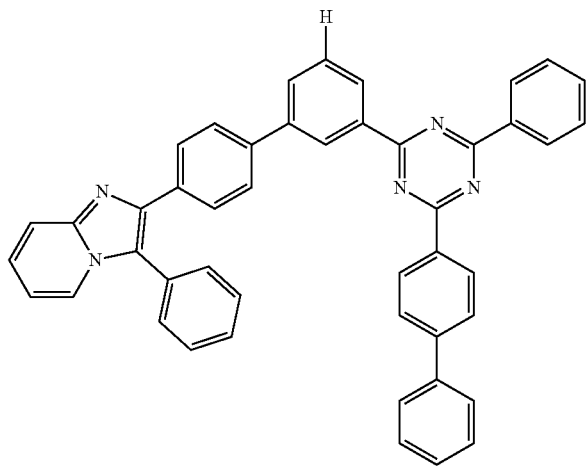
B 57
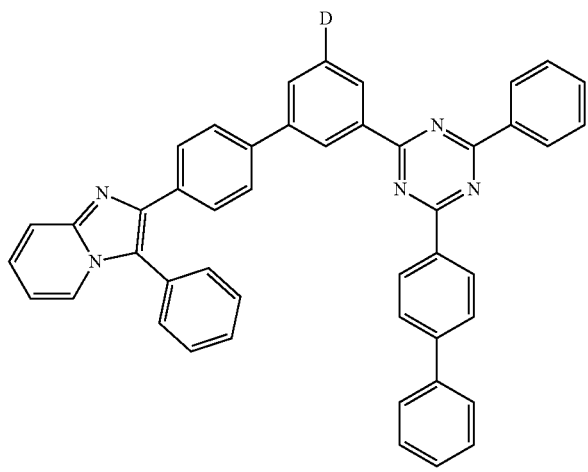 [SMILES: [2H]c1cc(-c2ccc(-c3nc4ccccn4c3-c3ccccc3)cc2)cc(-c2nc(-c3ccccc3)nc(-c3ccc(-c4ccccc4)cc3)n2)c1]

-continued
B 58
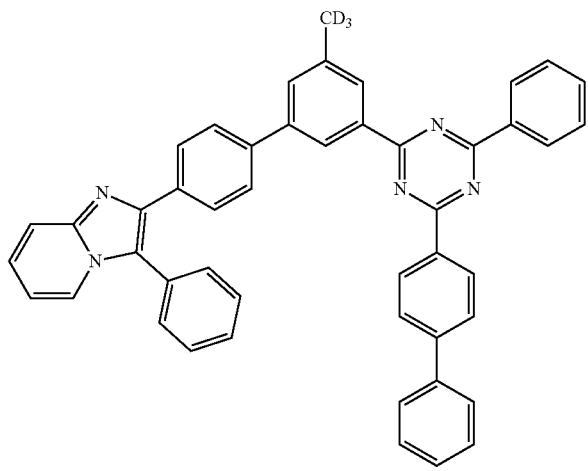 [SMILES: [2H]C([2H])([2H])c1cc(-c2ccc(-c3nc4ccccn4c3-c3ccccc3)cc2)cc(-c2nc(-c3ccccc3)nc(-c3ccc(-c4ccccc4)cc3)n2)c1]
B 59
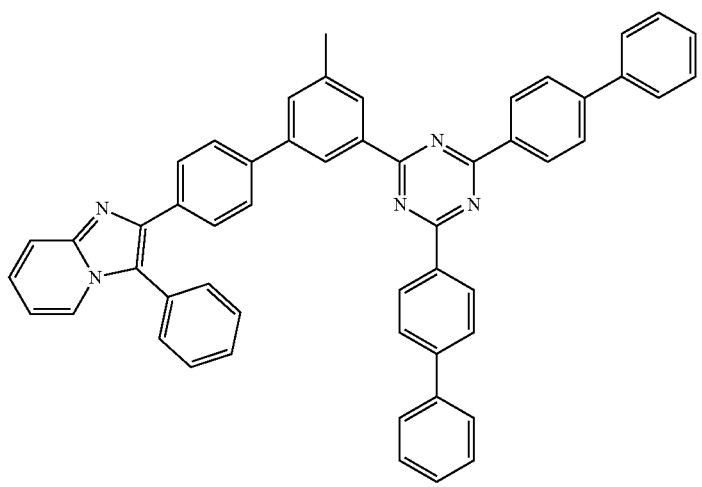 [SMILES: Cc1cc(-c2ccc(-c3nc4ccccn4c3-c3ccccc3)cc2)cc(-c2nc(-c3ccc(-c4ccccc4)cc3)nc(-c3ccc(-c4ccccc4)cc3)n2)c1]
B 60
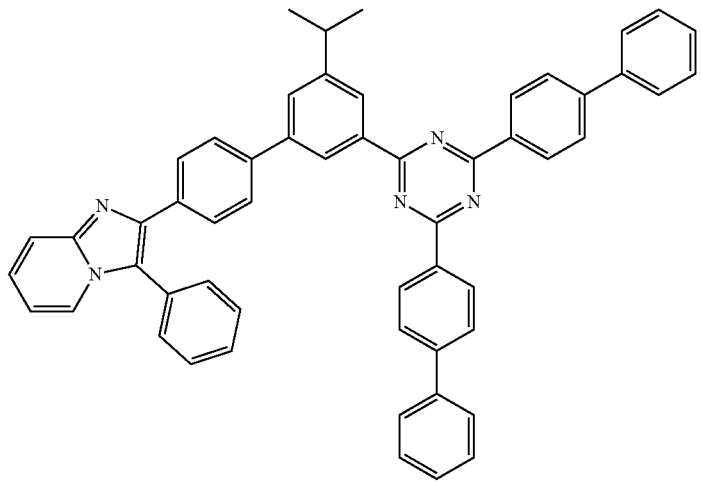 [SMILES: CC(C)c1cc(-c2ccc(-c3nc4ccccn4c3-c3ccccc3)cc2)cc(-c2nc(-c3ccc(-c4ccccc4)cc3)nc(-c3ccc(-c4ccccc4)cc3)n2)c1]

-continued
B 61
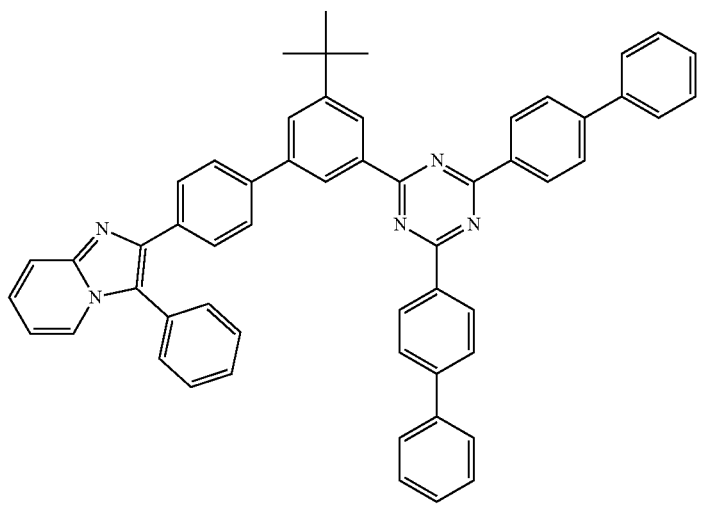 [SMILES: CC(C)(C)c1cc(-c2ccc(-c3nc4ccccn4c3-c3ccccc3)cc2)cc(-c2nc(-c3ccc(-c4ccccc4)cc3)nc(-c3ccc(-c4ccccc4)cc3)n2)c1]
B 62
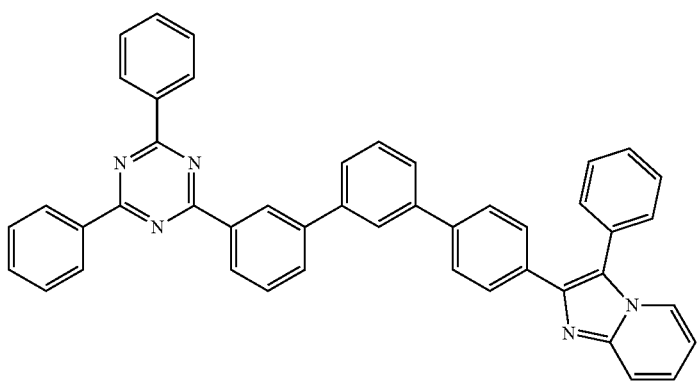 [SMILES: c1ccc(-c2nc(-c3ccccc3)nc(-c3cccc(-c4cccc(-c5ccc(-c6nc7ccccn7c6-c6ccccc6)cc5)c4)c3)n2)cc1]
B 63
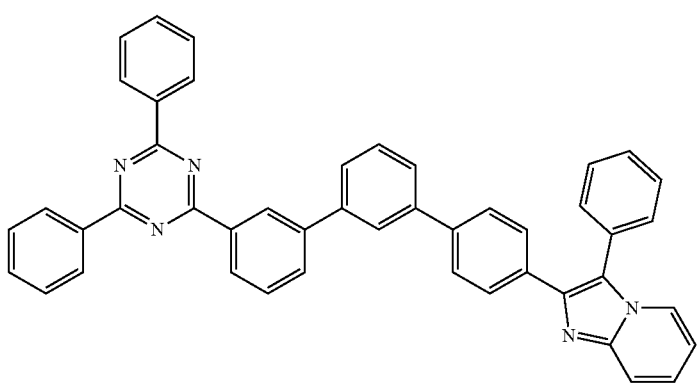 [SMILES: c1ccc(-c2nc(-c3ccccc3)nc(-c3cccc(-c4cccc(-c5ccc(-c6nc7ccccn7c6-c6ccccc6)cc5)c4)c3)n2)cc1]
B 64
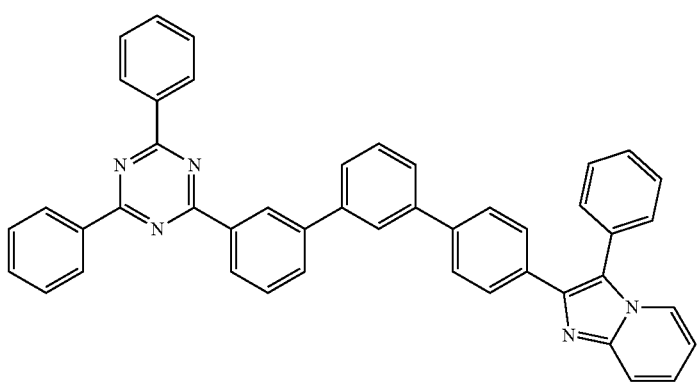 [SMILES: c1ccc(-c2nc(-c3ccccc3)nc(-c3cccc(-c4cccc(-c5ccc(-c6nc7ccccn7c6-c6ccccc6)cc5)c4)c3)n2)cc1]

B 65
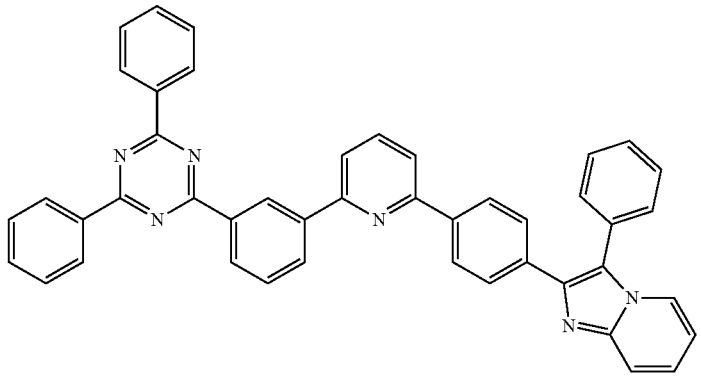 [SMILES: c1ccc(-c2nc(-c3ccccc3)nc(-c3cccc(-c4cccc(-c5ccc(-c6nc7ccccn7c6-c6ccccc6)cc5)n4)c3)n2)cc1]
B 66
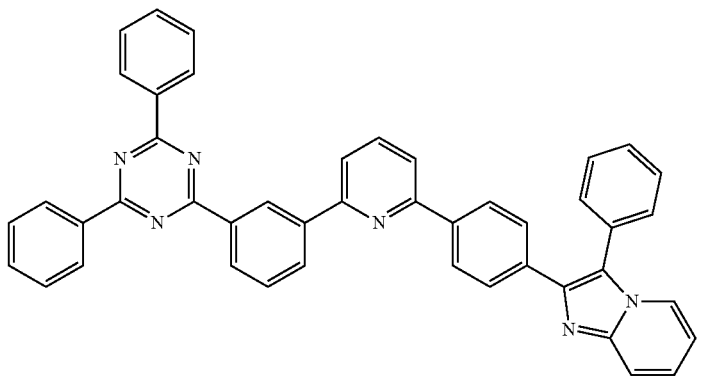 [SMILES: c1ccc(-c2nc(-c3ccccc3)nc(-c3cccc(-c4cccc(-c5ccc(-c6nc7ccccn7c6-c6ccccc6)cc5)n4)c3)n2)cc1]
B 67
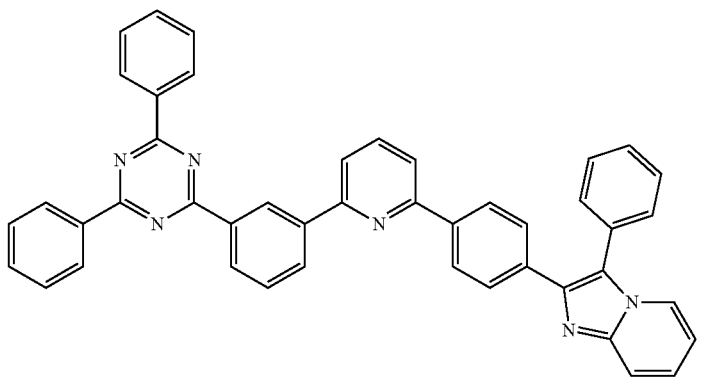 [SMILES: c1ccc(-c2nc(-c3ccccc3)nc(-c3cccc(-c4cccc(-c5ccc(-c6nc7ccccn7c6-c6ccccc6)cc5)n4)c3)n2)cc1]
B 68
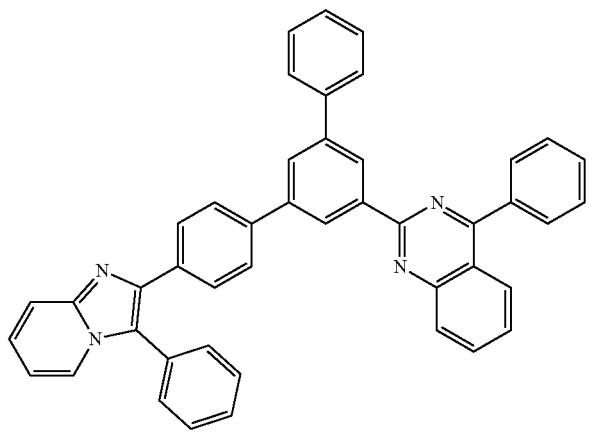 [SMILES: c1ccc(-c2cc(-c3ccc(-c4nc5ccccn5c4-c4ccccc4)cc3)cc(-c3nc(-c4ccccc4)c4ccccc4n3)c2)cc1]

B 69
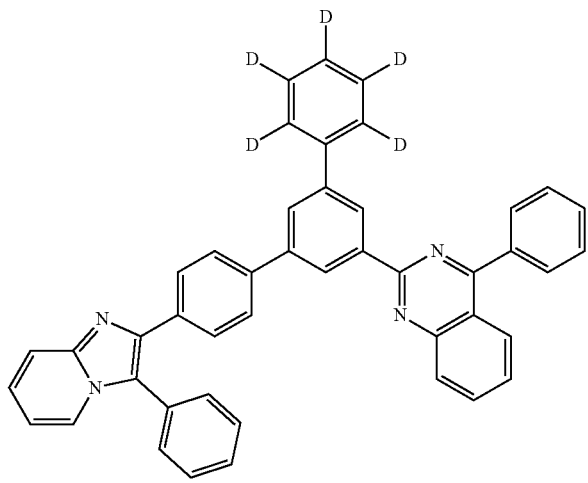 [SMILES: [2H]c1c([2H])c([2H])c(-c2cc(-c3ccc(-c4nc5ccccn5c4-c4ccccc4)cc3)cc(-c3nc(-c4ccccc4)c4ccccc4n3)c2)c([2H])c1[2H]]
B 70
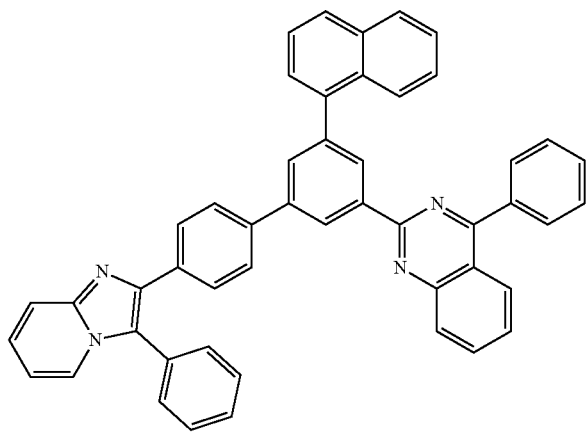 [SMILES: c1ccc(-c2nc(-c3cc(-c4ccc(-c5nc6ccccn6c5-c5ccccc5)cc4)cc(-c4cccc5ccccc45)c3)nc3ccccc23)cc1]
B 71
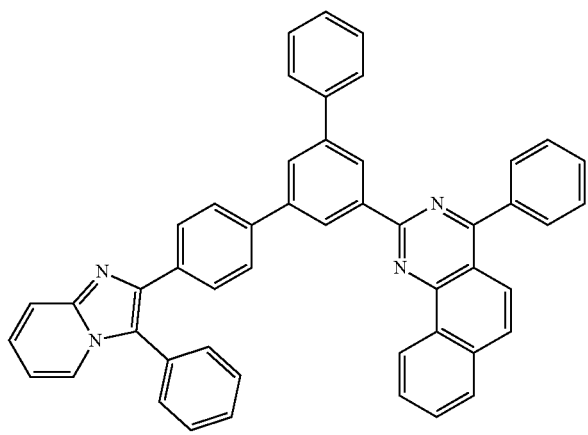 [SMILES: c1ccc(-c2cc(-c3ccc(-c4nc5ccccn5c4-c4ccccc4)cc3)cc(-c3nc(-c4ccccc4)c4ccc5ccccc5c4n3)c2)cc1]

B 72
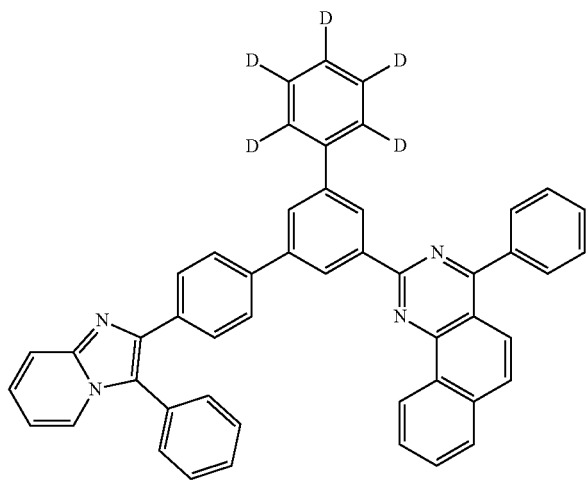 [SMILES: [2H]c1c([2H])c([2H])c(-c2cc(-c3ccc(-c4nc5ccccn5c4-c4ccccc4)cc3)cc(-c3nc(-c4ccccc4)c4ccc5ccccc5c4n3)c2)c([2H])c1[2H]]
B 73
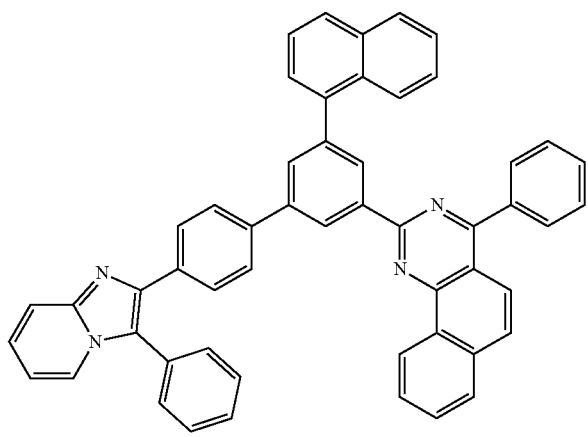 [SMILES: c1ccc(-c2nc(-c3cc(-c4ccc(-c5nc6ccccn6c5-c5ccccc5)cc4)cc(-c4cccc5ccccc45)c3)nc3c2ccc2ccccc23)cc1]
B 74
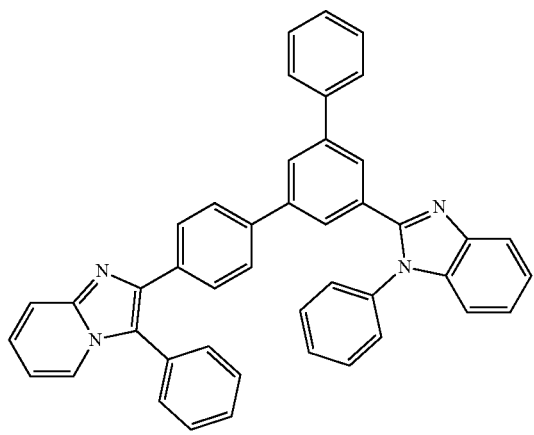 [SMILES: c1ccc(-c2cc(-c3ccc(-c4nc5ccccn5c4-c4ccccc4)cc3)cc(-c3nc4ccccc4n3-c3ccccc3)c2)cc1]

-continued
B 75
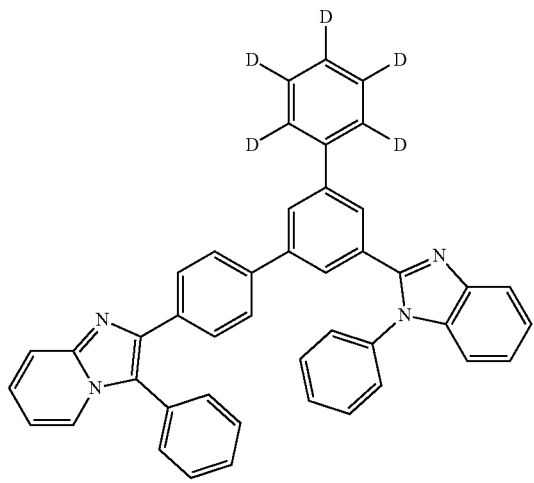 [SMILES: [2H]c1c([2H])c([2H])c(-c2cc(-c3ccc(-c4nc5ccccn5c4-c4ccccc4)cc3)cc(-c3nc4ccccc4n3-c3ccccc3)c2)c([2H])c1[2H]]
B 76
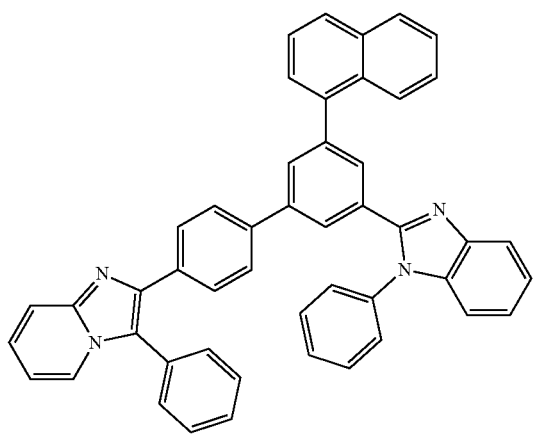 [SMILES: c1ccc(-c2c(-c3ccc(-c4cc(-c5cccc6ccccc56)cc(-c5nc6ccccc6n5-c5ccccc5)c4)cc3)nc3ccccn23)cc1]
B 77
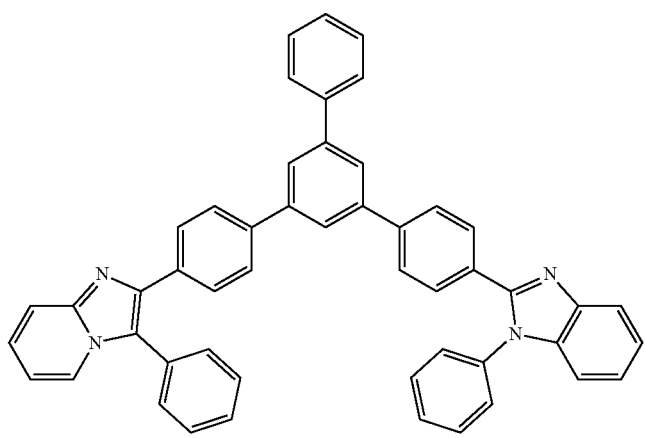 [SMILES: c1ccc(-c2cc(-c3ccc(-c4nc5ccccn5c4-c4ccccc4)cc3)cc(-c3ccc(-c4nc5ccccc5n4-c4ccccc4)cc3)c2)cc1]

-continued
B 78
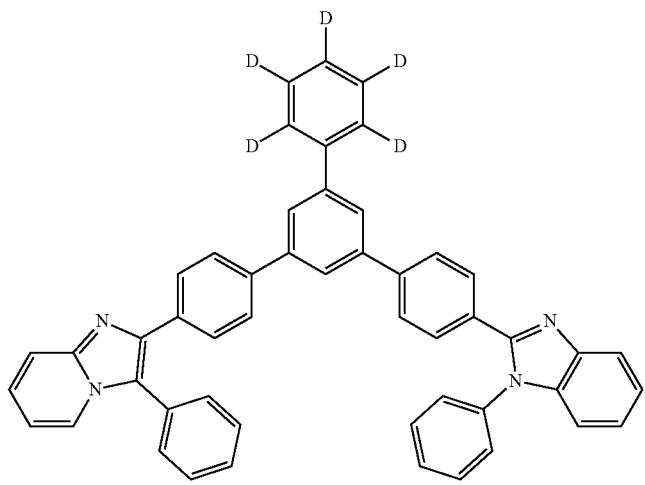 [SMILES: [2H]c1c([2H])c([2H])c(-c2cc(-c3ccc(-c4nc5ccccn5c4-c4ccccc4)cc3)cc(-c3ccc(-c4nc5ccccc5n4-c4ccccc4)cc3)c2)c([2H])c1[2H]]
B 79
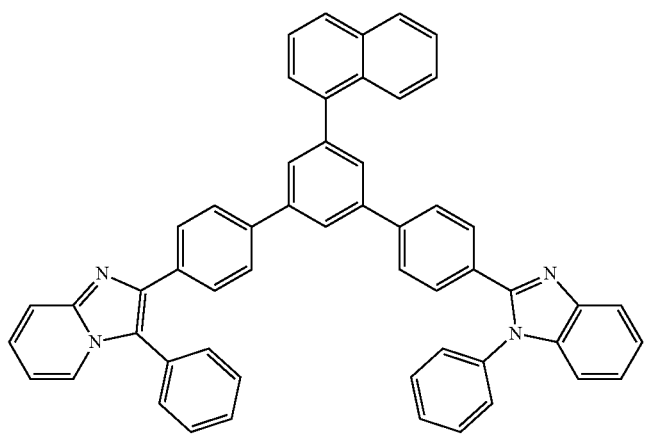 [SMILES: c1ccc(-c2c(-c3ccc(-c4cc(-c5ccc(-c6nc7ccccc7n6-c6ccccc6)cc5)cc(-c5cccc6ccccc56)c4)cc3)nc3ccccn23)cc1]
B 80
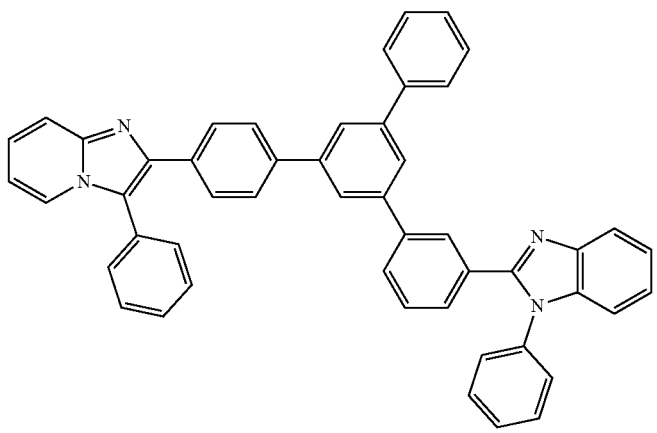 [SMILES: c1ccc(-c2cc(-c3ccc(-c4nc5ccccn5c4-c4ccccc4)cc3)cc(-c3cccc(-c4nc5ccccc5n4-c4ccccc4)c3)c2)cc1]

-continued
B 81
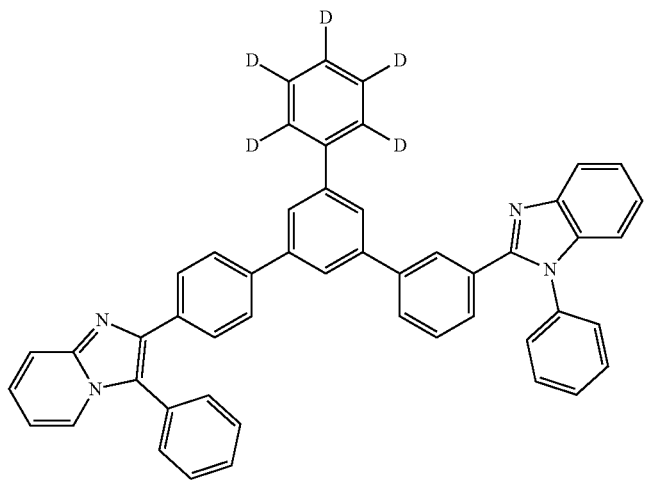 [SMILES: [2H]c1c([2H])c([2H])c(-c2cc(-c3ccc(-c4nc5ccccn5c4-c4ccccc4)cc3)cc(-c3cccc(-c4nc5ccccc5n4-c4ccccc4)c3)c2)c([2H])c1[2H]]
B 82
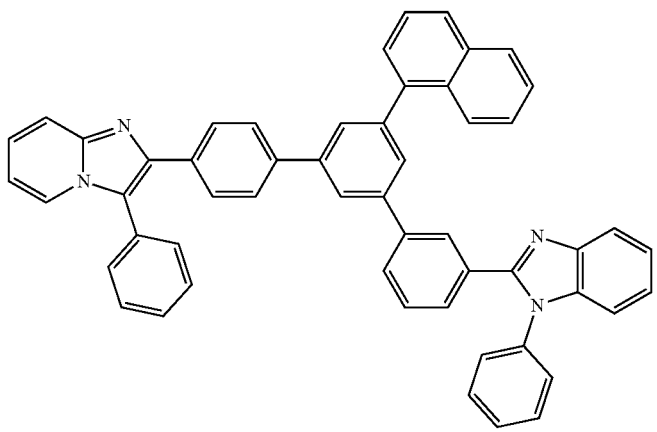 [SMILES: c1ccc(-c2c(-c3ccc(-c4cc(-c5cccc(-c6nc7ccccc7n6-c6ccccc6)c5)cc(-c5cccc6ccccc56)c4)cc3)nc3ccccn23)cc1]
B 83
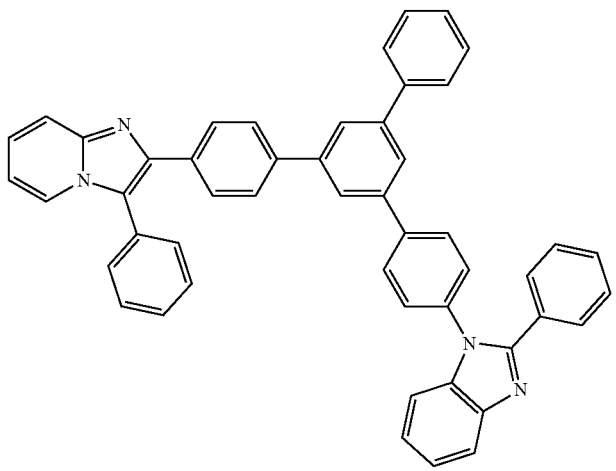 [SMILES: c1ccc(-c2cc(-c3ccc(-c4nc5ccccn5c4-c4ccccc4)cc3)cc(-c3ccc(-n4c(-c5ccccc5)nc5ccccc54)cc3)c2)cc1]

-continued
B 84
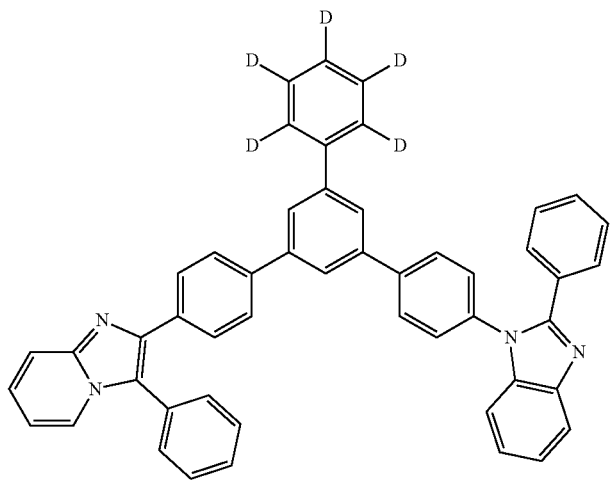 [SMILES: [2H]c1c([2H])c([2H])c(-c2cc(-c3ccc(-c4nc5ccccn5c4-c4ccccc4)cc3)cc(-c3ccc(-n4c(-c5ccccc5)nc5ccccc54)cc3)c2)c([2H])c1[2H]]
B 85
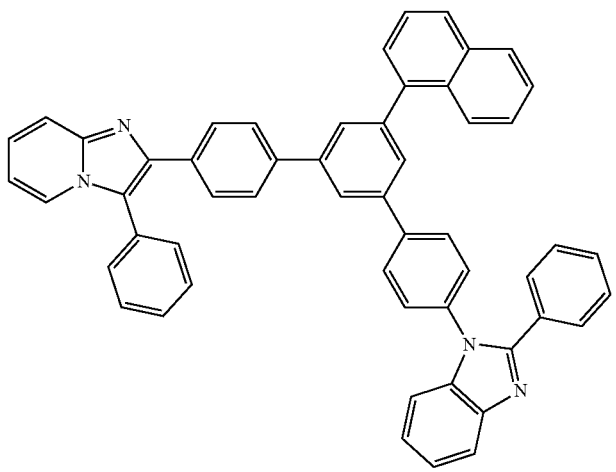 [SMILES: c1ccc(-c2nc3ccccc3n2-c2ccc(-c3cc(-c4ccc(-c5nc6ccccn6c5-c5ccccc5)cc4)cc(-c4cccc5ccccc45)c3)cc2)cc1]
B 86
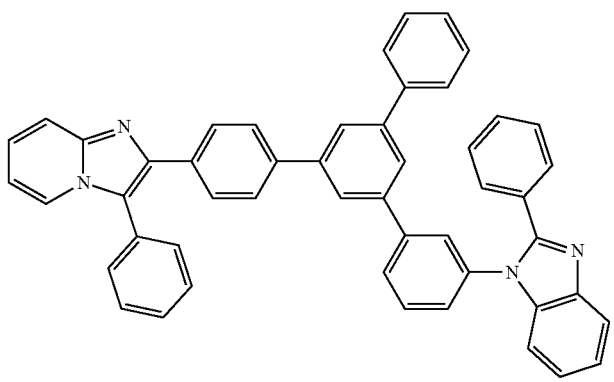 [SMILES: c1ccc(-c2cc(-c3ccc(-c4nc5ccccn5c4-c4ccccc4)cc3)cc(-c3cccc(-n4c(-c5ccccc5)nc5ccccc54)c3)c2)cc1]

-continued
B 87
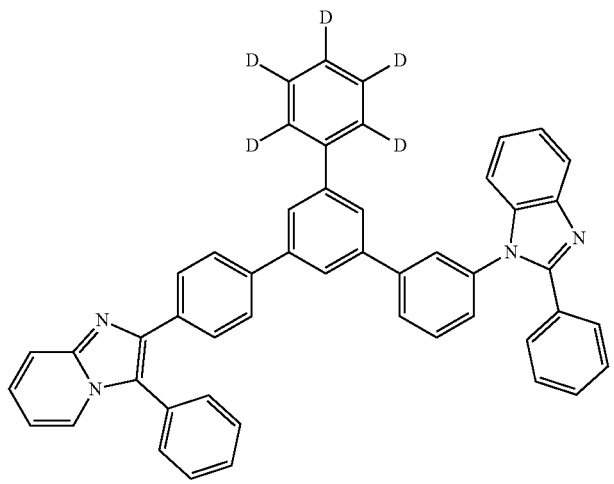 [SMILES: [2H]c1c([2H])c([2H])c(-c2cc(-c3ccc(-c4nc5ccccn5c4-c4ccccc4)cc3)cc(-c3cccc(-n4c(-c5ccccc5)nc5ccccc54)c3)c2)c([2H])c1[2H]]
B 88
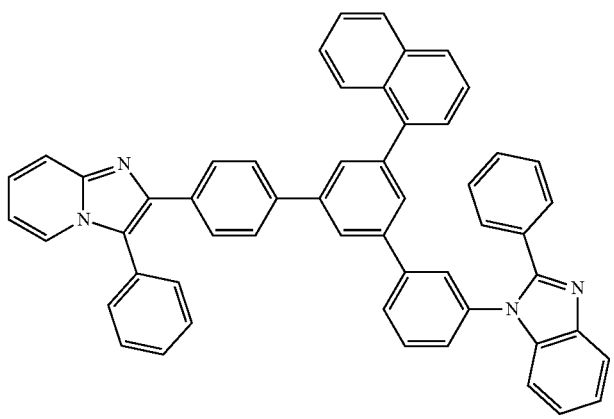 [SMILES: c1ccc(-c2nc3ccccc3n2-c2cccc(-c3cc(-c4ccc(-c5nc6ccccn6c5-c5ccccc5)cc4)cc(-c4cccc5ccccc45)c3)c2)cc1]
B 89
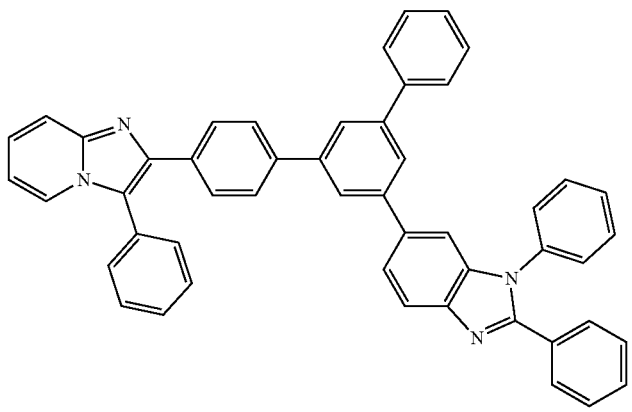 [SMILES: c1ccc(-c2cc(-c3ccc(-c4nc5ccccn5c4-c4ccccc4)cc3)cc(-c3ccc4nc(-c5ccccc5)n(-c5ccccc5)c4c3)c2)cc1]

-continued
B 90
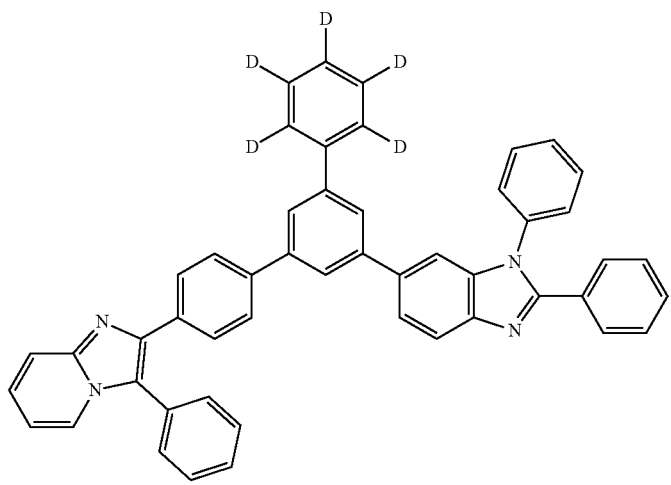 [SMILES: [2H]c1c([2H])c([2H])c(-c2cc(-c3ccc(-c4nc5ccccn5c4-c4ccccc4)cc3)cc(-c3ccc4nc(-c5ccccc5)n(-c5ccccc5)c4c3)c2)c([2H])c1[2H]]
B 91
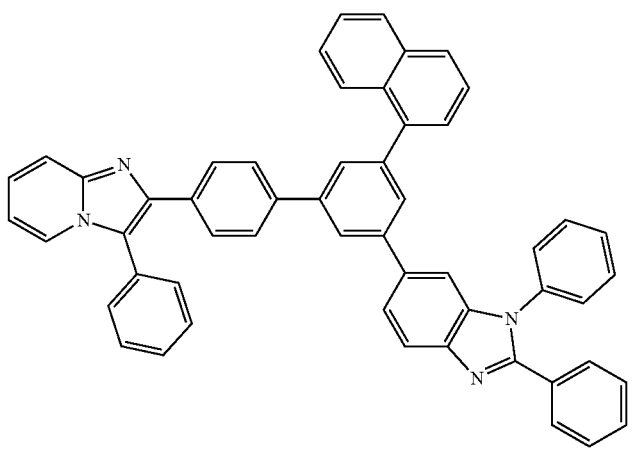 [SMILES: c1ccc(-c2nc3ccc(-c4cc(-c5ccc(-c6nc7ccccn7c6-c6ccccc6)cc5)cc(-c5cccc6ccccc56)c4)cc3n2-c2ccccc2)cc1]
B 92
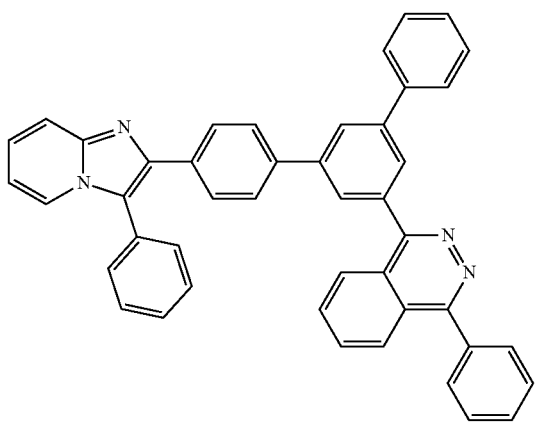 [SMILES: c1ccc(-c2cc(-c3ccc(-c4nc5ccccn5c4-c4ccccc4)cc3)cc(-c3nnc(-c4ccccc4)c4ccccc34)c2)cc1]

| -continued |
|---|
| B 93 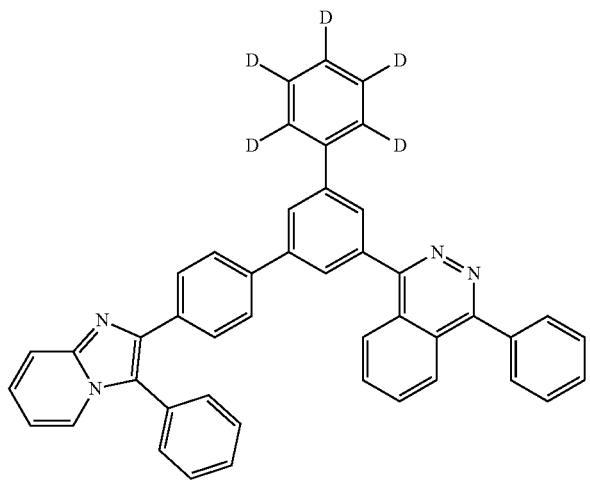 [SMILES: [2H]c1c([2H])c([2H])c(-c2cc(-c3ccc(-c4nc5ccccn5c4-c4ccccc4)cc3)cc(-c3nnc(-c4ccccc4)c4ccccc34)c2)c([2H])c1[2H]] |
| B 94 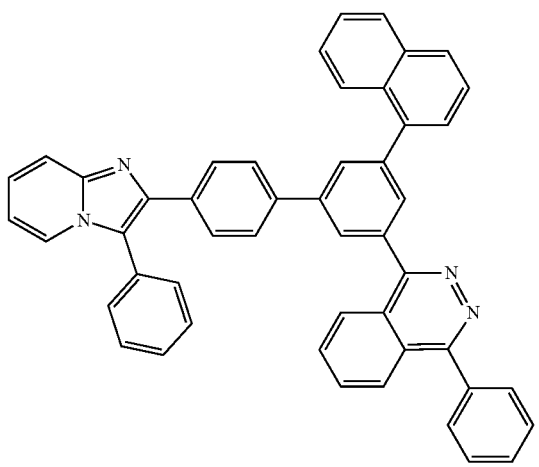 [SMILES: c1ccc(-c2nnc(-c3cc(-c4ccc(-c5nc6ccccn6c5-c5ccccc5)cc4)cc(-c4cccc5ccccc45)c3)c3ccccc23)cc1] |
| B 95 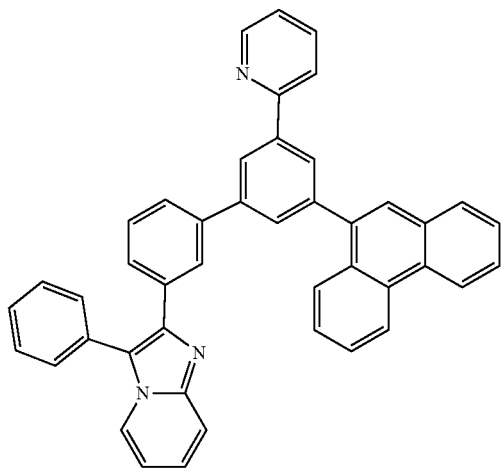 [SMILES: c1ccc(-c2c(-c3cccc(-c4cc(-c5ccccn5)cc(-c5cc6ccccc6c6ccccc56)c4)c3)nc3ccccn23)cc1] |

-continued
B 96
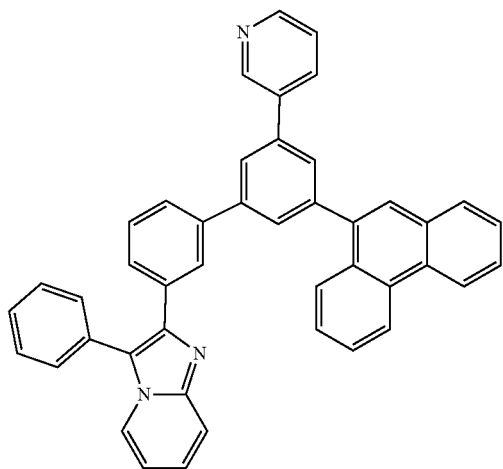 [SMILES: c1ccc(-c2c(-c3cccc(-c4cc(-c5cccnc5)cc(-c5cc6ccccc6c6ccccc56)c4)c3)nc3ccccn23)cc1]
B 97
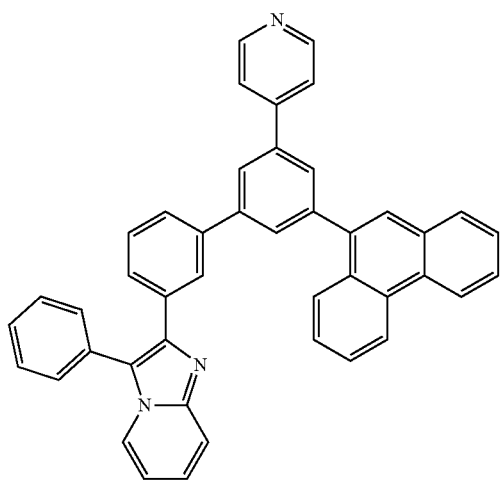 [SMILES: c1ccc(-c2c(-c3cccc(-c4cc(-c5ccncc5)cc(-c5cc6ccccc6c6ccccc56)c4)c3)nc3ccccn23)cc1]
B 98
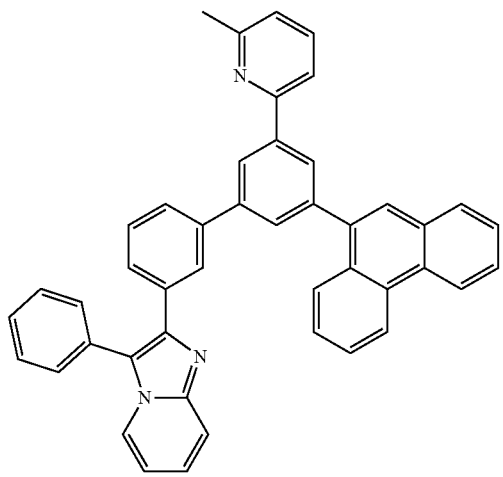 [SMILES: Cc1cccc(-c2cc(-c3cccc(-c4nc5ccccn5c4-c4ccccc4)c3)cc(-c3cc4ccccc4c4ccccc34)c2)n1]

B 99
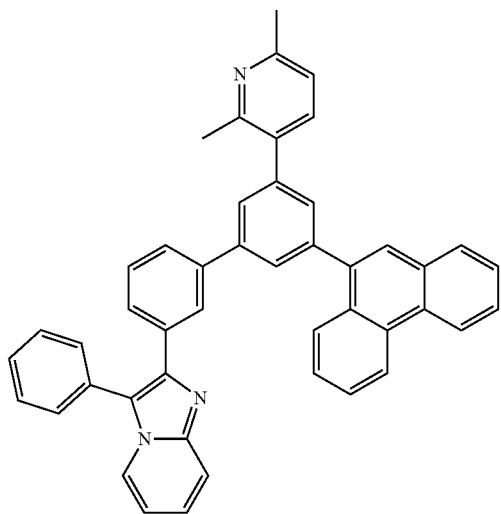 [SMILES: Cc1ccc(-c2cc(-c3cccc(-c4nc5ccccn5c4-c4ccccc4)c3)cc(-c3cc4ccccc4c4ccccc34)c2)c(C)n1]
B 100
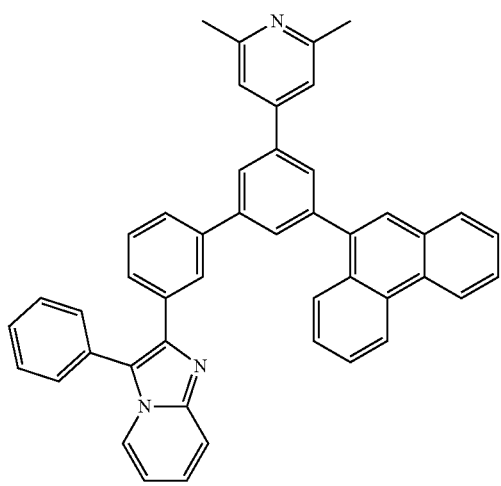 [SMILES: Cc1cc(-c2cc(-c3cccc(-c4nc5ccccn5c4-c4ccccc4)c3)cc(-c3cc4ccccc4c4ccccc34)c2)cc(C)n1]
B 101
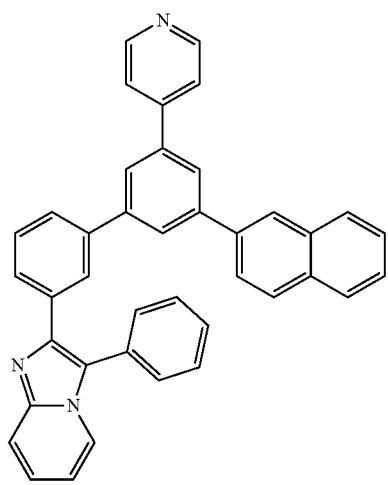 [SMILES: c1ccc(-c2c(-c3cccc(-c4cc(-c5ccncc5)cc(-c5ccc6ccccc6c5)c4)c3)nc3ccccn23)cc1]

-continued
B 102
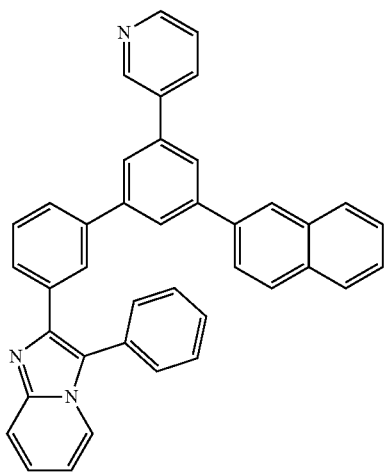 [SMILES: c1ccc(-c2c(-c3cccc(-c4cc(-c5cccnc5)cc(-c5ccc6ccccc6c5)c4)c3)nc3ccccn23)cc1]
B 103
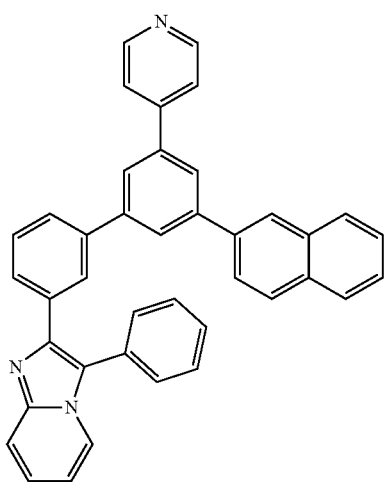 [SMILES: c1ccc(-c2c(-c3cccc(-c4cc(-c5ccncc5)cc(-c5ccc6ccccc6c5)c4)c3)nc3ccccn23)cc1]
B 104
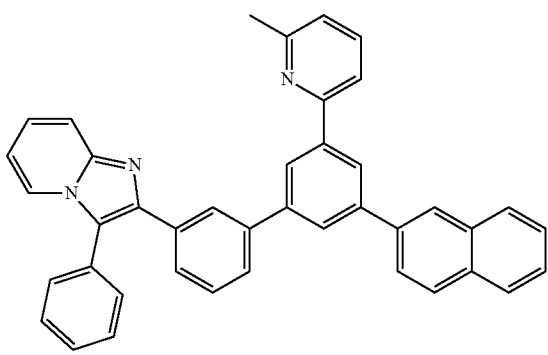 [SMILES: Cc1cccc(-c2cc(-c3cccc(-c4nc5ccccn5c4-c4ccccc4)c3)cc(-c3ccc4ccccc4c3)c2)n1]

B 105
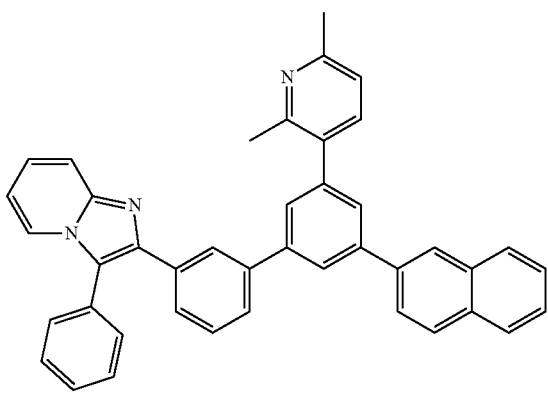 [SMILES: Cc1ccc(-c2cc(-c3cccc(-c4nc5ccccn5c4-c4ccccc4)c3)cc(-c3ccc4ccccc4c3)c2)c(C)n1]
B 106
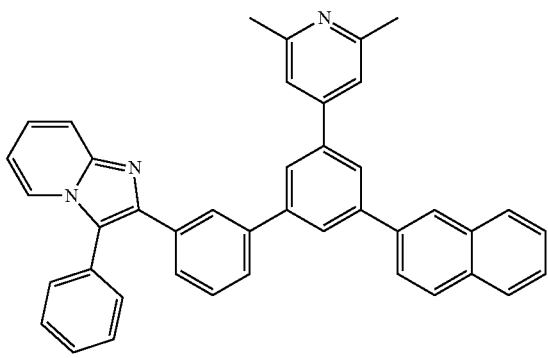 [SMILES: Cc1cc(-c2cc(-c3cccc(-c4nc5ccccn5c4-c4ccccc4)c3)cc(-c3ccc4ccccc4c3)c2)cc(C)n1]
B 107
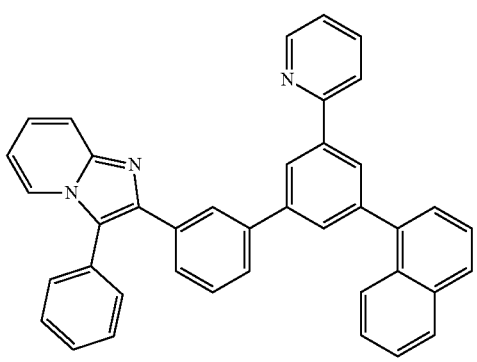
B 108
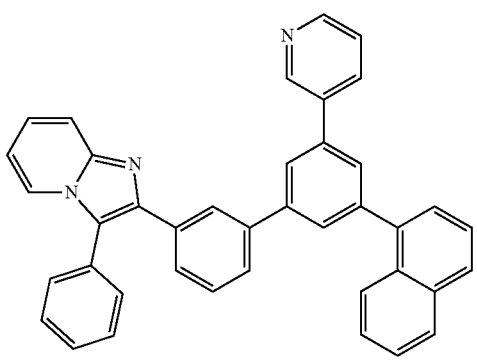 [SMILES: c1ccc(-c2c(-c3cccc(-c4cc(-c5cccnc5)cc(-c5cccc6ccccc56)c4)c3)nc3ccccn23)cc1]

-continued
B 109
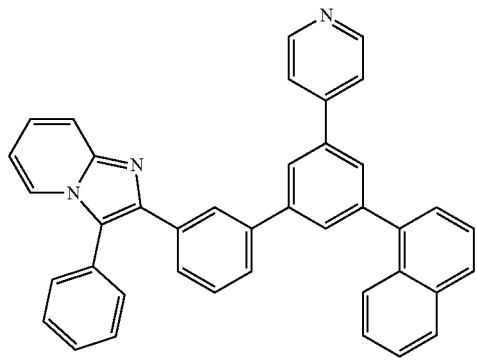 [SMILES: c1ccc(-c2c(-c3cccc(-c4cc(-c5ccncc5)cc(-c5cccc6ccccc56)c4)c3)nc3ccccn23)cc1]
B 110
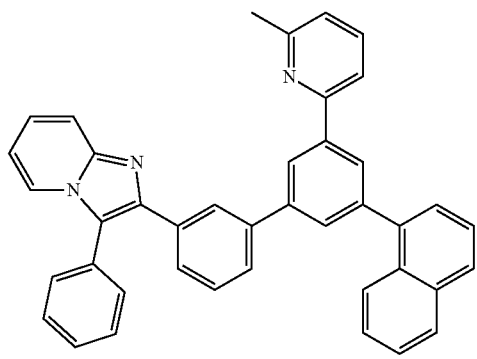 [SMILES: Cc1cccc(-c2cc(-c3cccc(-c4nc5ccccn5c4-c4ccccc4)c3)cc(-c3cccc4ccccc34)c2)n1]
B 111
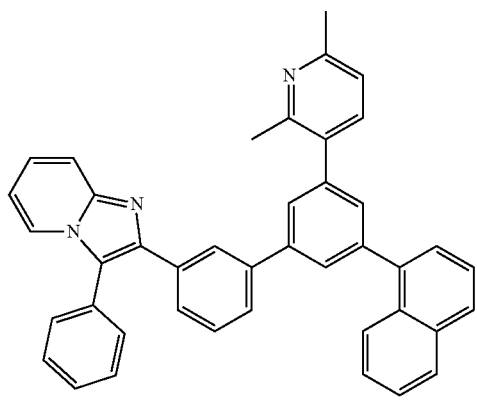 [SMILES: Cc1ccc(-c2cc(-c3cccc(-c4nc5ccccn5c4-c4ccccc4)c3)cc(-c3cccc4ccccc34)c2)c(C)n1]
B 112
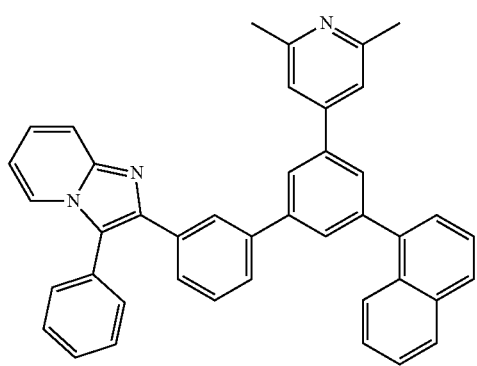 [SMILES: Cc1cc(-c2cc(-c3cccc(-c4nc5ccccn5c4-c4ccccc4)c3)cc(-c3cccc4ccccc34)c2)cc(C)n1]

B 113
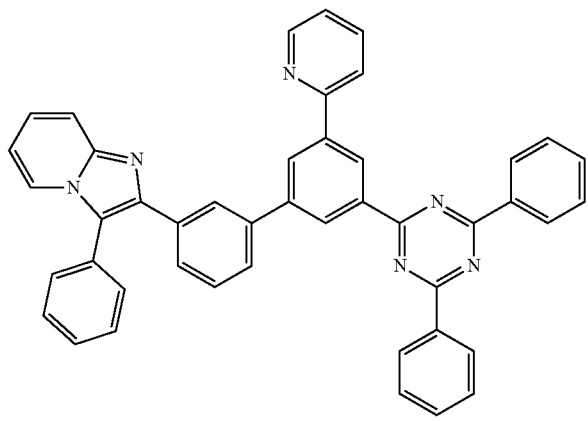 [SMILES: c1ccc(-c2nc(-c3ccccc3)nc(-c3cc(-c4cccc(-c5nc6ccccn6c5-c5ccccc5)c4)cc(-c4ccccn4)c3)n2)cc1]
B 114
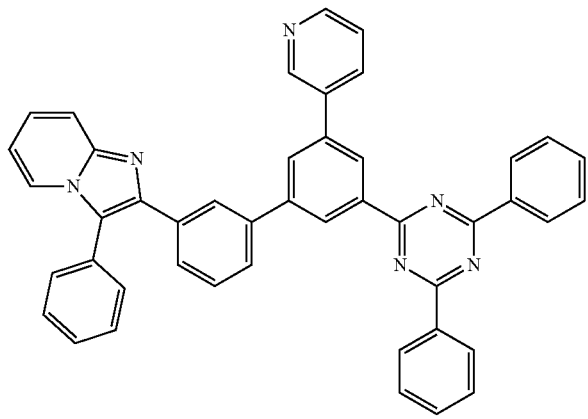 [SMILES: c1ccc(-c2nc(-c3ccccc3)nc(-c3cc(-c4cccnc4)cc(-c4cccc(-c5nc6ccccn6c5-c5ccccc5)c4)c3)n2)cc1]
B 115
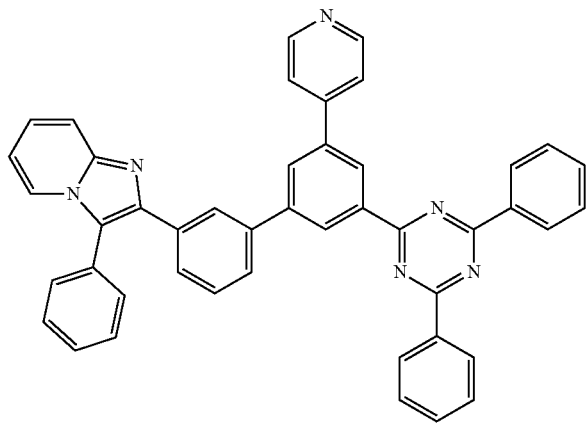 [SMILES: c1ccc(-c2nc(-c3ccccc3)nc(-c3cc(-c4ccncc4)cc(-c4cccc(-c5nc6ccccn6c5-c5ccccc5)c4)c3)n2)cc1]

B 116
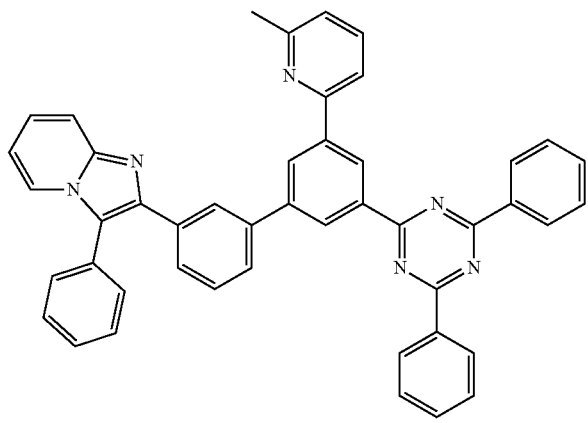 [SMILES: Cc1cccc(-c2cc(-c3cccc(-c4nc5ccccn5c4-c4ccccc4)c3)cc(-c3nc(-c4ccccc4)nc(-c4ccccc4)n3)c2)n1]
B 117
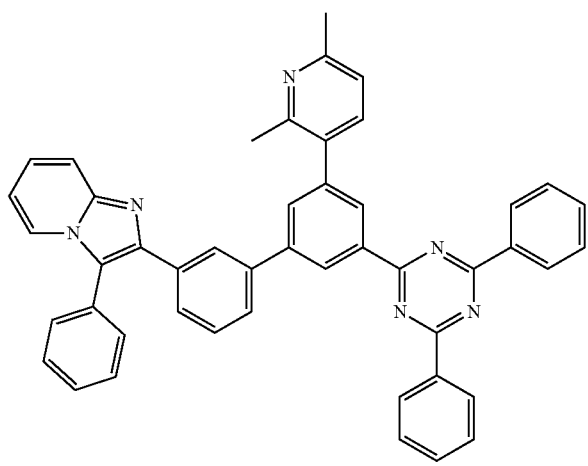 [SMILES: Cc1ccc(-c2cc(-c3cccc(-c4nc5ccccn5c4-c4ccccc4)c3)cc(-c3nc(-c4ccccc4)nc(-c4ccccc4)n3)c2)c(C)n1]
B 118
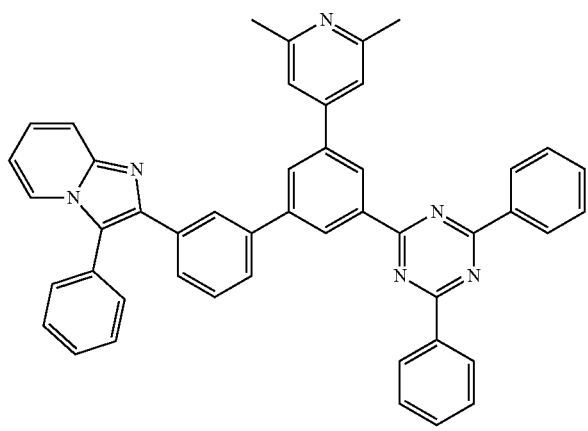 [SMILES: Cc1cc(-c2cc(-c3cccc(-c4nc5ccccn5c4-c4ccccc4)c3)cc(-c3nc(-c4ccccc4)nc(-c4ccccc4)n3)c2)cc(C)n1]

-continued
B 119
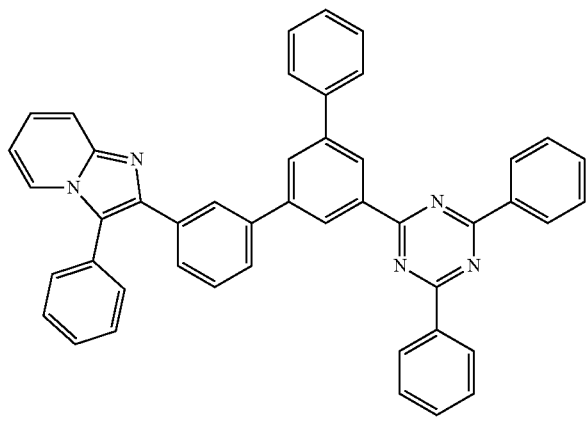 [SMILES: c1ccc(-c2cc(-c3cccc(-c4nc5ccccn5c4-c4ccccc4)c3)cc(-c3nc(-c4ccccc4)nc(-c4ccccc4)n3)c2)cc1]
B 120
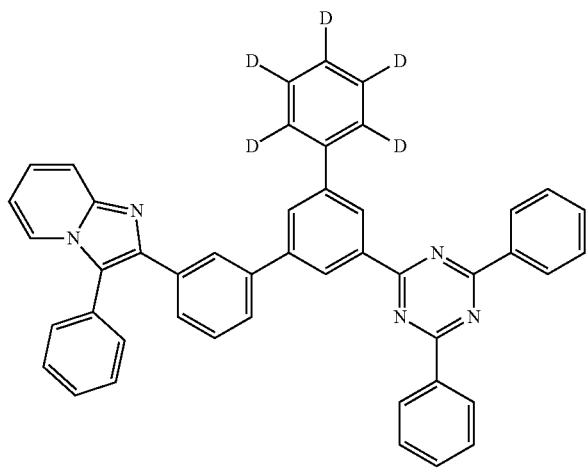 [SMILES: [2H]c1c([2H])c([2H])c(-c2cc(-c3cccc(-c4nc5ccccn5c4-c4ccccc4)c3)cc(-c3nc(-c4ccccc4)nc(-c4ccccc4)n3)c2)c([2H])c1[2H]]
B 121
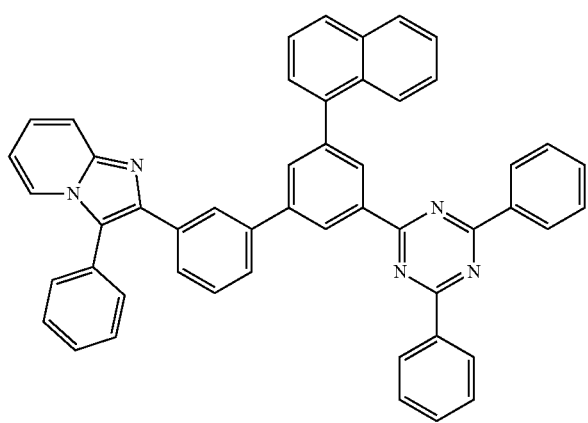 [SMILES: c1ccc(-c2nc(-c3ccccc3)nc(-c3cc(-c4cccc(-c5nc6ccccn6c5-c5ccccc5)c4)cc(-c4cccc5ccccc45)c3)n2)cc1]

-continued
B 122
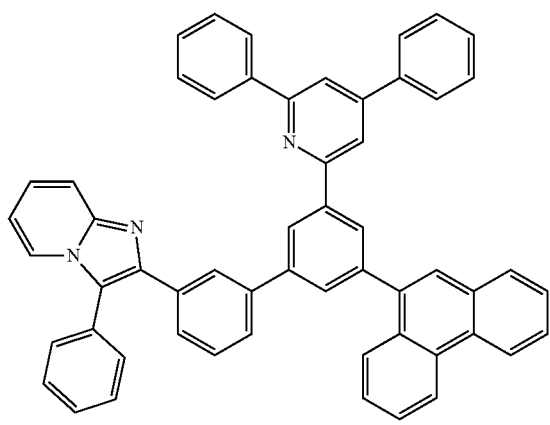 [SMILES: c1ccc(-c2cc(-c3ccccc3)nc(-c3cc(-c4cccc(-c5nc6ccccn6c5-c5ccccc5)c4)cc(-c4cc5ccccc5c5ccccc45)c3)c2)cc1]
B 123
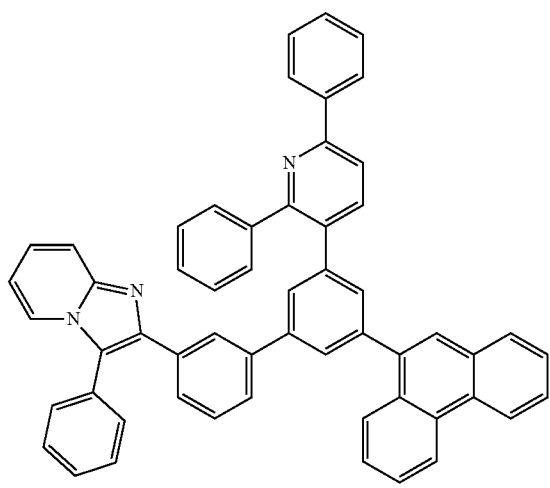 [SMILES: c1ccc(-c2ccc(-c3cc(-c4cccc(-c5nc6ccccn6c5-c5ccccc5)c4)cc(-c4cc5ccccc5c5ccccc45)c3)c(-c3ccccc3)n2)cc1]
B 124
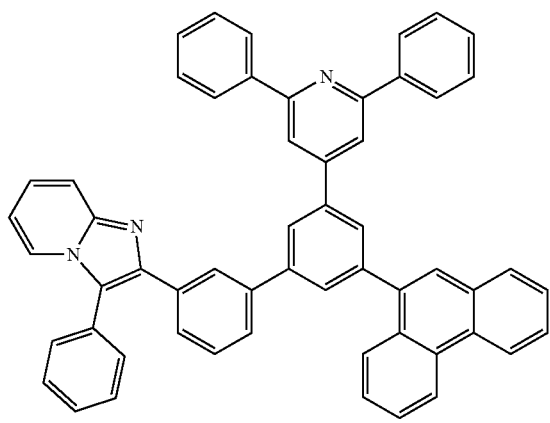 [SMILES: c1ccc(-c2cc(-c3cc(-c4cccc(-c5nc6ccccn6c5-c5ccccc5)c4)cc(-c4cc5ccccc5c5ccccc45)c3)cc(-c3ccccc3)n2)cc1]

-continued
B 125
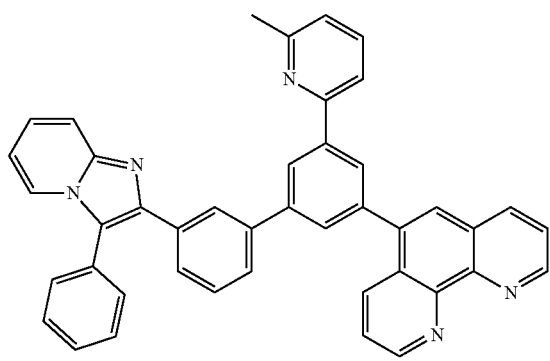 [SMILES: Cc1cccc(-c2cc(-c3cccc(-c4nc5ccccn5c4-c4ccccc4)c3)cc(-c3cc4cccnc4c4ncccc34)c2)n1]
B 126
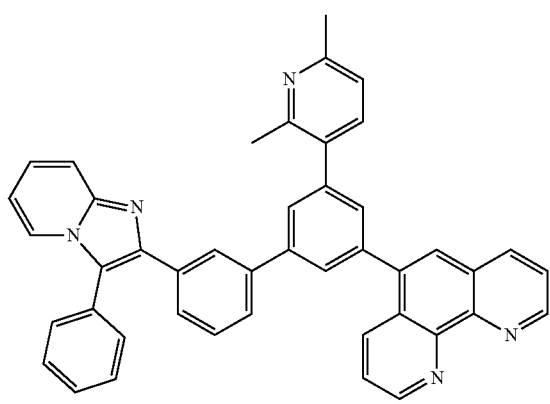 [SMILES: Cc1ccc(-c2cc(-c3cccc(-c4nc5ccccn5c4-c4ccccc4)c3)cc(-c3cc4cccnc4c4ncccc34)c2)c(C)n1]
B 127
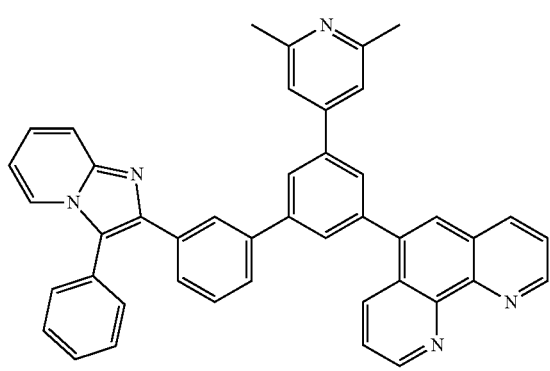 [SMILES: Cc1cc(-c2cc(-c3cccc(-c4nc5ccccn5c4-c4ccccc4)c3)cc(-c3cc4cccnc4c4ncccc34)c2)cc(C)n1]
B 128
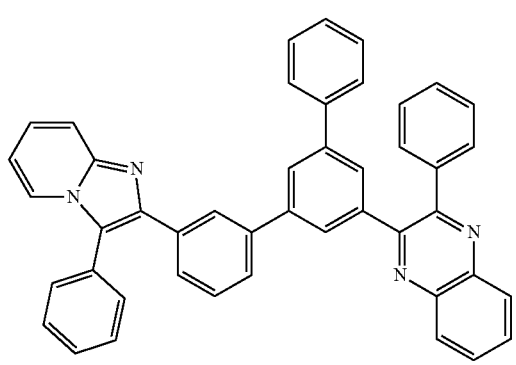 [SMILES: c1ccc(-c2cc(-c3cccc(-c4nc5ccccn5c4-c4ccccc4)c3)cc(-c3nc4ccccc4nc3-c3ccccc3)c2)cc1]

-continued
B 129
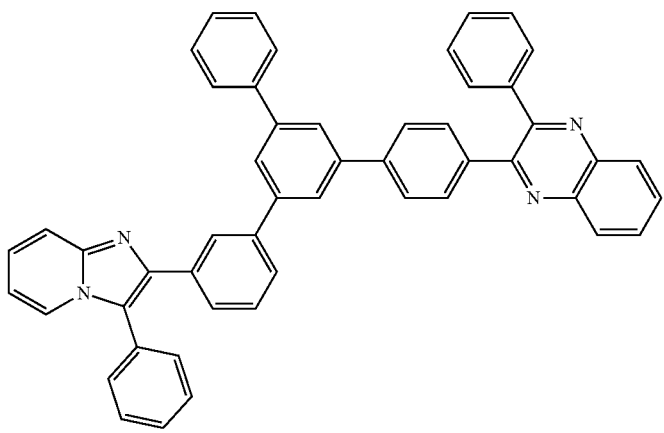 [SMILES: c1ccc(-c2cc(-c3ccc(-c4nc5ccccc5nc4-c4ccccc4)cc3)cc(-c3cccc(-c4nc5ccccn5c4-c4ccccc4)c3)c2)cc1]
B 130
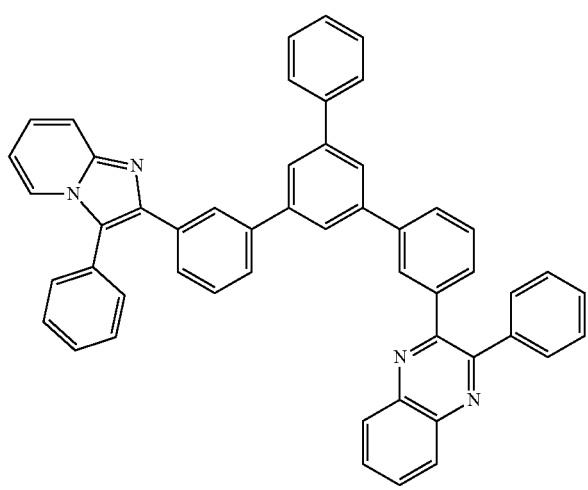 [SMILES: c1ccc(-c2cc(-c3cccc(-c4nc5ccccc5nc4-c4ccccc4)c3)cc(-c3cccc(-c4nc5ccccn5c4-c4ccccc4)c3)c2)cc1]
B 131
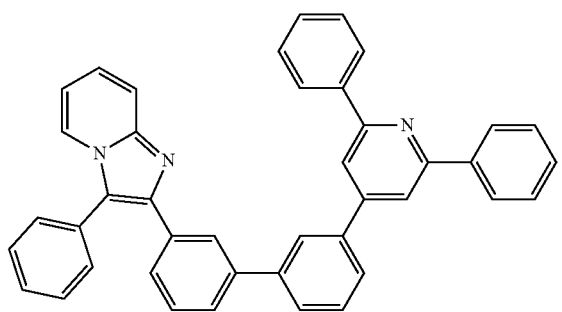 [SMILES: c1ccc(-c2cc(-c3cccc(-c4cccc(-c5nc6ccccn6c5-c5ccccc5)c4)c3)cc(-c3ccccc3)n2)cc1]
B 132
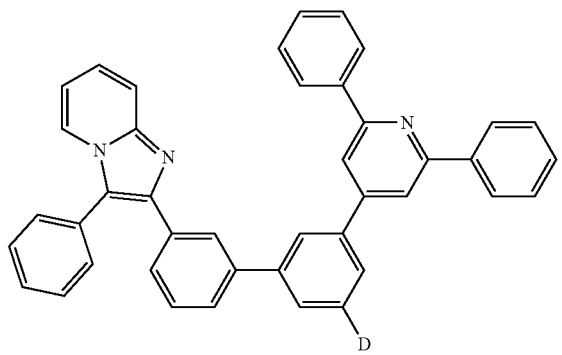 [SMILES: [2H]c1cc(-c2cccc(-c3nc4ccccn4c3-c3ccccc3)c2)cc(-c2cc(-c3ccccc3)nc(-c3ccccc3)c2)c1]

B 133
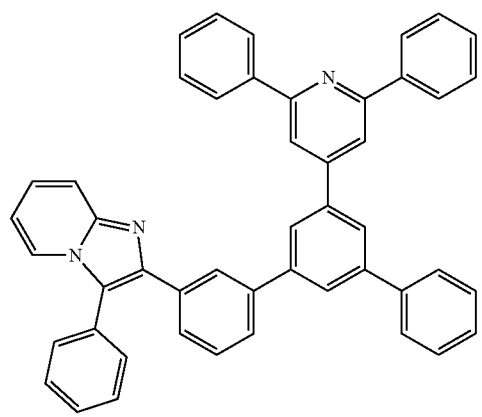 [SMILES: c1ccc(-c2cc(-c3cccc(-c4nc5ccccn5c4-c4ccccc4)c3)cc(-c3cc(-c4ccccc4)nc(-c4ccccc4)c3)c2)cc1]
B 134
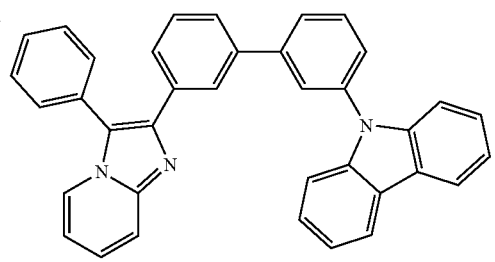 [SMILES: c1ccc(-c2c(-c3cccc(-c4cccc(-n5c6ccccc6c6ccccc65)c4)c3)nc3ccccn23)cc1]
B 135
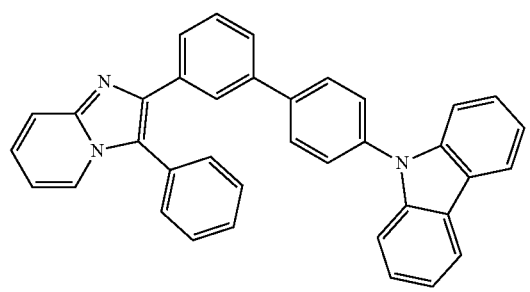 [SMILES: c1ccc(-c2c(-c3cccc(-c4ccc(-n5c6ccccc6c6ccccc65)cc4)c3)nc3ccccn23)cc1]
B 136
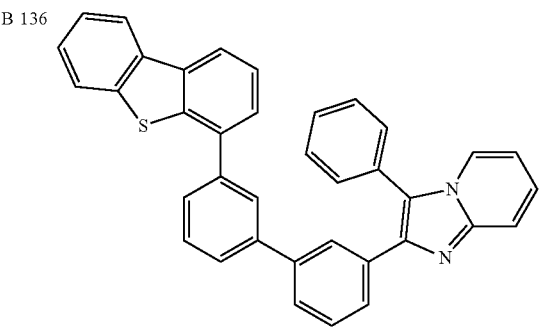

B 137
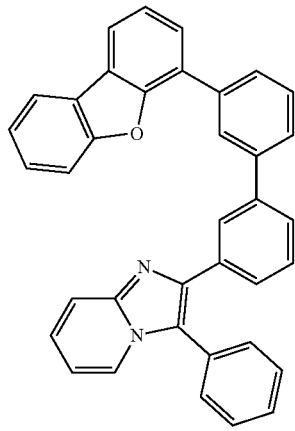 [SMILES: c1ccc(-c2c(-c3cccc(-c4cccc(-c5cccc6c5oc5ccccc56)c4)c3)nc3ccccn23)cc1]
B 138
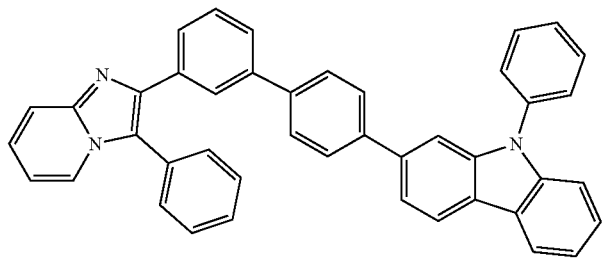 [SMILES: c1ccc(-c2c(-c3cccc(-c4ccc(-c5ccc6c7ccccc7n(-c7ccccc7)c6c5)cc4)c3)nc3ccccn23)cc1]
B 139
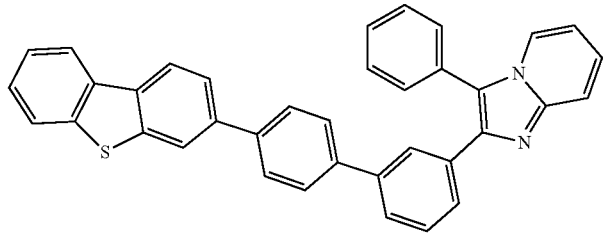 [SMILES: c1ccc(-c2c(-c3cccc(-c4ccc(-c5ccc6c(c5)sc5ccccc56)cc4)c3)nc3ccccn23)cc1]
B 140
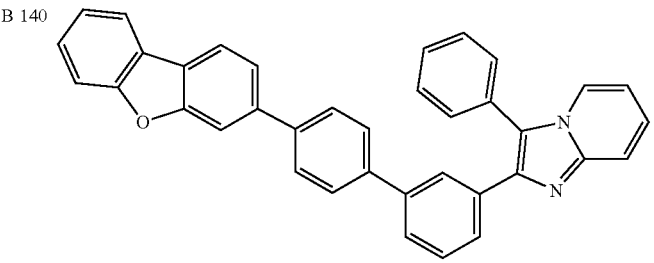
B 141
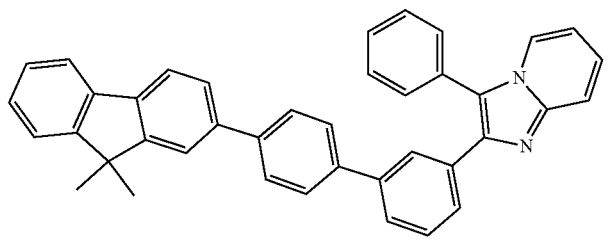 [SMILES: CC1(C)c2ccccc2-c2ccc(-c3ccc(-c4cccc(-c5nc6ccccn6c5-c5ccccc5)c4)cc3)cc21]

B 142
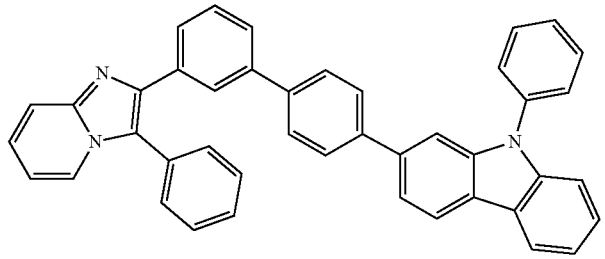 [SMILES: c1ccc(-c2c(-c3cccc(-c4ccc(-c5ccc6c7ccccc7n(-c7ccccc7)c6c5)cc4)c3)nc3ccccn23)cc1]
B 143
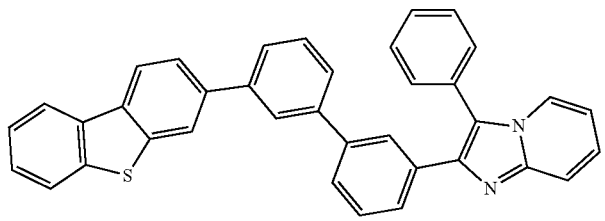 [SMILES: c1ccc(-c2c(-c3cccc(-c4cccc(-c5ccc6c(c5)sc5ccccc56)c4)c3)nc3ccccn23)cc1]
B 144
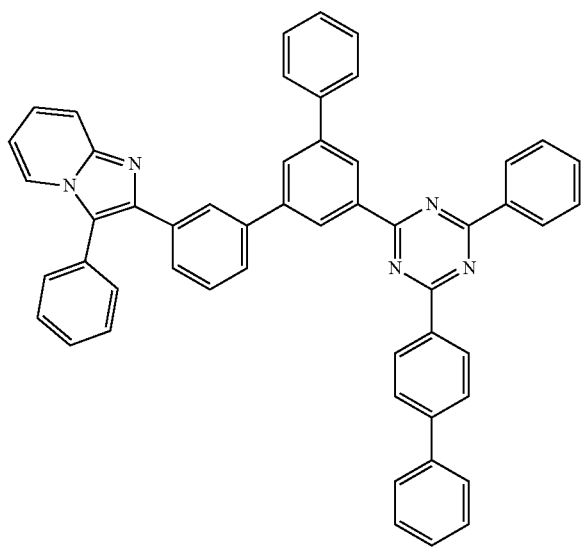 [SMILES: c1ccc(-c2ccc(-c3nc(-c4ccccc4)nc(-c4cc(-c5ccccc5)cc(-c5cccc(-c6nc7ccccn7c6-c6ccccc6)c5)c4)n3)cc2)cc1]
B 145
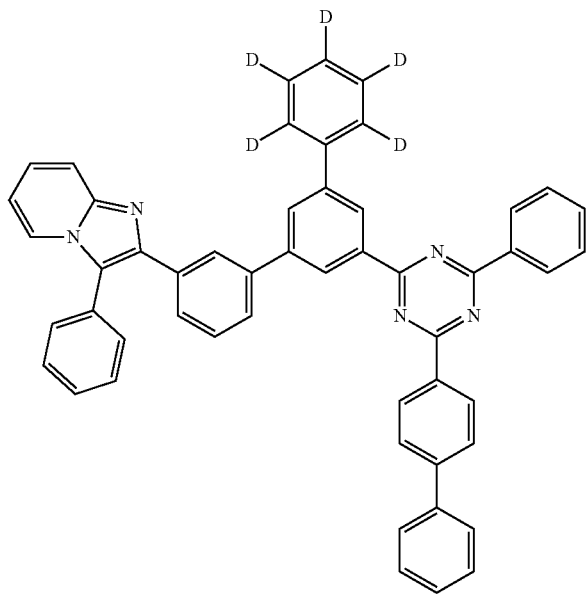 [SMILES: [2H]c1c([2H])c([2H])c(-c2cc(-c3cccc(-c4nc5ccccn5c4-c4ccccc4)c3)cc(-c3nc(-c4ccccc4)nc(-c4ccc(-c5ccccc5)cc4)n3)c2)c([2H])c1[2H]]

B 146
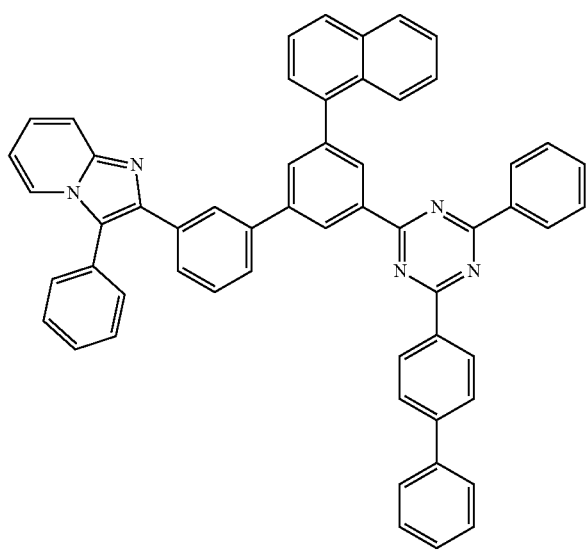 [SMILES: c1ccc(-c2ccc(-c3nc(-c4ccccc4)nc(-c4cc(-c5cccc(-c6nc7ccccn7c6-c6ccccc6)c5)cc(-c5cccc6ccccc56)c4)n3)cc2)cc1]
B 147
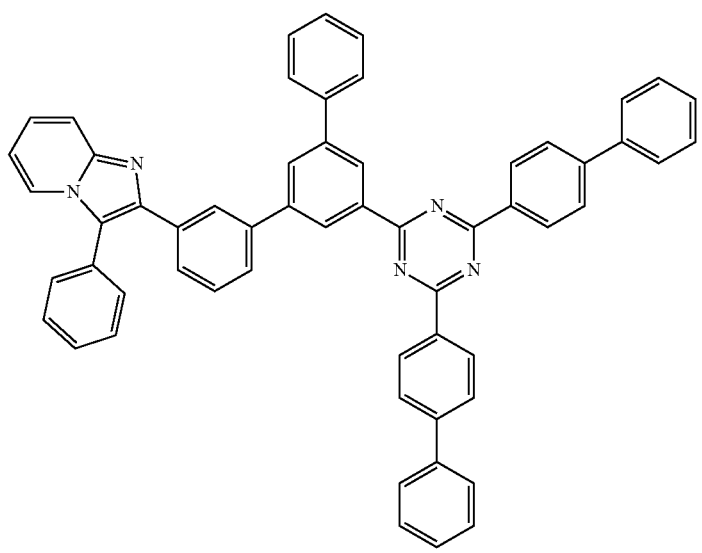 [SMILES: c1ccc(-c2ccc(-c3nc(-c4ccc(-c5ccccc5)cc4)nc(-c4cc(-c5ccccc5)cc(-c5cccc(-c6nc7ccccn7c6-c6ccccc6)c5)c4)n3)cc2)cc1]

B 148
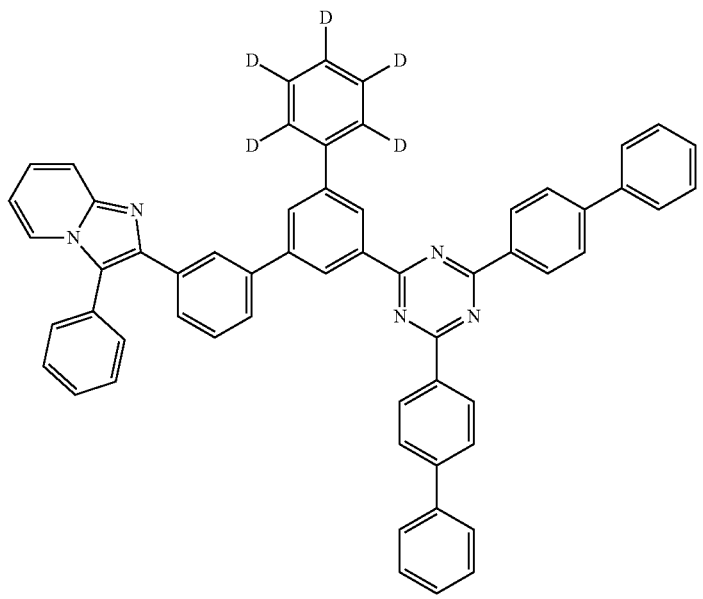 [SMILES: [2H]c1c([2H])c([2H])c(-c2cc(-c3cccc(-c4nc5ccccn5c4-c4ccccc4)c3)cc(-c3nc(-c4ccc(-c5ccccc5)cc4)nc(-c4ccc(-c5ccccc5)cc4)n3)c2)c([2H])c1[2H]]
B 149
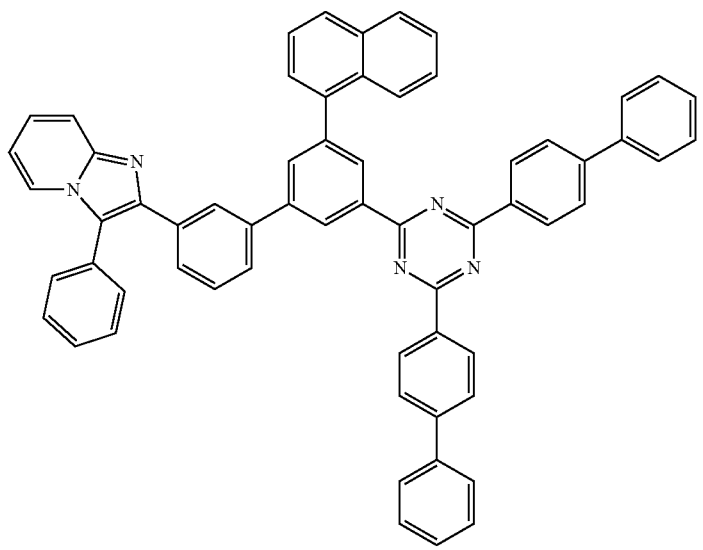 [SMILES: c1ccc(-c2ccc(-c3nc(-c4ccc(-c5ccccc5)cc4)nc(-c4cc(-c5cccc(-c6nc7ccccn7c6-c6ccccc6)c5)cc(-c5cccc6ccccc56)c4)n3)cc2)cc1]
B 150
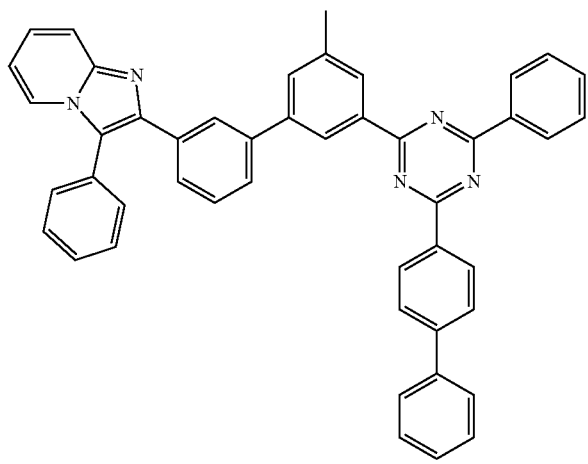 [SMILES: Cc1cc(-c2cccc(-c3nc4ccccn4c3-c3ccccc3)c2)cc(-c2nc(-c3ccccc3)nc(-c3ccc(-c4ccccc4)cc3)n2)c1]

-continued
B 151
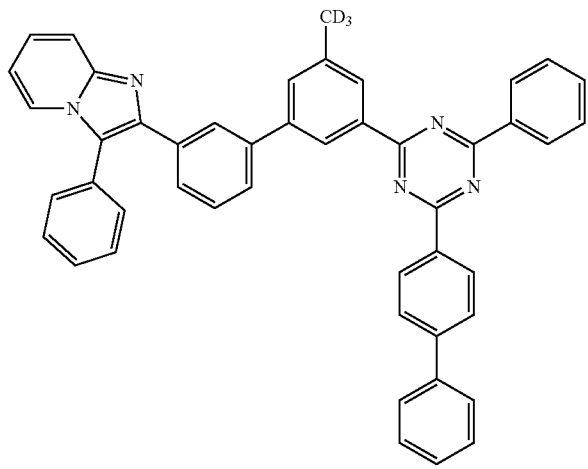 [SMILES: [2H]C([2H])([2H])c1cc(-c2cccc(-c3nc4ccccn4c3-c3ccccc3)c2)cc(-c2nc(-c3ccccc3)nc(-c3ccc(-c4ccccc4)cc3)n2)c1]
B 152
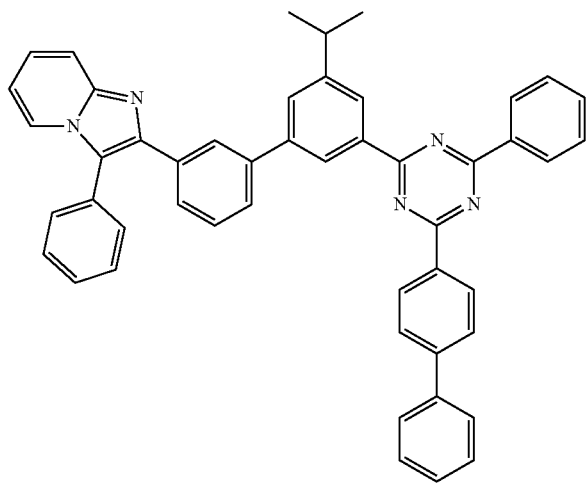 [SMILES: CC(C)c1cc(-c2cccc(-c3nc4ccccn4c3-c3ccccc3)c2)cc(-c2nc(-c3ccccc3)nc(-c3ccc(-c4ccccc4)cc3)n2)c1]
B 153
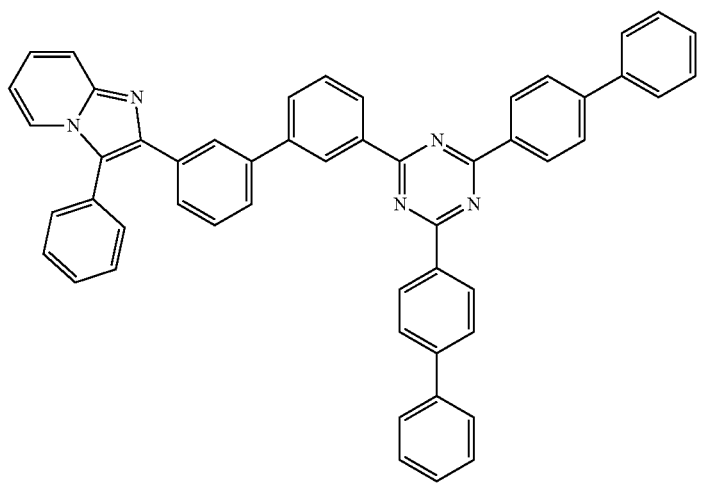 [SMILES: c1ccc(-c2ccc(-c3nc(-c4ccc(-c5ccccc5)cc4)nc(-c4cccc(-c5cccc(-c6nc7ccccn7c6-c6ccccc6)c5)c4)n3)cc2)cc1]

-continued
B 154
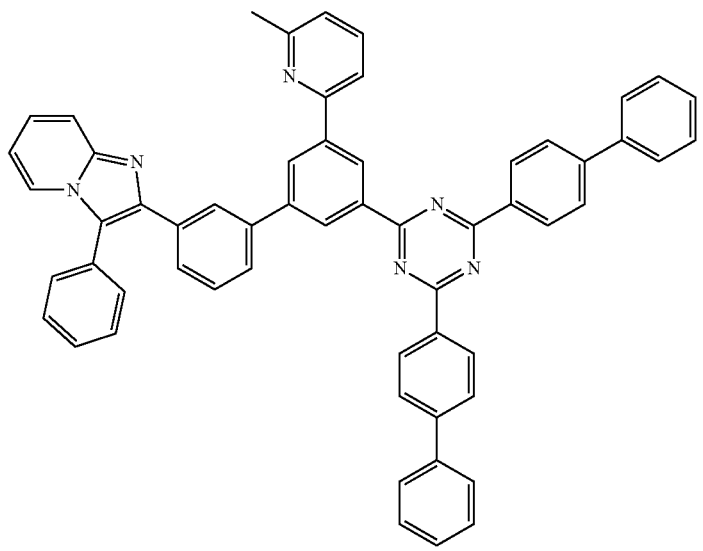 [SMILES: Cc1cccc(-c2cc(-c3cccc(-c4nc5ccccn5c4-c4ccccc4)c3)cc(-c3nc(-c4ccc(-c5ccccc5)cc4)nc(-c4ccc(-c5ccccc5)cc4)n3)c2)n1]
B 155
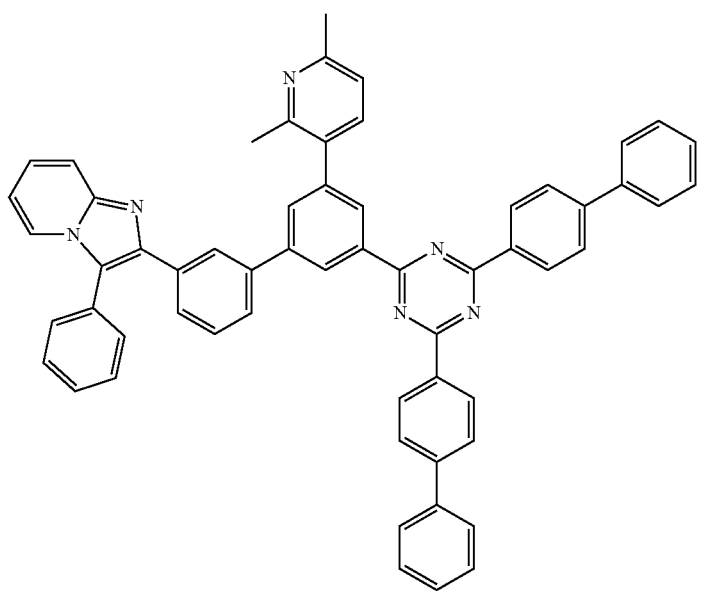 [SMILES: Cc1ccc(-c2cc(-c3cccc(-c4nc5ccccn5c4-c4ccccc4)c3)cc(-c3nc(-c4ccc(-c5ccccc5)cc4)nc(-c4ccc(-c5ccccc5)cc4)n3)c2)c(C)n1]
B 156
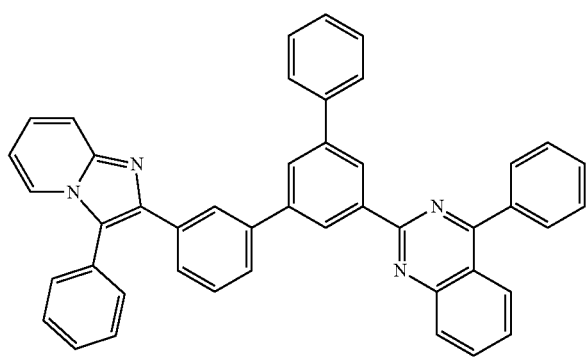 [SMILES: c1ccc(-c2cc(-c3cccc(-c4nc5ccccn5c4-c4ccccc4)c3)cc(-c3nc(-c4ccccc4)c4ccccc4n3)c2)cc1]

-continued
B 157
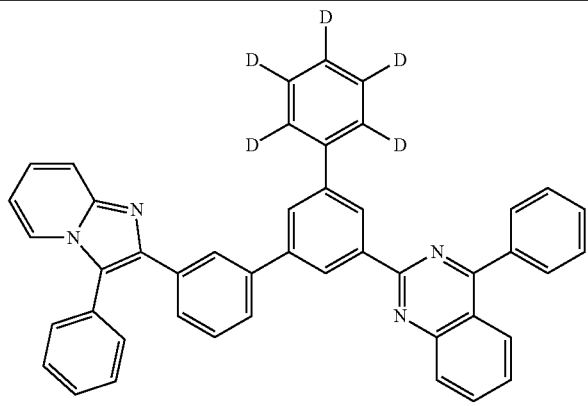
B 158
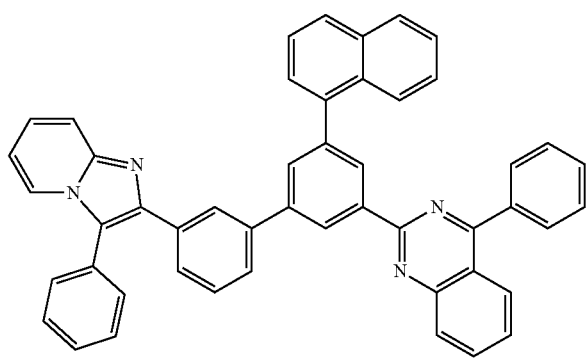 [SMILES: c1ccc(-c2nc(-c3cc(-c4cccc(-c5nc6ccccn6c5-c5ccccc5)c4)cc(-c4cccc5ccccc45)c3)nc3ccccc23)cc1]
B 159
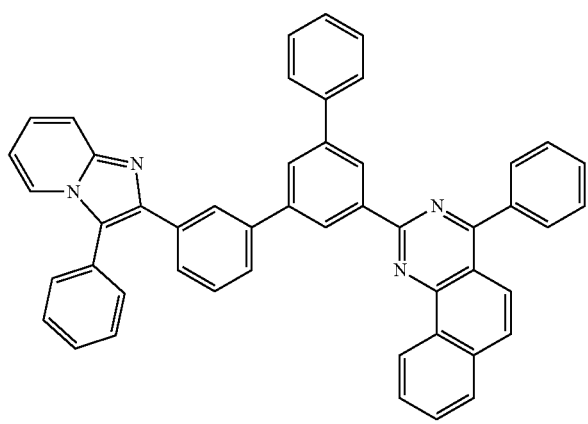 [SMILES: c1ccc(-c2cc(-c3cccc(-c4nc5ccccn5c4-c4ccccc4)c3)cc(-c3nc(-c4ccccc4)c4ccc5ccccc5c4n3)c2)cc1]
B 160
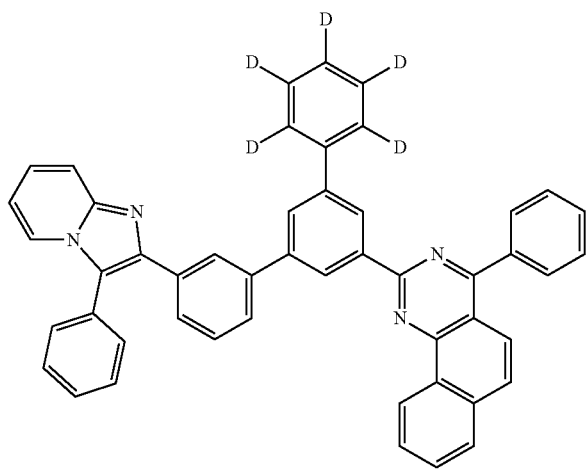 [SMILES: [2H]c1c([2H])c([2H])c(-c2cc(-c3cccc(-c4nc5ccccn5c4-c4ccccc4)c3)cc(-c3nc(-c4ccccc4)c4ccc5ccccc5c4n3)c2)c([2H])c1[2H]]

B 161
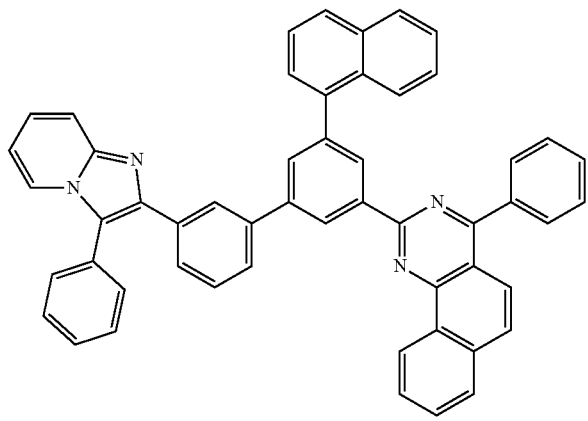 [SMILES: c1ccc(-c2nc(-c3cc(-c4cccc(-c5nc6ccccn6c5-c5ccccc5)c4)cc(-c4cccc5ccccc45)c3)nc3c2ccc2ccccc23)cc1]
B 162
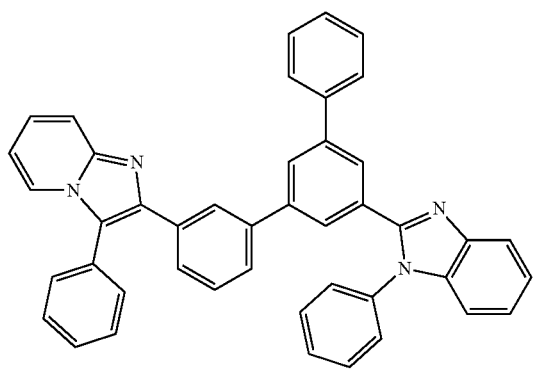 [SMILES: c1ccc(-c2cc(-c3cccc(-c4nc5ccccn5c4-c4ccccc4)c3)cc(-c3nc4ccccc4n3-c3ccccc3)c2)cc1]
B 163
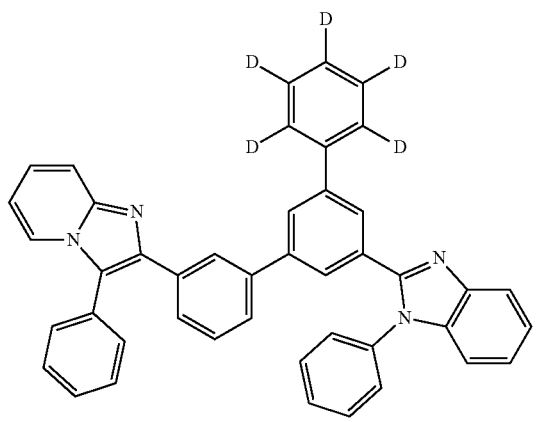 [SMILES: [2H]c1c([2H])c([2H])c(-c2cc(-c3cccc(-c4nc5ccccn5c4-c4ccccc4)c3)cc(-c3nc4ccccc4n3-c3ccccc3)c2)c([2H])c1[2H]]
B 164
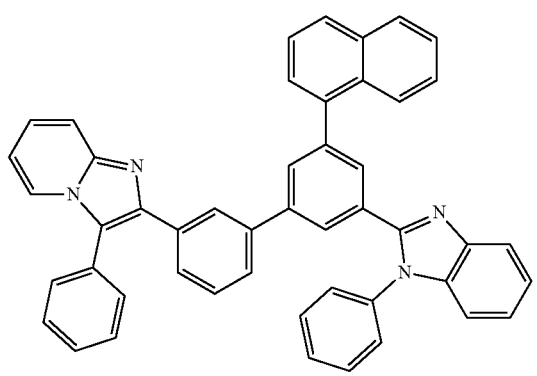 [SMILES: c1ccc(-c2c(-c3cccc(-c4cc(-c5cccc6ccccc56)cc(-c5nc6ccccc6n5-c5ccccc5)c4)c3)nc3ccccn23)cc1]

B 165
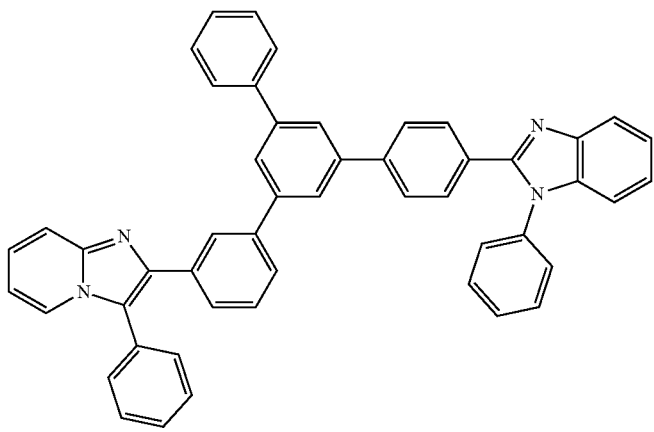 [SMILES: c1ccc(-c2cc(-c3ccc(-c4nc5ccccc5n4-c4ccccc4)cc3)cc(-c3cccc(-c4nc5ccccn5c4-c4ccccc4)c3)c2)cc1]
B 166
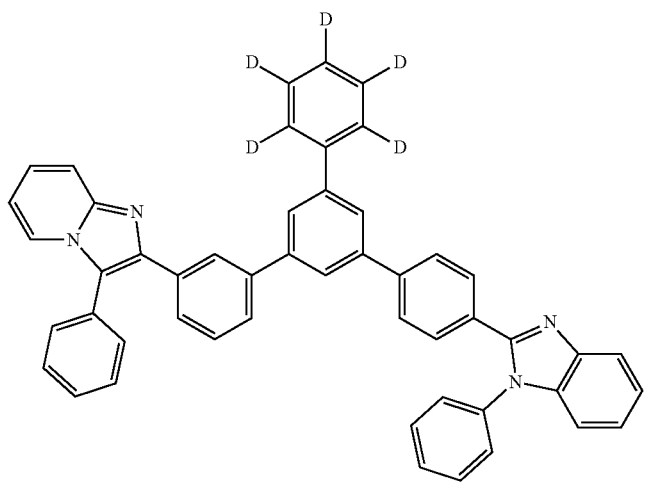 [SMILES: [2H]c1c([2H])c([2H])c(-c2cc(-c3ccc(-c4nc5ccccc5n4-c4ccccc4)cc3)cc(-c3cccc(-c4nc5ccccn5c4-c4ccccc4)c3)c2)c([2H])c1[2H]]
B 167
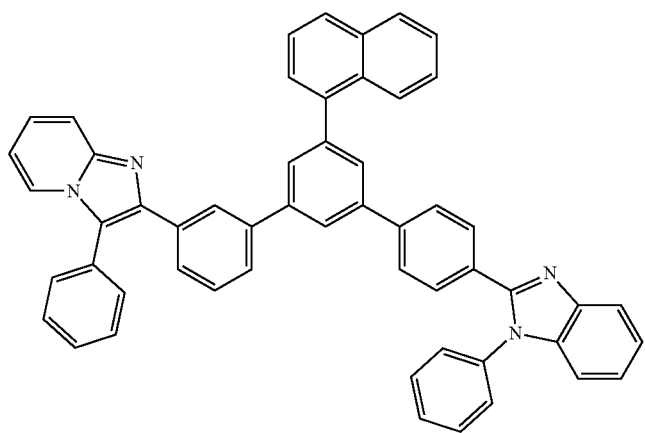 [SMILES: c1ccc(-c2c(-c3cccc(-c4cc(-c5ccc(-c6nc7ccccc7n6-c6ccccc6)cc5)cc(-c5cccc6ccccc56)c4)c3)nc3ccccn23)cc1]

B 168
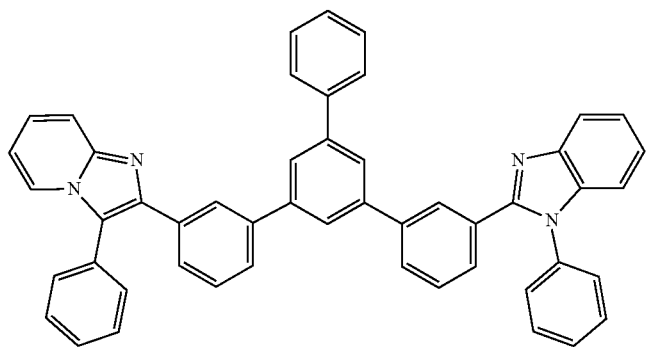 [SMILES: c1ccc(-c2cc(-c3cccc(-c4nc5ccccn5c4-c4ccccc4)c3)cc(-c3cccc(-c4nc5ccccc5n4-c4ccccc4)c3)c2)cc1]
B 169
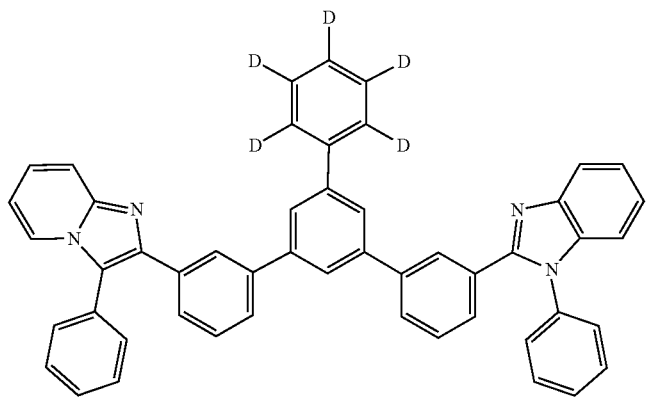 [SMILES: [2H]c1c([2H])c([2H])c(-c2cc(-c3cccc(-c4nc5ccccn5c4-c4ccccc4)c3)cc(-c3cccc(-c4nc5ccccc5n4-c4ccccc4)c3)c2)c([2H])c1[2H]]
B 170
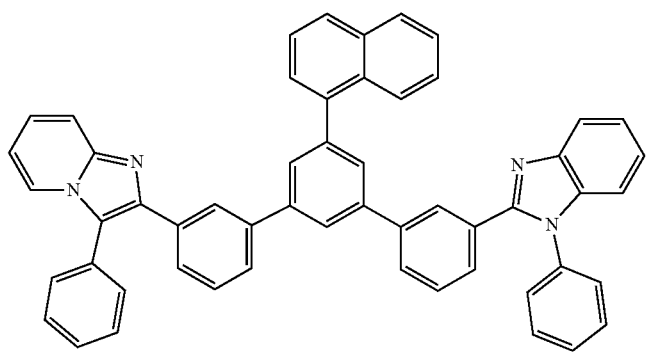 [SMILES: c1ccc(-c2c(-c3cccc(-c4cc(-c5cccc(-c6nc7ccccc7n6-c6ccccc6)c5)cc(-c5cccc6ccccc56)c4)c3)nc3ccccn23)cc1]
B 171
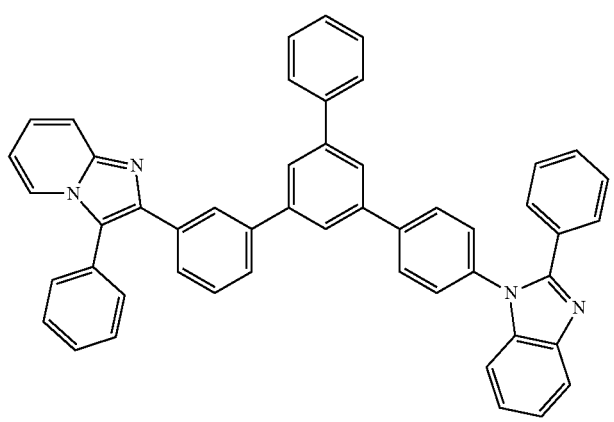 [SMILES: c1ccc(-c2cc(-c3ccc(-n4c(-c5ccccc5)nc5ccccc54)cc3)cc(-c3cccc(-c4nc5ccccn5c4-c4ccccc4)c3)c2)cc1]

-continued
B 172
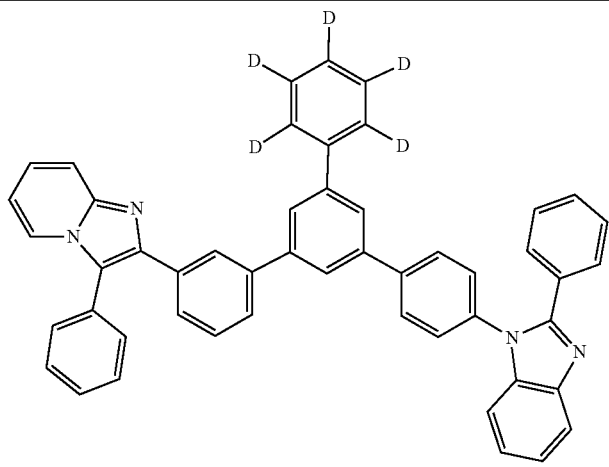
B 173
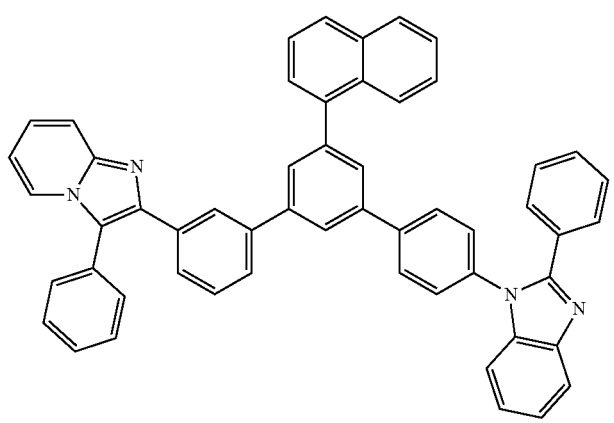 [SMILES: c1ccc(-c2nc3ccccc3n2-c2ccc(-c3cc(-c4cccc(-c5nc6ccccn6c5-c5ccccc5)c4)cc(-c4cccc5ccccc45)c3)cc2)cc1]
B 174
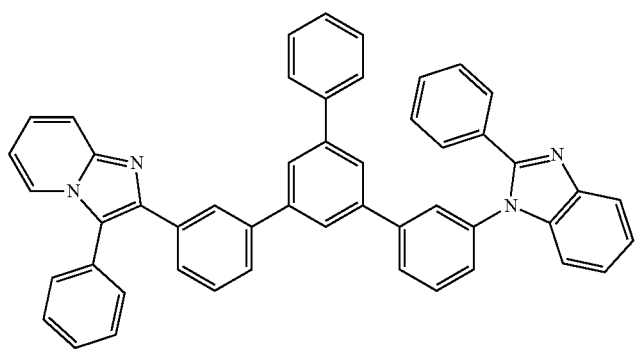 [SMILES: c1ccc(-c2cc(-c3cccc(-c4nc5ccccn5c4-c4ccccc4)c3)cc(-c3cccc(-n4c(-c5ccccc5)nc5ccccc54)c3)c2)cc1]
B 175
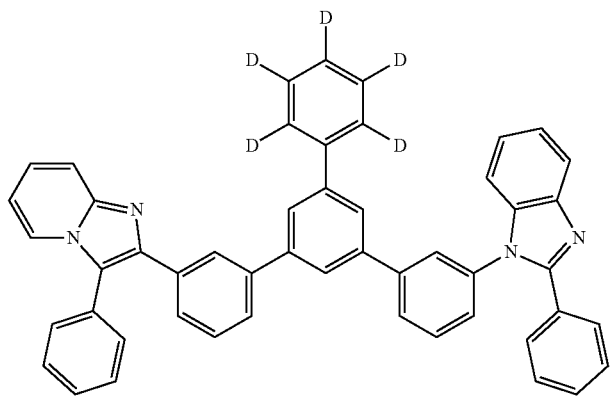 [SMILES: [2H]c1c([2H])c([2H])c(-c2cc(-c3cccc(-c4nc5ccccn5c4-c4ccccc4)c3)cc(-c3cccc(-n4c(-c5ccccc5)nc5ccccc54)c3)c2)c([2H])c1[2H]]

B 176
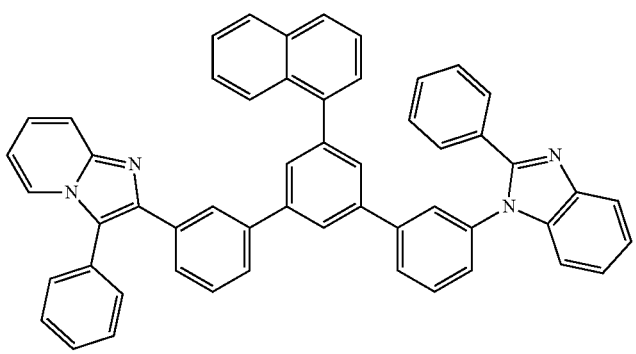 [SMILES: c1ccc(-c2nc3ccccc3n2-c2cccc(-c3cc(-c4cccc(-c5nc6ccccn6c5-c5ccccc5)c4)cc(-c4cccc5ccccc45)c3)c2)cc1]
B 177
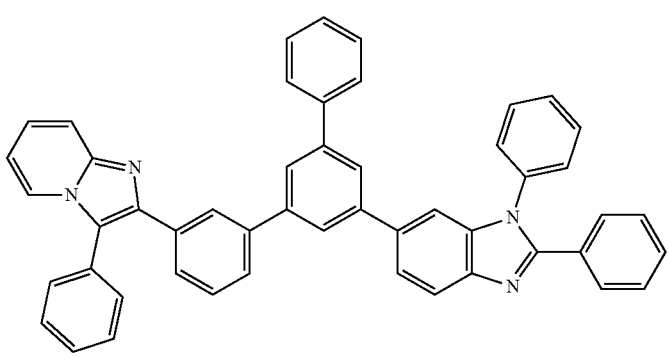 [SMILES: c1ccc(-c2cc(-c3cccc(-c4nc5ccccn5c4-c4ccccc4)c3)cc(-c3ccc4nc(-c5ccccc5)n(-c5ccccc5)c4c3)c2)cc1]
B 178
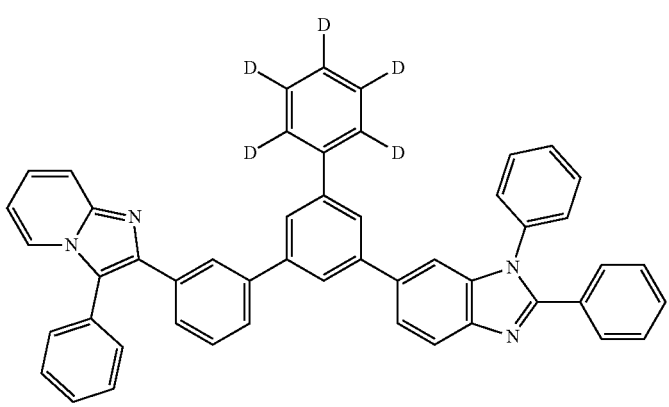 [SMILES: [2H]c1c([2H])c([2H])c(-c2cc(-c3cccc(-c4nc5ccccn5c4-c4ccccc4)c3)cc(-c3ccc4nc(-c5ccccc5)n(-c5ccccc5)c4c3)c2)c([2H])c1[2H]]
B 179
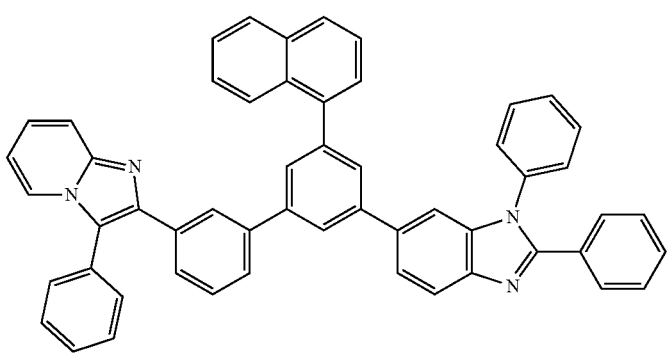 [SMILES: c1ccc(-c2nc3ccc(-c4cc(-c5cccc(-c6nc7ccccn7c6-c6ccccc6)c5)cc(-c5cccc6ccccc56)c4)cc3n2-c2ccccc2)cc1]

B 180
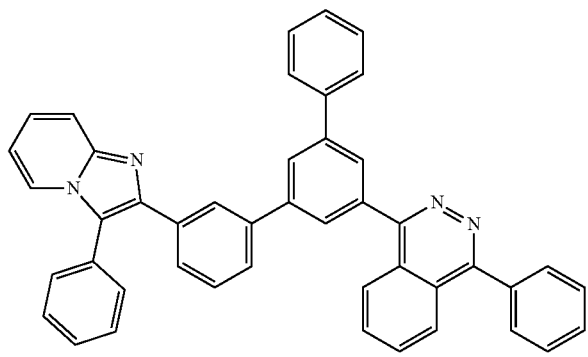 [SMILES: c1ccc(-c2cc(-c3cccc(-c4nc5ccccn5c4-c4ccccc4)c3)cc(-c3nnc(-c4ccccc4)c4ccccc34)c2)cc1]
B 181
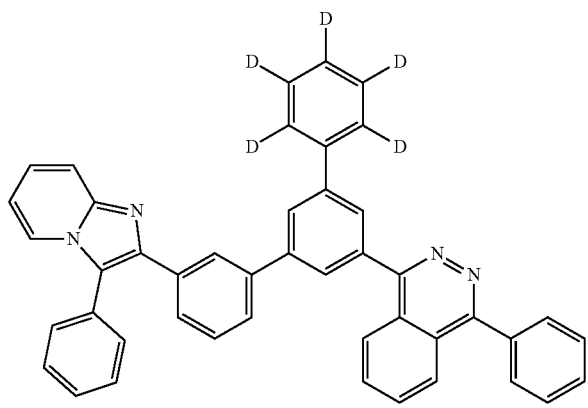 [SMILES: [2H]c1c([2H])c([2H])c(-c2cc(-c3cccc(-c4nc5ccccn5c4-c4ccccc4)c3)cc(-c3nnc(-c4ccccc4)c4ccccc34)c2)c([2H])c1[2H]]
B 182
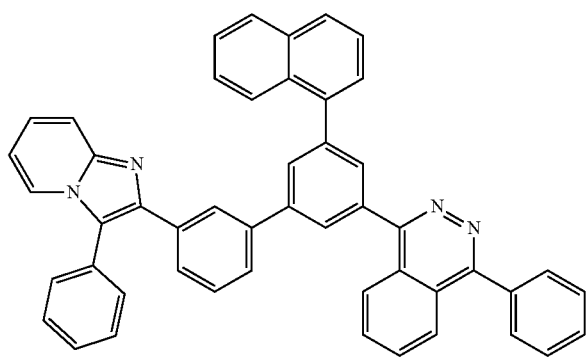 [SMILES: c1ccc(-c2nnc(-c3cc(-c4cccc(-c5nc6ccccn6c5-c5ccccc5)c4)cc(-c4cccc5ccccc45)c3)c3ccccc23)cc1]
B 183
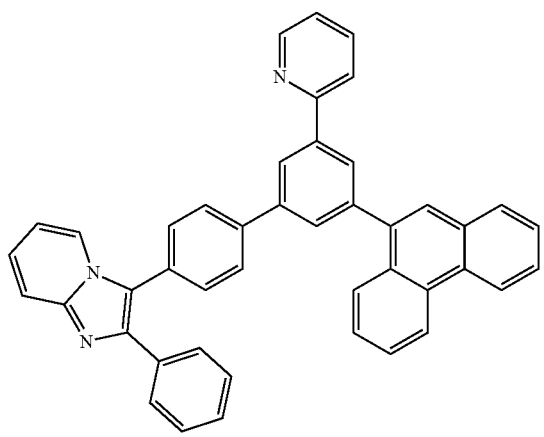 [SMILES: c1ccc(-c2nc3ccccn3c2-c2ccc(-c3cc(-c4ccccn4)cc(-c4cc5ccccc5c5ccccc45)c3)cc2)cc1]

-continued
B 184
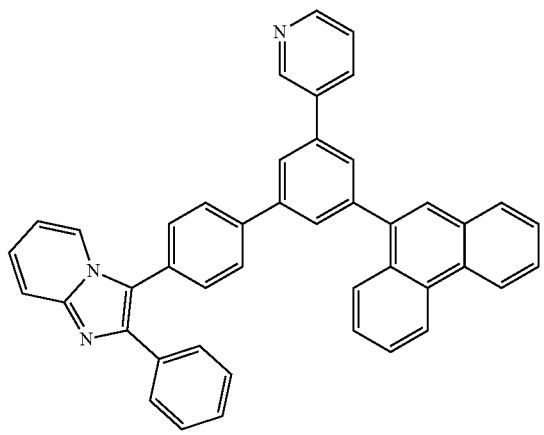 [SMILES: c1ccc(-c2nc3ccccn3c2-c2ccc(-c3cc(-c4cccnc4)cc(-c4cc5ccccc5c5ccccc45)c3)cc2)cc1]
B 185
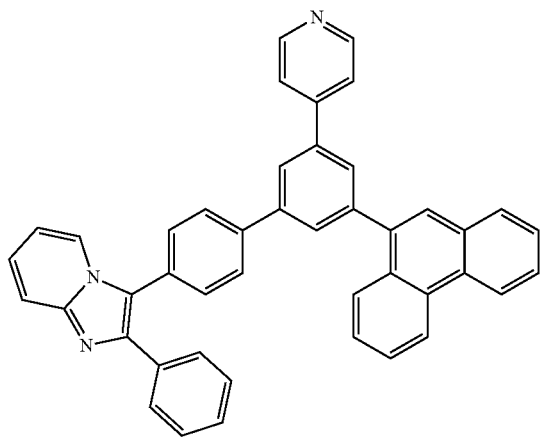 [SMILES: c1ccc(-c2nc3ccccn3c2-c2ccc(-c3cc(-c4ccncc4)cc(-c4cc5ccccc5c5ccccc45)c3)cc2)cc1]
B 186
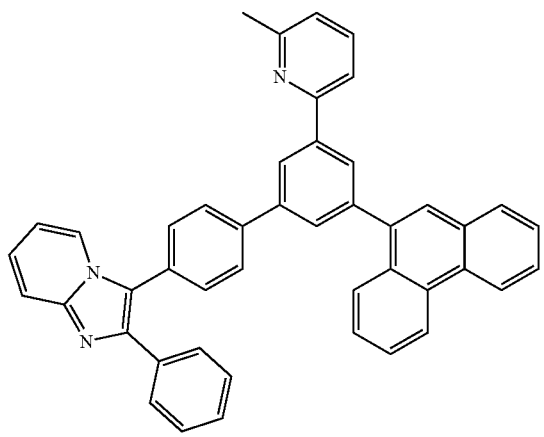 [SMILES: Cc1cccc(-c2cc(-c3ccc(-c4c(-c5ccccc5)nc5ccccn45)cc3)cc(-c3cc4ccccc4c4ccccc34)c2)n1]

B 187
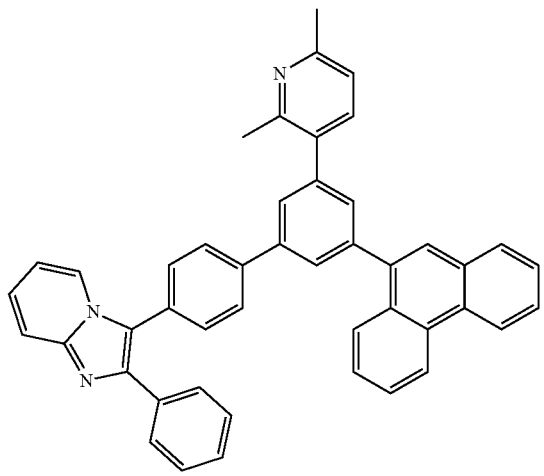 [SMILES: Cc1ccc(-c2cc(-c3ccc(-c4c(-c5ccccc5)nc5ccccn45)cc3)cc(-c3cc4ccccc4c4ccccc34)c2)c(C)n1]
B 188
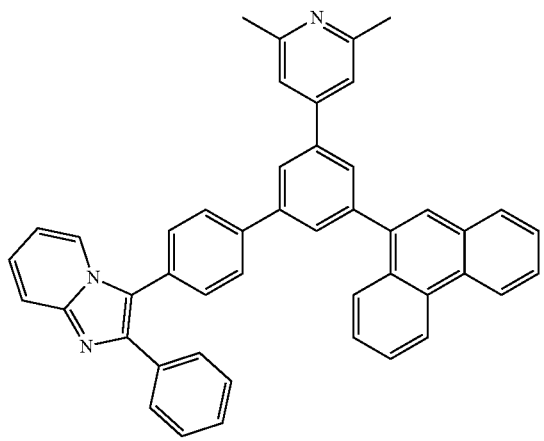 [SMILES: Cc1cc(-c2cc(-c3ccc(-c4c(-c5ccccc5)nc5ccccn45)cc3)cc(-c3cc4ccccc4c4ccccc34)c2)cc(C)n1]
B 189
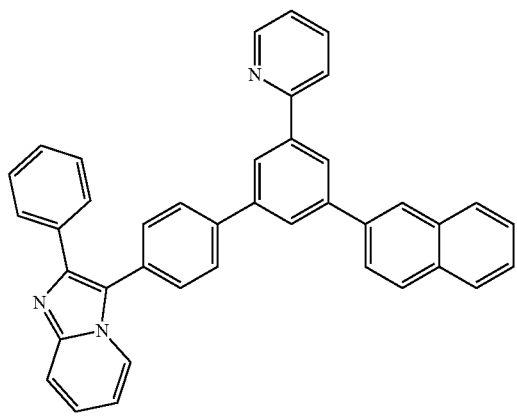 [SMILES: c1ccc(-c2nc3ccccn3c2-c2ccc(-c3cc(-c4ccc5ccccc5c4)cc(-c4ccccn4)c3)cc2)cc1]

B 190
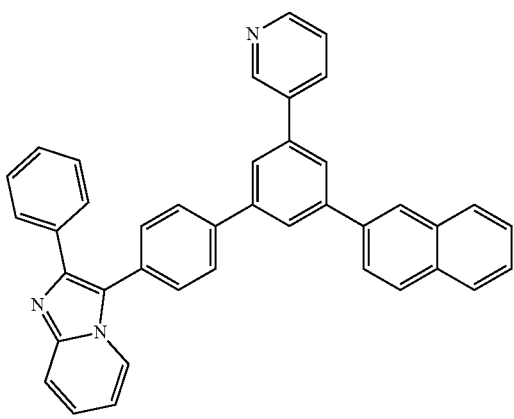 [SMILES: c1ccc(-c2nc3ccccn3c2-c2ccc(-c3cc(-c4cccnc4)cc(-c4ccc5ccccc5c4)c3)cc2)cc1]
B 191
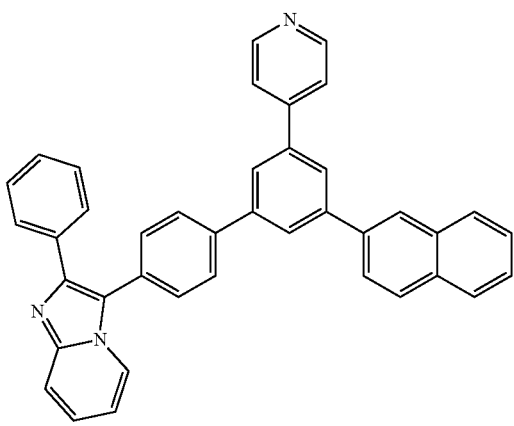 [SMILES: c1ccc(-c2nc3ccccn3c2-c2ccc(-c3cc(-c4ccncc4)cc(-c4ccc5ccccc5c4)c3)cc2)cc1]
B 192
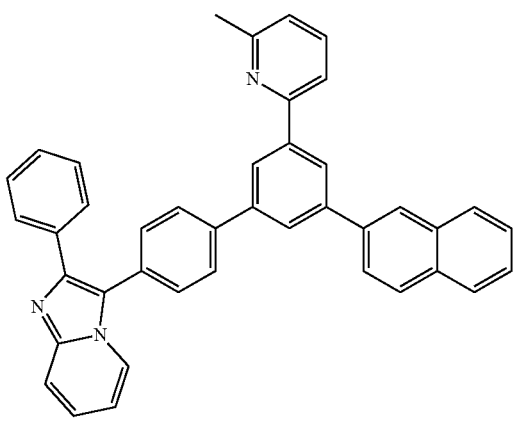 [SMILES: Cc1cccc(-c2cc(-c3ccc(-c4c(-c5ccccc5)nc5ccccn45)cc3)cc(-c3ccc4ccccc4c3)c2)n1]

B 193
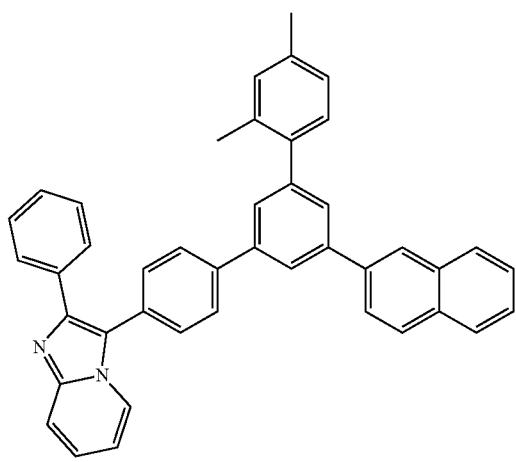 [SMILES: Cc1ccc(-c2cc(-c3ccc(-c4c(-c5ccccc5)nc5ccccn45)cc3)cc(-c3ccc4ccccc4c3)c2)c(C)c1]
B 194
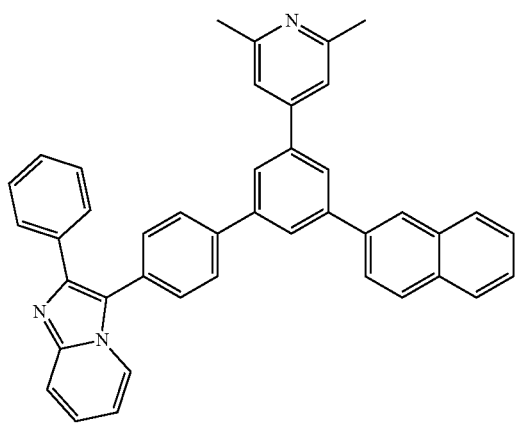 [SMILES: Cc1cc(-c2cc(-c3ccc(-c4c(-c5ccccc5)nc5ccccn45)cc3)cc(-c3ccc4ccccc4c3)c2)cc(C)n1]
B 195
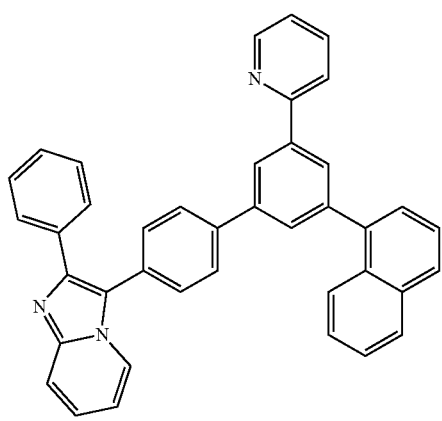 [SMILES: c1ccc(-c2nc3ccccn3c2-c2ccc(-c3cc(-c4ccccn4)cc(-c4cccc5ccccc45)c3)cc2)cc1]

-continued
B 196
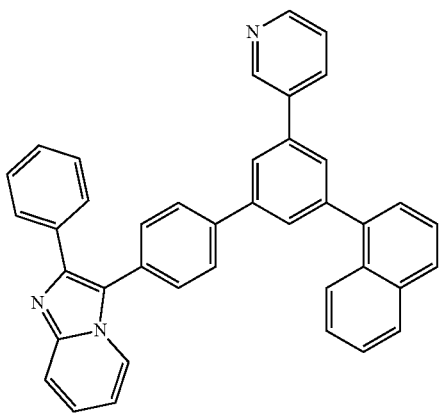 [SMILES: c1ccc(-c2nc3ccccn3c2-c2ccc(-c3cc(-c4cccnc4)cc(-c4cccc5ccccc45)c3)cc2)cc1]
B 197
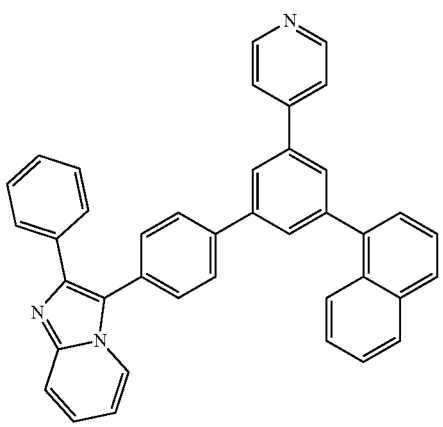 [SMILES: c1ccc(-c2nc3ccccn3c2-c2ccc(-c3cc(-c4ccncc4)cc(-c4cccc5ccccc45)c3)cc2)cc1]
B 198
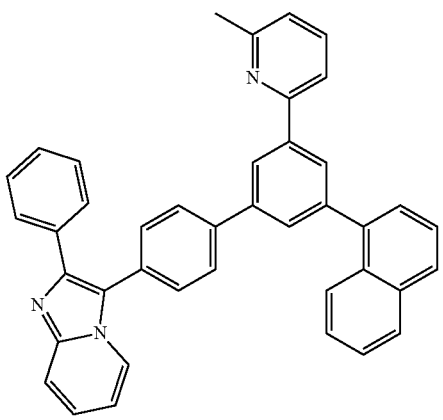 [SMILES: Cc1cccc(-c2cc(-c3ccc(-c4c(-c5ccccc5)nc5ccccn45)cc3)cc(-c3cccc4ccccc34)c2)n1]

-continued
B 199
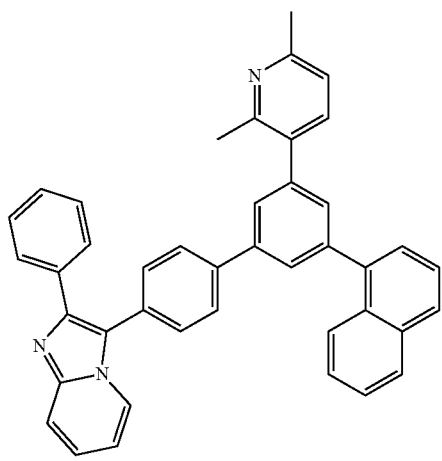 [SMILES: Cc1ccc(-c2cc(-c3ccc(-c4c(-c5ccccc5)nc5ccccn45)cc3)cc(-c3cccc4ccccc34)c2)c(C)n1]
B 200
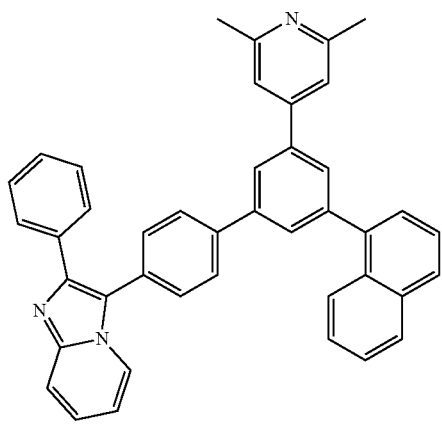 [SMILES: Cc1cc(-c2cc(-c3ccc(-c4c(-c5ccccc5)nc5ccccn45)cc3)cc(-c3cccc4ccccc34)c2)cc(C)n1]
B 201
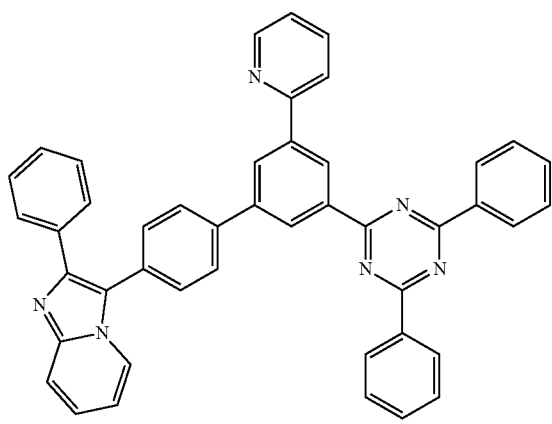

-continued
B 202
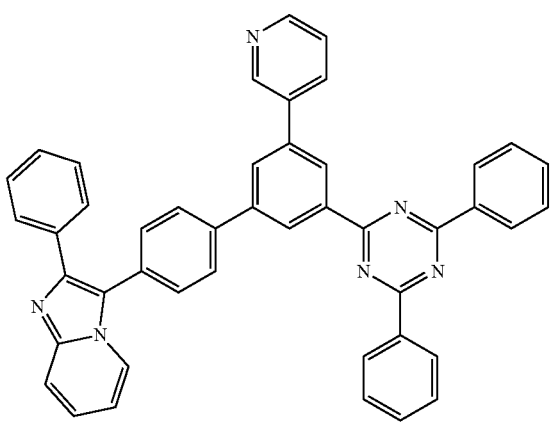 [SMILES: c1ccc(-c2nc(-c3ccccc3)nc(-c3cc(-c4ccc(-c5c(-c6ccccc6)nc6ccccn56)cc4)cc(-c4cccnc4)c3)n2)cc1]
B 203
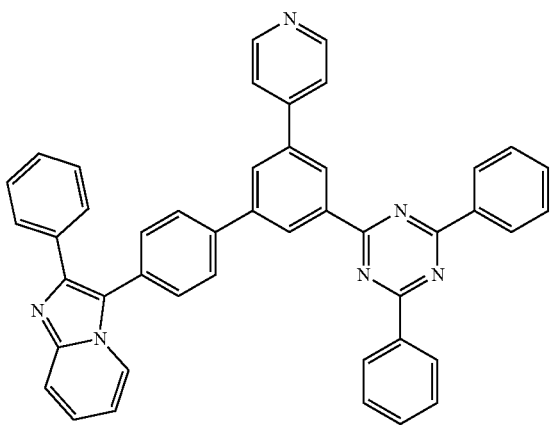 [SMILES: c1ccc(-c2nc(-c3ccccc3)nc(-c3cc(-c4ccncc4)cc(-c4ccc(-c5c(-c6ccccc6)nc6ccccn56)cc4)c3)n2)cc1]
B 204
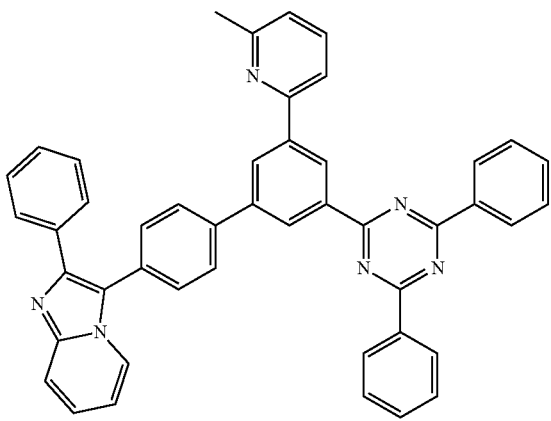 [SMILES: Cc1cccc(-c2cc(-c3ccc(-c4c(-c5ccccc5)nc5ccccn45)cc3)cc(-c3nc(-c4ccccc4)nc(-c4ccccc4)n3)c2)n1]

B 205
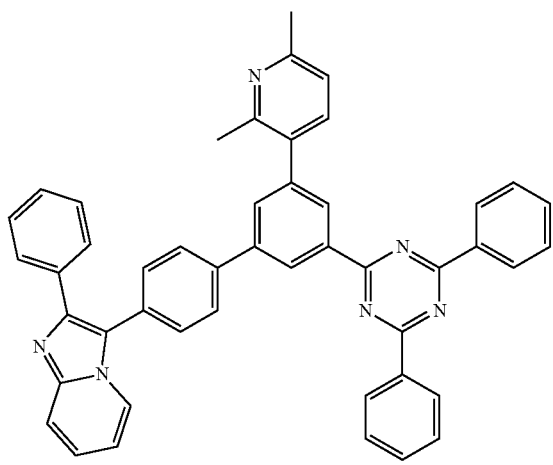 [SMILES: Cc1ccc(-c2cc(-c3ccc(-c4c(-c5ccccc5)nc5ccccn45)cc3)cc(-c3nc(-c4ccccc4)nc(-c4ccccc4)n3)c2)c(C)n1]
B 206
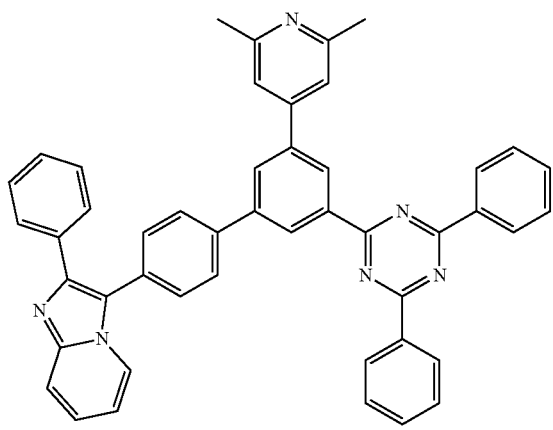 [SMILES: Cc1cc(-c2cc(-c3ccc(-c4c(-c5ccccc5)nc5ccccn45)cc3)cc(-c3nc(-c4ccccc4)nc(-c4ccccc4)n3)c2)cc(C)n1]
B 207
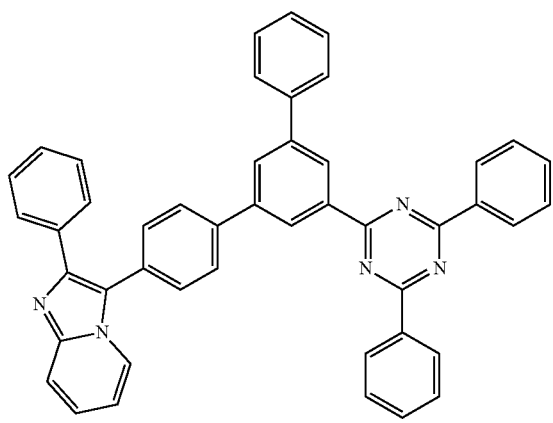 [SMILES: c1ccc(-c2cc(-c3ccc(-c4c(-c5ccccc5)nc5ccccn45)cc3)cc(-c3nc(-c4ccccc4)nc(-c4ccccc4)n3)c2)cc1]

-continued
B 208
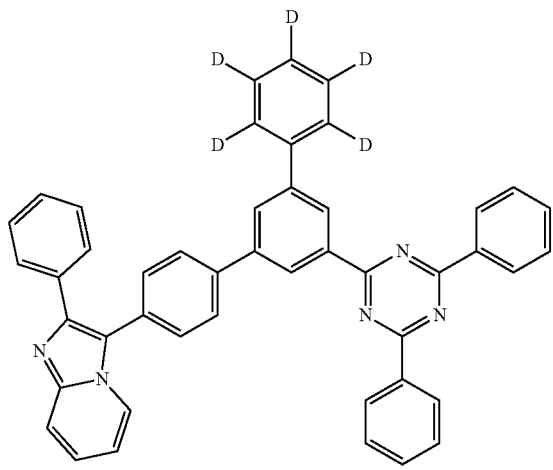 [SMILES: [2H]c1c([2H])c([2H])c(-c2cc(-c3ccc(-c4c(-c5ccccc5)nc5ccccn45)cc3)cc(-c3nc(-c4ccccc4)nc(-c4ccccc4)n3)c2)c([2H])c1[2H]]
B 209
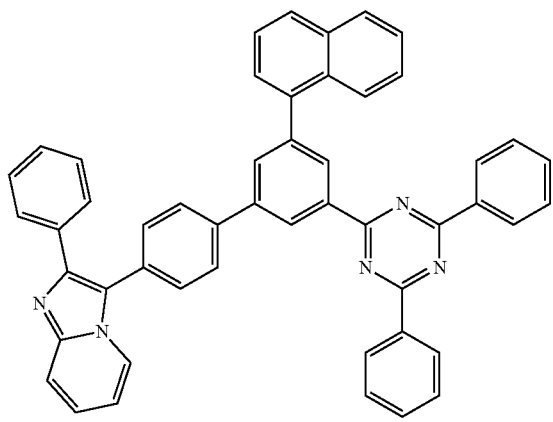 [SMILES: c1ccc(-c2nc(-c3ccccc3)nc(-c3cc(-c4ccc(-c5c(-c6ccccc6)nc6ccccn56)cc4)cc(-c4cccc5ccccc45)c3)n2)cc1]
B 210
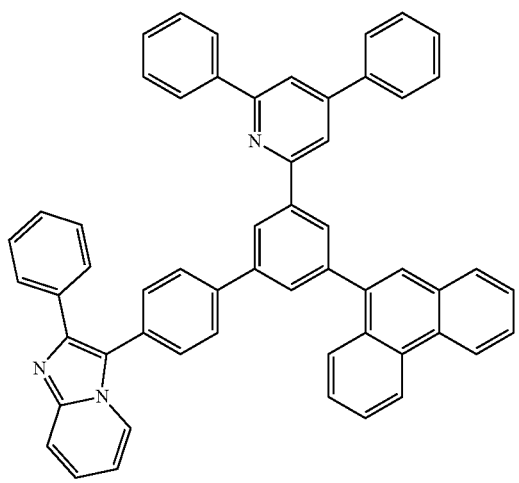 [SMILES: c1ccc(-c2cc(-c3ccccc3)nc(-c3cc(-c4ccc(-c5c(-c6ccccc6)nc6ccccn56)cc4)cc(-c4cc5ccccc5c5ccccc45)c3)c2)cc1]

-continued
B 211
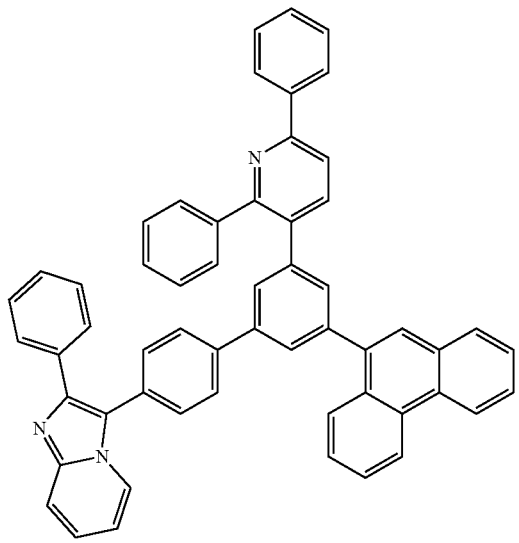 [SMILES: c1ccc(-c2ccc(-c3cc(-c4ccc(-c5c(-c6ccccc6)nc6ccccn56)cc4)cc(-c4cc5ccccc5c5ccccc45)c3)c(-c3ccccc3)n2)cc1]
B 212
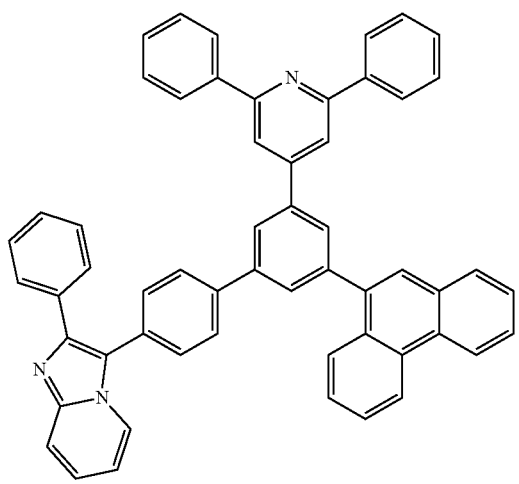 [SMILES: c1ccc(-c2cc(-c3cc(-c4ccc(-c5c(-c6ccccc6)nc6ccccn56)cc4)cc(-c4cc5ccccc5c5ccccc45)c3)cc(-c3ccccc3)n2)cc1]
B 213
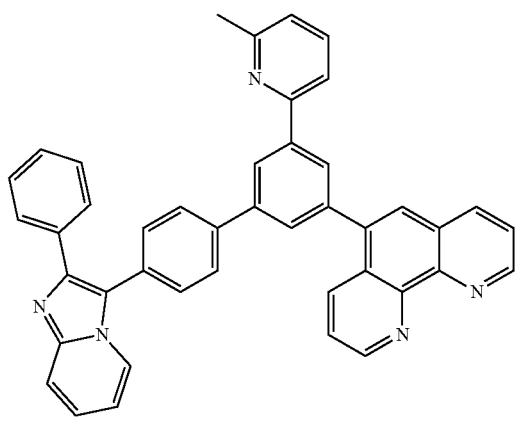 [SMILES: Cc1cccc(-c2cc(-c3ccc(-c4c(-c5ccccc5)nc5ccccn45)cc3)cc(-c3cc4cccnc4c4ncccc34)c2)n1]

B 214
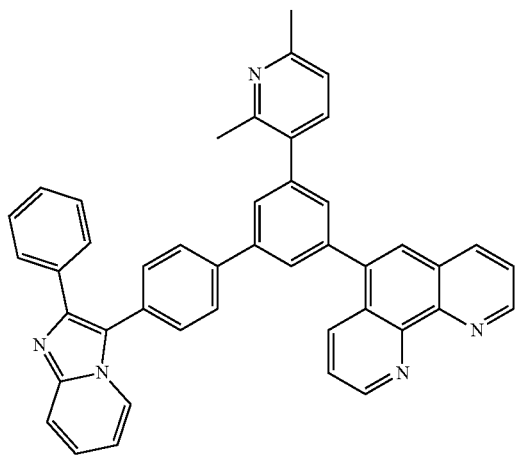 [SMILES: Cc1ccc(-c2cc(-c3ccc(-c4c(-c5ccccc5)nc5ccccn45)cc3)cc(-c3cc4cccnc4c4ncccc34)c2)c(C)n1]
B 215
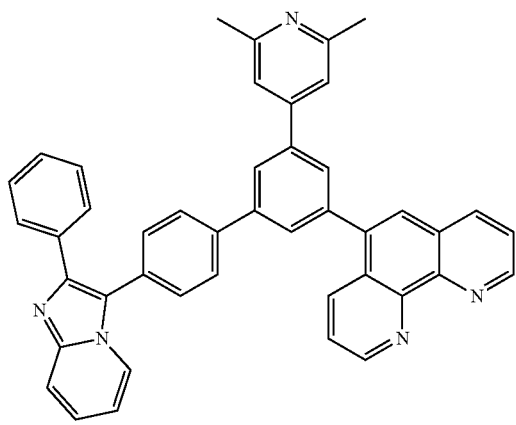 [SMILES: Cc1cc(-c2cc(-c3ccc(-c4c(-c5ccccc5)nc5ccccn45)cc3)cc(-c3cc4cccnc4c4ncccc34)c2)cc(C)n1]
B 216
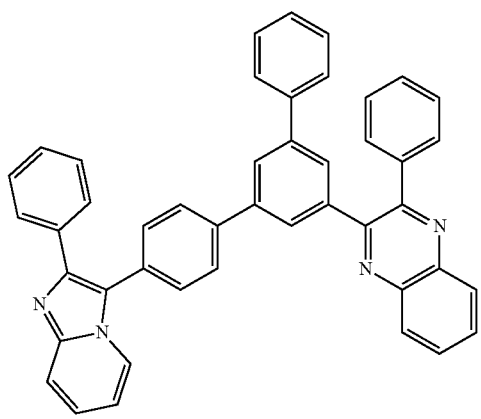 [SMILES: c1ccc(-c2cc(-c3ccc(-c4c(-c5ccccc5)nc5ccccn45)cc3)cc(-c3nc4ccccc4nc3-c3ccccc3)c2)cc1]

-continued
B 217
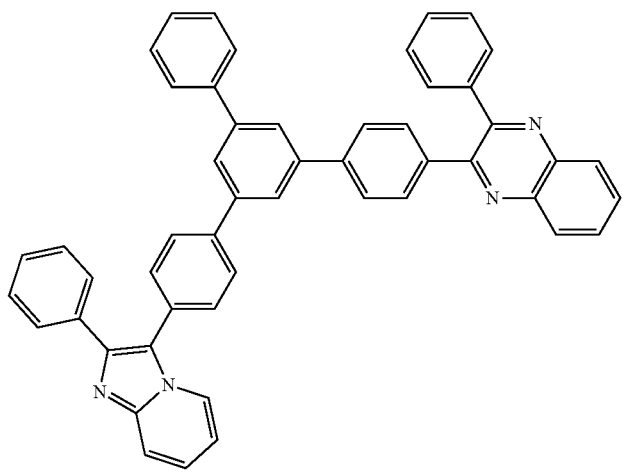 [SMILES: c1ccc(-c2cc(-c3ccc(-c4nc5ccccc5nc4-c4ccccc4)cc3)cc(-c3ccc(-c4c(-c5ccccc5)nc5ccccn45)cc3)c2)cc1]
B 218
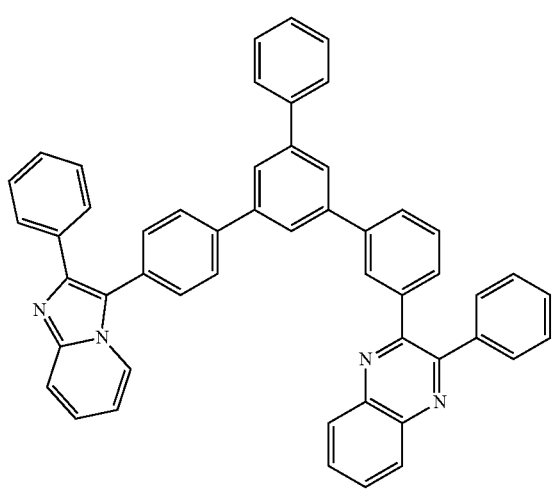 [SMILES: c1ccc(-c2cc(-c3ccc(-c4c(-c5ccccc5)nc5ccccn45)cc3)cc(-c3cccc(-c4nc5ccccc5nc4-c4ccccc4)c3)c2)cc1]
B 219
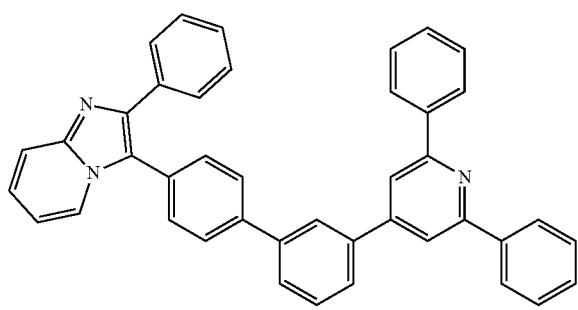 [SMILES: c1ccc(-c2cc(-c3cccc(-c4ccc(-c5c(-c6ccccc6)nc6ccccn56)cc4)c3)cc(-c3ccccc3)n2)cc1]
B 220
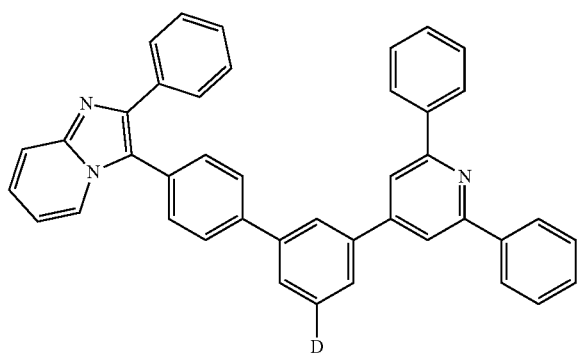 [SMILES: [2H]c1cc(-c2ccc(-c3c(-c4ccccc4)nc4ccccn34)cc2)cc(-c2cc(-c3ccccc3)nc(-c3ccccc3)c2)c1]

-continued
B 221
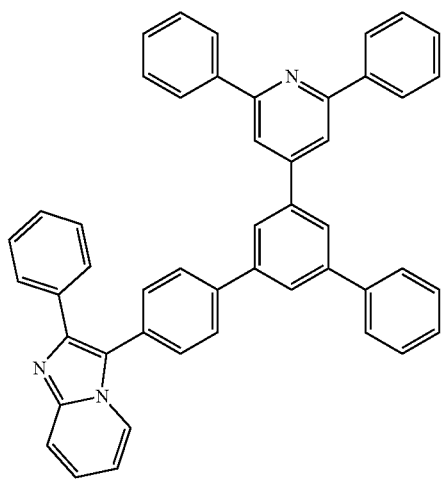 [SMILES: c1ccc(-c2cc(-c3ccc(-c4c(-c5ccccc5)nc5ccccn45)cc3)cc(-c3cc(-c4ccccc4)nc(-c4ccccc4)c3)c2)cc1]
B 222
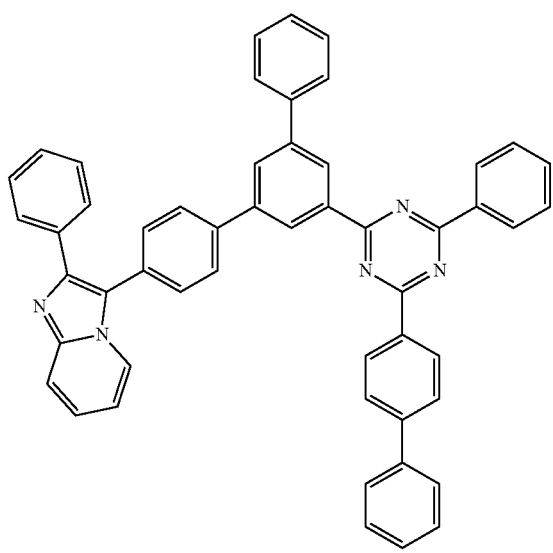 [SMILES: c1ccc(-c2ccc(-c3nc(-c4ccccc4)nc(-c4cc(-c5ccccc5)cc(-c5ccc(-c6c(-c7ccccc7)nc7ccccn67)cc5)c4)n3)cc2)cc1]
B 223
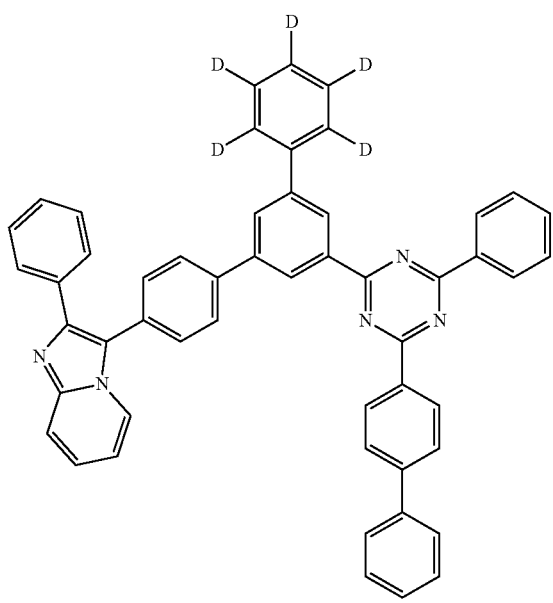 [SMILES: [2H]c1c([2H])c([2H])c(-c2cc(-c3ccc(-c4c(-c5ccccc5)nc5ccccn45)cc3)cc(-c3nc(-c4ccccc4)nc(-c4ccc(-c5ccccc5)cc4)n3)c2)c([2H])c1[2H]]

B 224
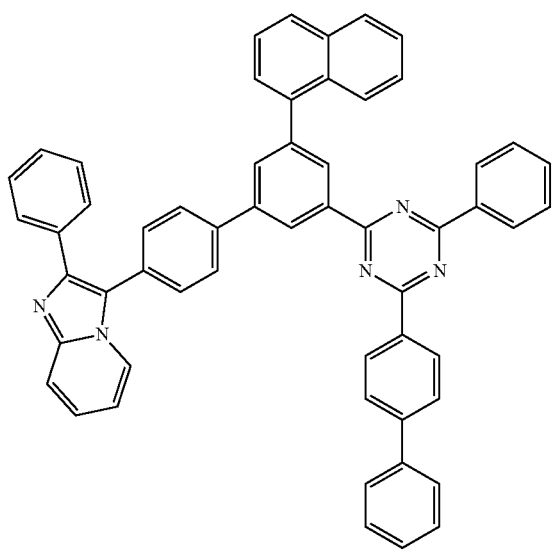 [SMILES: c1ccc(-c2ccc(-c3nc(-c4ccccc4)nc(-c4cc(-c5ccc(-c6c(-c7ccccc7)nc7ccccn67)cc5)cc(-c5cccc6ccccc56)c4)n3)cc2)cc1]
B 225
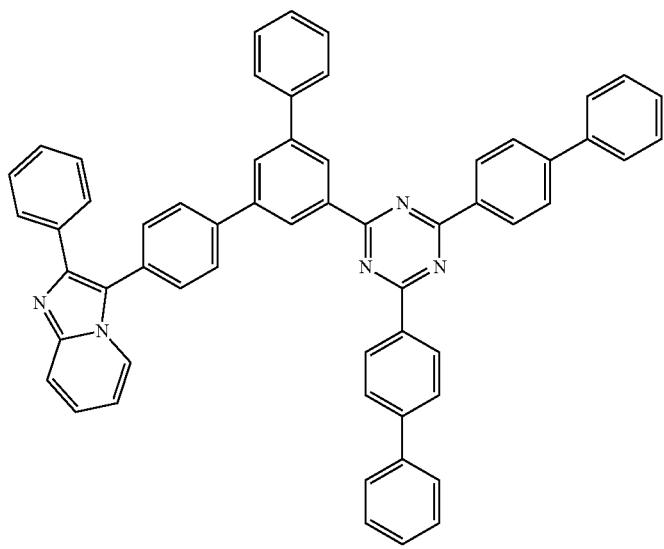 [SMILES: c1ccc(-c2ccc(-c3nc(-c4ccc(-c5ccccc5)cc4)nc(-c4cc(-c5ccccc5)cc(-c5ccc(-c6c(-c7ccccc7)nc7ccccn67)cc5)c4)n3)cc2)cc1]

-continued
B 226
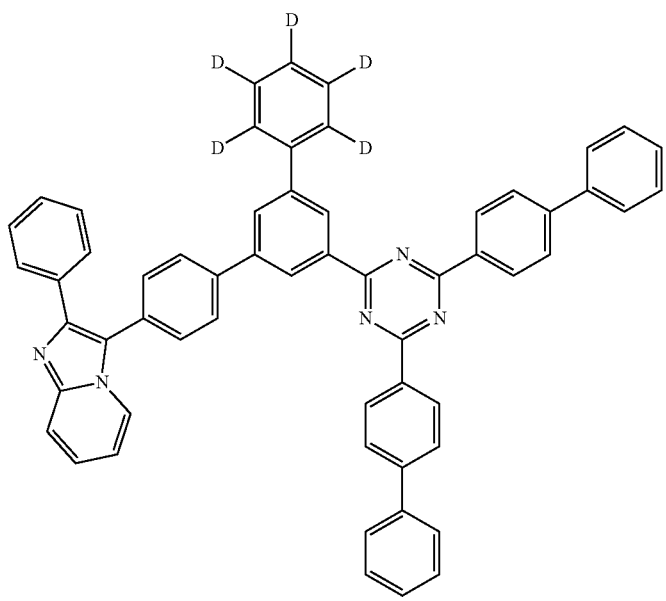 [SMILES: [2H]c1c([2H])c([2H])c(-c2cc(-c3ccc(-c4c(-c5ccccc5)nc5ccccn45)cc3)cc(-c3nc(-c4ccc(-c5ccccc5)cc4)nc(-c4ccc(-c5ccccc5)cc4)n3)c2)c([2H])c1[2H]]
B 227
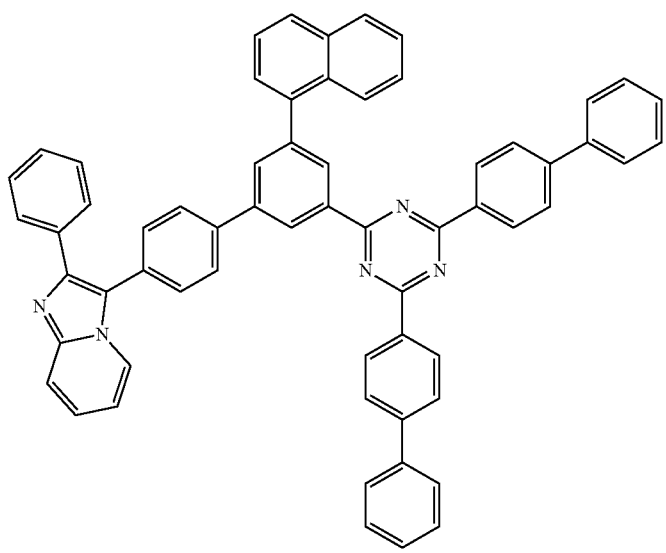 [SMILES: c1ccc(-c2ccc(-c3nc(-c4ccc(-c5ccccc5)cc4)nc(-c4cc(-c5ccc(-c6c(-c7ccccc7)nc7ccccn67)cc5)cc(-c5cccc6ccccc56)c4)n3)cc2)cc1]
B 228
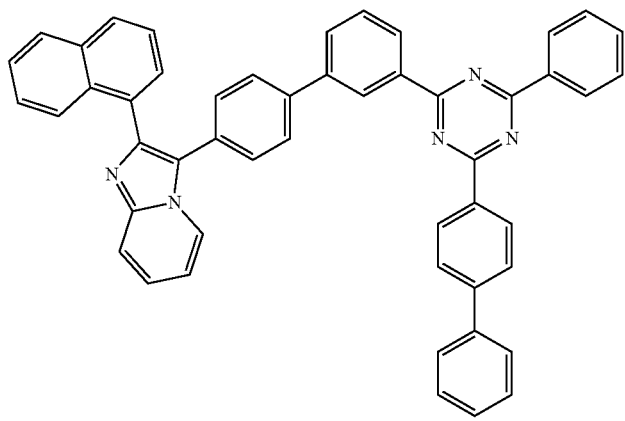 [SMILES: c1ccc(-c2ccc(-c3nc(-c4ccccc4)nc(-c4cccc(-c5ccc(-c6c(-c7cccc8ccccc78)nc7ccccn67)cc5)c4)n3)cc2)cc1]

-continued
B 229
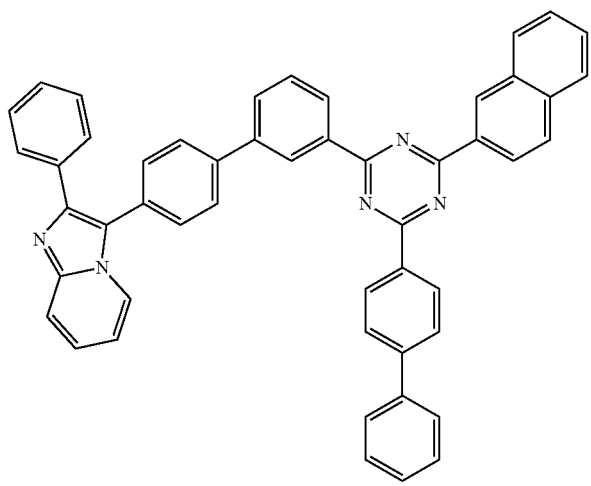 [SMILES: c1ccc(-c2ccc(-c3nc(-c4cccc(-c5ccc(-c6c(-c7ccccc7)nc7ccccn67)cc5)c4)nc(-c4ccc5ccccc5c4)n3)cc2)cc1]
B 230
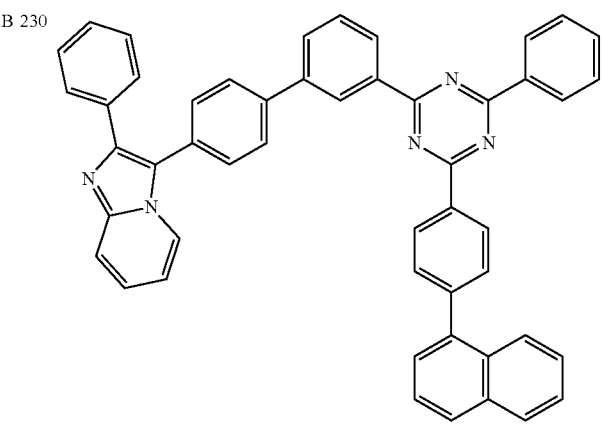
B 231
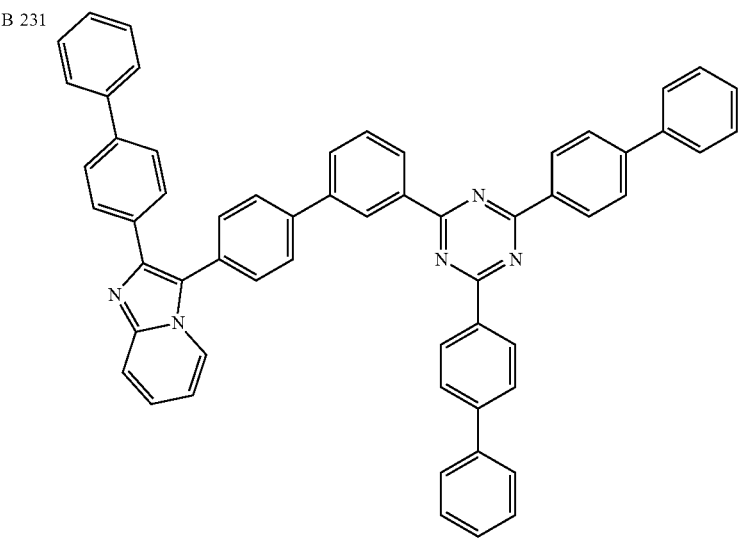

B 232
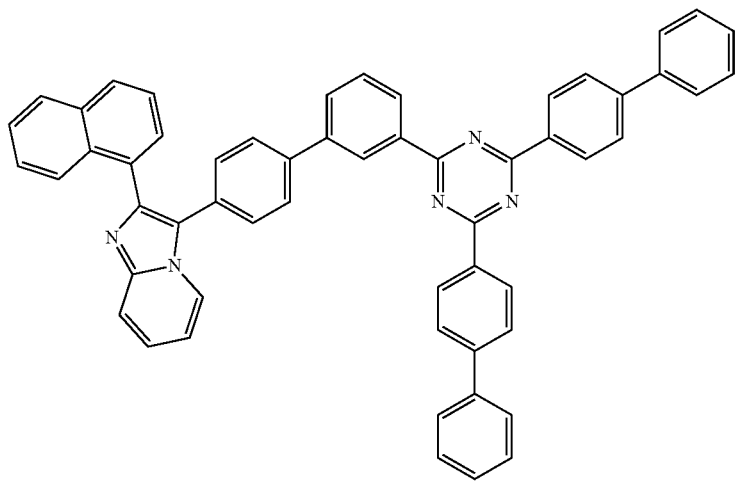 [SMILES: c1ccc(-c2ccc(-c3nc(-c4ccc(-c5ccccc5)cc4)nc(-c4cccc(-c5ccc(-c6c(-c7cccc8ccccc78)nc7ccccn67)cc5)c4)n3)cc2)cc1]
B 233
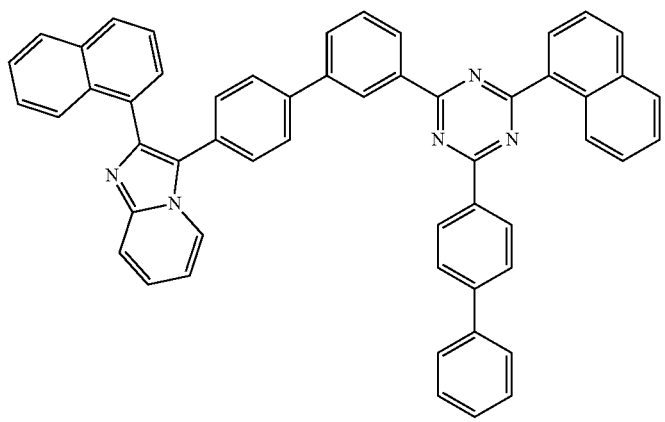 [SMILES: c1ccc(-c2ccc(-c3nc(-c4cccc(-c5ccc(-c6c(-c7cccc8ccccc78)nc7ccccn67)cc5)c4)nc(-c4cccc5ccccc45)n3)cc2)cc1]
B 234
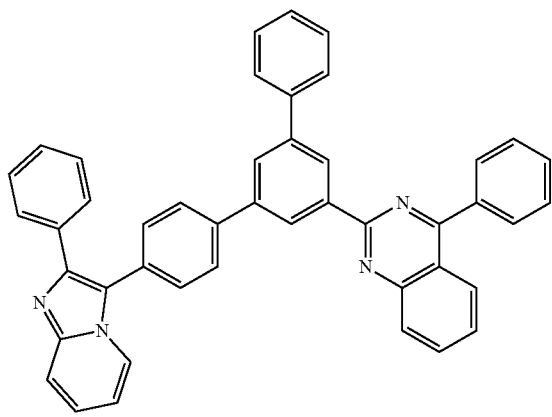 [SMILES: c1ccc(-c2cc(-c3ccc(-c4c(-c5ccccc5)nc5ccccn45)cc3)cc(-c3nc(-c4ccccc4)c4ccccc4n3)c2)cc1]

-continued
B 235
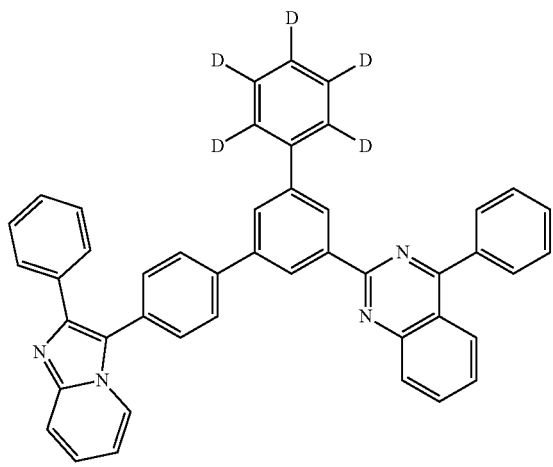 [SMILES: [2H]c1c([2H])c([2H])c(-c2cc(-c3ccc(-c4c(-c5ccccc5)nc5ccccn45)cc3)cc(-c3nc(-c4ccccc4)c4ccccc4n3)c2)c([2H])c1[2H]]
B 236
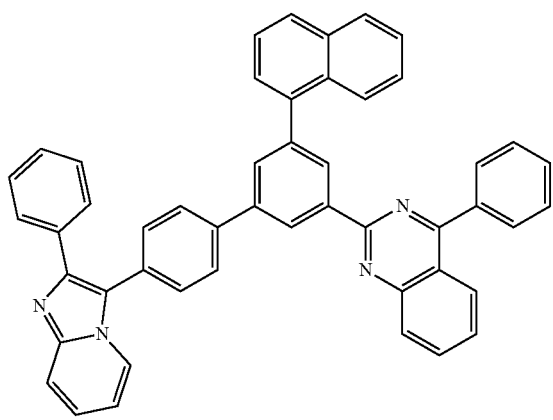 [SMILES: c1ccc(-c2nc3ccccn3c2-c2ccc(-c3cc(-c4nc(-c5ccccc5)c5ccccc5n4)cc(-c4cccc5ccccc45)c3)cc2)cc1]
B 237
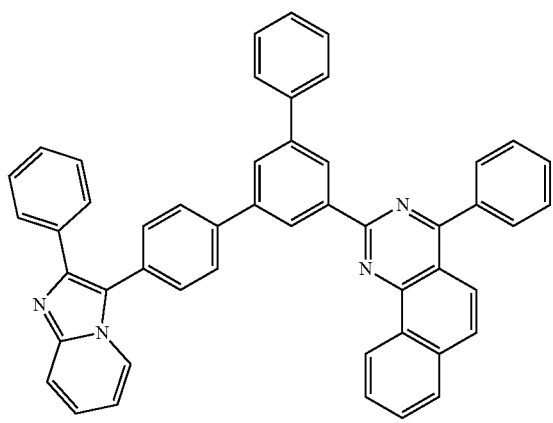 [SMILES: c1ccc(-c2cc(-c3ccc(-c4c(-c5ccccc5)nc5ccccn45)cc3)cc(-c3nc(-c4ccccc4)c4ccc5ccccc5c4n3)c2)cc1]

-continued
B 238
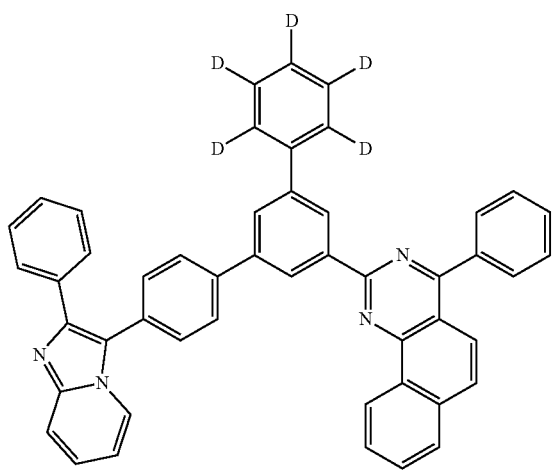 [SMILES: [2H]c1c([2H])c([2H])c(-c2cc(-c3ccc(-c4c(-c5ccccc5)nc5ccccn45)cc3)cc(-c3nc(-c4ccccc4)c4ccc5ccccc5c4n3)c2)c([2H])c1[2H]]
B 239
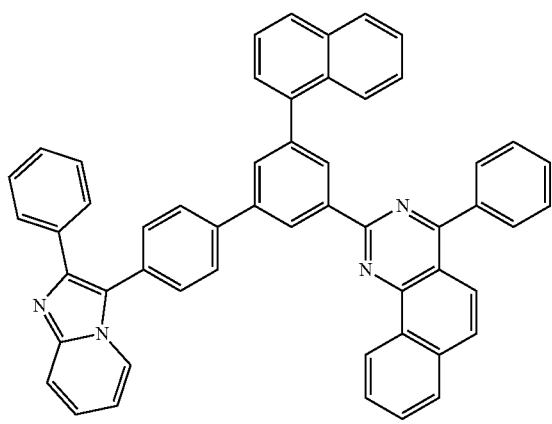 [SMILES: c1ccc(-c2nc3ccccn3c2-c2ccc(-c3cc(-c4nc(-c5ccccc5)c5ccc6ccccc6c5n4)cc(-c4cccc5ccccc45)c3)cc2)cc1]
B 240
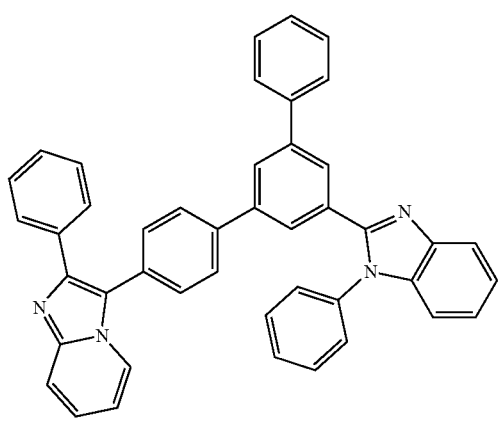 [SMILES: c1ccc(-c2cc(-c3ccc(-c4c(-c5ccccc5)nc5ccccn45)cc3)cc(-c3nc4ccccc4n3-c3ccccc3)c2)cc1]

-continued
B 241
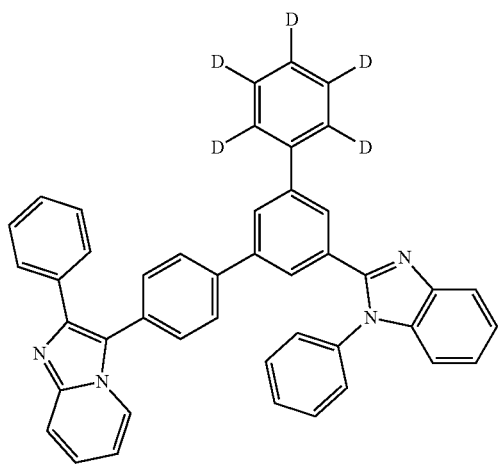 [SMILES: [2H]c1c([2H])c([2H])c(-c2cc(-c3ccc(-c4c(-c5ccccc5)nc5ccccn45)cc3)cc(-c3nc4ccccc4n3-c3ccccc3)c2)c([2H])c1[2H]]
B 242
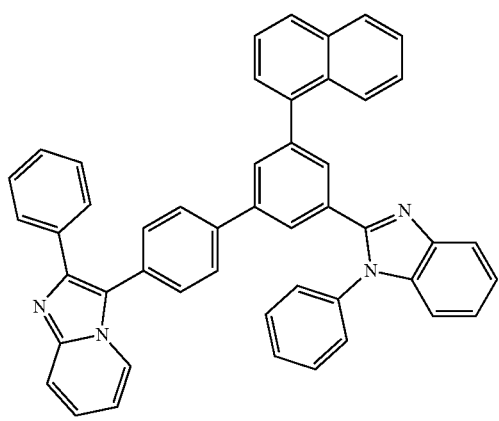 [SMILES: c1ccc(-c2nc3ccccn3c2-c2ccc(-c3cc(-c4cccc5ccccc45)cc(-c4nc5ccccc5n4-c4ccccc4)c3)cc2)cc1]
B 243
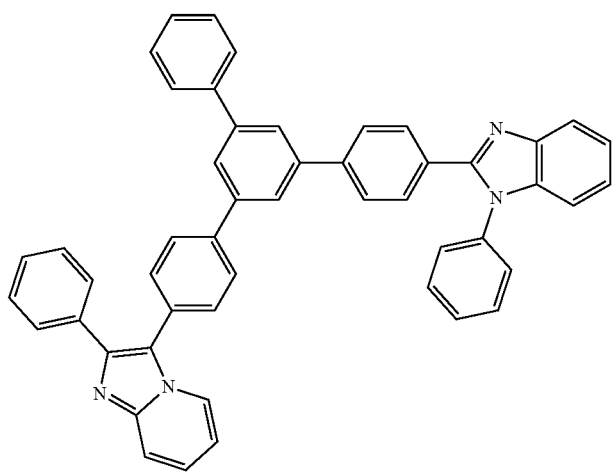 [SMILES: c1ccc(-c2cc(-c3ccc(-c4nc5ccccc5n4-c4ccccc4)cc3)cc(-c3ccc(-c4c(-c5ccccc5)nc5ccccn45)cc3)c2)cc1]

-continued
B 244
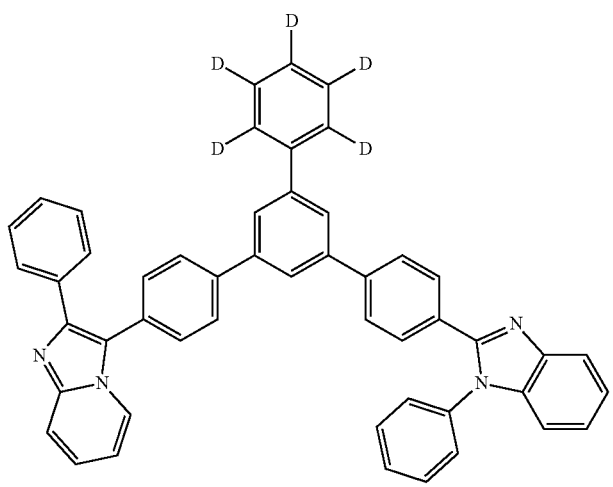 [SMILES: [2H]c1c([2H])c([2H])c(-c2cc(-c3ccc(-c4nc5ccccc5n4-c4ccccc4)cc3)cc(-c3ccc(-c4c(-c5ccccc5)nc5ccccn45)cc3)c2)c([2H])c1[2H]]
B 245
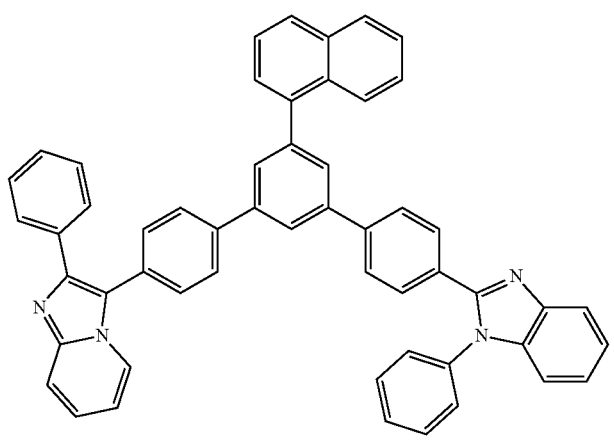 [SMILES: c1ccc(-c2nc3ccccn3c2-c2ccc(-c3cc(-c4ccc(-c5nc6ccccc6n5-c5ccccc5)cc4)cc(-c4cccc5ccccc45)c3)cc2)cc1]
B 246
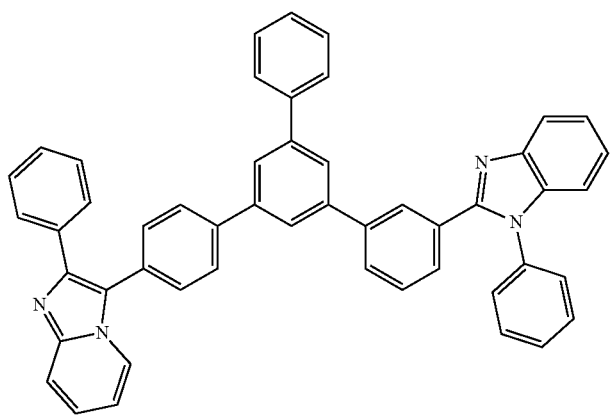 [SMILES: c1ccc(-c2cc(-c3ccc(-c4c(-c5ccccc5)nc5ccccn45)cc3)cc(-c3cccc(-c4nc5ccccc5n4-c4ccccc4)c3)c2)cc1]

B 247
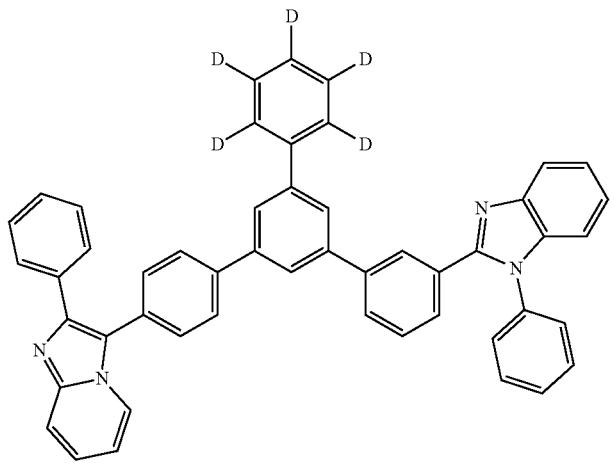 [SMILES: [2H]c1c([2H])c([2H])c(-c2cc(-c3ccc(-c4c(-c5ccccc5)nc5ccccn45)cc3)cc(-c3cccc(-c4nc5ccccc5n4-c4ccccc4)c3)c2)c([2H])c1[2H]]
B 248
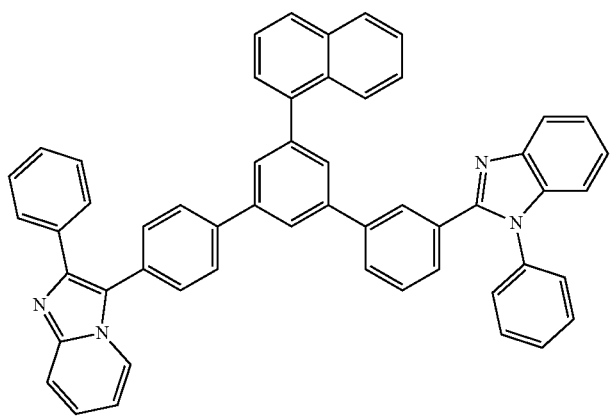 [SMILES: c1ccc(-c2nc3ccccn3c2-c2ccc(-c3cc(-c4cccc(-c5nc6ccccc6n5-c5ccccc5)c4)cc(-c4cccc5ccccc45)c3)cc2)cc1]
B 249
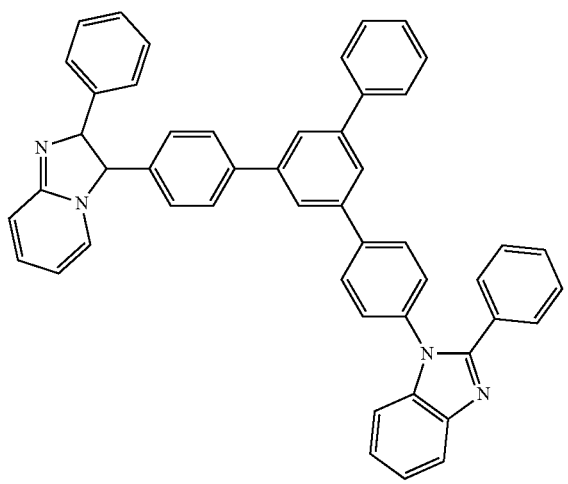 [SMILES: C1=CC2=NC(c3ccccc3)C(c3ccc(-c4cc(-c5ccccc5)cc(-c5ccc(-n6c(-c7ccccc7)nc7ccccc76)cc5)c4)cc3)N2C=C1]

-continued
B 250
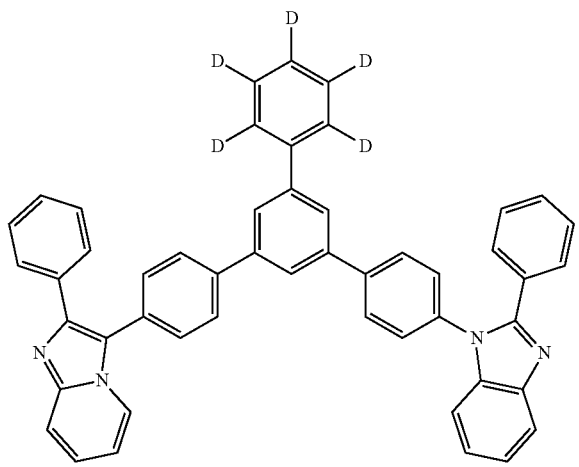 [SMILES: [2H]c1c([2H])c([2H])c(-c2cc(-c3ccc(-c4c(-c5ccccc5)nc5ccccn45)cc3)cc(-c3ccc(-n4c(-c5ccccc5)nc5ccccc54)cc3)c2)c([2H])c1[2H]]
B 251
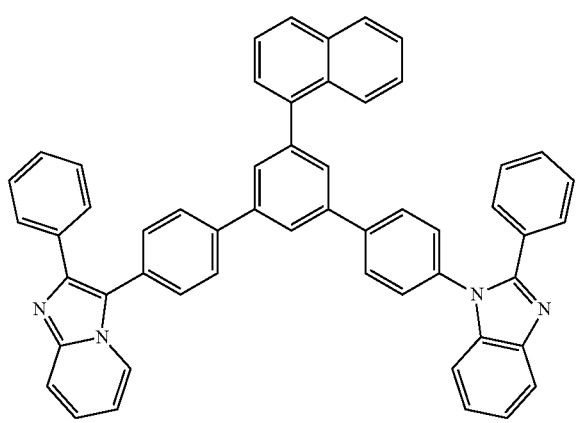 [SMILES: c1ccc(-c2nc3ccccn3c2-c2ccc(-c3cc(-c4ccc(-n5c(-c6ccccc6)nc6ccccc65)cc4)cc(-c4cccc5ccccc45)c3)cc2)cc1]
B 252
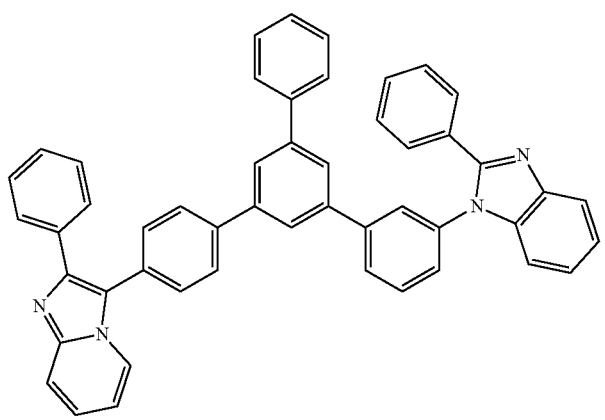 [SMILES: c1ccc(-c2cc(-c3ccc(-c4c(-c5ccccc5)nc5ccccn45)cc3)cc(-c3cccc(-n4c(-c5ccccc5)nc5ccccc54)c3)c2)cc1]

B 253
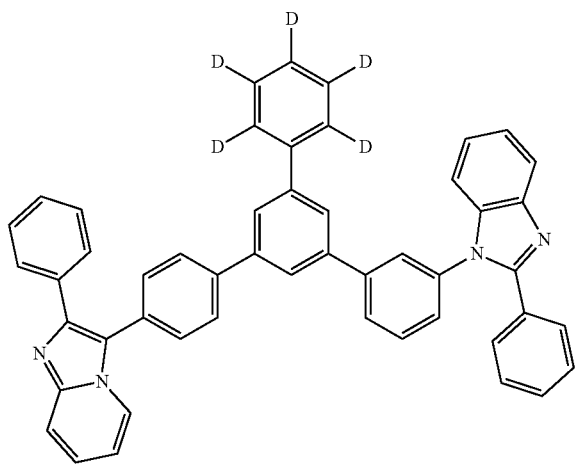 [SMILES: [2H]c1c([2H])c([2H])c(-c2cc(-c3ccc(-c4c(-c5ccccc5)nc5ccccn45)cc3)cc(-c3cccc(-n4c(-c5ccccc5)nc5ccccc54)c3)c2)c([2H])c1[2H]]
B 254
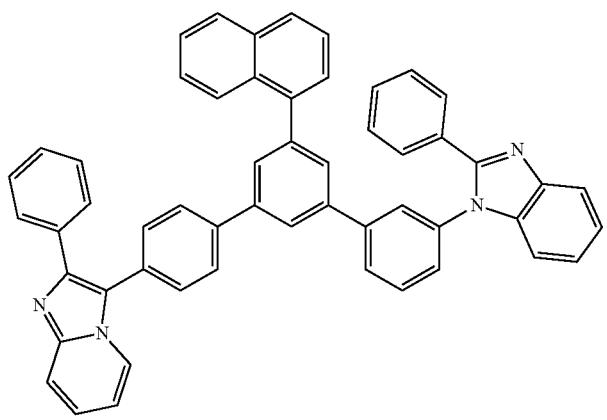 [SMILES: c1ccc(-c2nc3ccccn3c2-c2ccc(-c3cc(-c4cccc(-n5c(-c6ccccc6)nc6ccccc65)c4)cc(-c4cccc5ccccc45)c3)cc2)cc1]
B 255
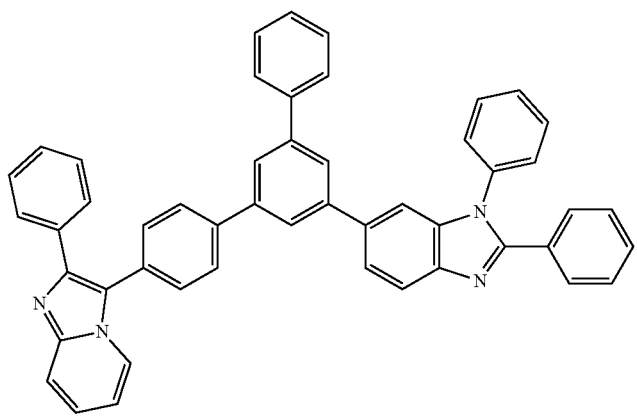 [SMILES: c1ccc(-c2cc(-c3ccc(-c4c(-c5ccccc5)nc5ccccn45)cc3)cc(-c3ccc4nc(-c5ccccc5)n(-c5ccccc5)c4c3)c2)cc1]

-continued
B 256
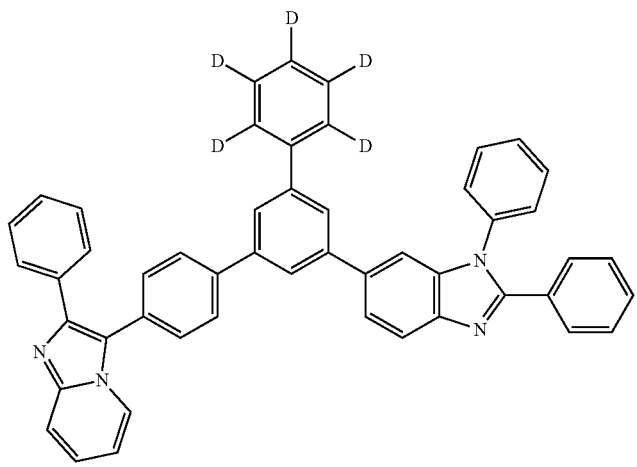 [SMILES: [2H]c1c([2H])c([2H])c(-c2cc(-c3ccc(-c4c(-c5ccccc5)nc5ccccn45)cc3)cc(-c3ccc4nc(-c5ccccc5)n(-c5ccccc5)c4c3)c2)c([2H])c1[2H]]
B 257
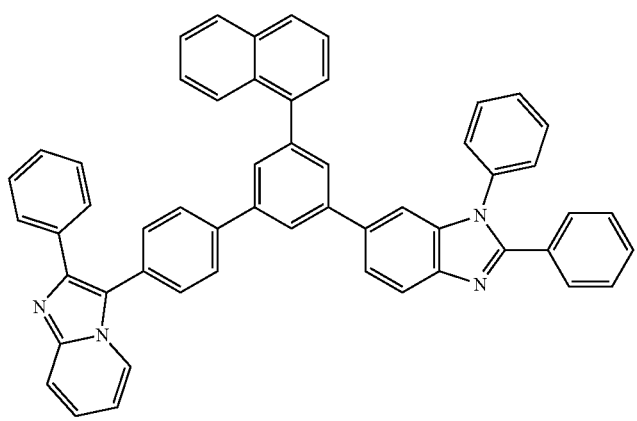 [SMILES: c1ccc(-c2nc3ccccn3c2-c2ccc(-c3cc(-c4ccc5nc(-c6ccccc6)n(-c6ccccc6)c5c4)cc(-c4cccc5ccccc45)c3)cc2)cc1]
B 258
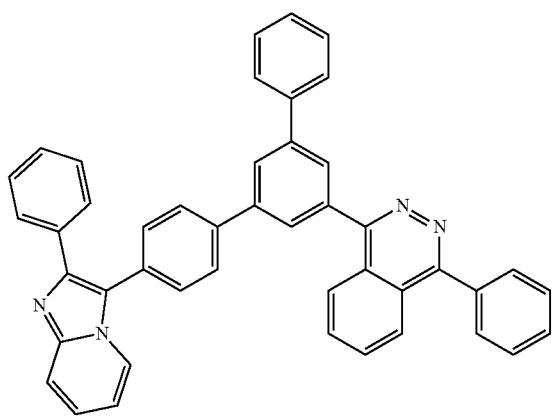 [SMILES: c1ccc(-c2cc(-c3ccc(-c4c(-c5ccccc5)nc5ccccn45)cc3)cc(-c3nnc(-c4ccccc4)c4ccccc34)c2)cc1]

-continued
B 259
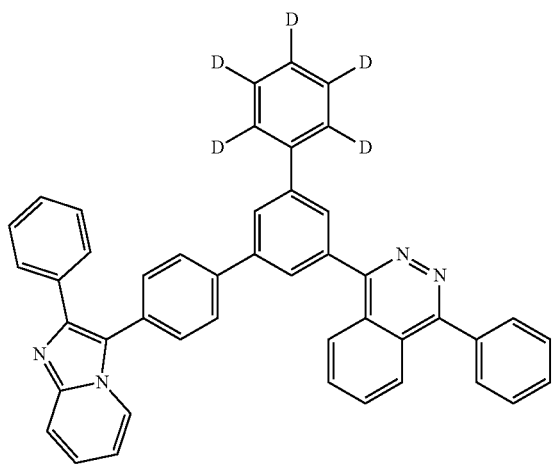 [SMILES: [2H]c1c([2H])c([2H])c(-c2cc(-c3ccc(-c4c(-c5ccccc5)nc5ccccn45)cc3)cc(-c3nnc(-c4ccccc4)c4ccccc34)c2)c([2H])c1[2H]]
B 260
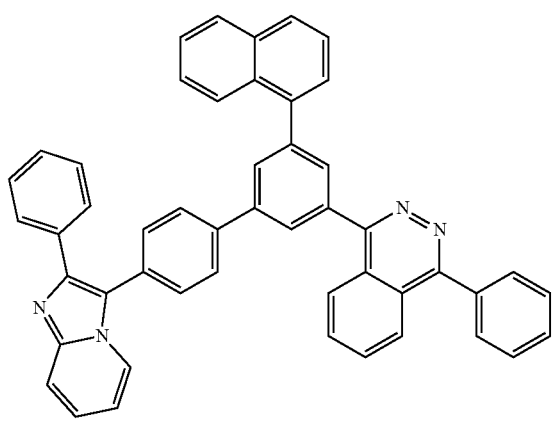 [SMILES: c1ccc(-c2nc3ccccn3c2-c2ccc(-c3cc(-c4cccc5ccccc45)cc(-c4nnc(-c5ccccc5)c5ccccc45)c3)cc2)cc1]
B 261
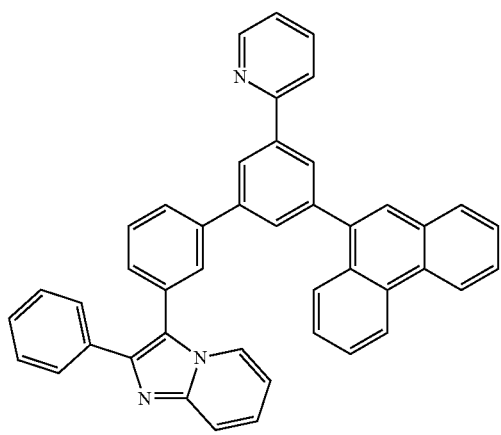 [SMILES: c1ccc(-c2nc3ccccn3c2-c2cccc(-c3cc(-c4ccccn4)cc(-c4cc5ccccc5c5ccccc45)c3)c2)cc1]

B 262
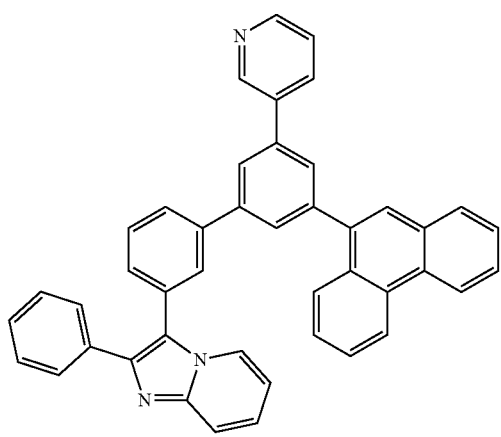 [SMILES: c1ccc(-c2nc3ccccn3c2-c2cccc(-c3cc(-c4cccnc4)cc(-c4cc5ccccc5c5ccccc45)c3)c2)cc1]
B 263
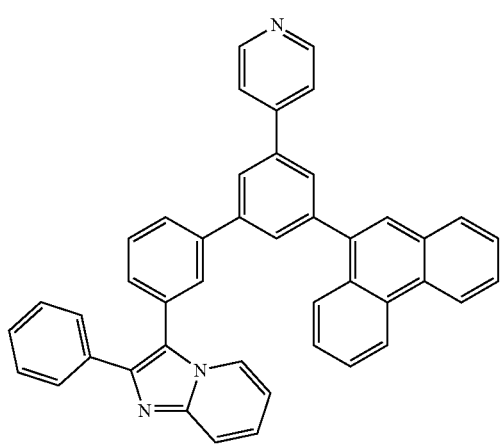 [SMILES: c1ccc(-c2nc3ccccn3c2-c2cccc(-c3cc(-c4ccncc4)cc(-c4cc5ccccc5c5ccccc45)c3)c2)cc1]
B 264
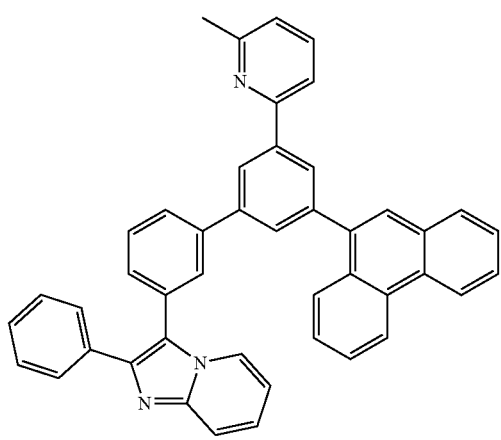 [SMILES: Cc1cccc(-c2cc(-c3cccc(-c4c(-c5ccccc5)nc5ccccn45)c3)cc(-c3cc4ccccc4c4ccccc34)c2)n1]

B 265 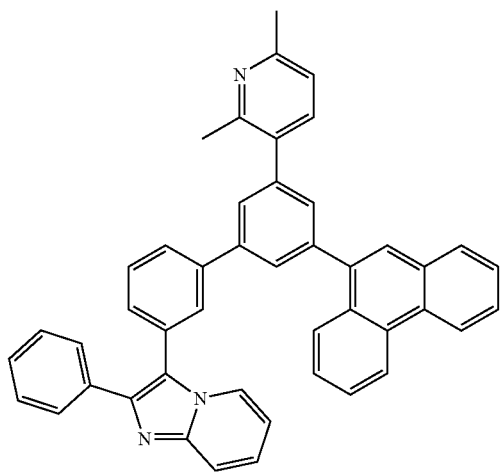 [SMILES: Cc1ccc(-c2cc(-c3cccc(-c4c(-c5ccccc5)nc5ccccn45)c3)cc(-c3cc4ccccc4c4ccccc34)c2)c(C)n1]
B 266 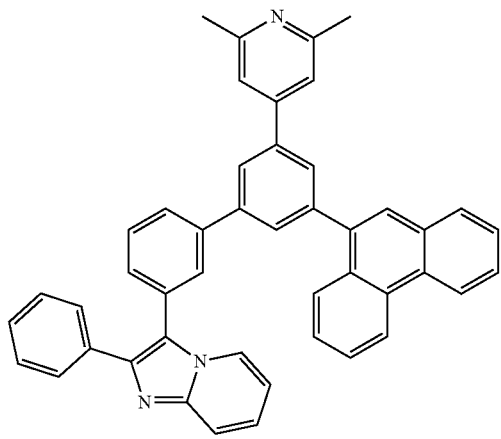 [SMILES: Cc1cc(-c2cc(-c3cccc(-c4c(-c5ccccc5)nc5ccccn45)c3)cc(-c3cc4ccccc4c4ccccc34)c2)cc(C)n1]
B 267 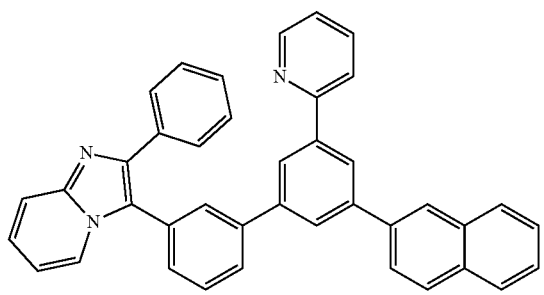 [SMILES: c1ccc(-c2nc3ccccn3c2-c2cccc(-c3cc(-c4ccc5ccccc5c4)cc(-c4ccccn4)c3)c2)cc1]
B 268 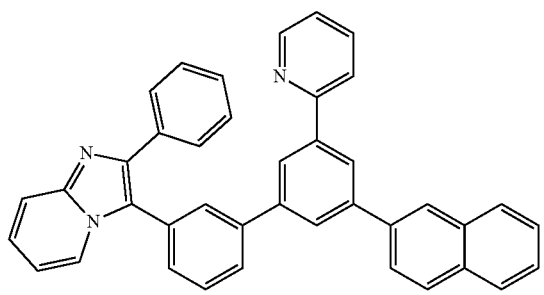 [SMILES: c1ccc(-c2nc3ccccn3c2-c2cccc(-c3cc(-c4ccc5ccccc5c4)cc(-c4ccccn4)c3)c2)cc1]

-continued
B 269
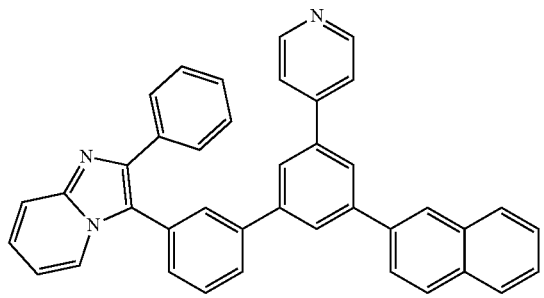 [SMILES: c1ccc(-c2nc3ccccn3c2-c2cccc(-c3cc(-c4ccncc4)cc(-c4ccc5ccccc5c4)c3)c2)cc1]
B 270
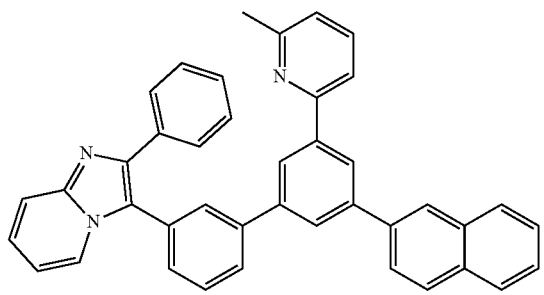 [SMILES: Cc1cccc(-c2cc(-c3cccc(-c4c(-c5ccccc5)nc5ccccn45)c3)cc(-c3ccc4ccccc4c3)c2)n1]
B 271
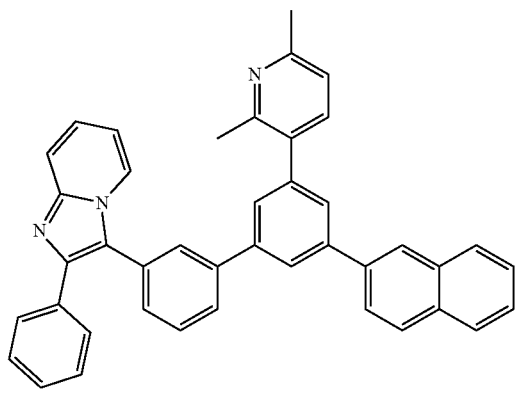 [SMILES: Cc1ccc(-c2cc(-c3cccc(-c4c(-c5ccccc5)nc5ccccn45)c3)cc(-c3ccc4ccccc4c3)c2)c(C)n1]
B 272
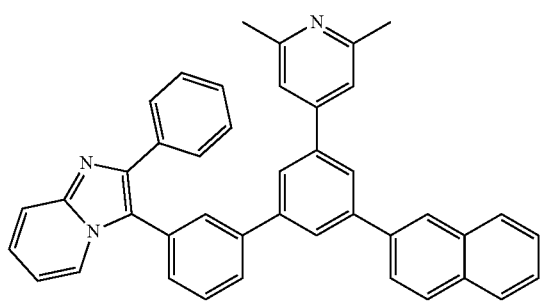 [SMILES: Cc1cc(-c2cc(-c3cccc(-c4c(-c5ccccc5)nc5ccccn45)c3)cc(-c3ccc4ccccc4c3)c2)cc(C)n1]
B 273
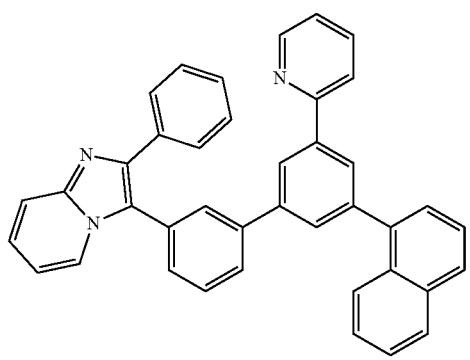 [SMILES: c1ccc(-c2nc3ccccn3c2-c2cccc(-c3cc(-c4ccccn4)cc(-c4cccc5ccccc45)c3)c2)cc1]

B 274
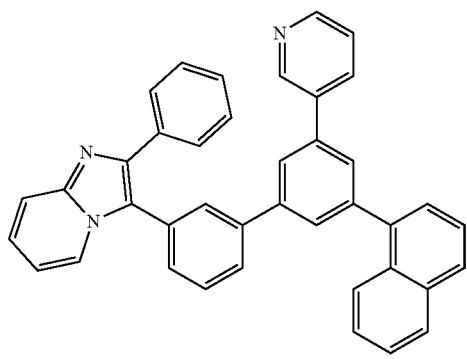 [SMILES: c1ccc(-c2nc3ccccn3c2-c2cccc(-c3cc(-c4cccnc4)cc(-c4cccc5ccccc45)c3)c2)cc1]
B 275
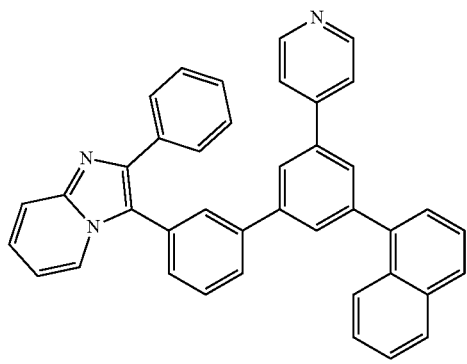 [SMILES: c1ccc(-c2nc3ccccn3c2-c2cccc(-c3cc(-c4ccncc4)cc(-c4cccc5ccccc45)c3)c2)cc1]
B 276
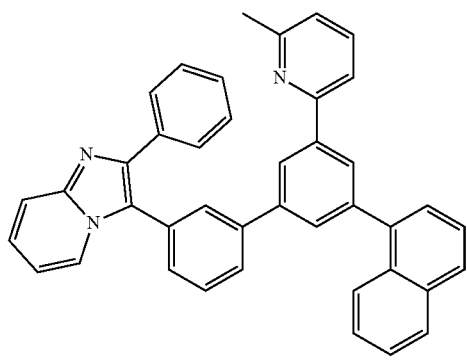 [SMILES: Cc1cccc(-c2cc(-c3cccc(-c4c(-c5ccccc5)nc5ccccn45)c3)cc(-c3cccc4ccccc34)c2)n1]
B 277
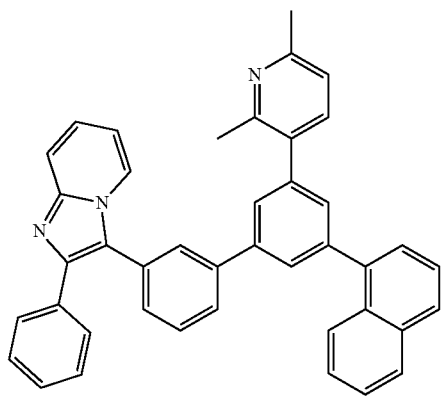 [SMILES: Cc1ccc(-c2cc(-c3cccc(-c4c(-c5ccccc5)nc5ccccn45)c3)cc(-c3cccc4ccccc34)c2)c(C)n1]

-continued
B 278
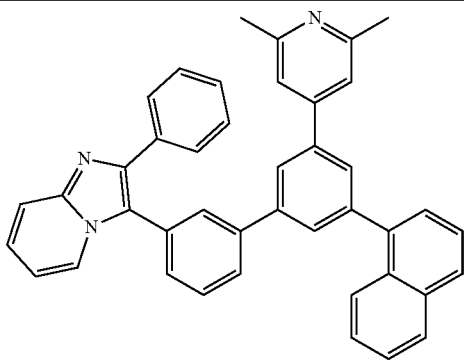
B 279
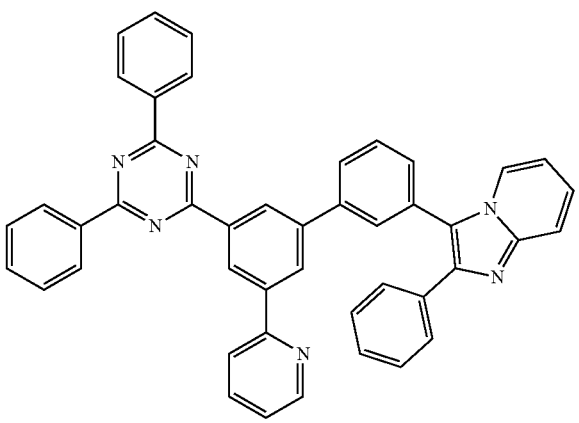 [SMILES: c1ccc(-c2nc(-c3ccccc3)nc(-c3cc(-c4cccc(-c5c(-c6ccccc6)nc6ccccn56)c4)cc(-c4ccccn4)c3)n2)cc1]
B 280
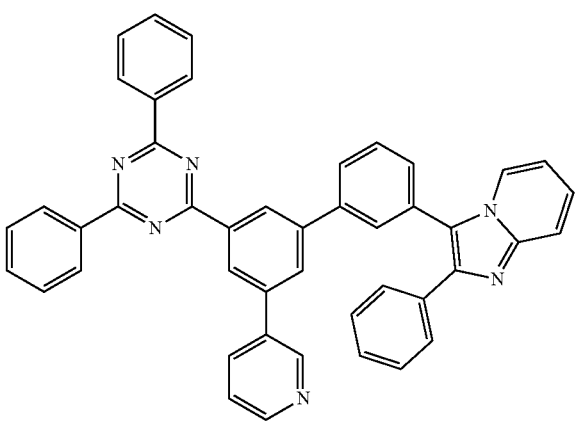 [SMILES: c1ccc(-c2nc(-c3ccccc3)nc(-c3cc(-c4cccnc4)cc(-c4cccc(-c5c(-c6ccccc6)nc6ccccn56)c4)c3)n2)cc1]
B 281
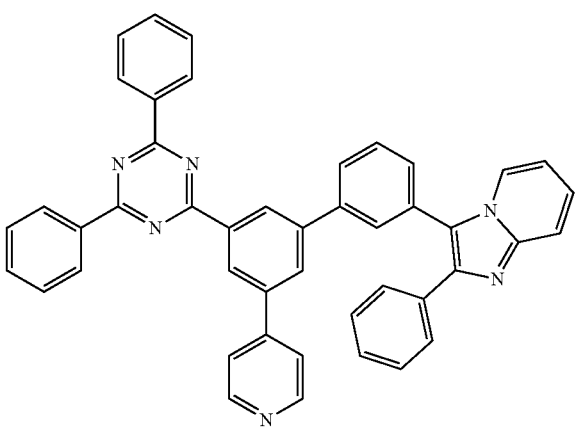 [SMILES: c1ccc(-c2nc(-c3ccccc3)nc(-c3cc(-c4ccncc4)cc(-c4cccc(-c5c(-c6ccccc6)nc6ccccn56)c4)c3)n2)cc1]

-continued
B 282
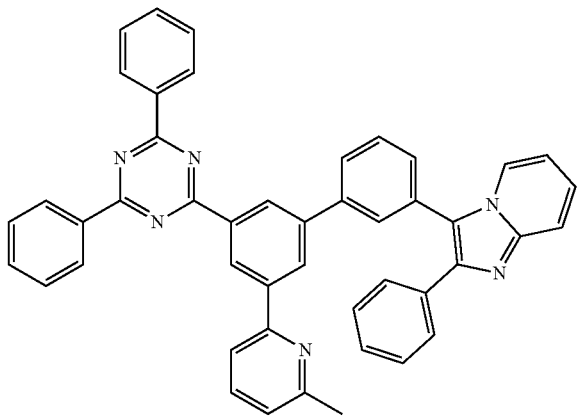 [SMILES: Cc1cccc(-c2cc(-c3cccc(-c4c(-c5ccccc5)nc5ccccn45)c3)cc(-c3nc(-c4ccccc4)nc(-c4ccccc4)n3)c2)n1]
B 283
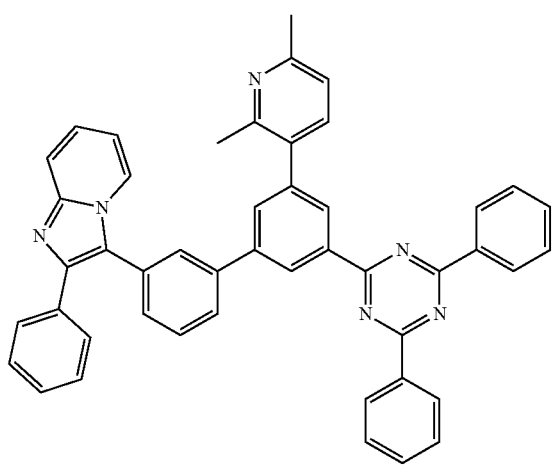 [SMILES: Cc1ccc(-c2cc(-c3cccc(-c4c(-c5ccccc5)nc5ccccn45)c3)cc(-c3nc(-c4ccccc4)nc(-c4ccccc4)n3)c2)c(C)n1]
B 284
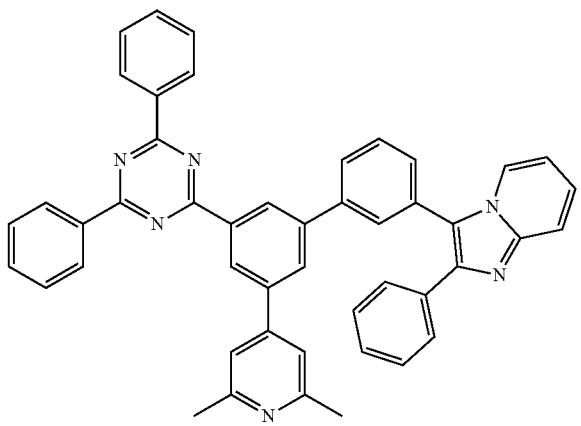 [SMILES: Cc1cc(-c2cc(-c3cccc(-c4c(-c5ccccc5)nc5ccccn45)c3)cc(-c3nc(-c4ccccc4)nc(-c4ccccc4)n3)c2)cc(C)n1]

B 285
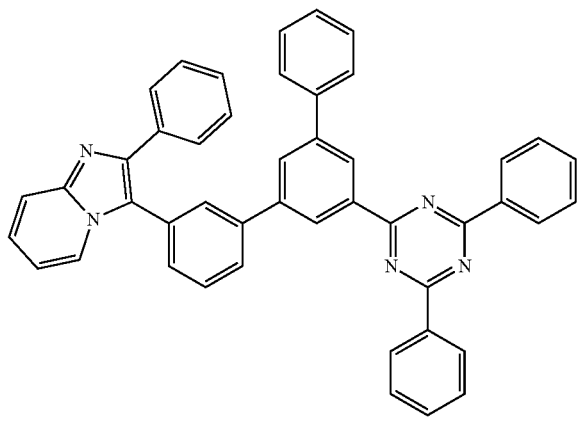 [SMILES: c1ccc(-c2cc(-c3cccc(-c4c(-c5ccccc5)nc5ccccn45)c3)cc(-c3nc(-c4ccccc4)nc(-c4ccccc4)n3)c2)cc1]
B 286
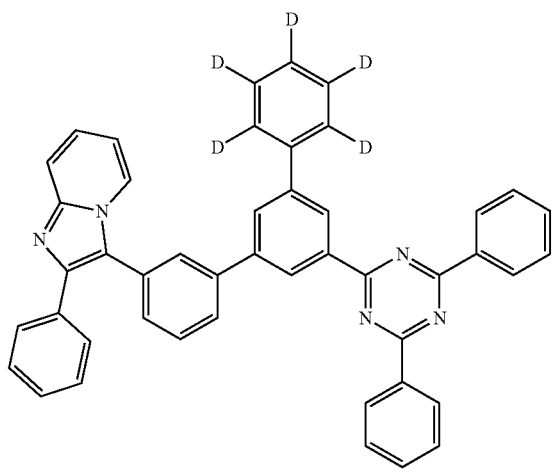 [SMILES: [2H]c1c([2H])c([2H])c(-c2cc(-c3cccc(-c4c(-c5ccccc5)nc5ccccn45)c3)cc(-c3nc(-c4ccccc4)nc(-c4ccccc4)n3)c2)c([2H])c1[2H]]
B 287
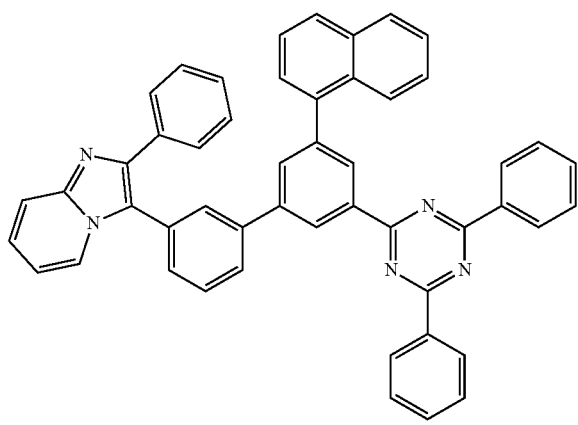 [SMILES: c1ccc(-c2nc(-c3ccccc3)nc(-c3cc(-c4cccc(-c5c(-c6ccccc6)nc6ccccn56)c4)cc(-c4cccc5ccccc45)c3)n2)cc1]

B 288
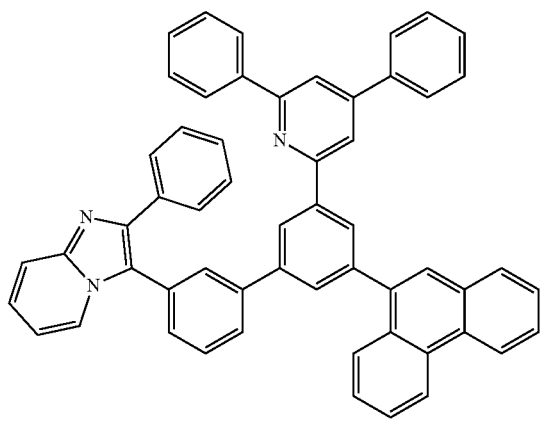 [SMILES: c1ccc(-c2cc(-c3ccccc3)nc(-c3cc(-c4cccc(-c5c(-c6ccccc6)nc6ccccn56)c4)cc(-c4cc5ccccc5c5ccccc45)c3)c2)cc1]
B 289
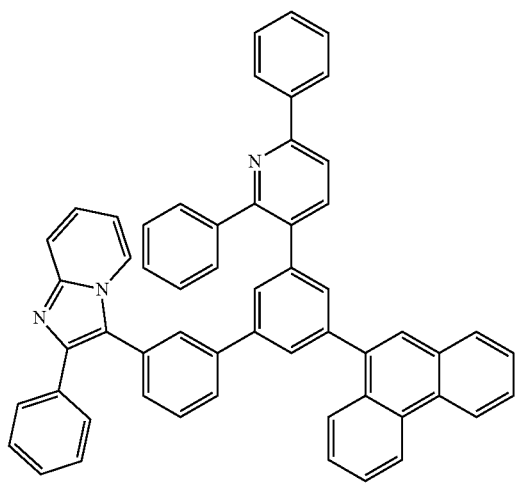 [SMILES: c1ccc(-c2ccc(-c3cc(-c4cccc(-c5c(-c6ccccc6)nc6ccccn56)c4)cc(-c4cc5ccccc5c5ccccc45)c3)c(-c3ccccc3)n2)cc1]
B 290
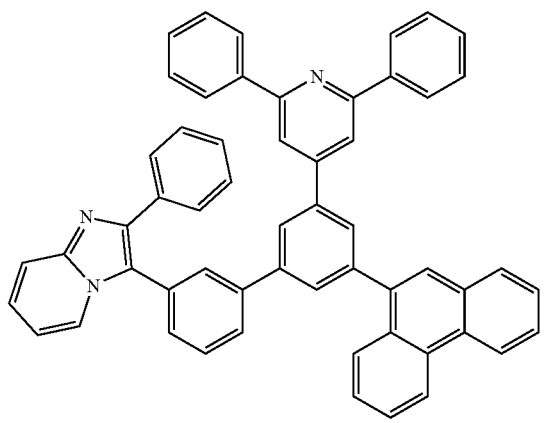 [SMILES: c1ccc(-c2cc(-c3cc(-c4cccc(-c5c(-c6ccccc6)nc6ccccn56)c4)cc(-c4cc5ccccc5c5ccccc45)c3)cc(-c3ccccc3)n2)cc1]

-continued
B 291
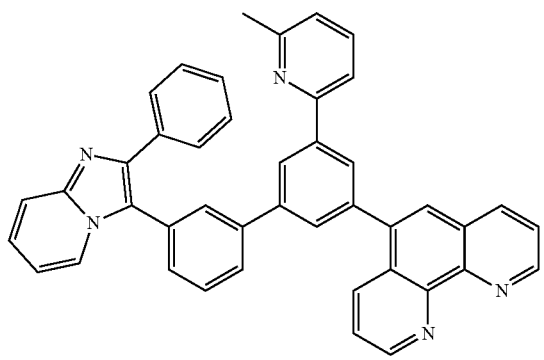 [SMILES: Cc1cccc(-c2cc(-c3cccc(-c4c(-c5ccccc5)nc5ccccn45)c3)cc(-c3cc4cccnc4c4ncccc34)c2)n1]
B 292
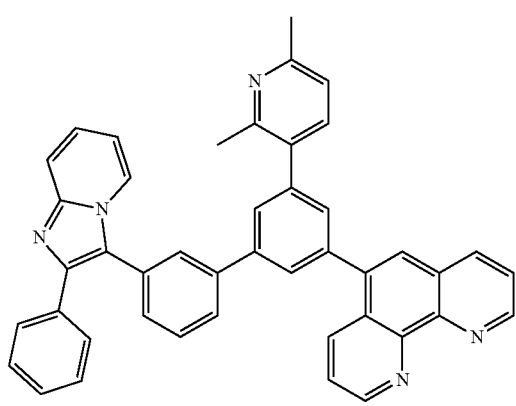 [SMILES: Cc1ccc(-c2cc(-c3cccc(-c4c(-c5ccccc5)nc5ccccn45)c3)cc(-c3cc4cccnc4c4ncccc34)c2)c(C)n1]
B 293
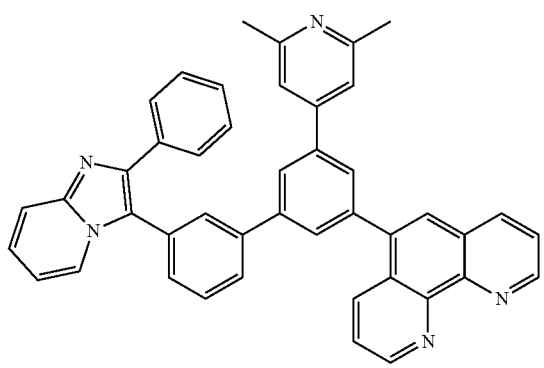 [SMILES: Cc1cc(-c2cc(-c3cccc(-c4c(-c5ccccc5)nc5ccccn45)c3)cc(-c3cc4cccnc4c4ncccc34)c2)cc(C)n1]
B 294
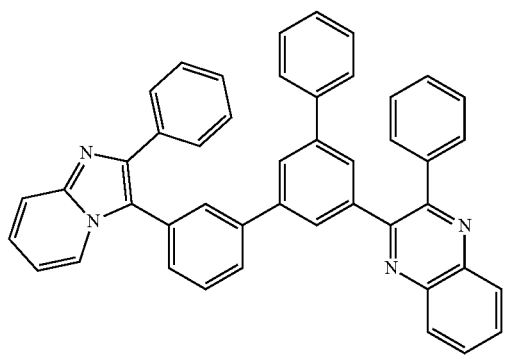 [SMILES: c1ccc(-c2cc(-c3cccc(-c4c(-c5ccccc5)nc5ccccn45)c3)cc(-c3nc4ccccc4nc3-c3ccccc3)c2)cc1]

-continued
B 295
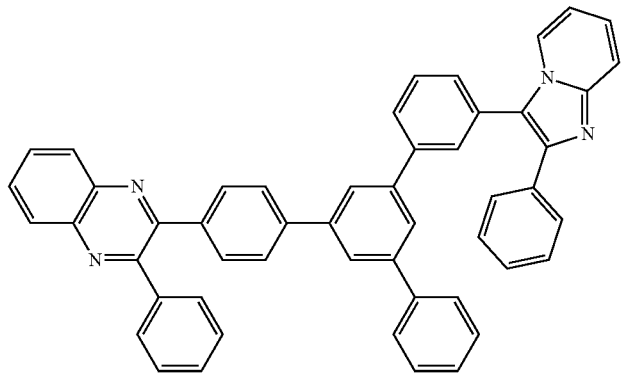 [SMILES: c1ccc(-c2cc(-c3ccc(-c4nc5ccccc5nc4-c4ccccc4)cc3)cc(-c3cccc(-c4c(-c5ccccc5)nc5ccccn45)c3)c2)cc1]
B 296
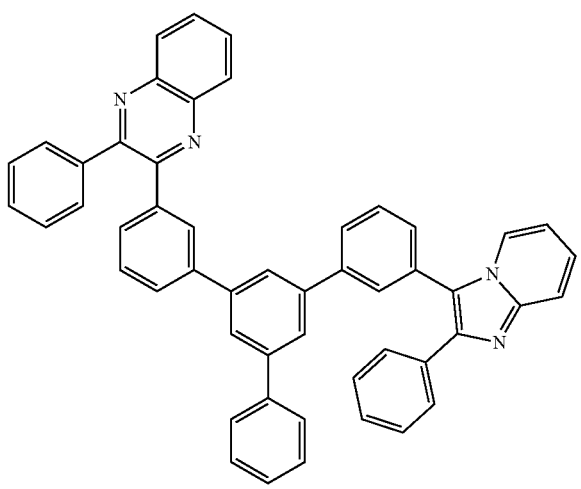 [SMILES: c1ccc(-c2cc(-c3cccc(-c4nc5ccccc5nc4-c4ccccc4)c3)cc(-c3cccc(-c4c(-c5ccccc5)nc5ccccn45)c3)c2)cc1]
B 297
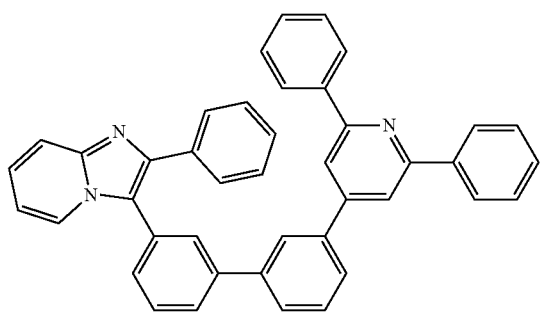 [SMILES: c1ccc(-c2cc(-c3cccc(-c4cccc(-c5c(-c6ccccc6)nc6ccccn56)c4)c3)cc(-c3ccccc3)n2)cc1]
B 298
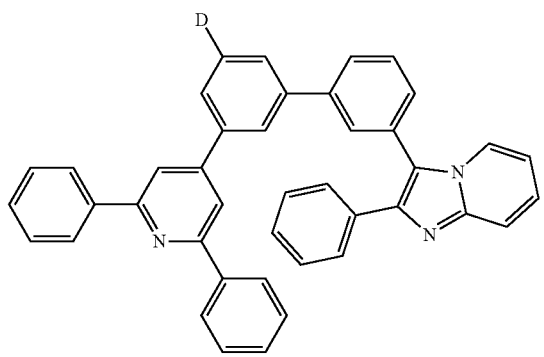 [SMILES: [2H]c1cc(-c2cccc(-c3c(-c4ccccc4)nc4ccccn34)c2)cc(-c2cc(-c3ccccc3)nc(-c3ccccc3)c2)c1]

-continued
B 299
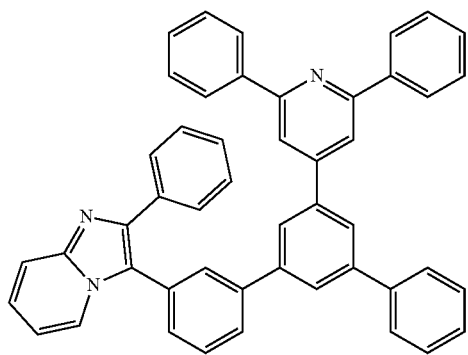 [SMILES: c1ccc(-c2cc(-c3cccc(-c4c(-c5ccccc5)nc5ccccn45)c3)cc(-c3cc(-c4ccccc4)nc(-c4ccccc4)c3)c2)cc1]
B 300
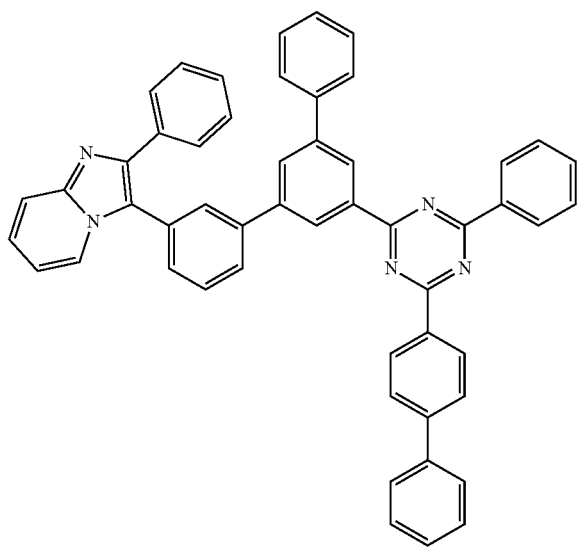 [SMILES: c1ccc(-c2ccc(-c3nc(-c4ccccc4)nc(-c4cc(-c5ccccc5)cc(-c5cccc(-c6c(-c7ccccc7)nc7ccccn67)c5)c4)n3)cc2)cc1]
B 301
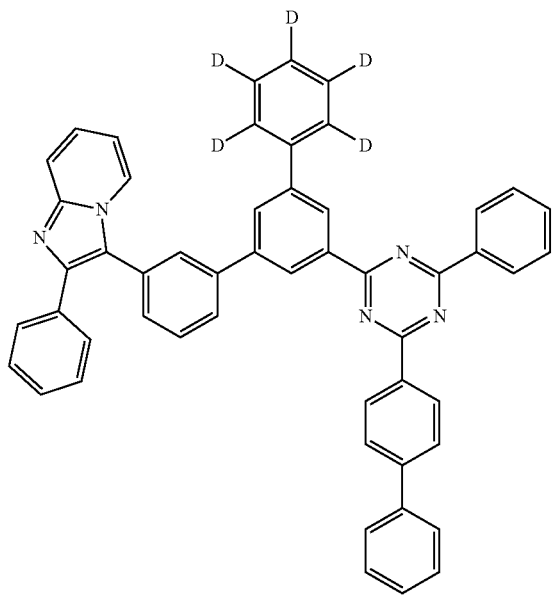 [SMILES: [2H]c1c([2H])c([2H])c(-c2cc(-c3cccc(-c4c(-c5ccccc5)nc5ccccn45)c3)cc(-c3nc(-c4ccccc4)nc(-c4ccc(-c5ccccc5)cc4)n3)c2)c([2H])c1[2H]]

B 302
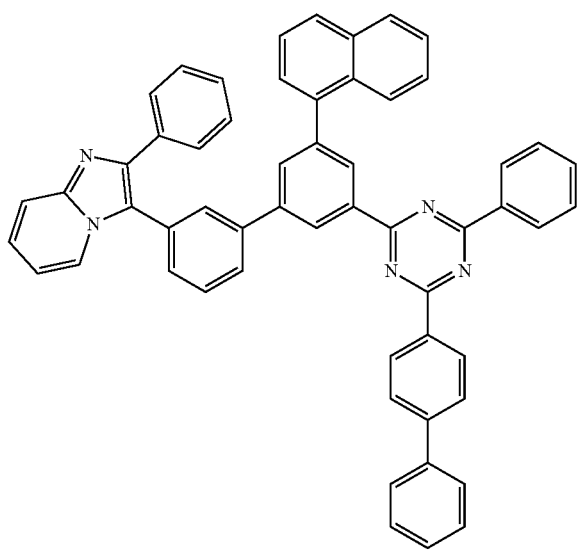 [SMILES: c1ccc(-c2ccc(-c3nc(-c4ccccc4)nc(-c4cc(-c5cccc(-c6c(-c7ccccc7)nc7ccccn67)c5)cc(-c5cccc6ccccc56)c4)n3)cc2)cc1]
B 303
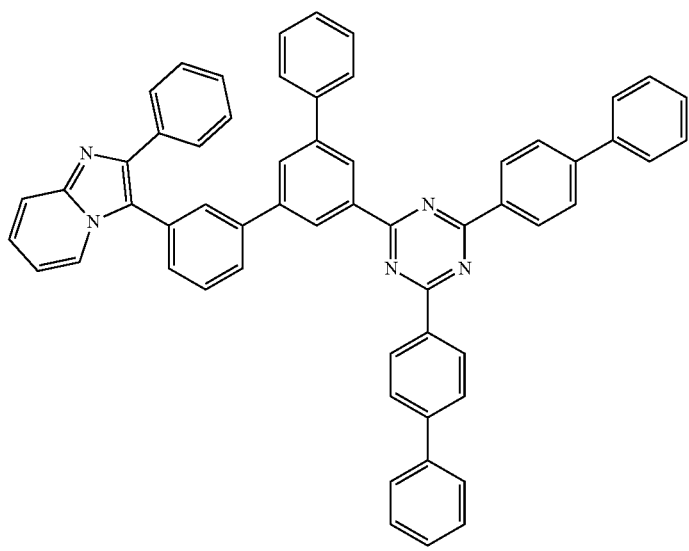 [SMILES: c1ccc(-c2ccc(-c3nc(-c4ccc(-c5ccccc5)cc4)nc(-c4cc(-c5ccccc5)cc(-c5cccc(-c6c(-c7ccccc7)nc7ccccn67)c5)c4)n3)cc2)cc1]

-continued
B 304
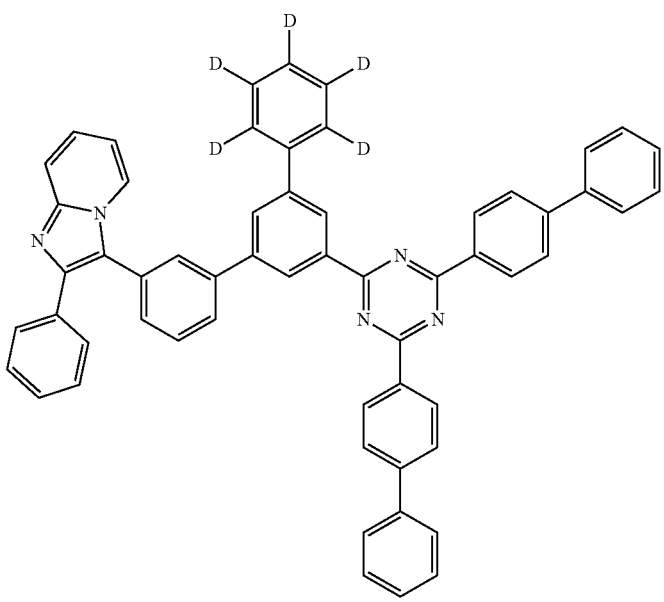 [SMILES: [2H]c1c([2H])c([2H])c(-c2cc(-c3cccc(-c4c(-c5ccccc5)nc5ccccn45)c3)cc(-c3nc(-c4ccc(-c5ccccc5)cc4)nc(-c4ccc(-c5ccccc5)cc4)n3)c2)c([2H])c1[2H]]
B 305
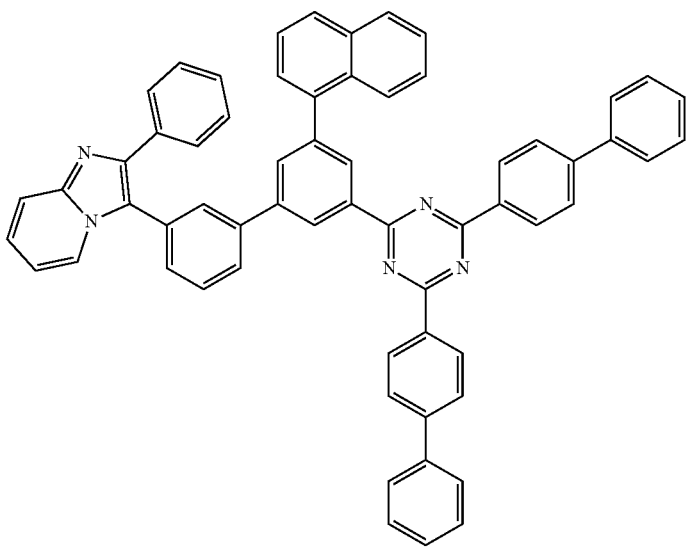 [SMILES: c1ccc(-c2ccc(-c3nc(-c4ccc(-c5ccccc5)cc4)nc(-c4cc(-c5cccc(-c6c(-c7ccccc7)nc7ccccn67)c5)cc(-c5cccc6ccccc56)c4)n3)cc2)cc1]
B 306
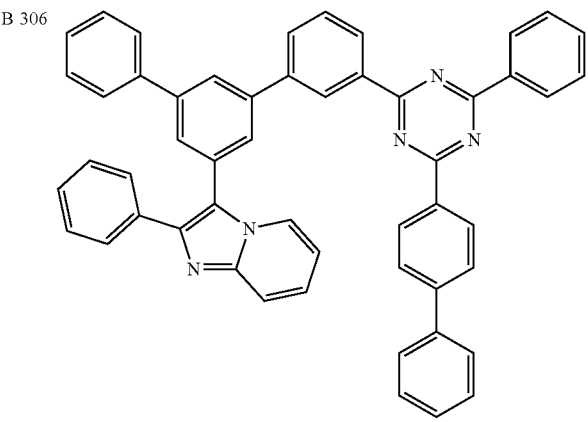

B 307
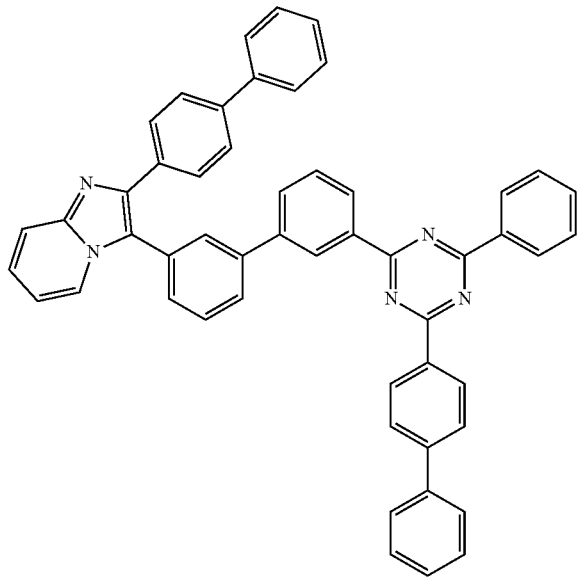 [SMILES: c1ccc(-c2ccc(-c3nc(-c4ccccc4)nc(-c4cccc(-c5cccc(-c6c(-c7ccc(-c8ccccc8)cc7)nc7ccccn67)c5)c4)n3)cc2)cc1]
B 308
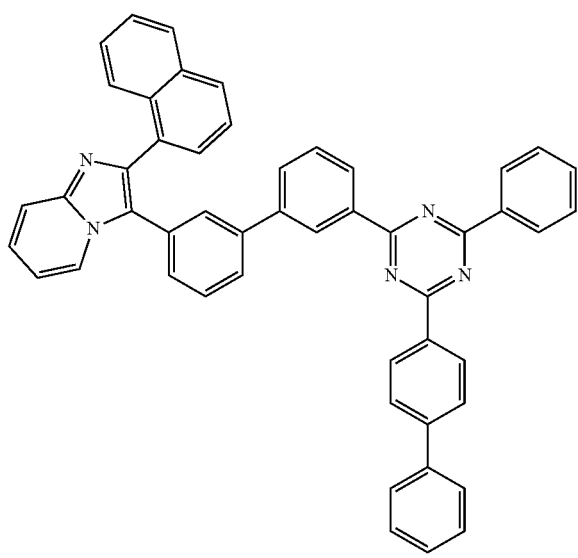 [SMILES: c1ccc(-c2ccc(-c3nc(-c4ccccc4)nc(-c4cccc(-c5cccc(-c6c(-c7cccc8ccccc78)nc7ccccn67)c5)c4)n3)cc2)cc1]
B 309
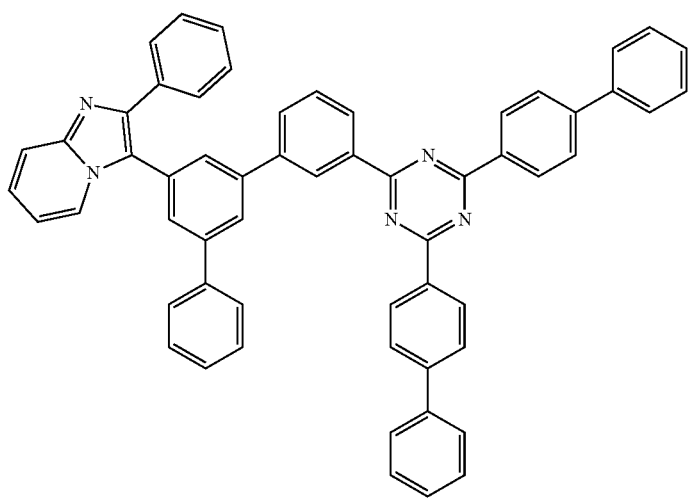 [SMILES: c1ccc(-c2ccc(-c3nc(-c4ccc(-c5ccccc5)cc4)nc(-c4cccc(-c5cc(-c6ccccc6)cc(-c6c(-c7ccccc7)nc7ccccn67)c5)c4)n3)cc2)cc1]

-continued
B 310
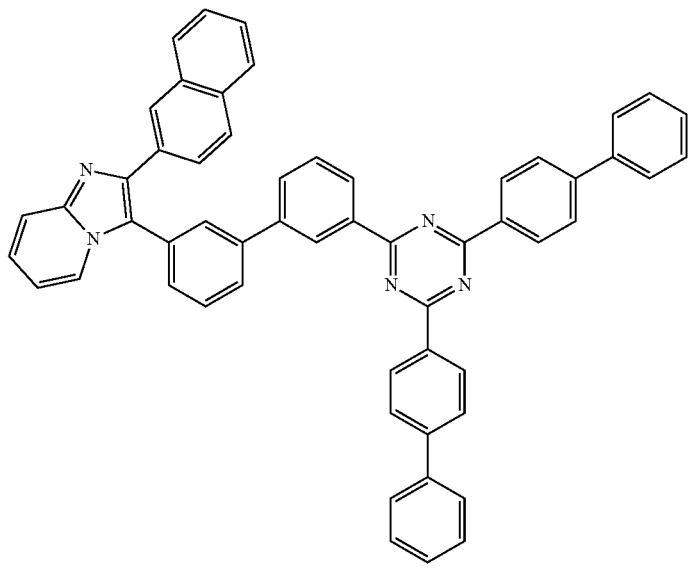 [SMILES: c1ccc(-c2ccc(-c3nc(-c4ccc(-c5ccccc5)cc4)nc(-c4cccc(-c5cccc(-c6c(-c7ccc8ccccc8c7)nc7ccccn67)c5)c4)n3)cc2)cc1]
B 311
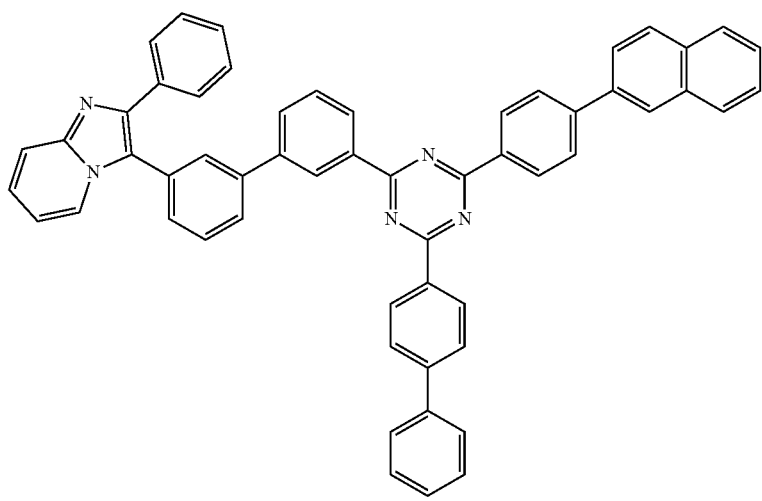 [SMILES: c1ccc(-c2ccc(-c3nc(-c4ccc(-c5ccc6ccccc6c5)cc4)nc(-c4cccc(-c5cccc(-c6c(-c7ccccc7)nc7ccccn67)c5)c4)n3)cc2)cc1]
B 312
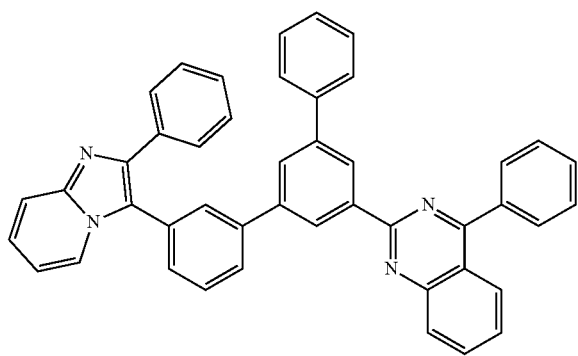 [SMILES: c1ccc(-c2cc(-c3cccc(-c4c(-c5ccccc5)nc5ccccn45)c3)cc(-c3nc(-c4ccccc4)c4ccccc4n3)c2)cc1]

B 313 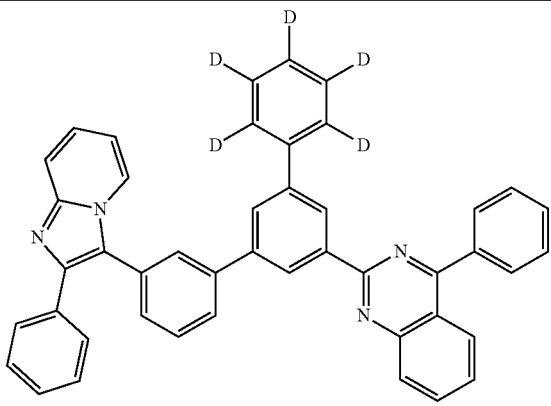
B 314 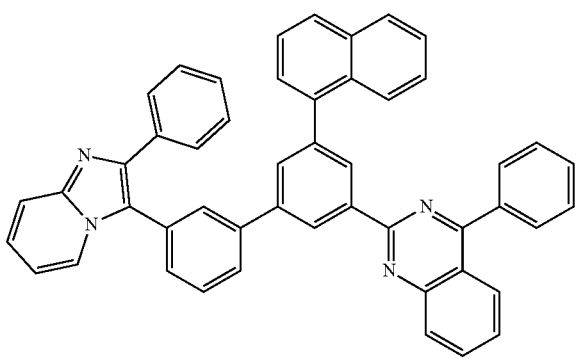 [SMILES: c1ccc(-c2nc3ccccn3c2-c2cccc(-c3cc(-c4nc(-c5ccccc5)c5ccccc5n4)cc(-c4cccc5ccccc45)c3)c2)cc1]
B 315 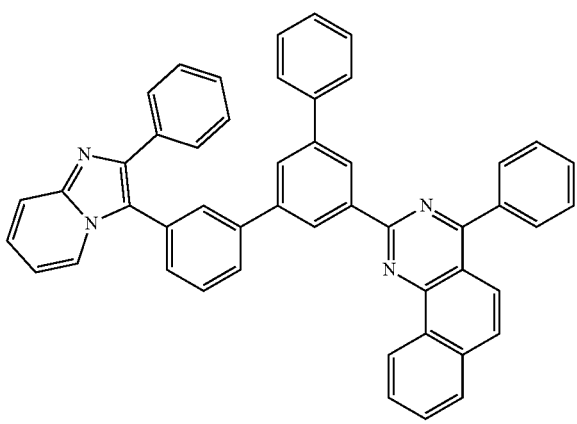 [SMILES: c1ccc(-c2cc(-c3cccc(-c4c(-c5ccccc5)nc5ccccn45)c3)cc(-c3nc(-c4ccccc4)c4ccc5ccccc5c4n3)c2)cc1]
B 316 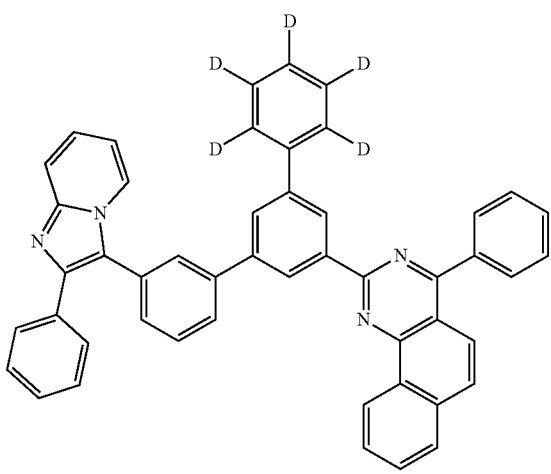 [SMILES: [2H]c1c([2H])c([2H])c(-c2cc(-c3cccc(-c4c(-c5ccccc5)nc5ccccn45)c3)cc(-c3nc(-c4ccccc4)c4ccc5ccccc5c4n3)c2)c([2H])c1[2H]]

B 317
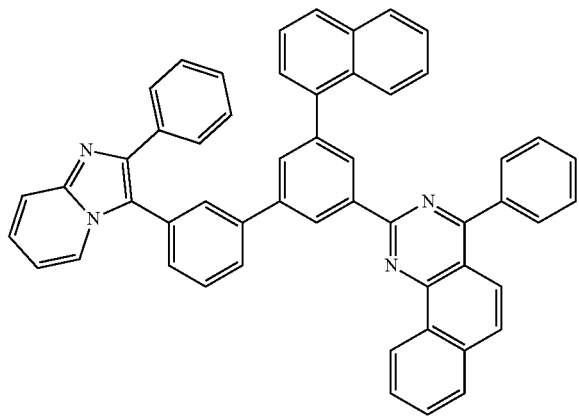 [SMILES: c1ccc(-c2nc3ccccn3c2-c2cccc(-c3cc(-c4nc(-c5ccccc5)c5ccc6ccccc6c5n4)cc(-c4cccc5ccccc45)c3)c2)cc1]
B 318
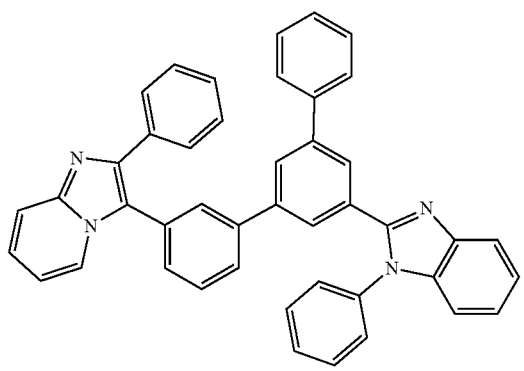 [SMILES: c1ccc(-c2cc(-c3cccc(-c4c(-c5ccccc5)nc5ccccn45)c3)cc(-c3nc4ccccc4n3-c3ccccc3)c2)cc1]
B 319
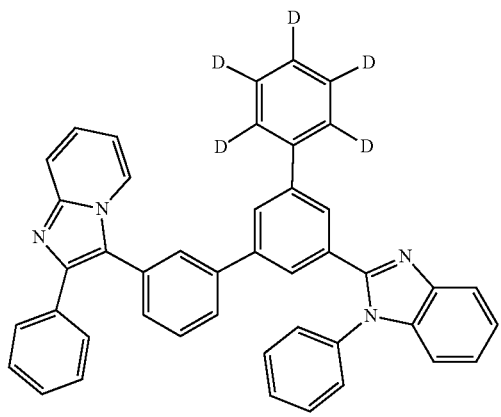 [SMILES: [2H]c1c([2H])c([2H])c(-c2cc(-c3cccc(-c4c(-c5ccccc5)nc5ccccn45)c3)cc(-c3nc4ccccc4n3-c3ccccc3)c2)c([2H])c1[2H]]
B 320
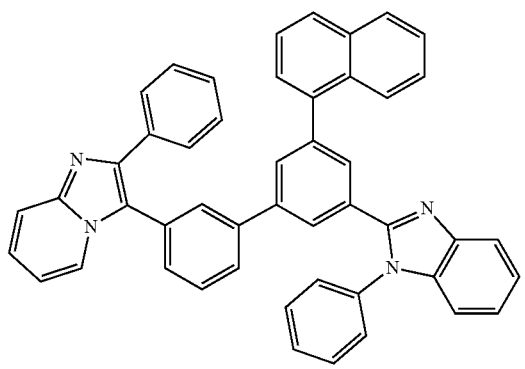 [SMILES: c1ccc(-c2nc3ccccn3c2-c2cccc(-c3cc(-c4cccc5ccccc45)cc(-c4nc5ccccc5n4-c4ccccc4)c3)c2)cc1]

-continued
B 321
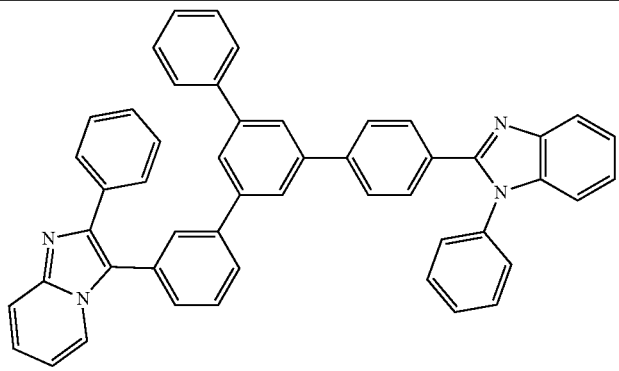
B 322
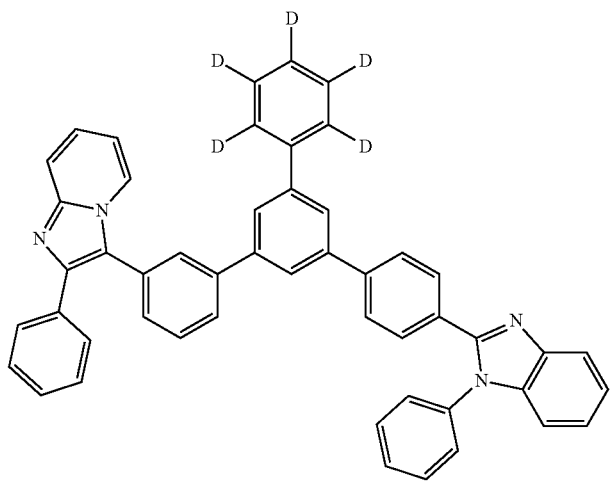 [SMILES: [2H]c1c([2H])c([2H])c(-c2cc(-c3ccc(-c4nc5ccccc5n4-c4ccccc4)cc3)cc(-c3cccc(-c4c(-c5ccccc5)nc5ccccn45)c3)c2)c([2H])c1[2H]]
B 323
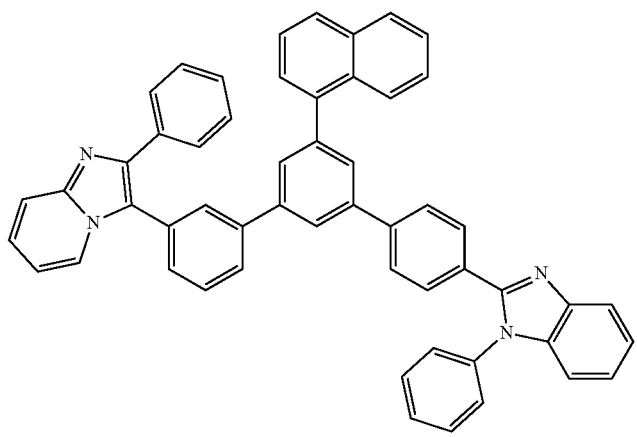 [SMILES: c1ccc(-c2nc3ccccn3c2-c2cccc(-c3cc(-c4ccc(-c5nc6ccccc6n5-c5ccccc5)cc4)cc(-c4cccc5ccccc45)c3)c2)cc1]
B 324
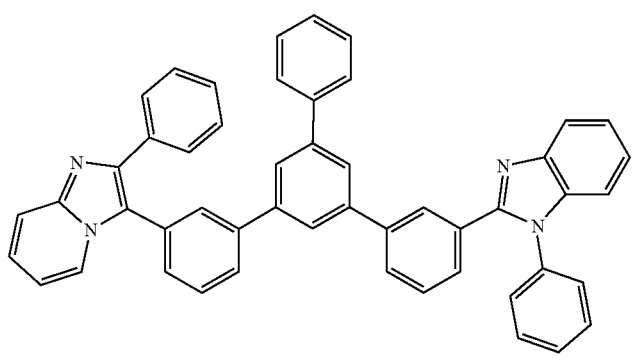 [SMILES: c1ccc(-c2cc(-c3cccc(-c4nc5ccccc5n4-c4ccccc4)c3)cc(-c3cccc(-c4c(-c5ccccc5)nc5ccccn45)c3)c2)cc1]

B 325
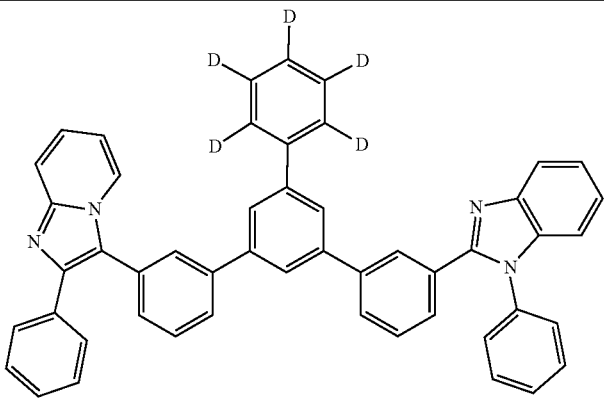
B 326
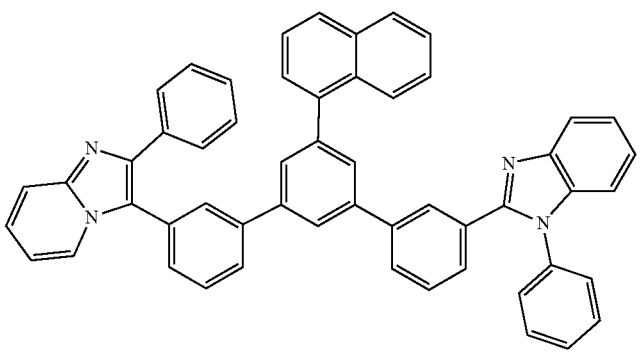 [SMILES: c1ccc(-c2nc3ccccn3c2-c2cccc(-c3cc(-c4cccc(-c5nc6ccccc6n5-c5ccccc5)c4)cc(-c4cccc5ccccc45)c3)c2)cc1]
B 327
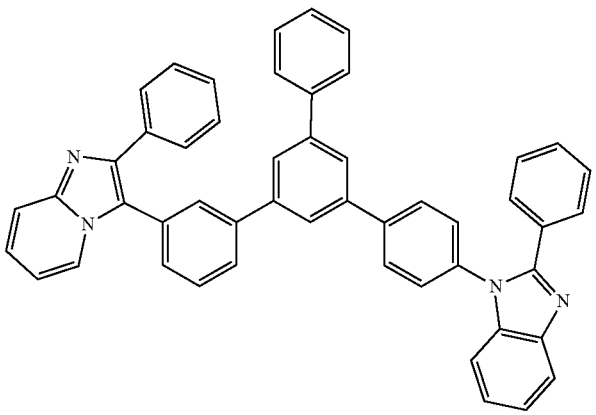 [SMILES: c1ccc(-c2cc(-c3ccc(-n4c(-c5ccccc5)nc5ccccc54)cc3)cc(-c3cccc(-c4c(-c5ccccc5)nc5ccccn45)c3)c2)cc1]
B 328
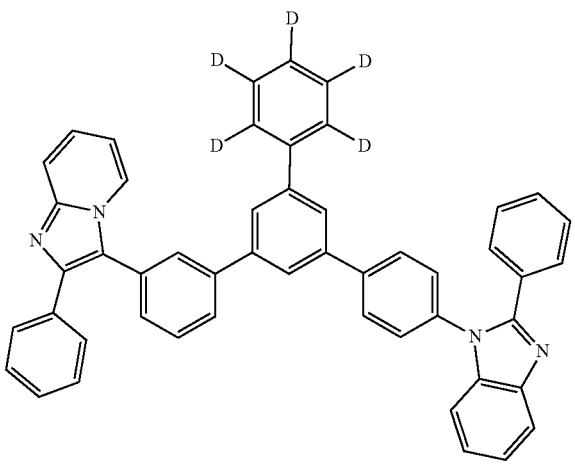 [SMILES: [2H]c1c([2H])c([2H])c(-c2cc(-c3ccc(-n4c(-c5ccccc5)nc5ccccc54)cc3)cc(-c3cccc(-c4c(-c5ccccc5)nc5ccccn45)c3)c2)c([2H])c1[2H]]

B 329
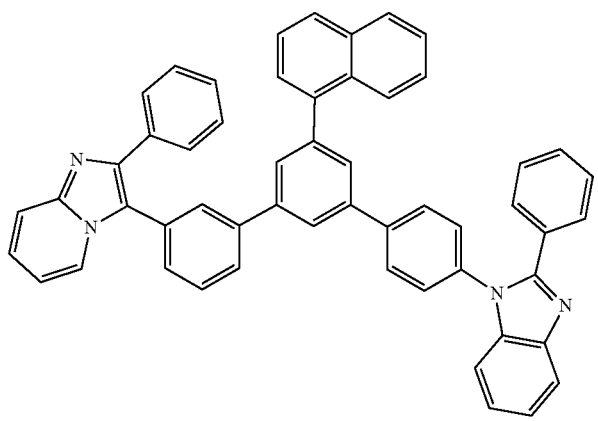 [SMILES: c1ccc(-c2nc3ccccn3c2-c2cccc(-c3cc(-c4ccc(-n5c(-c6ccccc6)nc6ccccc65)cc4)cc(-c4cccc5ccccc45)c3)c2)cc1]
B 330
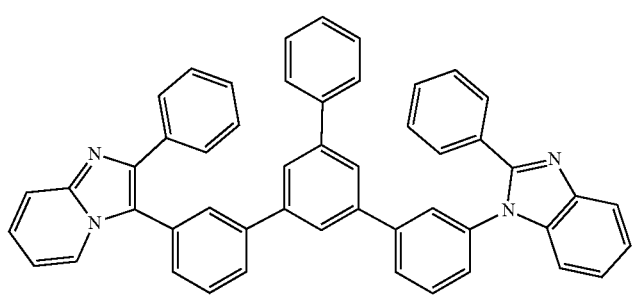 [SMILES: c1ccc(-c2cc(-c3cccc(-c4c(-c5ccccc5)nc5ccccn45)c3)cc(-c3cccc(-n4c(-c5ccccc5)nc5ccccc54)c3)c2)cc1]
B 331
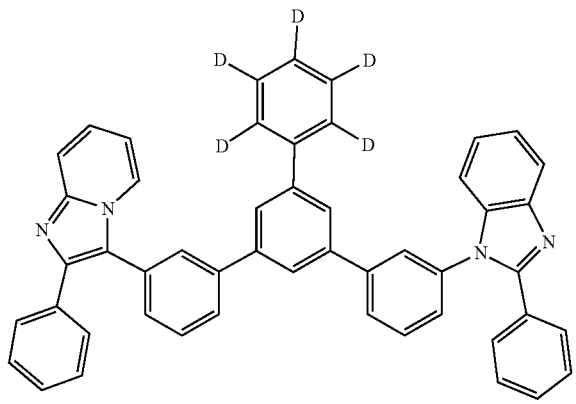 [SMILES: [2H]c1c([2H])c([2H])c(-c2cc(-c3cccc(-c4c(-c5ccccc5)nc5ccccn45)c3)cc(-c3cccc(-n4c(-c5ccccc5)nc5ccccc54)c3)c2)c([2H])c1[2H]]
B 332
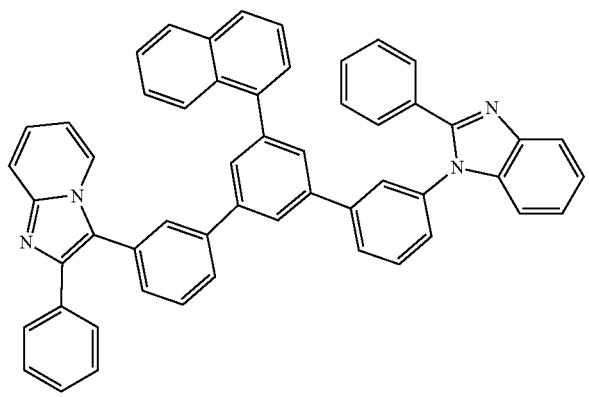 [SMILES: c1ccc(-c2nc3ccccn3c2-c2cccc(-c3cc(-c4cccc(-n5c(-c6ccccc6)nc6ccccc65)c4)cc(-c4cccc5ccccc45)c3)c2)cc1]

-continued
B 333
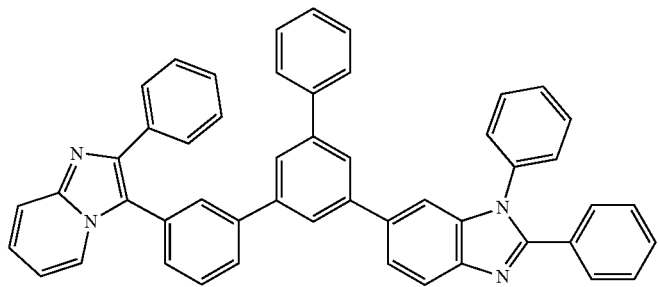 [SMILES: c1ccc(-c2cc(-c3cccc(-c4c(-c5ccccc5)nc5ccccn45)c3)cc(-c3ccc4nc(-c5ccccc5)n(-c5ccccc5)c4c3)c2)cc1]
B 334
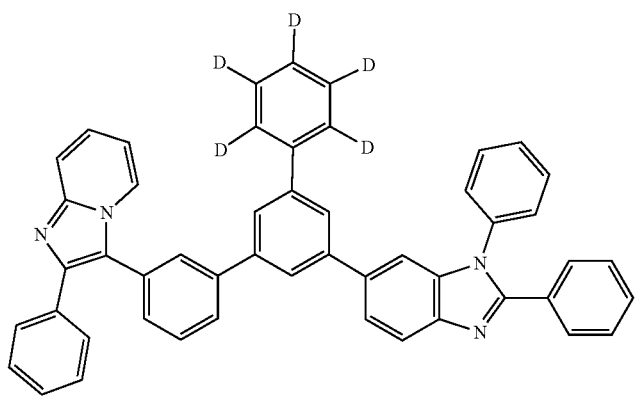 [SMILES: [2H]c1c([2H])c([2H])c(-c2cc(-c3cccc(-c4c(-c5ccccc5)nc5ccccn45)c3)cc(-c3ccc4nc(-c5ccccc5)n(-c5ccccc5)c4c3)c2)c([2H])c1[2H]]
B 335
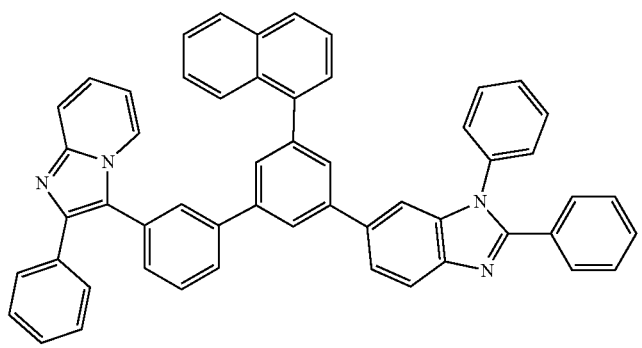 [SMILES: c1ccc(-c2nc3ccccn3c2-c2cccc(-c3cc(-c4ccc5nc(-c6ccccc6)n(-c6ccccc6)c5c4)cc(-c4cccc5ccccc45)c3)c2)cc1]
B 336
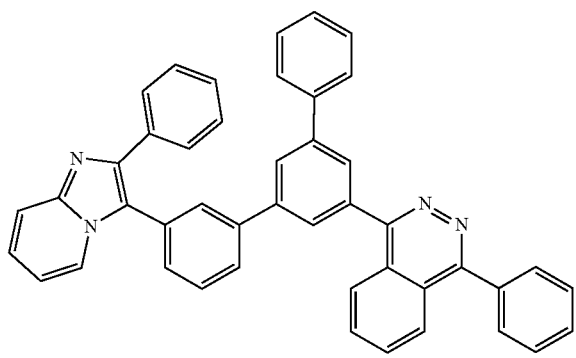 [SMILES: c1ccc(-c2cc(-c3cccc(-c4c(-c5ccccc5)nc5ccccn45)c3)cc(-c3nnc(-c4ccccc4)c4ccccc34)c2)cc1]

B 337
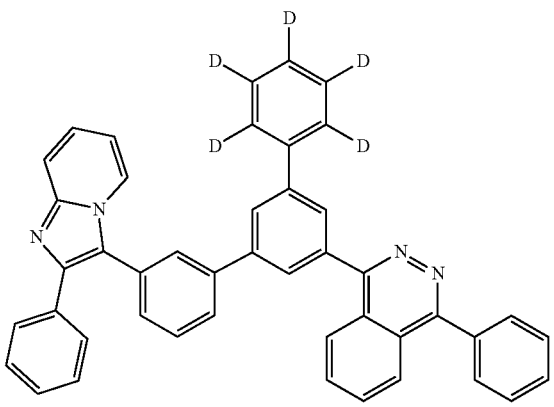 [SMILES: [2H]c1c([2H])c([2H])c(-c2cc(-c3cccc(-c4c(-c5ccccc5)nc5ccccn45)c3)cc(-c3nnc(-c4ccccc4)c4ccccc34)c2)c([2H])c1[2H]]
B 338
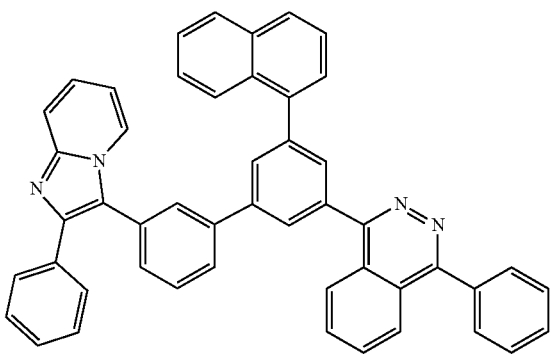 [SMILES: c1ccc(-c2nc3ccccn3c2-c2cccc(-c3cc(-c4cccc5ccccc45)cc(-c4nnc(-c5ccccc5)c5ccccc45)c3)c2)cc1]
B 339
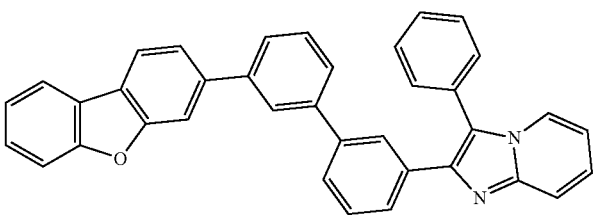 [SMILES: c1ccc(-c2c(-c3cccc(-c4cccc(-c5ccc6c(c5)oc5ccccc56)c4)c3)nc3ccccn23)cc1]
B 340
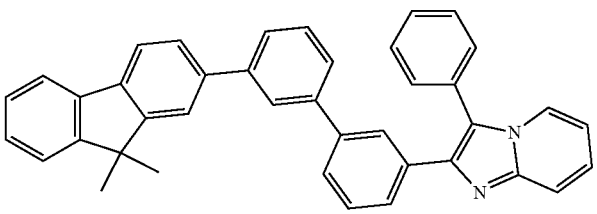 [SMILES: CC1(C)c2ccccc2-c2ccc(-c3cccc(-c4cccc(-c5nc6ccccn6c5-c5ccccc5)c4)c3)cc21]
B 341
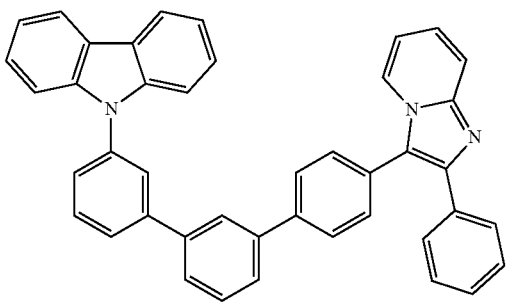 [SMILES: c1ccc(-c2nc3ccccn3c2-c2ccc(-c3cccc(-c4cccc(-n5c6ccccc6c6ccccc65)c4)c3)cc2)cc1]

-continued
B 342
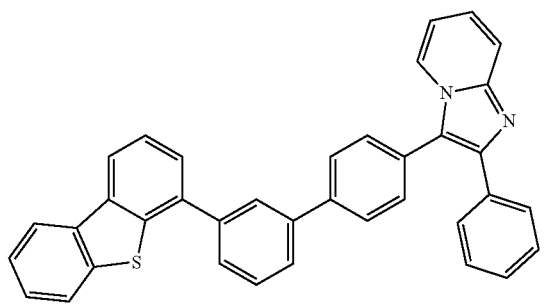
B 343
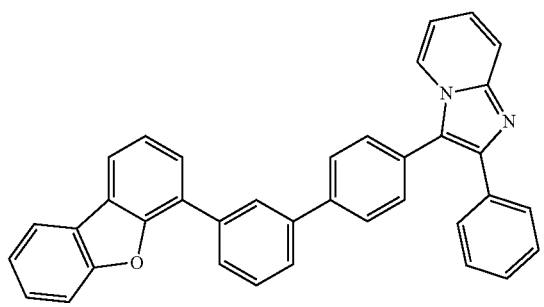 [SMILES: c1ccc(-c2nc3ccccn3c2-c2ccc(-c3cccc(-c4cccc5c4oc4ccccc45)c3)cc2)cc1]
B 344
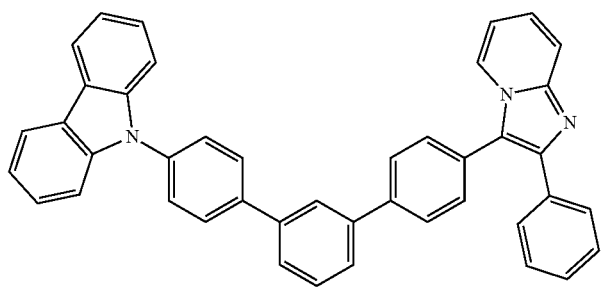 [SMILES: c1ccc(-c2nc3ccccn3c2-c2ccc(-c3cccc(-c4ccc(-n5c6ccccc6c6ccccc65)cc4)c3)cc2)cc1]
B 345
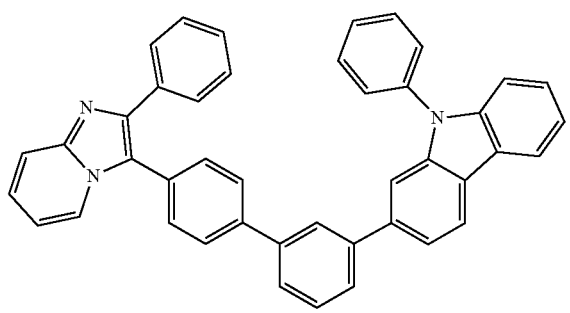 [SMILES: c1ccc(-c2nc3ccccn3c2-c2ccc(-c3cccc(-c4ccc5c6ccccc6n(-c6ccccc6)c5c4)c3)cc2)cc1]
B 346
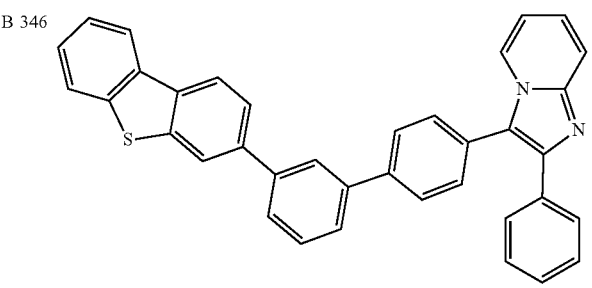

-continued
B 347
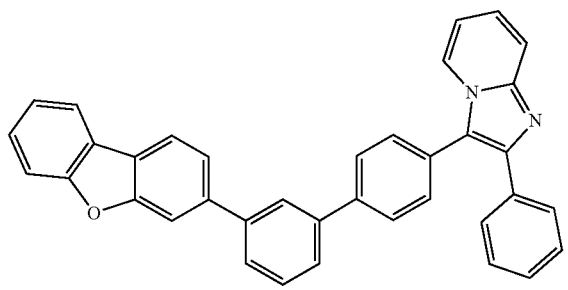 [SMILES: c1ccc(-c2nc3ccccn3c2-c2ccc(-c3cccc(-c4ccc5c(c4)oc4ccccc45)c3)cc2)cc1]
B 348
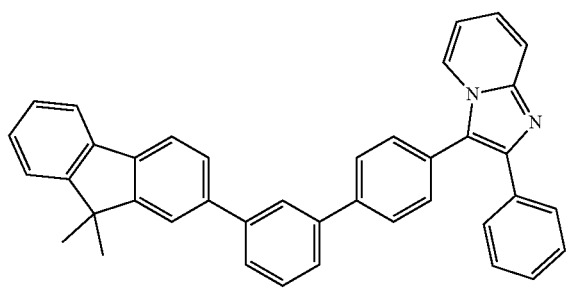 [SMILES: CC1(C)c2ccccc2-c2ccc(-c3cccc(-c4ccc(-c5c(-c6ccccc6)nc6ccccn56)cc4)c3)cc21]
B 349
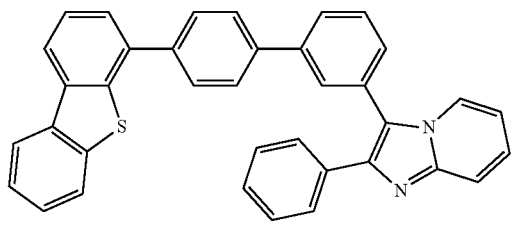 [SMILES: c1ccc(-c2nc3ccccn3c2-c2cccc(-c3ccc(-c4cccc5c4sc4ccccc45)cc3)c2)cc1]
B 350
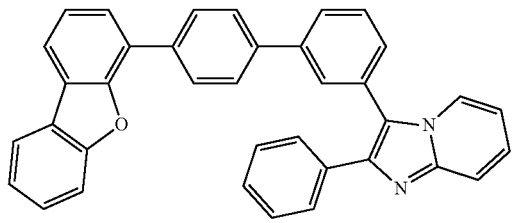 [SMILES: c1ccc(-c2nc3ccccn3c2-c2cccc(-c3ccc(-c4cccc5c4oc4ccccc45)cc3)c2)cc1]
B 351
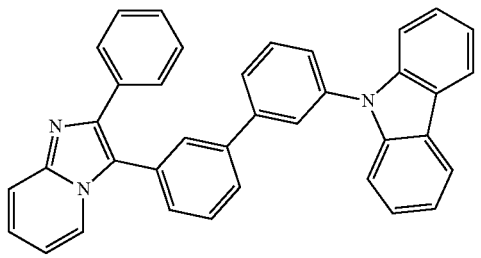 [SMILES: c1ccc(-c2nc3ccccn3c2-c2cccc(-c3cccc(-n4c5ccccc5c5ccccc54)c3)c2)cc1]
B 352
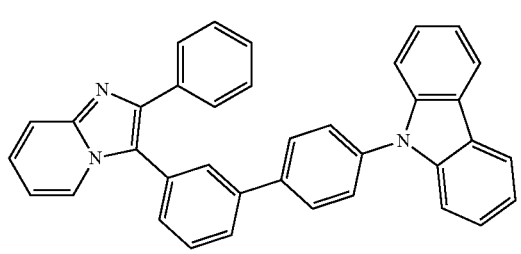 [SMILES: c1ccc(-c2nc3ccccn3c2-c2cccc(-c3ccc(-n4c5ccccc5c5ccccc54)cc3)c2)cc1]

-continued
B 353
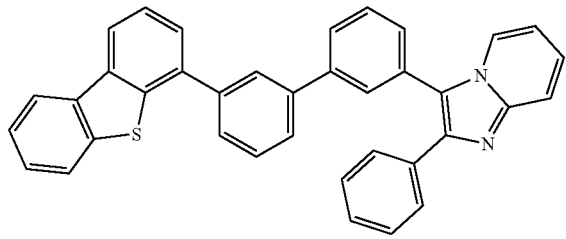 [SMILES: c1ccc(-c2nc3ccccn3c2-c2cccc(-c3cccc(-c4cccc5c4sc4ccccc45)c3)c2)cc1]
B 354
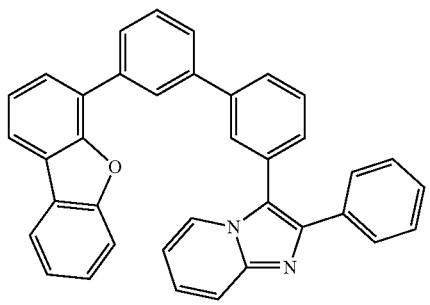 [SMILES: c1ccc(-c2nc3ccccn3c2-c2cccc(-c3cccc(-c4cccc5c4oc4ccccc45)c3)c2)cc1]
B 355
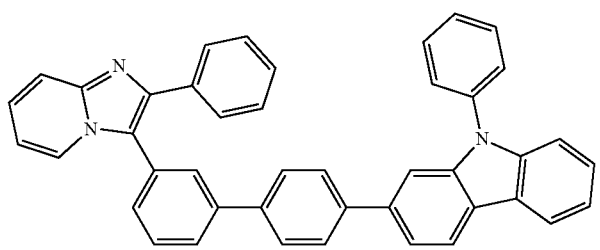 [SMILES: c1ccc(-c2nc3ccccn3c2-c2cccc(-c3ccc(-c4ccc5c6ccccc6n(-c6ccccc6)c5c4)cc3)c2)cc1]
B 356
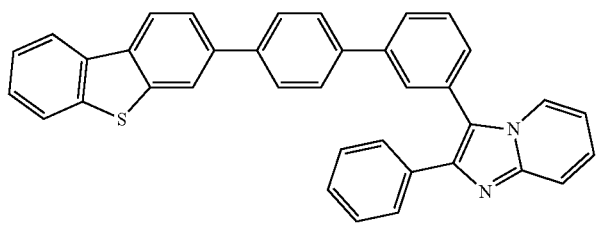
B 357
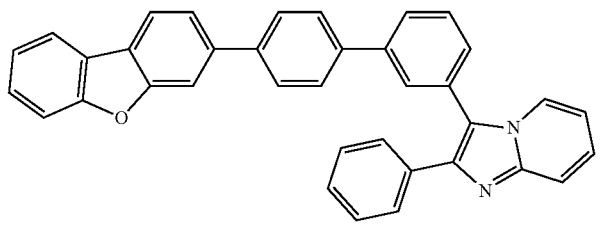 [SMILES: c1ccc(-c2nc3ccccn3c2-c2cccc(-c3ccc(-c4ccc5c(c4)oc4ccccc45)cc3)c2)cc1]
B 358
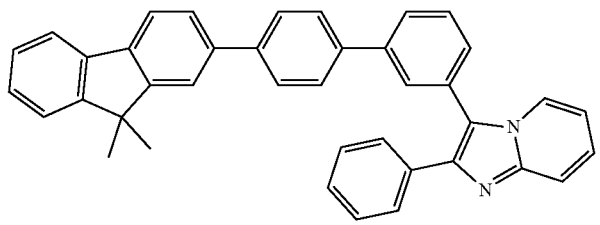

-continued
B 359
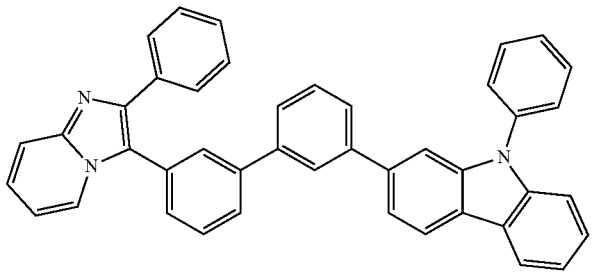 [SMILES: c1ccc(-c2nc3ccccn3c2-c2cccc(-c3cccc(-c4ccc5c6ccccc6n(-c6ccccc6)c5c4)c3)c2)cc1]
B 360
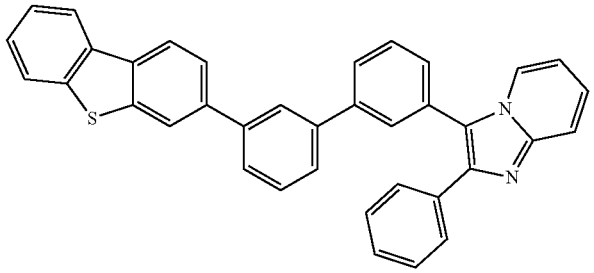
B 361
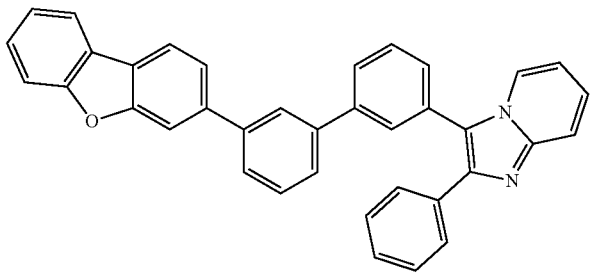 [SMILES: c1ccc(-c2nc3ccccn3c2-c2cccc(-c3cccc(-c4ccc5c(c4)sc4ccccc45)c3)c2)cc1]
B 362
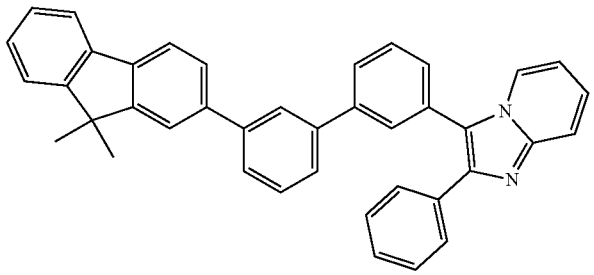
13. An application of the compound according to claim 1 in an OLED apparatus.
14. The application according to claim 13 in the OLED apparatus, characterized in that the compound is taken an electron transmission material, a hole barrier layer material and a light extraction layer material.
* * * * *